United States Patent
Shiraishi et al.

(10) Patent No.: US 7,649,001 B2
(45) Date of Patent: Jan. 19, 2010

(54) FUSED BENZENE DERIVATIVE AND USE

(75) Inventors: Mitsuru Shiraishi, Amagasaki (JP); Takahito Hara, Los Angles, CA (US); Masami Kusaka, Kobe (JP); Naoyuki Kanzaki, Ibaraki (JP); Satoshi Yamamoto, Ibaraki (JP); Toshio Miyawaki, Nishinomiya (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 679 days.

(21) Appl. No.: 10/524,452

(22) PCT Filed: Aug. 11, 2003

(86) PCT No.: PCT/JP03/10228

§ 371 (c)(1),
(2), (4) Date: Aug. 29, 2005

(87) PCT Pub. No.: WO2004/016576

PCT Pub. Date: Feb. 26, 2004

(65) Prior Publication Data

US 2006/0106067 A1    May 18, 2006

(30) Foreign Application Priority Data

Aug. 12, 2002    (JP) .............................. 2002-235275

(51) Int. Cl.
*A61K 31/454*    (2006.01)
*C07D 409/02*    (2006.01)

(52) U.S. Cl. ...................... 514/320; 514/319; 514/324; 514/422; 546/196; 546/202; 546/205; 548/525; 548/527; 548/550; 548/551

(58) Field of Classification Search ............... 514/319, 514/320, 324, 422; 546/196, 202, 205; 548/525, 548/527, 550, 551
See application file for complete search history.

(56) References Cited

U.S. PATENT DOCUMENTS

| 6,211,225 B1 * | 4/2001 | Takaki et al. ................. 514/422 |
| 7,223,788 B2 * | 5/2007 | Schwink et al. ............. 514/426 |
| 2001/0012905 A1 | 8/2001 | Shershukov et al. |
| 2004/0122001 A1 | 6/2004 | Agejas-Chicharro et al. |
| 2006/0287327 A1 * | 12/2006 | Labrie et al. ................. 514/249 |

FOREIGN PATENT DOCUMENTS

| EP | 1136079 A1 | 9/2001 |
| EP | 1424080 A1 | 6/2004 |
| EP | 1466902 A1 | 10/2004 |
| JP | 2002/88073 | 8/2000 |
| WO | WO 92/03426 | 3/1992 |
| WO | WO 94/13659 | 6/1994 |
| WO | WO 95/14004 | 5/1995 |
| WO | WO 97/25323 | 7/1997 |
| WO | WO 01/02392 A1 | 1/2001 |
| WO | WO 02/00617 A2 | 1/2002 |
| WO | WO 02/00653 A2 | 1/2002 |
| WO | WO 02/11209 A2 | 2/2002 |
| WO | WO 02/24702 A1 | 3/2002 |
| WO | WO 02/100822 A1 | 12/2002 |
| WO | WO 03/006455 A1 | 1/2003 |
| WO | WO 03/075958 | 11/2003 |
| WO | WO 03/102188 | 1/2004 |

OTHER PUBLICATIONS

Sun et al. "preparation of imidazo . . . " CA 138:153537 (2003).*
Vincent et al. "Role of thiol groups in . . . " CA 89:102701 (1978).*
Salvati et al. "Synthesis of selective androgen . . . " CA 136:85823 (2002).*
Ulla Karvonen, et al., "Interaction of Androgen Receptors with Androgen Response Element in Intact Cells", The Journal of Biological Chemistry, (1997), pp. 15973-15979, vol. 272, No. 25.

(Continued)

*Primary Examiner*—Celia Chang
(74) *Attorney, Agent, or Firm*—Edwards Angell Palmer & Dodge LLP; David G. Conlin; Lisa Swiszcz Hazzard

(57) ABSTRACT

The present invention provides a compound represented by the general formula:

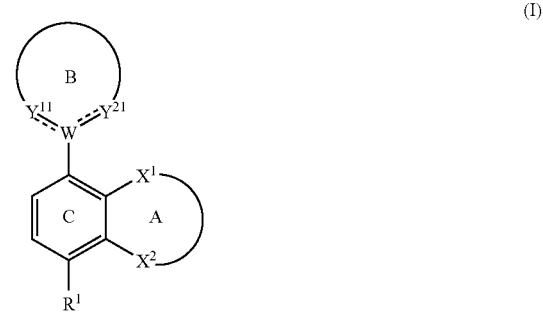

(I)

[wherein Ring A represents an optionally substituted 5- to 8-membered ring, Ring B represents a further optionally substituted 4- to 10-membered ring, Ring C represents a further optionally substituted benzene ring, $X^1$ represents carbon atom, $X^2$ represents a carbon atom, an oxygen atom, etc., W represents a nitrogen atom, etc., $Y^{11}$ represents a group represented by the formula $CR^2R^{3'}$ (wherein $R^2$ represents a hydrogen atom, a cyano group, a nitro group, etc., and $R^{3'}$ represents a hydrogen atom, a cyano group, a nitro group, etc., respectively), $Y^{21}$ represents a group represented by the formula $CR^4R^{5'}$ (wherein $R^4$ represents a hydrogen atom, a cyano group, a nitro group, etc., and $R^{5'}$ represents a hydrogen atom, a cyano group, a nitro group, etc., respectively), etc., and $R^1$ represents an electron-withdrawing group, respectively. The formula ═══
represents a single bond or a double bond] or a salt thereof, which is useful as an androgen receptor modulator.

9 Claims, No Drawings

OTHER PUBLICATIONS

Marcian E. Van Dort, et al., "Design, Synthesis, and Pharmacological Characterization of 4-[4,4-Dimethyl-3-(4-hydroxybuty1)-5-oxo-2-thioxo-1-imidazolidinyl]-2-iodobenzonitrile as a High-Affinity Nonsteroidal Androgen Receptor Ligand", J. Med. Chem., (2000), pp. 3344-3347, vol. 43, No. 17.

Tammy Wang, et al., "Palladium-Catalyzed Mircrowave-Assisted Amination of 1-Bromonaphthalenes and 5- and 8-Bromoquinolines", Organic Letters, (2003), pp. 897-900, vol. 5, No. 6.

Toshihiko Okamoto, et al., "Reaction Mechanism in Aromatic Heterocyclic Compounds. III. Kinetics of the Reaction of 4-Haloquinoline 1-Oxides and Related Compounds with Piperidine", Chem. Pharm. Bull, (1960), pp. 892-899, vol. 8.

* cited by examiner

FUSED BENZENE DERIVATIVE AND USE

This application is the National Phase filing of International Patent Application No. PCT/JP03/10228, filed Aug. 11, 2003.

TECHNICAL FIELD

The present invention relates to a condensed benzene derivative useful as an androgen receptor modulator and a method for preparing the same, etc.

BACKGROUND ART

Androgens synthesized in the testis and the adrenal cortex, bind to an androgen receptor at the target organ, and exert various physiological activities. Natural androgens all belong to C19 steroids chemically. The chief androgen among them is testosterone, which is synthesized at testis, incorporated into target cells and has strong physiological activity. For females, the adrenal cortex is a major source for androgens.

Androgens have actions of developing and maintaining the functions of reproductive organs (prostate, seminal vesicle, epididymis, vas deferens, etc.), sexual differentiation at fetal stage, formation of sperm, expression of secondary sexual characteristics (induction of masculinization for muscle/backbone, voice, fat distribution, etc.), promoting protein anabolism at muscle, etc., and actions for bone metabolism, etc. Therefore, insufficiency of androgen such as androgen deficiency by testis function disorders and castration, etc. is linked to various diseases and decrease of QOL (quality of life). For this, androgen supplement therapy is usually carried out. In addition to testosterone, synthetic androgens having different balance of androgen action have been investigated, and applied in clinical practice.

On the other hand, in the case that androgens are associated with the progress of diseases, androgen deprivation therapy is carried out. For example, for androgen-dependent prostate cancer, testosterone level is lowered by castration operation or GnRH agonist administration, to increase therapeutic effects.

In the case of androgen supplements, testosterone or synthetic androgens are usually used. However, these substances have steroid backbones, and sometimes give a great burden to the liver, or exhibit actions of other steroid hormones. Therefore, an androgen receptor modulator having non-steroidal backbone (especially, agonist) is considered to be useful for improving diseases by deficient androgen actions (hypogonadism, male climacteric disturbance, etc.) and in diseases which is expected to be improved by actions of androgen (osteoporosis, etc.).

Furthermore, the present inventors have investigated and found that if the testosterone level is lowered by a castration operation or GnRH agonist administration, there may be cancer acquiring growth ability under such a lowered testosterone, and in such cancer, androgen agonists exhibit anti-tumor actions conversely.

Therefore, the object of the present invention is to provide an androgen receptor modulator (especially, agonist) having a non-steroidal backbone, to solve such problems.

DISCLOSURE OF INVENTION

The present inventors have made extensive studies considering the above-mentioned circumstances, and as a result, have found that a compound represented by the general formula (I) has excellent action as an androgen receptor modulator capable of accomplishing the above-mentioned objects, and reached completion of the present invention.

That is, the present invention relates to:

[1] A compound represented by the general formula:

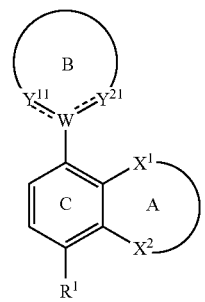

(I)

[wherein Ring A represents an optionally substituted 5- to 8-membered ring, Ring B represents a further optionally substituted 4- to 10-membered ring, Ring C represents a further optionally substituted benzene ring, $X^1$ represents an optionally substituted carbon atom, and $X^2$ represents an optionally substituted carbon atom, an oxygen atom or a group represented by the formula $S(O)_k$ (wherein k represents 0, 1 or 2), respectively. W represents a nitrogen atom, or when Ring A is an optionally substituted benzene ring, a group represented by the formula $CR^a$ (wherein $R^a$ represents a bond, a hydrogen atom, a hydroxy group or an optionally substituted alkoxy group). $Y^{11}$ represents a group represented by the formula $CR^2R^{3'}$ (wherein $R^2$ represents a hydrogen atom, a cyano group, a nitro group, an optionally substituted acyl group, an optionally esterified or amidated carboxyl group or an optionally substituted hydrocarbon group, and $R^{3'}$ represents a bond, a hydrogen atom, a cyano group, a nitro group, an optionally substituted acyl group, an optionally esterified or amidated carboxyl group or an optionally substituted hydrocarbon group, respectively), and $Y^{21}$ represents 1] when W is a nitrogen atom, a group represented by the formula $CR^4R^{5'}$ (wherein $R^4$ represents a hydrogen atom, a cyano group, a nitro group, an optionally substituted acyl group, an optionally esterified or amidated carboxyl group or an optionally substituted hydrocarbon group, and $R^{5'}$ represents a bond, a hydrogen atom, a cyano group, a nitro group, an optionally substituted acyl group, an optionally esterified or amidated carboxyl group or an optionally substituted hydrocarbon group, respectively), an optionally substituted nitrogen atom, an oxygen atom or a group represented by the formula $S(O)_m$ (wherein m represents 0, 1 or 2), and 2) when W is a group represented by the formula $CR^a$ (wherein the symbol is as defined above), a group represented by the formula $CR^4R^{5'}$ (wherein each symbol is as defined above) or a nitrogen atom (provided that when $Y^{21}$ is a nitrogen atom and W is a group represented by the formula $CR^a$ (wherein the symbol is as defined above), the bond between $CR^a$ and $Y^{21}$ is a double bond), respectively, and when Ring B is a further optionally substituted bicyclic ring, $CR^2$ in $Y^{11}$ or $CR^4$ or the nitrogen atom in $Y^{21}$ may constitute a part of Ring B. $R^1$ represents an electron-withdrawing group. The formula ==== represents a single bond or a double bond] or a salt thereof, except the case that 1) W is a nitrogen atom and Ring B is an optionally substituted piperazine ring, 2) Ring A is an optionally substituted benzene ring, $R^1$ is a nitro group or an optionally substituted sulfamoyl group, W is a nitrogen atom, Ring B is an octahydro[1,2-a]pyrazine ring, a homopiperazine ring in which the nitrogen atom is optionally substituted with an alkyl group or a 2,5-diazabicyclo[2,2,1]heptane ring in which the nitrogen atom is optionally substituted with an alkyl group,
3) Ring A is an optionally substituted, optionally saturated furan ring or pyran ring, $R^1$ is a halogen atom, W is a nitrogen atom, and Ring B is a pyrrolidine ring substituted with an optionally substituted amino group at the position 3,
4) W is a group represented by the formula $CR^a$ (wherein the symbol is as defined above), and Ring B is an optionally substituted piperidine ring bonding to Ring C at the position 4 or an optionally substituted 1,2,5,6-tetrahydropyridine ring bonding to Ring C at the position 4, and
5) the compound is 1-[4-(1-piperidinyl)-1-naphthyl]ethanone, 4-(1-piperidinyl)-1-nitronaphthalene, 4-(1-piperidinyl)-1-naphthonitrile and 4-(1-pyrrolidinyl)-1-nitronaphthalene;

[2] The compound as described in the above-mentioned [1], wherein the compound is represented by the general formula:

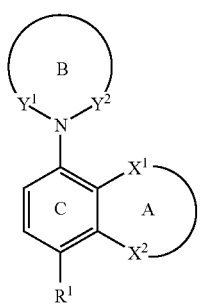

(Ia)

[wherein Ring A represents an optionally substituted 5- to 8-membered ring, Ring B represents a further optionally substituted 4- to 10-membered ring, Ring C represents a further-optionally substituted benzene ring, $X^1$ represents an optionally substituted carbon atom, and $X^2$ represents an optionally substituted carbon atom, an oxygen atom or a group represented by the formula $S(O)_k$ (wherein k represents 0, 1 or 2), respectively. $Y^1$ represents a group represented by the formula $CR^2R^3$ (wherein $R^2$ and $R^3$ are the same or different and represent a hydrogen atom, a cyano group, a nitro group, an optionally substituted acyl group, an optionally esterified or amidated carboxyl group or an optionally substituted hydrocarbon group, respectively), and $Y^2$ represents a group represented by the formula $CR^4R^5$ (wherein $R^4$ and $R^5$ are the same or different and represent a hydrogen atom, a cyano group, a nitro group, an optionally substituted acyl group, an optionally esterified or amidated carboxyl group or an optionally substituted hydrocarbon group, respectively), an optionally substituted nitrogen atom, an oxygen atom or a group represented by the formula $S(O)_m$ (wherein m represents 0, 1 or 2), respectively, and when Ring B is a further optionally substituted bicyclic ring, $CR^2$ in $Y^1$ or $CR^4$ in $Y^2$ may constitute a part of Ring B. $R^1$ represents an electron-withdrawing group], except the case that
1) Ring B is an optionally substituted piperazine ring,
2) Ring A is an optionally substituted benzene ring, $R^1$ is a nitro group or an optionally substituted sulfamoyl group, Ring B is an octahydro[1,2-a]pyrazine ring, a homopiperazine ring in which the nitrogen atom is optionally substituted with an alkyl group or a 2,5-diazabicyclo[2,2,1]heptane ring in which the nitrogen atom is optionally substituted with an alkyl group,
3) Ring A is an optionally substituted, optionally saturated furan ring or pyran ring, $R^1$ is a halogen atom, and Ring B is a pyrrolidine ring substituted with an optionally substituted amino group at the position 3, and
4) the compound is 1-[4-(1-piperidinyl)-1-naphthyl]ethanone, 4-(1-piperidinyl)-1-nitronaphthalene, 4-(1-piperidinyl)-1-naphthonitrile and 4-(1-pyrrolidinyl)-1-nitronaphthalene;

[3] The compound as described in the above-mentioned [1], wherein Ring A is an optionally substituted benzene ring, an optionally substituted thiophene ring or an optionally substituted furan ring;

[4] The compound as described in the above-mentioned [1], wherein Ring B is an optionally substituted pyrrolidine ring, an optionally substituted piperidine ring, an optionally substituted morpholine ring, an optionally substituted thiomorpholine ring, an optionally substituted pyrazoline ring, an optionally substituted pyrazolidine ring, an optionally substituted isoxazoline ring, an optionally substituted cyclopentane ring, an optionally substituted cyclopentene ring or an optionally substituted perhydroazepine ring;

[5] The compound as described in the above-mentioned [1], wherein $R^1$ is a cyano group, a nitro group, a halogen atom, an optionally substituted acyl group, an optionally esterified or amidated carboxyl group or a $C_{1-6}$ alkyl group substituted with 1 to 5 halogen atoms;

[6] The compound as described in the above-mentioned [1], wherein the substituent on Ring A or Ring B except for $R^a, R^2, R^{3'}, R^4$ and $R^{5'}$ is 1 to 6 groups selected from the group consisting of (1) a hydrogen atom, (2) a halogen atom, (3) a cyano group, (4) a nitro group, (5) a hydroxy group, (6) an optionally substituted amino group, (7) an optionally esterified or amidated carboxyl group, (8) an optionally substituted $C_{1-6}$ alkyl group, (9) an optionally substituted $C_{1-6}$ acyl group, (10) an optionally substituted $C_{1-6}$ alkoxy group, (11) a group represented by the formula $R^6S(O)_p$ (wherein $R^6$ represents an optionally substituted $C_{1-6}$alkyl group, and p represents 0, 1 or 2, respectively), (12) an oxo group, (13) a hydroxyimino group, (14) an optionally substituted $C_{1-6}$ alkoxyimino group and (15) an optionally substituted $C_{1-4}$ alkylenedioxy group;

[7] A compound represented by the general formula:

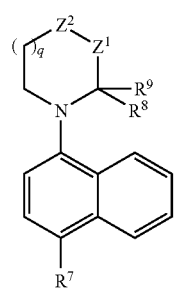

(IIa)

[wherein $R^7$ represents a cyano group, a nitro group, a halogen atom, an optionally substituted acyl group, an optionally esterified or amidated carboxyl group or a $C_{1-6}$ alkyl group substituted with 1 to 5 halogen atoms, $R^8$ and $R^9$ are the same or different and represent (1) a hydrogen atom, (2) a cyano group, (3) a nitro group, (4) a $C_{1-6}$ alkyl group optionally substituted with a halogen atom, a hydroxy group or a $C_{1-6}$ alkoxy group, (5) a $C_{1-6}$ acyl group optionally substituted with a halogen atom, a hydroxy group or a $C_{1-6}$ alkoxy group, (6) a $C_{1-6}$ alkoxy group optionally substituted with a halogen atom, a hydroxy group or a $C_{1-6}$ alkoxy group or (7) an optionally esterified or amidated carboxyl group, q represents 0, 1 or 2, $Z^1$ represents a carbonyl group, a carbon atom substituted with a hydroxyimino group or an optionally substituted $C_{1-6}$ alkoxyimino group, a carbon atom substituted with a $C_{1-4}$ alkylenedioxy group or a group represented by the formula:

(wherein $R^{10}$ and $R^{11}$ are the same or different and represent (1) a hydrogen atom, (2) a halogen atom, (3) a cyano group, (4) a nitro group, (5) a hydroxy group, (6) a $C_{1-6}$ alkyl group optionally substituted with a halogen atom, a hydroxy group or a $C_{1-6}$ alkoxy group, (7) a $C_{1-6}$ acyl group optionally substituted with a halogen atom, a hydroxy group or a $C_{1-6}$ alkoxy group, (8) a $C_{1-6}$ alkoxy group optionally substituted with a halogen atom, a hydroxy group or a $C_{1-6}$ alkoxy group, (9) an amino group optionally substituted with a $C_{1-6}$ alkyl group and/or a $C_{1-6}$ acyl group or (10) an optionally esterified or amidated carboxyl group, respectively), and $Z^2$ represents an oxygen atom, a sulfur atom, SO, $SO_2$, a carbonyl group, a carbon atom substituted with a hydroxyimino group or an optionally substituted $C_{1-6}$ alkoxyimino group, an amino group optionally substituted with a $C_{1-6}$ alkyl group or a $C_{1-6}$ acyl group, a carbon atom substituted with a $C_{1-4}$ alkylenedioxy group or a group represented by the formula:

(wherein $R^{12}$ and $R^{13}$ are the same or different and represent (1) a hydrogen atom, (2) a halogen atom, (3) a cyano group, (4) a nitro group, (5) a hydroxy group, (6) a $C_{1-6}$ alkyl group optionally substituted with a halogen atom, a hydroxy group or a $C_{1-6}$ alkoxy group, (7) a $C_{1-6}$ acyl group optionally substituted with a halogen atom, a hydroxy group or a $C_{1-6}$ alkoxy group, (8) a $C_{1-6}$ alkoxy group optionally substituted with a halogen atom, a hydroxy group or a $C_{1-6}$ alkoxy group, (9) an amino group optionally substituted with a $C_{1-6}$ alkyl group and/or a $C_{1-6}$ acyl group or (10) an optionally esterified or amidated carboxyl group, respectively), respectively] or a salt thereof, except the case that the compound is 1-[4-(1-piperidinyl)-1-naphthyl]ethanone, 4-(1-piperidinyl)-1-nitronaphthalene, 4-(1-piperidinyl)-1-naphthonitrile and 4-(1-pyrrolidinyl)-1-nitronaphthalene;

[8] A compound represented by the general formula:

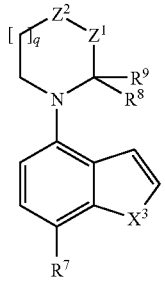

(IIb)

[wherein $X^3$ represents a sulfur atom or an oxygen atom, $R^7$ represents a cyano group, a nitro group, a halogen atom, an optionally substituted acyl group, an optionally esterified or amidated carboxyl group or a $C_{1-6}$ alkyl group substituted with 1 to 5 halogen atoms, $R^8$ and $R^9$ are the same or different and represent (1) a hydrogen atom, (2) a cyano group, (3) a nitro group, (4) a $C_{1-6}$ alkyl group optionally substituted with a halogen atom, a hydroxy group or a $C_{1-6}$ alkoxy group, (5) a $C_{1-6}$ acyl group optionally substituted with a halogen atom, a hydroxy group or a $C_{1-6}$ alkoxy group, (6) a $C_{1-6}$ alkoxy group optionally substituted with a halogen atom, a hydroxy group or a $C_{1-6}$ alkoxy group or (7) an optionally esterified or amidated carboxyl group, q represents 0, 1 or 2, $Z^1$ represents a carbonyl group, a carbon atom substituted with a hydroxyimino group or an optionally substituted $C_{1-6}$ alkoxyimino group, a carbon atom substituted with a $C_{1-4}$ alkylenedioxy group or a group represented by the formula:

(wherein $R^{10}$ and $R^{11}$ are the same or different and represent (1) a hydrogen atom, (2) a halogen atom, (3) a cyano group, (4) a nitro group, (5) a hydroxy group, (6) a $C_{1-6}$ alkyl group optionally substituted with a halogen atom, a hydroxy group or a $C_{1-6}$ alkoxy group, (7) a $C_{1-6}$ acyl group optionally substituted with a halogen atom, a hydroxy group or a $C_{1-6}$ alkoxy group, (8) a $C_{1-6}$ alkoxy group optionally substituted with a halogen atom, a hydroxy group or a $C_{1-6}$ alkoxy group, (9) an amino group optionally substituted with a $C_{1-6}$ alkyl group and/or a $C_{1-6}$ acyl group or (10) an optionally esterified or amidated carboxyl group, respectively), and $Z^2$ represents an oxygen atom, a sulfur atom, SO, $SO_2$, a carbonyl group, a carbon atom substituted with a hydroxyimino group or an optionally substituted $C_{1-6}$ alkoxyimino group, an amino group optionally substituted with a $C_{1-6}$ alkyl group or a $C_{1-6}$ acyl group, a carbon atom substituted with a $C_{1-4}$ alkylenedioxy group or a group represented by the formula:

(wherein $R^{12}$ and $R^{13}$ are the same or different and represent (1) a hydrogen atom, (2) a halogen atom, (3) a cyano group, (4) a nitro group, (5) a hydroxy group, (6) a $C_{1-6}$ alkyl group optionally substituted with a halogen atom, a hydroxy group or a $C_{1-6}$ alkoxy group, (7) a $C_{1-6}$ acyl group optionally substituted with a halogen atom, a hydroxy group or a $C_{1-6}$ alkoxy group, (8) a $C_{1-6}$ alkoxy group optionally substituted with a halogen atom, a hydroxy group or a $C_{1-6}$ alkoxy group, (9) an amino group optionally substituted with a $C_{1-6}$ alkyl group and/or a $C_{1-6}$ acyl group or (10) an optionally esterified or amidated carboxyl group, respectively), respectively] or a salt thereof, except the case that $X^3$ is an oxygen atom, $R^7$ is a halogen atom, q is 0, $R^8$ and $R^9$ are hydrogen atom, $Z^1$ is a group represented by the formula:

(wherein one of $R^{10}$ and $R^{11}$ represents a hydrogen atom and the other represents an amino group optionally substituted with a $C_{1-6}$ alkyl group and/or a $C_{1-6}$ acyl group), and $Z^2$ is a methylene group;

[9] 4-[4-(hydroxymethyl)-1-piperidinyl]-1-naphthonitrile, 4-[3-(hydroxymethyl)-1-piperidinyl]-1-naphthonitrile, 4-[3-(hydroxymethyl)-3-methyl-1-piperidinyl]-1-naphthonitrile, 4-(2-methyl-1-pyrrolidinyl)-1-naphthonitrile, 4-(2-ethyl-1-pyrrolidinyl)-1-naphthonitrile, 4-(2-vinyl-1-pyrrolidinyl)-1-naphthonitrile, 4-(2-isopropyl-1-pyrrolidinyl)-1-naphthonitrile, 4-(3-hydroxy-2-methyl-1-pyrrolidinyl)-1-naphthonitrile, 4-(3-methoxy-2-methyl-1-pyrrolidinyl)-1-naphthonitrile, 4-(3-methoxy-2-methyl-1-pyrrolidinyl)-1-naphthonitrile, 4-[3-(hydroxymethyl)-2-methyl-1-pyrrolidinyl]-1-naphthonitrile, 4-[3-(1-hydroxy-1-methylethyl)-2-methyl-1-pyrrolidinyl]-1-naphthonitrile, 1-(4-cyano-1-naphthyl)-2-methylpyrrolidine-3-carboxamide, 1-(4-cyano-1-naphthyl)-2-methylpyrrolidine-3-carbonitrile, 4-(2-methyl-1-pyrrolidinyl)-1-benzothiophene-7-carbonitrile, 4-(3-hydroxy-2-methyl-1-pyrrolidinyl)-1-benzothiophene-7-carbonitrile, 4-(4-hydroxy-2-methyl-1-pyrrolidinyl)-1-benzothiophene-7-carbonitrile or an optically active substance or a salt thereof;

[10] A method for preparing the compound as described in the above-mentioned [2] or a salt thereof, comprising subjecting a compound represented by the general formula:

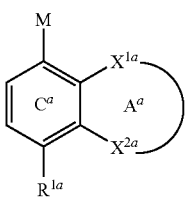

(III)

[wherein Ring $A^a$ represents an optionally substituted 5- to 8-membered ring, Ring $C^a$ represents a further optionally substituted benzene ring, $X^{1a}$ represents an optionally substituted carbon atom, $X^{2a}$ represents an optionally substituted carbon atom, an oxygen atom or a group represented by the formula $S(O)_k{}^a$ (wherein $k^a$ represents 0, 1 or 2), $R^{1a}$ represents an electron-withdrawing group, and M represents a leaving group, respectively] or a salt thereof and, a compound represented by the general formula:

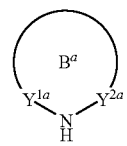

(IV)

[wherein Ring $B^a$ represents a further optionally substituted 4- to 10-membered ring, $Y^{1a}$ represents a group represented by the formula $CR^{2a}R^{3a}$ (wherein $R^{2a}$ and $R^{3a}$ are the same or different and represent a hydrogen atom, a cyano group, a nitro group, an optionally substituted acyl group, an optionally esterified or amidated carboxyl group or an optionally substituted hydrocarbon group, respectively), and $Y^{2a}$ represents a group represented by the formula $CR^{4a}R^{5a}$ (wherein $R^{4a}$ and $R^{5a}$ are the same or different and represent a hydrogen atom, a cyano group, a nitro group, an optionally substituted acyl group, an optionally esterified or amidated carboxyl group or an optionally substituted hydrocarbon group, respectively), an optionally substituted nitrogen atom, an oxygen atom or a group represented by the formula $S(O)_m{}^a$ (wherein $m^a$ represents 0, 1 or 2), respectively, or when Ring $B^a$ is a further optionally substituted bicyclic ring, $CR^{2a}$ in $Y^{1a}$ or $CR^{4a}$ or the nitrogen atom in $Y^{2a}$ may constitute a part of Ring B] or a salt thereof to a reaction, and if desired, eliminating the protective group;

[11] A prodrug of the compound as described in the above-mentioned [1], [7] or [8];

[12] A medicine comprising the compound as described in the above-mentioned [1], [7] or [8] or a salt or a prodrug thereof;

[13] The medicine as described in the above-mentioned [12], which is an androgen receptor modulator;

[14] The medicine as described in the above-mentioned [12], which is an androgen receptor agonist;

[15] An androgen receptor modulator comprising a compound represented by the general formula:

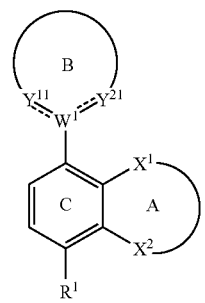

(I')

[wherein Ring A represents an optionally substituted 5- to 8-membered ring, Ring B represents a further optionally substituted 4- to 10-membered ring, Ring C represents a further optionally substituted benzene ring, $X^1$ represents an optionally substituted carbon atom, and $X^2$ represents an optionally substituted carbon atom, an oxygen atom or a group represented by the formula $S(O)_k$ (wherein k represents 0, 1 or 2), respectively. $W^1$ represents a nitrogen atom or a group represented by the formula $CR^a$ (wherein $R^a$ represents a bond, a hydrogen atom, a hydroxy group or an optionally substituted alkoxy group). $Y^{11}$ represents a group represented by the formula CR²R³' (wherein R² represents a hydrogen atom, a cyano group, a nitro group, an optionally substituted acyl group, an optionally esterified or amidated carboxyl group or an optionally substituted hydrocarbon group, and R³' represents a bond, a hydrogen atom, a cyano group, a nitro group, an optionally substituted acyl group, an optionally esterified or amidated carboxyl group or an optionally substituted hydrocarbon group, respectively), and Y²¹ represents a group represented by the formula CR⁴R⁵' (wherein R⁴ represents a hydrogen atom, a cyano group, a nitro group, an optionally substituted acyl group, an optionally esterified or amidated carboxyl group or an optionally substituted hydrocarbon group, and R⁵' represents a bond, a hydrogen atom, a cyano group, a nitro group, an optionally substituted acyl group, an optionally esterified or amidated carboxyl group or an optionally substituted hydrocarbon group, respectively), an optionally substituted nitrogen atom, an oxygen atom or a group represented by the formula S(O)$_m$ (wherein m represents 0, 1 or 2), respectively, and when Ring B is a further optionally substituted bicyclic ring, CR² in Y¹¹ or CR⁴ or the nitrogen atom in Y²¹ may constitute a part of Ring B. R¹ represents an electron-withdrawing group. The formula ⸺ represents a single bond or a double bond] or a salt or a prodrug thereof;

[16] The modulator as described in the above-mentioned [15], which is an androgen receptor agonist;

[17] An agent for preventing and/or treating hypogonadism or male climacteric disturbance comprising the modulator as described in the above-mentioned [15];

[18] An agent for preventing and/or treating osteoporosis comprising the modulator as described in the above-mentioned [15];

[19] An agent for preventing and/or treating hormone-resistant cancer comprising the modulator as described in the above-mentioned [15];

[20] The agent as described in the above-mentioned [19], wherein the hormone-resistant cancer is LHRH agonist-resistant cancer;

[21] The agent as described in the above-mentioned [19] or [20], wherein the cancer is prostate cancer;

[22] A method for preventing and/or treating hormone-resistant cancer, comprising administering an effective amount of an androgen receptor agonist to a mammal;

[23] An agent for preventing and/or treating hormone-resistant cancer, comprising an androgen receptor agonist;

[24] The agent as described in the above-mentioned [23], wherein the androgen receptor agonist is a non-steroidal compound;

[25] Use of the compound as described in the above-mentioned [1] or a salt or a prodrug thereof for manufacturing an androgen receptor agonist;

[26] Use of the compound as described in the above-mentioned [1] or a salt or a prodrug thereof for manufacturing an agent for preventing and/or treating cancer; and the like.

Furthermore, the present invention relates to:

[27] A medicine comprising the combination of the compound as described in the above-mentioned [1] or a salt or a prodrug thereof with an anticancer agent;

[28] A medicine comprising the combination of the compound as described in the above-mentioned [1] or a salt or a prodrug thereof with a hormonal therapeutic agent;

[29] The medicine as described in the above-mentioned [28], wherein the hormonal therapeutic agent is a LH-RH modulator;

[30] The medicine as described in the above-mentioned [29], wherein the LH-RH modulator is a LH-RH agonist;

[31] The medicine as described in the above-mentioned [30], wherein the LH-RH agonist is leuprorelin or a salt thereof;

[32] A method for preventing and/or treating cancer, comprising administering an effective amount of the compound as described in the above-mentioned [1] or a salt or a prodrug thereof to a mammal;

[33] A method for preventing and/or treating cancer, comprising administering to a mammal an effective amount of the compound as described in the above-mentioned [1] or a salt or a prodrug thereof in combination with an effective amount of other anticancer agent;

[34] A method for preventing and/or treating cancer, comprising administering to a mammal an effective amount of the compound as described in the above-mentioned [1] or a salt or a prodrug thereof in combination with an effective amount of a hormonal therapeutic agent;

[35] The method as described in the above-mentioned [34], wherein the hormonal therapeutic agent is a LH-RH modulator;

[36] The method as described in the above-mentioned [35], wherein the LH-RH modulator is a LH-RH agonist;

[37] The method as described in the above-mentioned [36], wherein the LH-RH agonist is leuprorelin or a salt thereof;

[38] A method for preventing and/or treating cancer, comprising administering an effective amount of the compound as described in the above-mentioned [1] or a salt or a prodrug thereof to a mammal after an administration other anticancer agent;

[39] A method for preventing and/or treating cancer, comprising administering an effective amount of the compound as described in the above-mentioned [1] or a salt or a prodrug thereof to a mammal before an application of surgery, radiotherapy, gene therapy, thermotherapy, cryotherapy and/or laser cauterization;

[40] A method for preventing and/or treating cancer, comprising administering an effective amount of the compound as described in the above-mentioned [1] or a salt or a prodrug thereof to a mammal after an application of surgery, radiotherapy, gene therapy, thermotherapy, cryotherapy and/or laser cauterization;

[41] A medicine comprising combination of the agent as described in the above-mentioned [13] with an anticancer agent;

[42] A medicine comprising combination of the agent as described in the above-mentioned [13] and a hormonal therapeutic agent;

[43] The medicine as described in the above-mentioned [42], wherein the hormonal therapeutic agent is a LH-RH modulator;

[44] The medicine as described in the above-mentioned [43], wherein the LH-RH modulator is a LH-RH agonist;

[45] The medicine as described in the above-mentioned [44], wherein the LH-RH agonist is leuprorelin or a salt thereof;

[46] The method for preventing and/or treating cancer, comprising administering to a mammal an effective amount of the agent as described in the above-mentioned [13];

[47] A method for preventing and/or treating cancer, comprising administering to a mammal an effective amount of the agent as described in the above-mentioned [13] in combination with an effective amount of other anticancer agent;

[48] A method of preventing and/or treating cancer, comprising administering to a mammal an effective amount of the agent as described in the above-mentioned [13] in combination with an effective amount of a hormonal therapeutic agent;

[49] The method as described in the above-mentioned [48], wherein the hormonal therapeutic agent is a LH-RH modulator;

[50] The method as described in the above-mentioned [49], wherein the LH-RH modulator is a LH-RH agonist;

[51] The method as described in the above-mentioned [50], wherein the LH-RH agonist is leuprorelin or a salt thereof;

[52] A method for preventing and/or treating cancer, comprising administering an effective amount of the agent as described in the above-mentioned [13] after an administration of other anticancer agent;

[53] A method for preventing and/or treating cancer, comprising administering an effective amount of the agent as described in the above-mentioned [13] to a mammal before an application of surgery, radiotherapy, gene therapy, thermotherapy, cryotherapy and/or laser cauterization; and

[54] A method for preventing and/or treating cancer, comprising administering an effective amount of the agent as described in the above-mentioned [13] to a mammal after an application of surgery, radiotherapy, gene therapy, thermotherapy, cryotherapy and/or laser cauterization, etc.

Further, the present invention relates to:

[55] The compound as described in the above-mentioned [2], wherein Ring A is an optionally substituted benzene ring;

[56] The compound as described in the above-mentioned [2], wherein Ring B is an optionally substituted pyrrolidine ring, an optionally substituted piperidine ring, an optionally substituted piperazine ring, an optionally substituted morpholine ring, an optionally substituted thiomorpholine ring or an optionally substituted perhydroazepine ring;

[57] The medicine as described in the above-mentioned [12], which is an agent for preventing and/or treating hypogonadism;

[58] The medicine as described in the above-mentioned [12], which is an agent for preventing and/or treating osteoporosis;

[59] The medicine as described in the above-mentioned [12], which is an agent for preventing and/or treating hormone-resistant cancer; and the like.

Hereinafter, the contents of the present invention will be explained specifically.

First, terms used in the present invention will be explained.

The "hydrocarbon group" in the "optionally substituted hydrocarbon group" represented by $R^2$, $R^{2a}$, $R^3$, $R^{3'}$, $R^{3a}$, $R^{4a}$, $R^5$, $R^{5'}$ and $R^{5a}$ includes, for example, an "aliphatic linear hydrocarbon group", an "alicyclic hydrocarbon group" and an "aromatic hydrocarbon group".

The "aliphatic linear hydrocarbon group" as an example of the hydrocarbon group includes, for example, a straight or branched aliphatic hydrocarbon group such as an alkyl group, an alkenyl group, an alkynyl group.

The "alkyl group" includes, for example, a $C_{1-10}$ alkyl group such as methyl, ethyl, n-propyl, isopropyl, n-butyl, isobutyl, sec-butyl, tert-butyl, n-pentyl, isopentyl, neopentyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methylheptyl, 1-ethylhexyl, n-octyl, 1-methylheptyl, nonyl, etc., preferably a $C_{1-6}$ alkyl (e.g., methyl, ethyl, n-propyl, isopropyl, n-butyl, sec-butyl, tert-butyl, etc.), etc.

The "alkenyl group" includes, for example, a $C_{2-10}$ alkenyl group such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc., preferably a $C_{2-6}$ alkenyl group, etc.

The alkynyl group includes, for example, a $C_{2-10}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl, preferably, $C_{2-6}$ alkynyl group, etc.

The "alicyclic hydrocarbon group" as an example of the hydrocarbon group includes, for example, a cycloalkyl group, a cycloalkenyl group, cycloalkanedienyl group and a saturated or unsaturated, monocyclic or fused polycyclic alicyclic hydrocarbon group such as a dicyclic or tricyclic fused ring of these groups and a $C_{6-14}$ aryl group (e.g., benzene, etc.), etc.

The "cycloalkyl group" includes, for example, a $C_{3-10}$ cycloalkyl such as cyclopropyl, cyclobutyl, cyclopentyl, cyclohexyl, cycloheptyl, cyclooctyl, cyclononyl, etc.

The "cycloalkenyl group" includes, for example, a $C_{3-10}$ cycloalkenyl group such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, etc.

The "cycloalkanedienyl group" includes, for example, a $C_{4-6}$ cycloalkanedienyl group such as 2,4-cyclopentadien-1-yl, 2,4-cyclohexadien-1-yl, 2,5-cyclohexanedien-1-yl, etc.

The "aromatic hydrocarbon group" as an example of the hydrocarbon group includes monocyclic or fused polycyclic aromatic hydrocarbon group, and is not particularly limited but preferably, a $C_{6-22}$ aromatic hydrocarbon group, more preferably, a $C_{6-18}$ aromatic hydrocarbon group, further preferably, a $C_{6-10}$ aromatic hydrocarbon group, etc. Specifically, for example, phenyl, o-tolyl, m-tolyl, p-tolyl, 2,3-xylyl, 2,4-xylyl, mesityl, o-cumenyl, m-cumenyl, p-cumenyl, α-methylbenzyl, benzhydryl, o-biphenyl, m-biphenyl, p-biphenylel, 1-naphthyl, 2-naphthyl, 2-indenyl, 2-anthryl, azulenyl, phenantholyl, fluorenyl, etc., among these, phenyl, 1-naphthyl, 2-naphthyl, 2-anthryl, etc. are preferable.

The "electron-withdrawing group" represented by $R^1$ and $R^{1a}$ is not particularly limited as long as it has tendency to attract electrons of others generally on the basis of hydrogen in the molecule, and is used in organic chemistry, but for example, a cyano group, a nitro group, a halogen atom, an optionally substituted acyl group, an optionally esterified or amidated carboxyl group or a $C_{1-6}$ alkyl group substituted with 1 to 5 halogen atoms, etc can be used.

The "$C_{1-6}$ alkyl group" in the "optionally substituted $C_{1-6}$ alkyl group" represented by $R^6$ and the "substituent on Ring A or Ring B except for $R^a$, $R^2$, $R^{3'}$, $R^4$ and $R^{5'}$" includes those as defined above.

The "$C_{1-6}$ alkoxy group" in the "optionally substituted $C_{1-6}$ alkoxy group" represented by the "substituent on Ring A or Ring B except for $R^a$, $R^2$, $R^{3'}$, $R^4$ and $R^{5'}$" includes, for example, methoxy, ethoxy, n-propoxy, isopropyloxy, n-butoxy, isobutyloxy, sec-butyloxy, tert-butyloxy, n-pentyloxy, isopentyloxy, neopentyloxy, n-hexyloxy, isohexyloxy, 1,1-dimethylbutyloxy, 2,2-dimethylbutyloxy, 3,3-dimethylbutyloxy and 2-ethylbutyloxy, etc., preferably, methoxy, ethoxy, n-propoxy, isopropyloxy, n-butoxy, etc.

The "alkoxy group" in the "optionally substituted alkoxy group" represented by $R^a$ includes a $C_{1-6}$ alkoxy group, preferably, for example, methoxy, ethoxy, n-propoxy, isopropyloxy, n-butoxy, isobutyloxy, sec-butyloxy, tert-butyloxy, n-pentyloxy, isopentyloxy, neopentyloxy, n-hexyloxy, isohexyloxy, 1,1-dimethylbutyloxy, 2,2-dimethylbutyloxy, 3,3-dimethylbutyloxy and 2-ethylbutyloxy, etc., preferably, methoxy, ethoxy, n-propoxy, isopropyloxy, n-butoxy, etc.

The "halogen atom" represented by $R^1$, $R^{1a}$, $R^7$, $R^{10}$, $R^{11}$, $R^{12}$, $R^{13}$ and the "substituent on Ring A or Ring B except for $R^a$, $R^2$, $R^{3'}$, $R^4$ and $R^{5'}$" includes a fluorine atom, a chlorine atom, a bromine atom or an iodine atom, etc., preferably, a fluorine atom or a chlorine atom, etc.

The "acyl group" in the "optionally substituted acyl group" represented by $R^1$, $R^{1a}$, $R^2$, $R^{2a}$, $R^3$, $R^{3'}$, $R^{3a}$, $R^4$, $R^{4a}$, $R^5$, $R^{5'}$, $R^{5a}$ and $R^7$ includes, for example, a lower ($C_{1-6}$) alkanoyl group such as formyl, acetyl, propionyl, butyryl, isobutyryl, valeryl, isovaleryl, pivaloyl and hexanoyl; a lower ($C_{3-7}$) alkenoyl group such as acryloyl, methacryloyl, crotonoyl and isocrotonoyl; a $C_{4-7}$ cycloalkanecarbonyl group such as a cyclopropanecarbonyl group, a cyclobutanecarbonyl group, a cyclopentanecarbonyl group and a cyclohexanecarbonyl group; a lower ($C_{1-4}$) alkanesulfonyl group such as mesyl, ethanesulfonyl and propanesulfonyl; a $C_{7-14}$ aroyl group such as benzoyl, p-toluoyl, 1-naphthoyl and 2-naphthoyl; a $C_{6-10}$ aryl lower ($C_{2-4}$) alkanoyl group such as phenylacetyl, phenylpropionyl, hydroatropoyl and phenylbutyryl; a $C_{6-10}$ aryl lower ($C_{3-5}$) alkenoyl group such as cinnamoyl and atropoyl; a $C_{6-10}$ arenesulfonyl group such as benzenesulfonyl and p-toluenesulfonyl group, etc.

The "$C_{1-6}$ acyl group" in the "optionally substituted $C_{1-6}$ acyl group" represented by the "substituent on Ring A or Ring B except for $R^a$, $R^2$, $R^{3'}$, $R^4$ and $R^{5'}$" includes a lower ($C_{1-6}$) alkanoyl group such as formyl, acetyl, propionyl, butyryl, isobutyryl, valeryl, isovaleryl, pivaloyl and hexanoyl; a lower ($C_{3-6}$) alkenoyl group such as acryloyl, methacryloyl, crotonoyl and isocrotonoyl; a $C_{4-6}$ cycloalkanecarbonyl group such as a cyclopropanecarbonyl group, a cyclobutanecarbonyl group and a cyclopentanecarbonyl group, etc.

The "optionally esterified or amidated carboxyl group" represented by $R^1$, $R^{1a}$, $R^2$, $R^{2a}$, $R^3$, $R^{3'}$, $R^{3a}$, $R^4$, $R^5$, $R^{5'}$, $R^{5a}$, $R^7$, $R^8$, $R^9$, $R^{10}$, $R^{11}$, $R^{12}$, $R^{13}$ and the "substituent on Ring A or Ring B except for $R^a$, $R^2$, $R^{3'}$, $R^4$ and $R^{5'}$" includes a carboxyl group, alkoxycarbonyl, aryloxycarbonyl, aralkyloxycarbonyl, carbamoyl, N-monosubstituted carbamoyl and N,N-disubstituted carbamoyl, etc.

The "alkoxycarbonyl" as used herein includes, for example, lower ($C_{1-6}$) alkoxycarbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl and neopentyloxycarbonyl, etc., among these preferably, $C_{1-3}$ alkoxycarbonyl such as methoxycarbonyl, ethoxycarbonyl and propoxycarbonyl, etc. The "lower alkoxycarbonyl" may have a substituent, and the substituent includes a hydroxy group, an optionally substituted amino group [the amino group, for example, may have 1 or 2 substituents such as a lower alkyl group (e.g., $C_{1-6}$ alkyl such as methyl, ethyl, propyl, isopropyl, butyl, isobutyl, tert-butyl, pentyl, hexyl, etc., preferably, methyl, ethyl, etc.) optionally substituted with 1 to 5 halogen atoms (e.g., fluorine, chlorine, bromine, iodine, etc.), an acyl group (e.g., $C_{1-6}$ alkanoyl such as formyl, acetyl, propionyl and pivaloyl, benzoyl, etc.), a carboxyl group and $C_{1-6}$ alkoxycarbonyl, etc.], a halogen atom (e.g., fluorine, chlorine, bromine, iodine, etc.), a nitro group, a cyano group, a lower alkoxy group (e.g., $C_{1-6}$alkoxy such as methoxy, ethoxy, n-propoxy, isopropoxy, n-butoxy, isobutoxy, sec-butoxy and tert-butoxy, etc., preferably, methoxy, ethoxy, etc.) optionally substituted with 1 to 5 halogen atoms (e.g., fluorine, chlorine, bromine, iodine, etc.), etc. Furthermore, these substituents may be the same or different and the number of substituents is preferably 1, 2 or 3 (more preferably 1 or 2).

The "aryloxycarbonyl" as used herein is preferably, for example, $C_{6-14}$ aryloxycarbonyl such as phenoxycarbonyl, 1-naphthoxycarbonyl, 2-naphthoxycarbonyl, 1-phenanthryloxycarbonyl, etc. The "aryloxycarbonyl" may have a substituent, and the substituent includes those such as the above-mentioned substituents in the "alkoxycarbonyl" as the substituent in the same number.

The "aralkyloxycarbonyl" as used herein is preferably, for example, $C_{7-14}$ aralkyloxycarbonyl such as benzyloxycarbonyl, phenethyloxycarbonyl, etc. (preferably, $C_{6-30}$ aryl-$C_{1-4}$ alkoxycarbonyl, etc.). The "aralkyloxycarbonyl" may have a substituent, and the substituent includes those such as the above-mentioned substituents in the "alkoxycarbonyl" as the substituent in the same number.

The "N-monosubstituted carbamoyl" as used herein includes, for example, lower alkyl (e.g., $C_{1-6}$alkyl such as methyl, ethyl, propyl, isopropyl, butyl, isobutyl, tert-butyl, pentyl, hexyl, etc.), lower alkenyl (e.g., $C_{2-6}$alkenyl such as vinyl, allyl, isopropenyl, propenyl, butenyl, pentenyl, hexenyl, etc.), cycloalkyl (e.g., $C_{3-6}$ cycloalkyl such as cyclopropyl, cyclobutyl, cyclopentyl and cyclohexyl, etc.), aryl (e.g., $C_{6-10}$ aryl such as phenyl, 1-naphthyl, 2-naphthyl, etc.), aralkyl (e.g., $C_{7-10}$ aralkyl such as benzyl and phenethyl, preferably, phenyl-$C_{1-4}$ alkyl, etc.), arylalkenyl (e.g., $C_{8-10}$ arylalkenyl such as cinnamyl, preferably, phenyl-$C_{2-4}$alkenyl, etc.), heterocyclic group (e.g., those such as the below-mentioned "heterocyclic group" in the "optionally substituted heterocyclic group" as a substituent, etc.), etc. The lower alkyl, lower alkenyl, cycloalkyl, aryl, aralkyl, arylalkenyl and the heterocyclic group may have a substituent, and the substituent includes those such as the above-mentioned substituents in the "alkoxycarbonyl" as the substituent in the same number.

The "N,N-disubstituted carbamoyl" as used herein means a carbamoyl group having two substituents on the nitrogen atom. Examples of one of the two substituents include those such as the above-mentioned substituents in the "N-monosubstituted carbamoyl" as the substituent, and examples of the other substituent includes, for example, lower alkyl (e.g., $C_{1-6}$alkyl such as methyl, ethyl, propyl, isopropyl, butyl, tert-butyl, pentyl, hexyl, etc.), $C_{3-7}$ cycloalkyl (e.g., cyclopropyl, cyclobutyl, cyclopentyl, cyclohexyl, etc.), $C_{7-10}$ aralkyl (e.g., benzyl and phenethyl, etc., preferably, phenyl-$C_{1-4}$alkyl, etc.), etc. Furthermore, the two substituents may form a cyclic amino together with the nitrogen atom, and in this case, the cyclic aminocarbamoyl includes, for example, a 3- to 8-membered (preferably, a 5- or 6-membered) cyclic aminocarbonyl such as 1-azetidinylcarbonyl, 1-pyrrolidinylcarbonyl, piperidinocarbonyl, morpholinocarbonyl, 1-piperazinylcarbonyl, and 1-piperazinylcarbonyl optionally having lower alkyl (e.g., $C_{1-6}$ alkyl such as methyl, ethyl, propyl, isopropyl, butyl, tert-butyl, pentyl, hexyl, etc.), aralkyl (e.g., $C_{7-10}$ aralkyl such as benzyl, phenethyl, etc.), aryl (e.g., $C_{6-10}$ aryl such as phenyl, 1-naphthyl, 2-naphthyl, etc.), etc. at the position 4, etc.

The "$C_{1-6}$ alkyl group substituted with 1 to 5 halogen atoms" represented by $R^1$, $R^{1a}$ and $R^7$ includes $C_{1-6}$ alkyl (e.g., methyl, ethyl, propyl, isopropyl, butyl, isobutyl, sec-butyl, tert-butyl, pentyl, hexyl, etc.) optionally having 1 to 5, preferably, 1 to 3 halogen atoms (e.g., fluorine, chlorine, bromine, iodine, etc.) etc., specifically, for example, fluoromethyl, chloromethyl, difluoromethyl, trichloromethyl, trifluoromethyl, 1-fluoroethyl, 2-bromoethyl, 2,2,2-trifluoroethyl, pentafluoroethyl, 2-fluoropropyl, 1,2-difluoropropyl, 3,3,3-trifluoropropyl, 1-fluorobutyl, 4,4,4-trifluorobutyl, 1-fluoropentyl, 5,5,5-trifluoropentyl, 1-fluorohexyl, 3,3-difluorohexyl, 6,6,6-trifluorohexyl, etc.

The "optionally substituted amino group" represented by the "substituent on Ring A or Ring B except for $R^1$, $R^2$, $R^{3'}$, $R^4$ and $R^{5'}$" includes groups such as the below-defined "optionally substituted amino group" in the "substituent".

The "$C_{1-6}$ alkoxyimino group" of the "optionally substituted $C_{1-6}$ alkoxyimino group" in the "carbon atom substituted with optionally substituted $C_{1-6}$ alkoxyimino group"

represented by $Z^1$ and $Z^2$, and the "$C_{1-6}$ alkoxyimino group" in the "optionally substituted $C_{1-6}$ alkoxyimino group" represented by the "substituent on Ring A or Ring B except for $R^1$, $R^2$, $R^{3'}$, $R^4$ and $R^{5'}$" include, for example, methoxyimino, ethoxyimino, n-propoxyimino, isopropyloxyimino, n-butoxyimino, isobutyloxyimino, sec-butyloxyimino, tert-butyloxyimino, n-pentyloxyimino, isopentyloxyimino, neopentyloxyimino, n-hexyloxyimino, isohexyloxyimino, 1,1-dimethylbutyloxyimino, 2,2-dimethylbutyloxyimino, 3,3-dimethylbutyloxyimino, 2-ethylbutyloxyimino, etc., preferably, methoxyimino, ethoxyimino, n-propoxyimino, isopropyloxyimino, n-butoxyimino, etc.

The "$C_{1-4}$ alkylenedioxy group" in the "carbon atom substituted with a $C_{1-4}$ alkylenedioxy group" represented by $Z^1$ and $Z^2$, and the "$C_{1-4}$ alkylenedioxy group" in the "optionally substituted $C_{1-4}$ alkylenedioxy group" represented by the "substituent on Ring A or Ring B except for $R^1$, $R^2$, $R^{3'}$, $R^4$ and $R^{5'}$" include, for example, a methylenedioxy group, an ethylenedioxy group, a propylenedioxy group, a butylenedioxy group, etc., preferably, a methylenedioxy group, an ethylenedioxy group.

The "$C_{1-6}$ alkyl group optionally substituted with a halogen atom, a hydroxy group or a $C_{1-6}$ alkoxy group" represented by $R^8$, $R^9$, $R^{10}$, $R^{11}$, $R^{12}$ and $R^{13}$ includes those substituted with 0 to 5, preferably 0 to 3 of the above-defined "halogen atom", a hydroxy group and the above-defined "$C_{1-6}$ alkoxy group" at the substitutable positions of the above-defined "$C_{1-6}$ alkyl group". It includes, for example, those substituted with 0 to 5, preferably, 0 to 3 of a fluorine atom, a chlorine atom, a bromine atom, an iodine atom; a hydroxy group; a $C_{1-6}$ alkoxy group such as methoxy, ethoxy, n-propoxy, isopropyloxy, n-butoxy, isobutyloxy, sec-butyloxy, tert-butyloxy, n-pentyloxy, isopentyloxy, neopentyloxy, n-hexyloxy, isohexyloxy, 1,1-dimethylbutyloxy, 2,2-dimethylbutyloxy, 3,3-dimethylbutyloxy and 2-ethylbutyloxy, at the substitutable positions of a $C_{1-6}$ alkyl group such as methyl, ethyl, n-propyl, isopropyl, n-butyl, isobutyl, sec-butyl, tert-butyl, n-pentyl, isopentyl, neopentyl, n-hexyl, isohexyl, 1,1-dimethylbutyl, 2,2-dimethylbutyl, 3,3-dimethylbutyl, 3,3-dimethylpropyl, 2-ethylbutyl and n-heptyl. It includes specifically methyl, fluoromethyl, chloromethyl, difluoromethyl, trichloromethyl, trifluoromethyl, hydroxymethyl, methoxymethyl, ethoxymethyl, pentyloxymethyl, ethyl, 1-fluoroethyl, 2-bromoethyl, 1,2-dichloroethyl, 1,2-dichloro-1-hydroxyethyl, 2,2,2-trifluoroethyl, pentafluoroethyl, 1-hydroxyethyl, 1,2-dihydroxyethyl, n-propyl, isopropyl, 1-hydroxypropyl, ethoxypropyl, 2-fluoropropyl, 1,2-difluoropropyl, 3,3,3-trifluoropropyl, n-butyl, isobutyl, 1-chlorobutyl, 4,4,4-trifluorobutyl, fluoromethoxybutyl, 1,1-dimethylbutyl, 2,2-dimethylbutyl, 3,3-dimethylbutyl, 1-hydroxy-2-fluoro-propyl, n-butyl, sec-butyl, tert-butyl, n-pentyl, isopentyl, neopentyl, 1-fluoropentyl, 5,5,5-trifluoropentyl, n-hexyl, isohexyl, 1-fluorohexyl, 3,3-difluorohexyl, 6,6,6-trifluorohexyl, etc.

The "$C_{1-6}$ acyl group optionally substituted with a halogen atom, a hydroxy group or a $C_{1-6}$ alkoxy group" represented by $R^8$, $R^9$, $R^{10}$, $R^{11}$, $R^{12}$ and $R^{13}$ includes those substituted with 0 to 5, preferably 0 to 3 of the above-defined "halogen atom", a hydroxy group and the above-defined "$C_{1-6}$ alkoxy group" at the substitutable positions of the above-defined "$C_{1-6}$ acyl group". It includes, for example, those substituted with 0 to 5, preferably, 0 to 3 of a fluorine atom, a chlorine atom, a bromine atom, an iodine atom; a hydroxy group; a $C_{1-6}$ alkoxy group such as methoxy, ethoxy, n-propoxy, isopropyloxy, n-butoxy, isobutyloxy, sec-butyloxy, tert-butyloxy, n-pentyloxy, isopentyloxy, neopentyloxy, n-hexyloxy, isohexyloxy, 1,1-dimethylbutyloxy, 2,2-dimethylbutyloxy, 3,3-dimethylbutyloxy and 2-ethylbutyloxy, at the substitutable positions of a $C_{1-6}$ acyl group such as formyl, acetyl, propionyl, butyryl, isobutyryl, valeryl, isovaleryl, pivaloyl, hexanoyl, acryloyl, methacryloyl, crotonoyl, isocrotonoyl, a cyclopropanecarbonyl group, a cyclobutanecarbonyl group and a cyclopentanecarbonyl group.

The "$C_{1-6}$ alkoxy group optionally substituted with a halogen atom, a hydroxy group or a $C_{1-6}$ alkoxy group" represented by $R^8$, $R^9$, $R^{10}$, $R^{11}$, $R^{12}$ and $R^{13}$ includes those substituted with 0 to 5, preferably 0 to 3 of the above-defined "halogen atom", a hydroxy group and the above-defined "$C_{1-6}$ alkoxy group" at the substitutable positions of the above-defined "$C_{1-6}$alkoxy group". It includes, for example, those substituted with 0 to 5, preferably, 0 to 3, a fluorine atom, a chlorine atom, a bromine atom, an iodine atom; a hydroxy group; a $C_{1-6}$ alkoxy group such as methoxy, ethoxy, n-propoxy, isopropyloxy, n-butoxy, isobutyloxy, sec-butyloxy, tert-butyloxy, n-pentyloxy, isopentyloxy, neopentyloxy, n-hexyloxy, isohexyloxy, 1,1-dimethylbutyloxy, 2,2-dimethylbutyloxy, 3,3-dimethylbutyloxy and 2-ethylbutyloxy at the substitutable positions of a $C_{1-6}$ alkoxy group such as methoxy, ethoxy, n-propoxy, isopropyloxy, n-butoxy, isobutyloxy, sec-butyloxy, tert-butyloxy, n-pentyloxy, isopentyloxy, neopentyloxy, n-hexyloxy, isohexyloxy, 1,1-dimethylbutyloxy, 2,2-dimethylbutyloxy, 3,3-dimethylbutyloxy and 2-ethylbutyloxy.

The "amino group optionally substituted with a $C_{1-6}$ alkyl group and/or a $C_{1-6}$ acyl group" represented by $R^{10}$, $R^{11}$, $R^{12}$ and $R^{13}$ includes those in which the amino group is substituted with 0 to 2 groups selected from a $C_{1-6}$ alkyl group such as methyl, ethyl, propyl, isopropyl, butyl, isobutyl, tert-butyl, pentyl and hexyl and a $C_{1-6}$ acyl group such as formyl, acetyl, propionyl, butyryl, isobutyryl, valeryl, isovaleryl, pivaloyl, hexanoyl, acryloyl, methacryloyl, crotonoyl, isocrotonoyl, a cyclopropanecarbonyl group, a cyclobutanecarbonyl group and a cyclopentanecarbonyl group.

The "amino group optionally substituted with a $C_{1-6}$ alkyl group or a $C_{1-6}$ acyl group" represented by $Z^2$ includes those in which the amino group is substituted with 0 to 2 groups selected from a $C_{1-6}$ alkyl group such as methyl, ethyl, propyl, isopropyl, butyl, isobutyl, tert-butyl, pentyl and hexyl and a $C_{1-6}$ acyl group such as formyl, acetyl, propionyl, butyryl, isobutyryl, valeryl, isovaleryl, pivaloyl, hexanoyl, acryloyl, methacryloyl, crotonoyl, isocrotonoyl, a cyclopropanecarbonyl group, a cyclobutanecarbonyl group and a cyclopentanecarbonyl group.

k, m, p, q, $k^a$ and $m^a$ represent 0, 1 or 2. Therefore, when k, m, p, $k^a$ and $m^a$ represent 0 in the formulae $S(O)_k$, $S(O)_m$, $S(O)_p$, $S(O)_k{}^a$ and $S(O)_m{}^a$, the formulae mean S; when k, m, p, $k^a$ and $m^a$ represent 1 in the formulae $S(O)_k$, $S(O)_m$, $S(O)_p$, $S(O)_k{}^a$ and $S(O)_m{}^a$, the formulae mean S(O); when k, m, p, $k^a$ and $m^a$ represent 2 in the formulae $S(O)_k$, $S(O)_m$, $S(O)_p$, $S(O)_k{}^a$ and $S(O)_m{}^a$, the formulae mean $S(O)_2$, respectively. Furthermore, when q represents 0, the formulae mean a chemical bond, when q represents 1, the formulae mean a methylene group, and when q represents 2, the formulae mean an ethylene group, respectively.

The "5- to 8-membered ring" in the "optionally substituted 5- to 8-membered ring" represented by Ring A and Ring $A^a$ includes, for example, "alicyclic hydrocarbon", "aromatic hydrocarbon", a "heterocycle", etc.

The "4- to 10-membered ring" in the "further optionally substituted 4- to 10-membered ring" represented by Ring B and Ring $B^a$ includes, for example, a "non-aromatic heterocycle", etc.

The "alicyclic hydrocarbon" includes, for example, cycloalkane, cycloalkene, cycloalkanediene and a saturated or unsaturated monocyclic or fused polycyclic $C_{5-8}$ or $C_{4-10}$ alicyclic hydrocarbon such as a bicyclic fused ring of these groups and benzene.

The "cycloalkane" includes, for example, $C_{3-10}$cycloalkane such as cyclopropane, cyclobutane, cyclopentane, cyclohexane, cycloheptane, cyclooctane, cyclononane, etc.

The "cycloalkene" includes, for example, $C_{3-10}$cycloalkene such as cyclopentene, cyclohexene, cyclobutene, etc.

The "cycloalkanediene" includes, for example, $C_{4-6}$ cycloalkanediene such as cyclopentadiene, cyclohexadiene, cyclohexanediene, etc.

The "aromatic hydrocarbon" includes monocyclic or fused polycyclic aromatic hydrocarbon, and is not particularly limited but preferably, $C_{6-8}$ aromatic hydrocarbon, more preferably, $C_6$ aromatic hydrocarbon, etc., specifically, for example, benzene, toluene, xylene, mesitylene, cumene, styrene, 1,2,3-trimethylbenzene, pentalene, etc., preferably, benzene, toluene, etc.

The "heterocycle" includes, for example, an aromatic heterocycle, a saturated or unsaturated non-aromatic heterocycle (an aliphatic heterocycle), etc., containing at least one (preferably, 1 to 4, further preferably, 1 to 2) hetero atoms of 1 to 3 kinds (preferably, 1 to 2 kinds) selected from an oxygen atom, a sulfur atom and a nitrogen atom, etc. as a ring-constituting atom (a ring atom), and is not particularly limited but preferably, 4- to 10-membered or 5- to 8-membered heterocycle, etc.

Specific examples of the "aromatic heterocycle" include 5- to 10-membered aromatic heterocycle, for example, a 5- or 6-membered aromatic monocyclic heterocycle (e.g., furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine, etc.), and a 8- to 10-membered aromatic fused heterocycle (e.g., 1H-pyrrolo[1,2-c]imidazole, pyrrolo[1,2-a]imidazol-4-ium, pyrrolo[1,2-c]imidazol-4-ium, pyrrolo[2,3-c]pyrazole, pyrrolo[3,2-c]pyrazole, pyrrolo[3,4-c]pyrazole, 1H-pyrrolo[3,2-c]pyrazole, pyrrolo[1,2-b]pyrazol-7-ium, 1H-furo[2,3-d]imidazole, 1H-furo[3,4-d]imidazole, 1H-furo[2,3-c]pyrazole, 1H-furo[2,3-d]imidazole, 1H-furo[3,2-c]pyrazole, 1H-furo[3,4-c]pyrazole, 1H-thieno[2,3-d]imidazole, thieno[2,3-b]furan, 4H-imidazo[4,5-d]thiazole, imidazo[2,1-b]thiazole, 5H-pyrrolo[1,2-c]imidazole, benzofuran, isobenzofuran, benzothiophene, indole, isoindole, 1H-indazole, benzoxazole, 1,2-benzoisoxazole, benzothiazole, benzopyran, 1,2-benzoisothiazole, 1H-benzotriazole, quinoline, isoquinoline, cinnoline, quinazoline, quinoxaline, phthalazine, naphthyridine, purine, pteridine, indolizine, pyrrolo[1,2-b]pyridazine, pyrazolo[1,5-a]pyridine, imidazo[1,2-a]pyridine, imidazo[1,5-a]pyridine, imidazo[1,2-b]pyridazine, imidazo[1,2-a]pyrimidine, 1,2,4-triazolo[4,3-a]pyridine, 1,2,4-triazolo[4,3-b]pyridazine, etc. (preferably, a heterocycle in which the above-mentioned 5- or 6-membered aromatic monocyclic heterocyclic group is fused with a benzene ring, or a heterocycle in which the same or different two heterocycles of the above-mentioned 5- or 6-membered aromatic monocyclic heterocyclic group are fused with each other, etc.)).

Specific examples of the "non-aromatic heterocycle" include, for example, oxetane, pyrroline, imidazoline, imidazolidine, pyrazoline, pyrazolidine, quinuclidine, aziridine, oxirane, azetidine, pyrrolidine, tetrahydrofuran, thiolane, piperidine, tetrahydropyran, dioxolane, thiazane, morpholine, thiomorpholine, piperazine, azepane, perhydroindole, perhydropyrrolo[2,3-d]pyridine, perhydropyrrolo[3,2-d]pyridine, and 7-azabicyclo[2,2,1]heptane, in addition to these, a 4- to 10-membered or 5- to 8-membered saturated or unsaturated (preferably, saturated) non-aromatic heterocycle (aliphatic heterocycle) such as a compound that the above-mentioned aromatic heterocycle is partially or completely saturated, and the like.

Herein, when Ring B is a further optionally substituted bicyclic ring, $CR^2$ in $Y^1$ or $CR^4$ or the nitrogen atom in $Y^2$ may constitute a part of Ring B.

Furthermore, when Ring $B^a$ is a further optionally substituted bicyclic ring, $CR^{2a}$ in $Y^{1a}$ or $CR^{4a}$ or the nitrogen atom in $Y^{2a}$ may constitute a part of Ring $B^a$.

Further, when Ring B is a further optionally substituted bicyclic ring, $CR^2$ in $Y^{11}$ or $CR^4$ or the nitrogen atom in $Y^{21}$ may constitute a part of Ring B.

The substituent in the present invention such as the substituent in the "optionally substituted hydrocarbon group" represented by $R^2$, $R^{2a}$, $R^3$, $R^{3'}$, $R^{3a}$, $R^4$, $R^{4a}$, $R^5$, $R^{5'}$ and $R^{5a}$ the substituent in the "optionally substituted 5- to 8-membered ring" represented by Ring A and Ring $A^a$; the substituent in the "further optionally substituted 4- to 10-membered ring" represented by Ring B and Ring $B^a$; the substituent in the "further optionally substituted benzene ring" represented by Ring C and Ring $C^a$; the substituent in the "optionally substituted benzene ring" of Ring A; the substituent in the "optionally substituted pyrrolidine ring", the "optionally substituted piperidine ring", the "optionally substituted piperazine ring", the "optionally substituted morpholine ring", the "optionally substituted thiomorpholine ring" or the "optionally substituted perhydroazepine ring" of Ring B is not particularly limited, but for example, (i) an optionally substituted alkyl group, (ii) an optionally substituted alkenyl group, (iii) an optionally substituted alkynyl group, (iv) an optionally substituted aryl group, (v) an optionally substituted aralkyl group, (vi) an optionally substituted cycloalkyl group, (vii) an optionally substituted cycloalkenyl group, (viii) an optionally substituted heterocyclic group, (ix) an optionally substituted amino group, (x) an optionally substituted imidoyl group (e.g., a group represented by the formula —C(U')═N—U [wherein U and U' represent a hydrogen atom or a substituent, respectively (U represents preferably a hydrogen atom), etc.], (xi) an optionally substituted amidino group (e.g., a group represented by the formula —C(NE'E")═N-E [wherein E, E' and E" represent a hydrogen atom or a substituent, respectively (E represents preferably a hydrogen atom)], etc.), (xii) an optionally substituted hydroxy group, (xiii) an optionally substituted thiol group, (xiv) an optionally substituted alkylsulfinyl group, (xv) an optionally esterified or amidated carboxyl group, (xvi) an optionally substituted thiocarbamoyl group, (xvii) an optionally substituted sulfamoyl group, (xviii) a halogen atom (e.g., fluorine, chlorine, bromine, iodine, etc., preferably, chlorine, bromine, etc.), (xix) a cyano group, (xx) an isocyano group, (xxi) a cyanate group, (xxii) an isocyanate group, (xxiii) a thiocyanate group, (xxiv) an isothiocyanate group, (xxv) a nitro group, (xxvi) a nitroso group, (xxvii) a sulfonic acid-derived acyl group, (xxviii) a carbonic acid-derived acyl group, (xxix) an oxo group, (xxx) a thioxo group, (xxxi) a $C_{1-4}$ alkylenedioxy group, etc. are used, These optional substituents may exist in the number of 1 to 5 (preferably, 1 to 3) at the substitutable positions.

The alkyl group in the "optionally substituted alkyl group" as the above-mentioned substituent includes, for example, $C_{1-6}$ alkyl such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, etc. Herein, the substituent of the alkyl group includes a lower alkoxy group (e.g., $C_{1-6}$ alkoxy such as methoxy, ethoxy, propoxy, etc.), a halogen atom (e.g., fluorine, chlorine, bromine, iodine, etc.), a lower alkyl group (e.g., $C_{1-6}$ alkyl such as methyl, ethyl, propyl, etc.), a lower alkenyl group (e.g., $C_{2-6}$ alkenyl such as vinyl, allyl, etc.), a lower alkynyl group (e.g., $C_{2-6}$ alkynyl such as ethynyl, propargyl, etc.), an optionally substituted amino group, an optionally substituted hydroxy group, a cyano group, an optionally substituted amidino group, a carboxy group, a lower alkoxycarbonyl group (e.g., $C_{1-6}$ alkoxycarbonyl such as methoxycarbonyl, ethoxycarbonyl, etc.), an optionally substituted carbamoyl group (e.g., a carbamoyl group optionally substituted with a $C_{1-6}$ alkyl group or an acyl group (e.g., formyl, $C_{2-6}$ alkanoyl, benzoyl, optionally halogenated $C_{1-6}$ alkoxycarbonyl, optionally halogenated $C_{1-6}$ alkylsulfonyl, benzenesulfonyl, etc.) optionally substituted with a 5- or 6-membered monocyclic aromatic heterocyclic group (e.g., pyridyl, etc.), 1-azetidinylcarbonyl, 1-pyrrolidinylcarbonyl, piperidinocarbonyl, morpholinocarbonyl, 1-piperazinylcarbonyl, etc.), etc. These optional substituents may exist at the substitutable positions in the number of 1 to 3.

The "optionally substituted amino group", the "optionally substituted hydroxy group" and the "optionally substituted amidino group" as the substituent of the above-mentioned "optionally substituted alkyl group" includes those such as the "optionally substituted amino group", the "optionally substituted hydroxy group" and the "optionally substituted amidino group" as the substituent of the below-described "optionally substituted aromatic ring", etc.

The alkenyl group in the "optionally substituted alkenyl group" as the above-mentioned substituent includes, for example, $C_{2-6}$ alkenyl such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc. Herein, the substituent of the alkenyl includes those such as the above-mentioned substituent in the "optionally substituted alkyl group" as the substituent in the same number.

The alkynyl group in the "optionally substituted alkynyl group" as the above-mentioned substituent includes, for example, $C_{2-6}$ alkynyl such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. Herein, the substituent of the alkynyl group includes those such as the above-mentioned substituent in the "optionally substituted alkyl group" as the substituent in the same number.

The aryl group in the "optionally substituted aryl group" as the above-mentioned substituent includes, for example, $C_{6-14}$ aryl such as phenyl, naphthyl, anthryl, phenantholyl, acenaphthylenyl, etc. Herein, the substituent of the aryl group includes those such as the above-mentioned substituent in the "optionally substituted alkyl-group" as the substituent in the same number.

The aralkyl group in the "optionally substituted aralkyl group" as the above-mentioned substituent includes, for example, $C_{7-11}$ aralkyl such as benzyl, phenethyl, naphthylmethyl, etc. Herein, the substituent of the aralkyl group includes those such as the above-mentioned substituent in the "optionally substituted alkyl group" as the substituent in the same number.

The cycloalkyl group in the "optionally substituted cycloalkyl group" as the above-mentioned substituent includes, for example, $C_{3-7}$ cycloalkyl such as cyclopropyl, cyclobutyl, cyclopentyl, cyclohexyl, cycloheptyl, etc. Herein, the substituent of the cycloalkyl group includes those such as the above-mentioned substituent in the "optionally substituted alkyl group" as the substituent in the same number.

The cycloalkenyl group in the "optionally substituted cycloalkenyl group" as the above-mentioned substituent includes, for example, $C_{3-7}$ cycloalkenyl such as cyclopropenyl, cyclobutenyl, cyclopentenyl, cyclohexenyl, etc. Herein, the substituent of the optionally substituted cycloalkenyl group includes those such as the above-mentioned substituent in the "optionally substituted alkyl group" as the substituent in the same number.

The heterocyclic group in the "optionally substituted heterocyclic group" as the above-mentioned substituent includes, for example, an aromatic heterocyclic group, a saturated or unsaturated non-aromatic heterocyclic group (an aliphatic heterocyclic group), etc., containing at least one (preferably, 1 to 4, further preferably, 1 to 2) hetero atoms of 1 to 3 kinds (preferably, 1 to 2 kinds) selected from an oxygen atom, a sulfur atom and a nitrogen atom, etc. as a ring-constituting atom (a ring atom).

Herein, the "aromatic heterocyclic group" includes, for example, a 5- or 6-membered monocyclic aromatic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and, for example, a 8 to 12-membered fused polycyclic aromatic heterocyclic group such as benzofuranyl, isobenzofuranyl, benzo[b]thienyl, indolyl, isoindolyl, 1H-indazolyl, benzindazolyl, benzoxazolyl, 1,2-benzoisoxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.

Herein, the "non-aromatic heterocyclic group" includes, for example, a 3- to 8-membered (preferably, 5- or 6-membered) saturated or unsaturated (preferably, saturated) non-aromatic heterocyclic group (aliphatic heterocyclic group) such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc., or non-aromatic heterocyclic group in which the double bonds of the above-mentioned monocyclic aromatic heterocyclic group or the fused polycyclic aromatic heterocyclic group are saturated partially or completely such as 1,2,3,4-tetrahydroquinolyl and 1,2,3,4-tetrahydroisoquinolyl, etc.

The substituent which the "optionally substituted heterocyclic group" as the substituent may have, includes a lower alkyl group (e.g., $C_{1-6}$ alkyl such as methyl, ethyl, propyl, etc.), a lower alkenyl group (e.g., $C_{2-6}$ alkenyl such as vinyl, allyl, etc.), a lower alkynyl group (e.g., $C_{2-6}$ alkynyl such as ethynyl, propargyl, etc.), an acyl group (e.g., $C_{1-6}$ alkanoyl such as formyl, acetyl, propionyl, pivaloyl, benzoyl, etc.), an optionally substituted amino group, an optionally substituted hydroxy group, a halogen atom (e.g., fluorine, chlorine, bromine, iodine, etc., preferably, chlorine, bromine, etc.), an optionally substituted imidoyl group, an optionally substituted amidino group, etc. These optional substituents may exist in the number of 1 to 5 (preferably, 1 to 3) at the substitutable positions.

The "optionally substituted amino group", the "optionally substituted hydroxy group", the "optionally substituted imidoyl group" and the "optionally substituted amidino group", which the "optionally substituted heterocyclic group" as the substituent may have, include those such as the "optionally substituted amino group", the "optionally substituted hydroxy group", the "optionally substituted imidoyl group" and the "optionally substituted amidino group" as the below-described substituent of the "optionally substituted aromatic ring", etc.

The substituent in the "optionally substituted amino group", the "optionally substituted imidoyl group", the "optionally substituted amidino group", the "optionally substituted hydroxy group" or the "optionally substituted thiol group" as the above-mentioned substituent, includes, for example, a lower alkyl group (e.g., $C_{1-6}$alkyl such as methyl, ethyl, propyl, isopropyl, butyl, isobutyl, tert-butyl, pentyl, hexyl, etc.) optionally substituted with a substituent selected from optionally halogenated $C_{1-6}$ alkoxy (e.g., methoxy, ethoxy, trifluoromethoxy, 2,2,2-trifluoroethoxy, trichloromethoxy, 2,2,2-trichloroethoxy, etc.) and a $C_{7-11}$ alkylaryl group (e.g., o-tolyl, m-tolyl, p-tolyl, xylyl, mesityl, etc., preferably, $C_{1-5}$alkyl-phenyl, etc.), an acyl group ($C_{1-6}$ alkanoyl (e.g., formyl, acetyl, propionyl and pivaloyl, etc.), benzoyl, a $C_{1-6}$ alkylsulfonyl (e.g., methanesulfonyl, etc.), benzenesulfonyl, etc.), an optionally halogenated $C_{1-6}$ alkoxycarbonyl group (e.g., methoxycarbonyl, ethoxycarbonyl, trifluoromethoxycarbonyl, 2,2,2-trifluoroethoxycarbonyl, trichloromethoxycarbonyl, 2,2,2-trichloroethoxycarbonyl, etc.), a $C_{1-6}$alkoxycarbonyl group optionally substituted with a phenyl group (e.g., benzyloxycarbonyl, etc.), aryl (e.g., $C_{6-10}$ aryl such as phenyl, 1-naphthyl, 2-naphthyl, etc.), aralkyl (e.g., $C_{7-10}$ aralkyl such as benzyl and phenethyl, preferably, phenyl-$C_{1-4}$ alkyl, etc.), arylalkenyl (e.g., $C_{8-10}$ arylalkenyl such as cinnamyl, preferably, phenyl-$C_{2-4}$ alkenyl, etc.), a heterocyclic group (those such as the "heterocyclic group" in the "optionally substituted heterocyclic group" as the above-mentioned substituent, preferably, pyridyl, further preferably, 4-pyridyl, etc.), etc. These optional substituents may exist at the substitutable positions in the number of 1 to 3.

Furthermore, the "amino group" in the "optionally substituted amino group" as the above-mentioned substituent may be substituted with an optionally substituted imidoyl group (e.g., a $C_{1-6}$alkylimidoyl (e.g., formylimidoyl, acetylimidoyl, etc.), a $C_{1-6}$ alkoxyimidoyl, a $C_{1-6}$ alkylthioimidoyl, amidino, etc.), an amino group optionally substituted with 1 or 2 $C_{1-6}$ alkyl groups, etc. These optional substituents may exist at the substitutable positions in the number of 1 or 2. Furthermore, the two substituents may form a cyclic amino group together with the nitrogen atom, and in such case, the cyclic amino group includes, for example, 3- to 8-membered (preferably, 5- or 6-membered) cyclic amino such as 1-azetidinyl, 1-pyrrolidinyl, piperidino, thiomorpholino, morpholino, 1-piperazinyl and 1-piperazinyl optionally having lower alkyl (e.g., $C_{1-6}$ alkyl such as methyl, ethyl, propyl, isopropyl, butyl, t-butyl, pentyl and hexyl, etc.), aralkyl (e.g., $C_{7-10}$ aralkyl such as benzyl, phenethyl, etc.), aryl (e.g., $C_{6-10}$ aryl such as phenyl, 1-naphthyl, 2-naphthyl, etc.), etc. at the position 4,1-pyrrolyl, 1-imidazolyl, etc.

The alkylsulfinyl group in the "optionally substituted alkylsulfinyl group" as the above-mentioned substituent includes $C_{1-6}$ alkylsulfinyl such as methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl and hexylsulfinyl. Herein, the substituent of the alkylsulfinyl includes those such as the above-mentioned substituent in the "optionally substituted alkyl" as the substituent in the same number.

The "optionally esterified or amidated carboxyl group" as the above-mentioned substituent includes a carboxyl group, alkoxycarbonyl, aryloxycarbonyl, aralkyloxycarbonyl, carbamoyl, N-monosubstituted carbamoyl and N,N-disubstituted carbamoyl.

Herein, the "alkoxycarbonyl" includes, for example, $C_{1-6}$ alkoxycarbonyl (lower alkoxycarbonyl) such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, etc., among these preferably, $C_{1-3}$ alkoxycarbonyl such as methoxycarbonyl, ethoxycarbonyl and propoxycarbonyl, etc. The "lower alkoxycarbonyl" may have a substituent, and the substituent includes a hydroxy group, an optionally substituted amino group [for example, the amino group may have 1 or 2 substituents, such as a lower alkyl group (e.g., $C_{1-6}$ alkyl such as methyl, ethyl, propyl, isopropyl, butyl, isobutyl, tert-butyl, pentyl, hexyl, etc., preferably, methyl, ethyl, etc.) optionally substituted with 1 to 5 halogen atoms (e.g., fluorine, chlorine, bromine, iodine, etc.), an acyl group (e.g., $C_{1-6}$alkanoyl such as formyl, acetyl, propionyl and pivaloyl, benzoyl, etc.), a carboxyl group and a $C_{1-6}$ alkoxycarbonyl.], a halogen atom (e.g., fluorine, chlorine, bromine, iodine, etc.), a nitro group, a cyano group, a lower alkoxy group (e.g., $C_{1-6}$ alkoxy such as methoxy, ethoxy, n-propoxy, isopropoxy, n-butoxy, isobutoxy, sec-butoxy and tert-butoxy, etc., preferably, methoxy, ethoxy, etc.) optionally substituted with 1 to 5 halogen atoms (e.g., fluorine, chlorine, bromine, iodine, etc.), etc. Furthermore, these substituents may be the same or different and the number of the substituent is preferably 1, 2 or 3 (more preferably 1 or 2).

Herein, the "aryloxycarbonyl" is preferably, for example, $C_{6-14}$ aryloxycarbonyl such as phenoxycarbonyl, 1-naphthoxycarbonyl, 2-naphthoxycarbonyl, 1-phenanthoxycarbonyl, etc. The "aryloxycarbonyl" may have a substituent, and the substituent includes those such as the above-mentioned substituents in the "alkoxycarbonyl" as the substituent in the same number.

Herein, the "aralkyloxycarbonyl" is preferably, for example, $C_{7-14}$ aralkyloxycarbonyl such as benzyloxycarbonyl, phenethyloxycarbonyl, etc. (preferably, $C_{6-10}$ aryl-$C_{1-4}$ alkoxy-carbonyl, etc.). The "aralkyloxycarbonyl" may have a substituent, and the substituent includes those such as the above-mentioned substituents in the "alkoxycarbonyl" as the substituent in the same number.

Herein, the "substituent" of the "N-monosubstituted carbamoyl" includes, for example, lower alkyl (e.g., $C_{1-6}$alkyl such as methyl, ethyl, propyl, isopropyl, butyl, isobutyl, tert-butyl, pentyl, hexyl, etc.), lower alkenyl (e.g., $C_{2-6}$alkenyl such as vinyl, allyl, isopropenyl, propenyl, butenyl, pentenyl, hexenyl, etc.), cycloalkyl (e.g., $C_{3-6}$ cycloalkyl such as cyclopropyl, cyclobutyl, cyclopentyl and cyclohexyl, etc.), aryl (e.g., $C_{6-10}$ aryl such as phenyl, 1-naphthyl, 2-naphthyl, etc.), aralkyl (e.g., $C_{7-10}$ aralkyl such as benzyl and phenethyl, preferably, phenyl-$C_{1-4}$ alkyl, etc.), arylalkenyl (e.g., $C_{8-10}$ arylalkenyl such as cinnamyl, preferably, phenyl-$C_{2-4}$ alkenyl, etc.), a heterocyclic group (e.g., those such as the "heterocyclic group" in the "optionally substituted heterocyclic group" as the above-mentioned substituent, etc.), etc. The lower alkyl, the lower alkenyl, the cycloalkyl, the aryl, the aralkyl, the arylalkenyl and the heterocyclic group may have a substituent, and the substituent includes those such as the above-mentioned substituents in the "alkoxycarbonyl" as the substituent in the same number.

Herein, the "N,N-disubstituted carbamoyl" means a carbamoyl group having two substituents on the nitrogen atom. Examples of one of the two substituents include those such as the above-mentioned substituent in the "N-monosubstituted carbamoyl" as the substituent, and examples of the other substituent include, for example, lower alkyl (e.g., $C_{1-6}$ alkyl such as methyl, ethyl, propyl, isopropyl, butyl, tert-butyl, pentyl, hexyl, etc.), $C_{3-7}$ cycloalkyl (e.g., cyclopropyl, cyclobutyl, cyclopentyl, cyclohexyl, etc.), $C_{7-10}$ aralkyl (e.g., benzyl and phenethyl, etc., preferably, phenyl-$C_{1-4}$alkyl, etc.), etc. Furthermore, the two substituents may form a cyclic amino together with the nitrogen atom, and in such case, the cyclic aminocarbamoyl includes, for example, a 3- to 8-membered (preferably, a 5- or 6-membered) cyclic aminocarbonyl such as 1-azetidinylcarbonyl, 1-pyrrolidinylcarbonyl, piperidinocarbonyl, morpholinocarbonyl, 1-piperazinylcarbonyl, and 1-piperazinylcarbonyl optionally having lower alkyl (e.g., $C_{1-6}$ alkyl such as methyl, ethyl, propyl, isopropyl, butyl, tert-butyl, pentyl, hexyl, etc.), aralkyl (e.g., $C_{7-10}$ aralkyl such as benzyl, phenethyl, etc.), aryl (e.g., $C_{6-10}$ aryl such as phenyl, 1-naphthyl, 2-naphthyl, etc.), etc. at the position 4, etc.

The substituent of the "optionally substituted thiocarbamoyl group" and the "optionally substituted sulfamoyl group" as the above-mentioned substituent includes those such as the substituent of the "N-monosubstituted carbamoyl" or the "N,N-disubstituted carbamoyl" in the "optionally esterified or amidated carboxyl group" as the above-mentioned substituent.

The "sulfonic acid-derived acyl" as the above-mentioned substituent includes, for example, those in which the one substituent on the nitrogen atom of the above-mentioned "N-monosubstituted carbamoyl" is bonded to sulfonyl, etc., preferably, acyl such as $C_{1-6}$ alkylsulfonyl such as methanesulfonyl and ethanesulfonyl.

The "carboxylic acid-derived acyl" as the substituent includes a hydrogen atom or those in which the one substituent on the nitrogen atom of the above-mentioned "N-monosubstituted carbamoyl" is bonded to carbonyl, preferably, acyl such as $C_{1-6}$ alkanoyl such as formyl, acetyl, propionyl and pivaloyl, and benzoyl.

The "$C_{1-4}$ alkylenedioxy group" as the substituent includes a methylenedioxy group, an ethylenedioxy group, a propylenedioxy group, a butylenedioxy group, etc., which may be substituted on the same carbon or different carbons.

The substituent in the "optionally substituted $C_{1-6}$ alkyl group" represented by $R^6$ and the "substituent on Ring A or Ring B except for $R^a$, $R^2$, $R^{3'}$, $R^4$ and $R^{5'}$" includes those such as the substituent used in the "optionally substituted alkyl group" as the above-mentioned substituent in the same number.

The substituent in the "optionally substituted $C_{1-6}$ alkoxy group" represented by the "substituent on Ring A or Ring B except for $R^a$, $R^2$, $R^{3'}$, $R^4$ and $R^{5'}$" includes those such as the substituent used in the "optionally substituted alkyl group" as the above-mentioned substituent in the same number.

The substituent in the "optionally substituted alkoxy group" represented by $R^a$ includes those such as the substituent used in the "optionally substituted alkyl group" as the above-mentioned substituent in the same number.

The substituent in the "optionally substituted acyl group" represented by $R^1$, $R^{1a}$, $R^2$, $R^{2a}$, $R^3$, $R^{3'}$, $R^{3a}$, $R^4$, $R^{4a}$, $R^5$, $R^{5'}$, $R^{5a}$ and $R^7$ includes those such as the substituent used in the "optionally substituted alkyl group" as the above-mentioned substituent in the same number.

The substituent in the "optionally substituted $C_{1-6}$ acyl group" represented by the "substituent on Ring A or Ring B except for $R^a$, $R^2$, $R^{3'}$, $R^4$ and $R^{5'}$" includes those such as substituent used in the "optionally substituted alkyl group" as the above-mentioned substituent in the same number.

The substituent in the "optionally substituted $C_{1-6}$ alkoxyimino group" in the "carbon atom substituted with an optionally substituted $C_{1-6}$ alkoxyimino group" represented by $Z^1$ and $Z^2$ and the "optionally substituted $C_{1-6}$ alkoxyimino group" represented by the "substituent on Ring A or Ring B except for $R^a$, $R^2$, $R^{3'}$, $R^4$ and $R^{5'}$" includes those such as substituent used in the "optionally substituted alkyl group" as the above-mentioned substituent in the same number.

The substituent in the "optionally substituted $C_{1-4}$ alkylenedioxy group" represented by the "substituent on Ring A or Ring B except for $R^a$, $R^2$, $R^{3'}$, $R^4$ and $R^{5'}$" includes those such as substituent used in the "optionally substituted alkyl group" as the above-mentioned substituent in the same number.

The "leaving group" represented by M includes, for example, halogen such as fluorine, chlorine, bromine and iodine, trifluoromethanesulfonate, p-toluenesulfonate, methanesulfonyl, etc.

Ring A and Ring $A^a$, and Ring B and Ring $B^a$ may be substituted.

The substituent in the "optionally substituted carbon atom" represented by $X^1$, $X^2$, $X^{1a}$ and $X^{2a}$ includes 1 or 2 of those such as the above-mentioned substituent in the "optionally substituted hydrocarbon group" represented by $R^2$, $R^{2a}$, $R^3$, $R^{3'}$, $R^{3a}$, $R^4$, $R^{4a}$, $R^5$, $R^{5'}$ and $R^{5a}$. Here, when the "optionally substituted carbon atom" has no substituent, the carbon atom has 1 or 2 of hydrogen atom, and when the "optionally substituted carbon atom" has one substituent, the carbon atom has 0 or 1 of a hydrogen atom in addition to the substituent.

The substituent in the "optionally substituted nitrogen atom" represented by $Y^2$, $Y^{21}$ and $Y^{2a}$ includes those such as the substituent in the "optionally substituted amino group" as the substituent in the definition of the above-mentioned "substituent on Ring A or Ring B except for $R^a$, $R^2$, $R^{3'}$, $R^4$ and $R^{5'}$". Here, when the "optionally substituted nitrogen atom" has no substituent, the nitrogen atom has 0 or 1 of a hydrogen atom.

W and $W^1$ represent a nitrogen atom or a group represented by the formula $CR^a$ (wherein the symbol is as defined above), provided that when Ring A represents an optionally substituted benzene ring, W represents a group represented by the formula $CR^a$ (wherein the symbol is as defined above).

$Y^1$ represents a group represented by the formula $CR^2R^3$ (wherein each symbol is as defined above), and $Y^2$ represents a group represented by a group represented by the formula $CR^4R^5$ (wherein each symbol is as defined above), a nitrogen atom, an oxygen atom or a group represented by the formula $S(O)_m$ (wherein each symbol is as defined above), respectively.

$Y^{11}$ represents a group represented by the formula $CR^2R^{3'}$ (wherein each symbol is as defined above), and $Y^{21}$ represents 1) hen W is a nitrogen atom, a group represented by the formula $R^4R^{5'}$ (wherein each symbol is as defined above), a nitrogen atom, n oxygen atom or a group represented by the formula $S(O)_m$ (wherein each symbol is as defined above), or 2) when W is a group represented by the formula $CR^a$ (wherein the symbol is as defined above), a group represented by the formula $CR^4R^{5'}$ (wherein each symbol is as defined above) or a nitrogen atom (provided that when $Y^{21}$ is a nitrogen atom and W is a group represented by the formula $CR^a$ (wherein the symbol is as defined above), the bond between $CR^a$ and $Y^{21}$ is a double bond), respectively.

$Y^{1a}$ represents a group represented by the formula $CR^{2a}R^{3a}$ (wherein each symbol is as defined above), and $Y^{2a}$ represents a group represented by the formula $CR^{4a}R^{5a}$ (wherein each symbol is as defined above), a nitrogen atom, an oxygen atom or a group represented by the formula $S(O)_m{}^a$ (wherein each symbol is as defined above), respectively.

The compound of the present invention is a compound represented by the general formula:

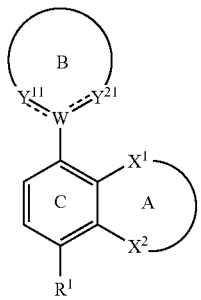

(I)

[wherein each symbol is as defined above] or a salt thereof, more preferably, a compound represented by the general formula:

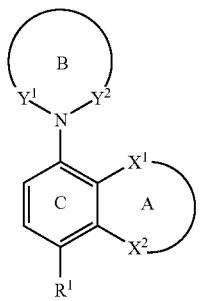

(Ia)

[wherein each symbol is as defined above] or a salt thereof, further preferably, a compound represented by the general formula:

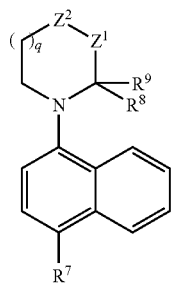

(IIa)

[wherein each symbol is as defined above] or a salt thereof, or a compound represented by the general formula:

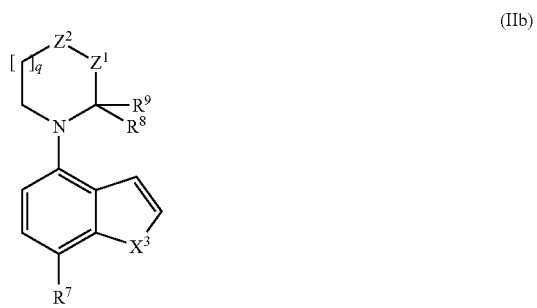

(IIb)

[wherein each symbol is as defined above] or a salt thereof.

Ring A or Ring $A^a$ includes, especially preferably, an optionally substituted benzene ring, an optionally substituted furan ring, an optionally substituted dihydrofuran ring, an optionally substituted cyclopentadiene ring, a cyclopentene ring, an optionally substituted cyclohexene ring, an optionally substituted cyclohexadiene ring, an optionally substituted dihydropyran ring, an optionally substituted pyran ring, an optionally substituted thiophene ring, an optionally substituted pyrrole ring, an optionally substituted pyridine ring, an optionally substituted pyrroline ring, an optionally substituted pyrrolidine ring, an optionally substituted piperidine ring, etc.

Ring B or Ring $B^a$ includes, especially preferably, an optionally substituted pyrroline ring, an optionally substituted pyrrolidine ring, an optionally substituted piperidine ring, an optionally substituted morpholine ring, an optionally substituted thiomorpholine ring or an optionally substituted perhydroazepine ring, etc.

$R^1$, $R^{1a}$ and $R^7$ include, especially preferably a cyano group, a nitro group, a halogen atom, a fluoromethyl group, a trifluoromethyl group, etc.

Substituents other than $R^2$, $R^{3'}$, $R^4$ and $R^{5'}$ on Ring B are especially preferably a hydrogen atom, a halogen atom, a cyano group, a nitro group, a hydroxy group, an optionally substituted $C_{1-6}$ alkyl group (e.g., a methyl group, an ethyl group, a propyl group, a fluoromethyl group, a hydroxymethyl group, a hydroxyethyl group, a hydroxypropyl group, a methoxymethyl group, etc.), a carbamoyl group, etc.

The compound of the present invention is preferably a compound represented by the above-mentioned general formula (I), etc., specifically, for example, 4-[4-(hydroxymethyl)-1-piperidinyl]-1-naphthonitrile, 4-[3-(hydroxymethyl)-1-piperidinyl]-1-naphthonitrile, 4-[3-(hydroxymethyl)-3-methyl-1-piperidinyl]-1-naphthonitrile, 4-(2-methyl-1-pyrrolidinyl)-1-naphthonitrile, 4-(2-ethyl-1-pyrrolidinyl)-1-naphthonitrile, 4-(2-vinyl-1-pyrrolidinyl)-1-naphthonitrile, 4-(2-isopropyl-1-pyrrolidinyl)-1-naphthonitrile, 4-(3-hydroxy-2-methyl-1-pyrrolidinyl)-1-naphthonitrile, 4-(3-methoxy-2-methyl-1-pyrrolidinyl)-1-naphthonitrile, 4-(4-methoxy-2-methyl-1-pyrrolidinyl)-1-naphthonitrile, 4-[3-(hydroxymethyl)-2-methyl-1-pyrrolidinyl]-1-naphthonitrile, 4-[3-(1-hydroxy-1-methylethyl)-2-methyl-1-pyrrolidinyl]-1-naphthonitrile, 1-(4-cyano-1-naphthyl)-2-methylpyrrolidine-3-carboxamide, 1-(4-cyano-1-naphthyl)-2-methylpyrrolidine-3-carbonitrile, 4-(2-methyl-1-pyrrolidinyl)-1-benzothiophene-7-carbonitrile, 4-(3-hydroxy-2-methyl-1-pyrrolidinyl)-1-benzothiophene-7-carbonitrile, 4-(4-hydroxy-2-methyl-1- pyrrolidinyl)-1-benzothiophene-7-carbonitrile or an optically active substance or a salt thereof can be preferably used.

In the compound of the present invention represented by the following general formula:

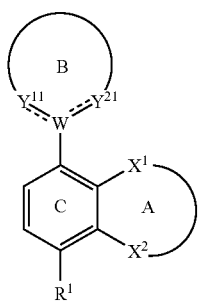

(I)

[wherein each symbol is as defined above], the compound in the case that "when Ring B is a further optionally substituted bicyclic ring, $CR^2$ in $Y^{11}$ or $CR^4$ or the nitrogen atom in $Y^{21}$ may constitute a part of Ring B", represents for example, a compound represented by the general formula:

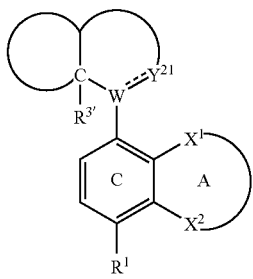

[wherein each symbol is as defined above] or, a compound represented by the general formula:

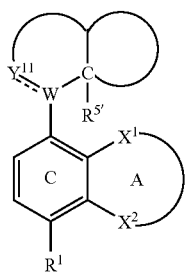

[wherein each symbol is as defined above] or, a compound represented by the general formula:

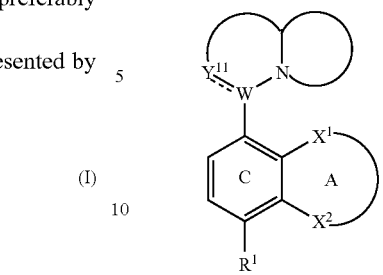

[wherein each symbol is as defined above], etc.

The compounds in the case that "when Ring $B^a$ is a further optionally substituted bicyclic ring, $CR^{2a}$ in $Y^{1a}$ or $CR^{4a}$ or the nitrogen atom in $Y^{2a}$ may constitute a part of Ring B" and "when Ring B is a further optionally substituted bicyclic ring, $CR^2$ in $Y^{11}$ or $CR^4$ or the nitrogen atom in $Y^{21}$ may constitute a part of Ring B" are similar to the above case.

[General Preparation]

The compound of the present invention (the compound represented by the general formula I, Ia, IIa, IIb, I', etc., hereinafter, also referred to as Compound (I), Compound (Ia), Compound (IIa), Compound (IIb), Compound (I'), etc., respectively) may be prepared by general organic synthesis methods or known synthesis methods, for example, by the following methods.

A compound of Compound (I) or Compound (I') in which W or $W^1$ is a nitrogen atom can be prepared by, for example, subjecting a compound represented by the formula:

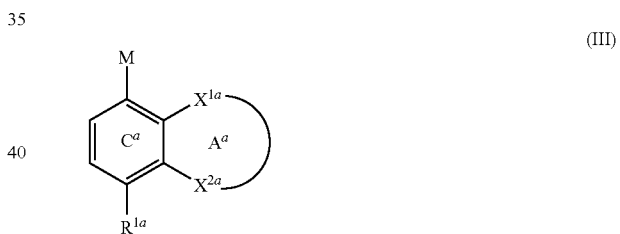

(III)

[wherein each symbol is as defined above] or a salt thereof, and a compound represented by the formula:

(IV)

[wherein each symbol is as defined above] or a salt thereof to a reaction, and if it has protective group, eliminating the protective group. The "leaving group" includes represented by M, for example, halogen such as fluorine, chlorine, bromine and iodine, trifluoromethanesulfonate, p-toluenesulfonate, methanesulfonyl, etc.

Compound (IV) or a salt thereof is used usually in an amount of 1 to 3 moles per 1 mole of Compound (III). The reaction can be facilitated, if necessary, by adding a base such as potassium carbonate, sodium carbonate, cesium carbonate, sodium hydrogen carbonate, sodium hydroxide, sodium t-butoxide, potassium t-butoxide, triethylamine, diisopropylamine (DIEA), pyridine, 4-(dimethylamino)pyridine (DMAP), 1,8-diazabicyclo[5,4,0]undec-7-ene (DBU), 1,5-diazabicyclo[4,3,0]non-5-ene (DBN). Further, transition metal catalyst (e.g., J.O.C., 1997, 62, pp 1264-1267) is suitably used as a catalyst.

The reaction can be carried out in an inert solvent, for example, methanol, ethanol, propanol, isopropanol, n-butanol, tetrahydrofuran, diethyl ether, acetonitrile, acetone, ethyl acetate, 1,2-dimethoxyethane, 1,4-dioxane, toluene, benzene, xylene, dichloromethane, chloroform, 1,2-dichloroethane, DMF, dimethylsulfoxide (DMSO), etc., or a mixed solvent thereof. The reaction is carried out at the temperature range of about 0° C. to 180° C. The reaction time is not particularly limited, usually 0.1 hour to 100 hours, preferably, 0.5 hours to 72 hours.

Furthermore, the compound of Compound (I) or Compound (I') in which W or $W^1$ is a nitrogen atom can be prepared by, for example, subjecting a compound represented by the formula:

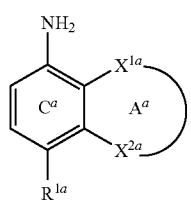
(V)

[wherein each symbol is as defined above] or a salt thereof and a compound represented formula:

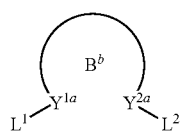
(VI)

[wherein $B^b$ represents a chain moiety to be Ring $B^a$ after cyclization with the amino group of the above-mentioned formula (V), and $L^1$ and $L^2$ are the same or different and represent a leaving group. Other symbols are as defined above.] to a reaction, and if it has protective group, eliminating the protective group. The "leaving group" represented by $L^1$ and $L^2$ may be the same or different and includes, for example, halogen such as fluorine, chlorine, bromine and iodine, and a sulfonyl group such as trifluoromethanesulfonyl, p-toluenesulfonyl, methanesulfonyl.

Compound (VI) is used in an amount of usually 1 to 3 moles per 1 mole of Compound (V) or a salt thereof. The reaction can be facilitated, if necessary, by adding a base such as potassium carbonate, sodium carbonate, cesium carbonate, sodium hydrogen carbonate, sodium hydroxide, triethylamine, diisopropylamine (DIEA), pyridine, 4-(dimethylamino)pyridine (DMAP), 1,8-diazabicyclo[5,4,0]undec-7-ene (DBU) and 1,5-diazabicyclo[4,3,0]non-5-ene (DBN), and sodium iodide, etc.

The reaction can be carried out in an inert solvent, for example, methanol, ethanol, propanol, isopropanol, n-butanol, tetrahydrofuran, diethyl ether, acetonitrile, acetone, ethyl acetate, 1,2-dimethoxyethane, 1,4-dioxane, toluene, benzene, xylene, dichloromethane, chloroform, 1,2-dichloroethane, DMF, dimethylsulfoxide (DMSO), etc., or mixed solvent thereof. The reaction is carried out at the temperature range of about 0° C. to 180° C. The reaction time is not particularly limited, usually 0.1 hour to 100 hours, preferably, 0.5 hours to 24 hours.

Furthermore, when Compound (I) or Compound (I') is a compound represented by the formula:

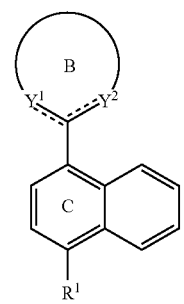
(VII)

[wherein each symbol is as defined above], it can be prepared, for example, by subjecting a compound represented by the formula:

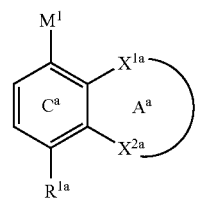
(VIII)

[wherein $M^1$ represents a leaving group or nitrile oxide and other symbols are as defined above] or a salt thereof and a compound represented by the formula:

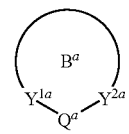
(IX)

[wherein $Q^a$ represents a carbonyl group or $CM^2$ ($M^2$ represents a leaving group), and other symbols are as defined above] or a compound represented by the formula:

[wherein $R^B$ and $R^C$ are the same or different and represent a hydrogen atom, a cyano group, a nitro group, an optionally substituted acyl group, an optionally esterified or amidated carboxyl group or an optionally substituted hydrocarbon group, respectively] or a salt thereof to a reaction, and if it has protective group, eliminating the protective group.

The "leaving group" represented by $M^1$ or $M^2$ includes, for example, halogen such as fluorine, chlorine, bromine and iodine, alkali metal, alkaline earth metal or metal halide thereof, zinc halide, tin halide, trifluoromethanesulfonate, p-toluenesulfonate, methanesulfonyl, dihydroxyborane, dialkoxyborane, etc.

The "optionally substituted acyl group", the "optionally esterified or amidated carboxyl group" and the "optionally substituted hydrocarbon group" represented by $R^B$ and $R^C$ includes those such as the definitions of "optionally substituted acyl group", the "optionally esterified or amidated carboxyl group" represented by the above-mentioned $R^1$, etc., and the "optionally substituted hydrocarbon group" represented by the above-mentioned $R^2$, etc.

Compound (IX), (X) or a salt thereof is used in an amount of usually 1 to 3 moles per 1 mole of Compound (VIII). The reaction can be facilitated, if necessary, by adding a base such as potassium carbonate, sodium carbonate, cesium carbonate, sodium hydrogen carbonate, sodium hydroxide, sodium t-butoxide, potassium t-butoxide, triethylamine, diisopropylamine (DIEA), pyridine, 4-(dimethylamino)pyridine (DMAP), 1,8-diazabicyclo[5,4,0]undec-7-ene (DBU) and 1,5-diazabicyclo[4,3,0]non-5-ene (DBN). Further, transition metal catalyst (e.g., J.O.C., 1997, 62, pp 1264-1267) is suitably used as a catalyst.

The reaction can be carried out in an inert solvent, for example, methanol, ethanol, propanol, isopropanol, n-butanol, tetrahydrofuran, diethyl ether, acetonitrile, acetone, ethyl acetate, 1,2-dimethoxyethane, 1,4-dioxane, toluene, benzene, xylene, dichloromethane, chloroform, 1,2-dichloroethane, DMF, dimethylsulfoxide (DMSO), etc., or a mixed solvent thereof. The reaction is carried out at the temperature range of about −80° C. to 180° C. The reaction time is not particularly limited, usually 0.1 hour to 100 hours, preferably, 0.5 hours to 72 hours.

Further, one or more substituents on Ring B in Compound (I) or Compound (I') can be converted to other substituents. For example, a carbonyl group can be reduced to produce alcohol, and the alcohol can be dehydrated to produce olefin, or the alcohol can be alkylated to produce ether according to a known method per se.

Compound (III), (IV), (V), (VI), (VII), (VIII), (IX) and (X) which are used as starting materials can be synthesized by a known method or modifications thereof, for example, by the methods described in the following Reference Examples.

Furthermore, the above-mentioned Compound (Ia), (IIa) or (IIb) can also be synthesized by the above-mentioned method or known method or modifications thereof.

Herein, the group in the above-mentioned formulae may be protected with a protective group which is generally used in an organic synthesis, and after reaction, if desired, the protective group can be eliminated by a known method.

The thus obtained compound represented by the general formula (I), (Ia), (IIa), (IIb) or (I'), etc. (hereinafter, also referred to as Compound (I), etc.) can be isolated and purified by known separation and purification methods such as concentration, concentration under reduced pressure, solvent extraction, pH adjustment, salting out, crystallization, recrystallization, re-dissolution, chromatography, etc.

When Compound (I), etc. is obtained as a free form, it can be converted into a salt according to a conventional method or modifications thereof, and conversely when Compound (I), etc. is obtained as a salt, it can be converted into a free form or another salt according to a conventional method modifications thereof.

Compound (I), etc. may be hydrated or non-hydrated.

When Compound (I), etc. is obtained as a mixture of optically active substances, it can be separated into (S)-isomer or (R)-isomer with a known optical resolution per se.

Compound (I), etc. may be labeled with an isotope (e.g., $^3$H, $^{14}$C, etc.), etc.

The compounds in the present invention may form salts. Salts of the compounds are not particularly limited as long as they do not interfere with the reaction, and include, for example, a salt with an inorganic base, an ammonium salt, a salt with an organic base a salt with an inorganic acid, a salt with an organic acid, a salt with an amino acid, etc. Preferable examples of the salt with an inorganic base include an alkali metal salt such as sodium salt, potassium salt, etc.; an alkaline earth metal salt such as calcium salt, magnesium salt, etc.; aluminum salt; ammonium salt; etc. Preferable examples of the salt with an organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferable examples of the salt with an inorganic acid include a salt with hydrochloric acid, hydrobromic acid, nitric acid, sulfuric acid, phosphoric acid, etc. Preferable examples of the salt with an organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferable examples of the salt with a basic amino acid include a salt with arginine, lysine, ornithine, etc. Preferable examples of the salt with an acidic amino acid include a salt with aspartic acid, glutamic acid, etc.

The prodrug of Compound (I), etc. or a salt thereof (hereinafter, abbreviated to Compound (I)) means a compound which is converted to Compound (I) with a reaction using an enzyme, a gastric acid, etc. under the physiological condition in the living body, that is, a compound which is converted to Compound (I) with oxidation, reduction, hydrolysis, etc. according to an enzyme and a compound which is converted to Compound (I) with hydrolysis by gastric acid, etc. Examples of the prodrug of Compound (I) include a compound wherein an amino group of Compound (I) is substituted with acyl, alkyl, phosphoric acid, etc. (e.g., a compound wherein an amino group of Compound (I) is substituted with eicosanyl, alanyl, pentylaminocarbonyl, (5-methyl-2-oxo-1, 3-dioxolen-4-yl)methoxycarbonyl, tetrahydrofuranyl, pyrrolidylmethyl, pivaloyloxymethyl, tert-butyl, etc,); a compound wherein a hydroxy group of Compound (I) is substituted with acyl, alkyl, phosphoric acid, boric acid, etc. (e.g., a compound wherein a hydroxy group of Compound (I) is substituted with acetyl, palmitoyl, propanoyl, pivaloyl, succinyl, fumaryl, alanyl, dimethylaminomethylcarbonyl, etc.); a compound wherein a carboxyl group of Compound (I) is substituted with ester, amide, etc. (e.g., a compound wherein a carboxyl group of Compound (I) is substituted with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl) methyl ester, cyclohexyloxycarbonylethyl ester, methyl amide, etc.); etc. These prodrugs ca n be manufactured by the known method per se from Compound (I).

In addition, the prodrug of Compound (I) may be a compound which is converted into Compound (I) under the physiological conditions as described in "Pharmaceutical Research and Development", Vol. 7 (Molecular Design), pages 163-198 published in 1990 by Hirokawa Publishing Co.

Compound (I) of the present invention or a prodrug thereof (hereinafter, it may be abbreviated to a compound of the present invention) has androgen receptor modulator actions, especially an androgen receptor agonist actions, and can be used for preventing or treating diseases for which administration of an androgen receptor agonist is effective in a mammal. The diseases for which administration of an androgen receptor agonist is effective, include hypogonadism, osteoporosis, hormone-resistant cancer (especially LHRH agonist-resistant cancer), climacteric disturbance (especially male climacteric disturbance), anemia, atherosclerosis, Alzheimer's disease, erection failure, depression or wasting diseases, etc.

The compound of the present invention is useful as an agent of preventing or treating breast cancer, prostate cancer, cancer of the uterine body, cancer of the uterine cervix, ovary cancer, bladder cancer, thyroid cancer, bone tumor, penis cancer, especially, prostate cancer, which has acquired hormone-resistance, among various cancers.

The hormone-resistant cancer includes, for example, LHRH derivative-resistant cancer, preferably, LHRH agonist-resistant cancer.

The compound of the present invention has low toxicity, and can be used as a medicine as itself, or as a pharmaceutical composition for a mammal (e.g., human, horse, bovine, dog, cat, rat, mouse, rabbit, pig, monkey, etc.) by mixing with pharmaceutically acceptable carriers according to a known method per se.

The pharmaceutical composition may contain other active ingredients, for example, following drugs for hormone therapy, anticancer agents (e.g., chemotherapeutic agents, immunotherapeutic agents, or cell growth factor and inhibitors for the receptor actions, etc.), in combination with the compound of the present invention etc.

As a medicine for mammals such as humans, the compound of the present invention can be administered orally in the form of, for example, tablets, capsules (including soft capsules and microcapsules), powders, and granules, or parenterally in the form of injections, suppositories, and pellets. Examples of the "parenteral administration route" include intravenous, intramuscular, subcutaneous, intra-tissue, intranasal, intradermal, instillation, intracerebral, intrarectal, intravaginal, intraperitoneal, intratumoral, juxtaposition of tumor and administration directly to the lesion.

The dose of the compound of the present invention varies depending on route for administration, symptoms, etc. For example, in case of oral administration for patient (40 to 80 kg body weight) with breast cancer or prostate cancer as an anticancer agent, the daily dose is 0.1 mg to 200 mg/kg body weight, preferably 1 to 100 mg/kg body weight, more preferably 1 to 50 mg/kg body weight, and it can be administered once or twice or three times per day.

The compound of the present invention may be administrated orally or parenterally as solid formulation such as tablet, capsule, granule, powder, etc.; or liquid formulation such as syrup, injection, etc. as admixture with a pharmaceutically acceptable carrier.

Examples of the pharmaceutically acceptable carrier include various organic or inorganic carriers which are generally used in this field. For example, an excipient, a lubricant, a binder, a disintegrating agent, etc. are used in solid formulations, and a solvent, a solubilizer, a suspending agent, an isotonizing agent, a buffer, a soothing agent, etc. are used in liquid formulations. In addition, if desired, an appropriate additive such as an antiseptic, antioxidant, a colorant, a sweetener, etc. may be used.

Suitable examples of the excipient include lactose, sucrose, D-mannitol, starch, crystalline cellulose, light silicic acid anhydride, etc.

Suitable examples of the lubricant include magnesium stearate, calcium stearate, talc, colloidal silica, etc.

Suitable examples of the binder include crystalline cellulose, sucrose, D-mannitol, dextrin, hydroxypropyl cellulose, hydroxypropylmethyl cellulose, polyvinylpyrrolidone, etc.

Suitable examples of the disintegrating agent include starch, carboxymethyl cellulose, carboxymethyl cellulose calcium, croscarmellose sodium, sodium carboxymethyl starch, etc.

Suitable examples of the solvent include water for injection, alcohol, propylene glycol, macrogol, sesame oil, corn oil, etc.

Suitable examples of the solubilizer include polyethylene glycol, propylene glycol, D-mannitol, benzyl benzoate, ethanol, trisaminomethane, cholesterol, triethanolamine, sodium carbonate, sodium citrate, etc.

Suitable examples of the suspending agent include surfactants such as stearyl triethanolamine, sodium laurylsulfate, laurylaminopropionic acid, lecithin, benzalkonium chloride, benzethonium chloride, glycerin monostearate, etc.; hydrophilic polymers such as polyvinyl alcohol, polyvinylpyrrolidone, sodium carboxymethyl cellulose, methyl cellulose, hydroxymethyl cellulose hydroxyethyl cellulose, hydroxypropyl cellulose, etc.

Suitable examples of the isotonizing agent include sodium chloride, glycerin, D-mannitol, etc.

Suitable examples of the buffer include a buffer solution of phosphate, acetate, carbonate, citrate, etc. Suitable examples of the soothing agent include benzyl alcohol, etc.

Suitable examples of the antiseptic include paraoxybenzoates, chlorobutanol, benzyl alcohol phenethyl alcohol, dehydroacetic acid, sorbic acid, etc.

Suitable examples of the antioxidant include sulfites, ascorbic acid, etc.

A pharmaceutical composition can be manufactured by a conventional method by containing the compound of the present invention in a ratio of normally 0.1 to 95% (w/w) to the total amount of the preparation, although the ratio varies depending on dosage form, method of administration, carrier, etc.

A combination of (1) administering an effective amount of a compound of the present invention and (2) 1 to 3 selected from the group consisting of (i) administering an effective amount of other anti-cancer agents, (ii) administering an effective amount of hormonal therapeutic agents and (iii) non-drug therapy can prevent and/or treat cancer more effectively. The non-drug therapy includes, for example, surgery, radiotherapy, gene therapy, thermotherapy, cryotherapy, laser cauterization, etc., and two or more of these may be combined.

For example, the compound of the present invention can be administered to the same subject simultaneously with hormonal therapeutic agents, anticancer agents (e.g., chemotherapeutic agents, immunotherapeutic agents, or drugs that inhibit the activity of growth factors or growth factor receptors), antiemetic agents (hereinafter, these are abbreviated to as a combination drug).

Although the compound of the present invention exhibits excellent anticancer action even when used as a simple agent, its effect or QOL of patients can be enhanced by using it in combination with one or more of the combination drug(s) mentioned above (multi-agent co-administration).

The "hormonal therapeutic agents" include fosfestrol, diethylstylbestrol, chlorotrianiserin, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate, etc.), pill preparations, mepitiostane, testrolactone, aminoglutethimide, LH- RH agonists (e.g., goserelin acetate, buserelin, leuprorelin, etc.), droloxifene, epitiostanol, ethinylestradiol sulfonate, aromatase inhibitors (e.g., fadrozole hydrochloride, anastrozole, retrozole, exemestane, vorozole, formestane, etc.), antiandrogens (e.g., flutamide, bicartamide, nilutamide), 5α-reductase inhibitors (e.g., finasteride, epristeride, etc.), adrenocorticohormone drugs (e.g., dexamethasone, prednisolone, betamethasone, triamcinolone, etc.), androgen synthesis inhibitors (e.g., abiraterone etc.), retinoid and drugs that retard retinoid metabolism (e.g., liarozole, etc.), etc. and LH-RH derivatives are preferable.

The "chemotherapeutic agents" include alkylating agents, antimetabolites, anticancer antibiotics, plant-derived anticancer agents, etc.

The "alkylating agents" include nitrogen mustard, nitrogen mustard N-oxide hydrochloride, chlorambucil, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, carboquone, adozelesin, cystemustine, bizelesin etc.

The "antimetabolites" include mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, etc.), aminopterine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, and ambamustine, etc.

The "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, etc.

The "plant-derived anticancer agents" include etoposide, etoposide phosphate, vinblastine sulfate, vincristine sulfate, vindesine sulfate, teniposide, paclitaxel, docetaxel, DJ-927, vinorelbine, etc.

The "immunotherapeutic agents (BRM)" include picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, etc.

The "growth factor" in the "drugs that inhibit the activity of growth factors or growth factor receptors" includes any substances that promote cell proliferation, which are normally peptides having a molecular weight of not more than 20,000 that are capable of exhibiting their activity at low concentrations by binding to a receptor, including (1) EGF (epidermal growth factor) or substances possessing substantially the same activity as it [e.g., EGF, heregulin (HER2 ligand), etc.], (2) insulin or substances possessing substantially the same activity as it [e.g., insulin, IGF (insulin-like growth factor)-1, IGF-2, etc.], (3) FGF (fibroblast growth factor) or substances possessing substantially the same activity as it [e.g., acidic FGF, basic FGF, KGF (keratinocyte growth factor), FGF-10, etc.], (4) other cell growth factors [e.g., CSF (colony stimulating factor), EPO (erythropoietin), IL-2 (interleukin-2), NGF (nerve growth factor), PDGF (platelet-derived growth factor), TGF β (transforming growth factor β), HGF (hepatocyte growth factor), VEGF (vascular endothelial growth factor), etc.], etc.

The "growth factor receptors" include any receptors capable of binding to the aforementioned growth factors, including EGF receptor, heregulin receptor (HER2), insulin receptor, IGF receptor, FGF receptor-1 or FGF receptor-2, etc.

The "drugs that inhibit the activity of cell growth factor" include various kinase inhibitors, trastuzumab (Herceptin (trademark): (HER2 antibody)), imatinib mesilate, ZD1839, cetuximab, etc.

In addition to the aforementioned drugs, L-asparaginase, aceglatone, procarbazine hydrochloride, protoporphyrin-cobalt complex salt, mercuric hematoporphyrin-sodium, topoisomerase I inhibitors (e.g., irinotecan, nogitecan, exatecan (DX-8951f, DE-310, rubitecan, T-0128, etc.), topoisomerase II inhibitors (e.g., sobuzoxane, etc.), differentiation inducers (e.g., retinoid, vitamin D, etc.), angiogenesis inhibitors, α-blockers (e.g., tamsulosin hydrochloride), TZT-1027, etc., may be used.

The "antiemetic agents" includes 5-HT$_3$ antagonist such as ondansetron, tropisetron hydrochloride, azasetron, ramosetron, granisetron, dorasetron mesilate and palonosetron, a gastrointestinal tract motility promoter such as 5-HT$_4$ antagonist such as domperidone, mosapride and metoclopramide; a gastrointestinal tract motility regulator such as trimebutine; phenothiazine drugs such as prochlorperazine maleate, promethazine and tiethylperazine; anxiolytics such as haloperidole, phenol phthalate chlorpromazine, diazepam and droperidole; steroids such as dexamethasone, prednisolone, betamethasone and triamcinolone; other drugs such as dimethylhydric acid, diphenhydramine, hyoscin, hyoscin bromide and tetrabenazine, etc.

The LH-RH derivative includes an LH-RH derivative or salt thereof which is effective against hormone-dependent diseases, especially sex hormone-dependent diseases such as sex hormone-dependent cancers (e.g., prostate cancer, uterine cancer, breast cancer, hypophyseal tumor, hepatic cancer, etc.), prostatic hypertrophy, endometriosis, uterine myoma, precocious puberty, dysmenorrhea, amenorrhea, premenstrual syndrome, multilocular ovary syndrome, etc., and contraception (or infertility when rebound effect after drug withdrawal is applied). Further it includes an LH-RH derivative or salt thereof which is effective against benign tumor or malignant tumor which is sex hormone-independent and LH-RH sensitive.

Specific examples of the LH-RH derivatives or salt thereof include peptides described in "Treatment with GnRH analogs: Controversies and perspectives" issued in 1996 by The Parthenon Publishing Group Ltd., PCT Japanese Translation Patent Publication No. 91-503165, JP-A 91-101695, JP-A 95-97334 and JP-A 96-259460, etc.

The LH-RH derivative includes LH-RH agonists and LH-RH antagonists. The LH-RH antagonist includes, for example, a physiologically active peptide represented by the formula:

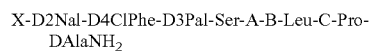
X-D2Nal-D4ClPhe-D3Pal-Ser-A-B-Leu-C-Pro-DAlaNH$_2$

[wherein X is N(4H$_2$-furoyl)Gly or NAc, A is a residue selected from NMeTyr, Tyr, Aph(Atz) and NMeAph(Atz), B is a residue selected from DLys(Nic), DCit, DLys(AzaglyNic), DLys(AzaglyFur), DhArg(Et$_2$), DAph(Atz) and DhCi, and C is Lys(Nisp), Arg or hArg(Et₂)] or a salt thereof, etc., especially preferably, abarelix, ganirelix, cetrorelix, 5-(N-benzyl-N-methylaminomethyl)-1-(2,6-difluorobenzyl)-6-[4-(3-methoxyureido)phenyl]-3-phenylthieno[2,3-d]pyrimidin-2,4(1H,3H)-dione, 5-(N-benzyl-N-methylaminomethyl)-1-(2,6-difluorobenzyl)-6-[4-(3-ethylureido)phenyl]-3-phenylthieno[2,3-d]pyrimidin-2,4(1H,3H)-dione, 5-(N-benzyl-N-methylaminomethyl)-1-(2,6-difluorobenzyl)-6-[4-(3-ethylureido)phenyl]-3-phenylthieno[2,3-d]pyrimidin-2,4(1H,3H)-dione hydrochloride, etc.

The LH-RH agonist includes, for example, a physiologically active peptide represented by the formula:

5-oxo-Pro-His-Trp-Ser-Tyr-Y-Leu-Arg-Pro-Z

[wherein Y is a residue selected from DLeu, DAla, DTrp, DSer(tBu), D2Nal and DHis(ImBzl) and Z is NH—C₂H₅ or Gly-NH₂] or a salt thereof, etc, especially, for example, goserelin acetate, buserelin, etc., suitably, a peptide wherein Y is DLeu, and Z is NH—C₂H₅ (that is, Peptide A represented by 5-oxo-Pro-His-Trp-Ser-Tyr-DLeu-Leu-Arg-Pro-NH—C₂H₅; leuprorelin) or a salt thereof (e.g., acetate).

The abbreviations for an amino acid, a peptide, a protecting group etc. in polypeptides described herein are based on abbreviations according to IUPAC-IUB Commission on Biochemical Nomenclature or conventional abbreviations in the art. In addition, when the amino acids have optical isomers, they represent L-form unless otherwise indicated.

Examples of abbreviations are shown below:
Abu: Aminobutyric acid
Aibu: 2-Aminobutyric acid
Ala: Alanine
Arg: Arginine
Gly: Glycine
His: Histidine
Ile: Isoleucine
Leu: Leucine
Met: Methionine
Nle: Norleucine
Nval: Norvaline
Phe: Phenylalanine
Phg: Phenylglycine
Pro: Proline
(Pyr)Glu: Pyroglutamic acid
Ser: Serine
Thr: Threonine
Trp: Tryptophan
Tyr: Tyrosine
Val: Valine
D2Nal: D-3-(2-naphthyl)alanine residue
DSer(tBu): O-tert-butyl-D-serine
DHis (ImBzl): N-benzyl-D-histidine
PAM: Phenylacetamidomethyl
Boc: t-Butyloxycarbonyl
Fmoc: 9-fluorenylmethyloxycarbonyl
Cl-Z: 2-Chloro-benzyloxycarbonyl
Br-Z: 2-Bromo-benzyloxycarbonyl
Bzl: Benzyl
Cl₂-Bzl: 2,6-Dichlorobenzyl
Tos: p-Toluenesulfonyl
HONb: N-hydroxy-5-norbornene-2,3-dicarboxyimide
HOBt: 1-Hydroxybenzotriazole
HOOBt: 3-Hydroxy-3,4-dihydro-4-oxo-1,2,3-benzotriazine
MeBzl: 4-Methylbenzyl
Bom: Benzyloxymethyl
Bum: t-Butoxymethyl
Trt: Trityl
DNP: Dinitrophenyl
DCC: N,N'-dicyclohexylcarbodiimide Among the above-mentioned these especially, the combination drug is preferably a LH-RH agonist (e.g., goserelin acetate, buserelin, leuprorelin, etc.), etc.

In combinations of the compound of the present invention and the combination drug, the administration time of the compound of the present invention and the combination drug is not restricted, and the compound of the present invention or the combination drug can be administered to the administration subject simultaneously, or may be administered at different times. The dosage of the combination drug may be determined according to the administration amount clinically used, and can be appropriately selected depending on the administration subject, administration route, disease, combination etc.

The administration mode of the compound of the present invention and the combination drug is not particularly limited, and it is sufficient that the compound of the present invention and the combination drug are combined in administration. Examples of such administration mode include the following methods: (1) The compound of the present invention and the combination drug are simultaneously produced to give a single preparation which is administered. (2) The compound of the present invention and the combination drug are separately produced to give two kinds of preparations which are administered simultaneously by the same administration route. (3) The compound of the present invention and the combination drug are separately produced to give two kinds of preparations which are administered by the same administration route only at the different times. (4) The compound of the present invention and the combination drug are separately produced to give two kinds of preparations which are administered simultaneously by different administration routes. (5) The compound of the present invention and the combination drug are separately produced to give two kinds of preparations which are administered by different administration routes at different times (for example, the compound of the present invention and the combination drug are administered in this order, or in the reverse order). Hereafter, these administration modes are referred to as the combination preparation of the present invention.

The combination preparation of the present invention has low toxicity, and for example, the compound of the present invention or (and) the above-mentioned combination drug can be mixed, according to a per se known method, with a pharmaceutically acceptable carrier to give pharmaceutical compositions, for example, tablets (including a sugar-coated tablet, film-coated tablet), powders, granules, capsules (including a soft capsule), solutions, injections, suppositories, sustained release agents etc. which can be safely administered orally or parenterally (e.g., local, rectum, vein, etc.). The injection can be administered by intravenous, intramuscular, subcutaneous, intra-tissue, intranasal, intradermal, instillation, intracerebral, intrarectal, intravaginal, intraperitoneal, intratumoral, juxtaposition of tumor and administration directly to the lesion.

The pharmaceutically acceptable carrier which may be used in production of the combination preparation includes those used for the above mentioned pharmaceutical composition of the present invention.

The compounding ratio of the compound of the present invention to the combination drug in the combination preparation of the present invention can be appropriately selected depending on the administration subject, administration route, diseases etc.

For example, the content of the compound of the present invention in the combination preparation differs depending on the form of preparation, and is usually from about 0.01% by weight to 100% by weight, preferably from about 0.1% by weight to 50% by weight, more preferably from about 0.5% by weight to 20% by weight, to the total of the preparation.

The content of the combination drug in the combination preparation of the present invention differs depending on the form of preparation, and is usually from about 0.01% by weight to 100% by weight, preferably from about 0.1% by weight to 50% by weight, more preferably from about 0.5% by weight to 20% by weight, to the total of the preparation.

The content of additives such as a carrier etc. in the combination preparation of the present invention differs depending on the form of preparation, and is usually from about 1% by weight to 99.99% by weight, preferably from about 10% by weight to 90% by weight, to the total of the preparation.

When the compound of the present invention and the combination drug are formulated separately, the same contents may be adopted.

These preparations can be manufactured by a per se known method commonly used in the pharmaceutical manufacturing process.

For example, the compound of the present invention and the combination drug can be made as an injection such as an aqueous injection together with a dispersing agent (e.g., Tween 80 (manufactured by Atlas Powder, US), HCO 60 (manufactured by Nikko Chemicals Co., Ltd.), polyethylene glycol, carboxymethyl cellulose, sodium alginate, hydroxypropylmethyl cellulose, dextrin etc.), a stabilizer (e.g., ascorbic acid, sodium pyrosulfite, etc.), a surfactant (e.g., Polysorbate 80, macrogol etc.), a solubilizer (e.g., glycerin, ethanol etc.), a buffer (e.g., phosphoric acid and alkali metal salt thereof, citric acid and alkali metal salt thereof, etc.), an isotonizing agent (e.g., sodium chloride, potassium chloride, mannitol, sorbitol, glucose etc.), a pH regulator (e.g., hydrochloric acid, sodium hydroxide etc.), an antiseptic (e.g., ethyl p-oxybenzoate, benzoic acid, methylparaben, propylparaben, benzyl alcohol etc.), a dissolving agent (e.g., conc. glycerin, meglumine etc.), a dissolution aid (e.g., propylene glycol, sucrose etc.), a soothing agent (e.g., glucose, benzyl alcohol etc.), etc., or an oily injection by dissolving, suspending or emulsifying them in a vegetable oil such as olive oil, sesame oil, cotton seed oil, corn oil etc. or a dissolution aid such as propylene glycol, and molding them.

In the case of a preparation for oral administration, the compound of the present invention and the combination drug can be made as a preparation for oral administration by adding an excipient (e.g., lactose, sucrose, starch etc.), a disintegrating agent (e.g., starch, calcium carbonate etc.), a binder (e.g., starch, arabic gum, carboxymethyl cellulose, polyvinylpyrrolidone, hydroxypropyl cellulose etc.), a lubricant (e.g., talc, magnesium stearate, polyethylene glycol 6000 etc.) etc., to the compound of the present invention or the combination drug, according to a per se known method, and compressing and molding the mixture, then if desired, coating the molded product by a per se known method for the purpose of masking of taste, enteric property or sustained release. The film forming agent includes, for example, hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragit (methacrylic acid/ acrylic acid copolymer, manufactured by Rohm, DE), pigment (e.g., iron oxide red, titanium dioxide, etc.) etc. The preparation for oral administration may be either a rapid release preparation or a sustained release preparation.

For example, in the case of a suppository, the compound of the present invention and the combination drug can be made into an oily or aqueous solid, semisolid or liquid suppository according to a per se known method. The oily substrate used in the above-mentioned composition includes, for example, glycerides of higher fatty acids [e.g., cacao butter, Witepsols (manufactured by Dynamite Nobel, DE), etc.], intermediate grade fatty acids [e.g., Miglyols (manufactured by Dynamite Nobel, DE), etc.], or vegetable oils (e.g., sesame oil, soy bean oil, cotton seed oil etc.), etc. Further, the aqueous base includes, for example, polyethylene glycols and propylene glycol, and the aqueous gel base includes, for example, natural gums, cellulose derivatives, vinyl polymers, acrylic acid polymers, etc.

The above-mentioned sustained release agent includes sustained release microcapsules, etc.

For obtaining a sustained release microcapsule, a per se known method can be adopted. For example, it is preferable to mold into a sustained release preparation shown in [2] below.

A compound of the present invention is preferably molded into an oral administration preparation such as a solid preparation (e.g., powder, granule, tablet, capsule, etc.) etc., or molded into a rectal administration preparation such as a suppository. Particularly, an oral administration preparation is preferable.

The combination drug can be made into the above-mentioned drug form depending on the kind of the drug.

In the following, there will be shown specifically [1] an injection of the compound of the present invention or the combination drug and preparation thereof, [2] a rapid release preparation or sustained release preparation of the compound of the present invention or the combination drug and preparation thereof and [3] a sublingual tablet, a buccal or an intraoral quick integrating agent of the compound of the present invention or the combination drug or preparation thereof.

[1] Injection and Preparation Thereof

It is preferred that an injection is prepared by dissolving the compound of the present invention or the combination drug in water. This injection may be allowed to contain a benzoate and/or a salicylate.

The injection is obtained by dissolving the compound of the present invention or the combination drug, and if desired, a benzoate and/or a salicylate, into water.

The above-mentioned salts of benzoic acid and salicylic acid include, for example, salts of alkali metals such as sodium, potassium etc., salts of alkaline earth metals such as calcium, magnesium etc., ammonium salts, meglumine salts, organic acid salts such as tromethamol, etc.

The concentration of the compound of the present invention or the combination drug in the injection is from 0.5 w/v % to 50 w/v %, preferably from about 3 w/v % to about 20 w/v %. The concentration of a salt of benzoic acid or/and a salt of salicylic acid is from 0.5 w/v % to 50 w/v %, preferably from 3 w/v % to 20 w/v %.

Conventional additives to be used in an injection may be appropriately added in a preparation of the present invention. Examples of the additives include a stabilizer (e.g., ascorbic acid, sodium pyrosulfite, etc.), a surfactant (e.g., Polysorbate 80, macrogol etc.), a solubilizer (e.g., glycerin, ethanol etc.), a buffer (e.g., phosphoric acid and alkali metal salt thereof, citric acid and alkali metal salt thereof, etc.), an isotonizing agent (e.g., sodium chloride, potassium chloride, etc.), a dispersing agent (e.g., hydroxypropylmethyl cellulose, dextrin), a pH regulator (e.g., hydrochloric acid, sodium hydroxide etc.), an antiseptic (e.g., ethyl p-oxybenzoate, benzoic acid etc.), a dissolving agent (e.g., conc. glycerin, meglumine etc.), a dissolution aid (e.g., propylene glycol, sucrose etc.), a soothing agent (e.g., glucose, benzyl alcohol etc.), etc. These additives are blended in a usual proportion generally employed in an injection.

It is advantageous that the pH of the injection is controlled from 2 to 12, preferably from 2.5 to 8.0 by addition of a pH regulator.

An injection is obtained by dissolving the compound of the present invention or the combination drug and if desired, a salt of benzoic acid and/or a salt of salicylic acid, and if necessary, the above-mentioned additives into water. These may be dissolved in any order, and can be appropriately dissolved in the same manner as in a conventional method of producing an injection.

An aqueous solution for injection may be advantageously heated, alternatively, for example, filter sterilization, high pressure heat sterilization, etc. can be conducted in the same manner as those for a usual injection, to provide an injection.

It may be advantageous that an aqueous solution for injection is subjected to high pressure heat sterilization at 100° C. to 121° C. for 5 minutes to 30 minutes.

Further, a preparation endowed with the antibacterial property of a solution may also be produced so that it can be used as a preparation which is divided and administered multiple-times.

[2] Sustained Release Preparation or Rapid Release Preparation, and Preparation Thereof Preferred is a sustained release preparation which is obtained, by coating a core containing the compound of the present invention or the combination drug with a film forming agent such as a water-insoluble substance, swellable polymer, etc., if desired. For example, a sustained release preparation for oral once-a-day administration is preferable.

The water insoluble substance used in a film forming agent includes, for example, a cellulose ether such as ethyl cellulose, butyl cellulose, etc.; a cellulose ester such as cellulose acetate, cellulose propionate, etc.; a polyvinyl ester such as polyvinyl acetate, polyvinyl butyrate, etc.; an acrylic acid polymer such as acrylic acid/methacrylic acid copolymer, methylmethacrylate copolymer, ethoxyethyl methacrylate/cinnamoethylmethacrylate/aminoalkyl methacrylate copolymer, polyacrylic acid, polymethacrylic acid, methacrylic acid alkyl amide copolymer, poly(methyl methacrylate), poly-methacrylate, polymethacryl amide, amino alkyl methacrylate copolymer, poly(methacrylic acid anhydride), glycidyl methacrylate copolymer, specially an Eudragit (manufactured by Rohm Pharma) such as Eudragit RS-100, RL-100, RS-30D, RL-30D, RL-PO, RS-PO (copolymer of ethyl acylate/methyl methacrylate/trimethyl chloride methacrylate/ammonium ethyl), Eudragit NE-30D (copolymer of methyl methacrylate/ethyl acrylate), etc., a hydrogenated oil such as hardened caster oil (e.g., Lovely wax (Freund Corporation), etc.), etc.; a wax such as carnauba wax, fatty acid glycerin ester, paraffin, etc.; polyglycerin fatty acid ester, etc.

The swellable polymer is preferably a polymer having acidic dissociating group and pH-dependent swelling property, and a polymer having acidic dissociating group which swells little in an area such as stomach and swells in a neutral area such as the small intestine or the large intestine.

The polymer having acidic dissociating group and pH-dependent swelling property includes, for example, crosslinkable polyacrylic polymer such as Carbomer 934P, 940, 941, 974P, 980, 1342 etc., polycarbophil, calcium polycarbophil (all are manufactured by BF Goodrich.), Hibiswako 103, 104, 105, 304 (all are manufactured by Wako Pure Chemical Industries, Ltd.), etc.

The film forming agent used in a sustained release preparation may further contain a hydrophilic substance.

The hydrophilic substance includes, for example, a polysaccharide optionally having sulfuric acid group such as pullulans, dextrin, arginic acid alkali metal salt, etc.; a polysaccharide having a hydroxyalkyl group or a carboxyalkyl group such as hydroxypropyl cellulose, hydroxypropyl methyl cellulose, sodium carboxymethyl cellulose, etc.; methyl cellulose; polyvinyl pyrrolidone; polyvinyl alcohol; polyethylene glycol; etc.

The content of water-insoluble substance in the film forming agent of sustained release preparation is about 30% (w/w) to about 90% (w/w), preferably about 35% (w/w) to about 80% (w/w), and more preferably about 40% (w/w) to about 75% (w/w). The content of swellable polymer is about 3% (w/w) to about 30% (w/w), preferably about 3% (w/w) to about 15% (w/w). The film forming agent may further contain a hydrophilic substance, in this case, the content of the hydrophilic substance in the film forming agent is about 50% (w/w) or less, preferably about 5% (w/w) to about 40% (w/w), and more preferably about 5% (w/w) to about 35% (w/w). This % (w/w) indicates % by weight based on a film forming agent composition which is obtained by removing a solvent (e.g., water, lower alcohols such as methanol, ethanol etc.) from a film forming agent liquid.

The sustained release preparation is manufactured by preparing a core containing drug as exemplified below, then, coating the resultant core with a film forming agent liquid prepared by heating and dissolving a water-insoluble substance, swellable polymer, etc. or by dissolving or dispersing it in a solvent.

I. Preparation of Core Containing a Drug

The form of a core containing a drug to be coated with a film forming agent (hereinafter, sometimes simply referred to as the core) is not particularly limited, and preferably, the core is formed into particles such as granules or fine particles.

When the core is composed of granules or fine particles, the average particle size thereof is preferably from about 150 to about 2,000 μm, further preferably, from about 500 μm to about 1,400 μm.

Preparation of the core can be conducted by a usual preparation. For example, it can be prepared by mixing a suitable excipient, binding agent, disintegrating agent, lubricant, stabilizer, etc. with a drug, and subjecting the mixture to wet-extrusion granulating method or fluidized bed granulating method, etc.

The content of drugs in a core is from about 0.5% (w/w) to about 95% (w/w), preferably from about 5.0% (w/w) to about 80% (w/w), further preferably from about 30% (w/w) to about 70% (w/w).

The excipient contained in the core includes, for example, saccharides such as sucrose, lactose, mannitol, glucose etc., starch, crystalline cellulose, calcium phosphate, corn starch etc. Among them, crystalline cellulose, corn starch are preferable.

The binders include, for example, polyvinyl alcohol, hydroxypropyl cellulose, polyethylene glycol, polyvinyl pyrrolidone, Pluronic F68, arabic gum, gelatin, starch, etc. The disintegrators include, for example, carboxymethyl cellulose calcium (ECG505), croscarmellose sodium (Ac-Di-Sol), crosslinkable polyvinyl pyrrolidone (crospovidone), low-substituted hydroxypropyl cellulose (L-HPC), etc. Among these, hydroxypropyl cellulose, polyvinyl pyrrolidone and low-substituted hydroxypropyl cellulose are preferable. The lubricants or the aggregation inhibitor includes, for example, talc, magnesium stearate and an inorganic salt thereof. The lubricant includes a polyethylene glycol, etc. The stabilizing agent includes an acid such as tartaric acid, citric acid, succinic acid, fumaric acid, maleic acid, etc.

In addition to the above-mentioned, the core can also be prepared by, for example, a rolling granulation method in which a drug or a mixture of the drug with an excipient, lubricant, etc. is added portionwise onto an inert carrier particle which is the core of the core while spraying a binder dissolved in a suitable solvent such as water, lower alcohol (e.g., methanol, ethanol, etc.) etc., a pan coating method, a fluidized bed coating method or a melt granulating method. The inert carrier particle includes, for example, those made of sucrose, lactose, starch, crystalline cellulose or waxes, and the average particle size thereof is preferably from about 100 µm to about 1,500 µm.

For the purpose of separating the drug contained in the core from the film forming agent, the surface of the core may be coated with a protective agent. The protective agent includes, for example, the above-mentioned hydrophilic substances, water-insoluble substances etc. The protective agent includes, preferably polyethylene glycol, and polysaccharides having a hydroxyalkyl group or carboxyalkyl group, more preferably, hydroxypropylmethyl cellulose and hydroxypropyl cellulose. The protective agent may contain a stabilizer such as acids such as tartaric acid, citric acid, succinic acid, fumaric acid, maleic acid etc., and a lubricant such as talc etc. When the protective agent is used, the coating amount is from about 1% (w/w) to about 15% (w/w), preferably from about 1% (w/w) to about 10% (w/w), further preferably from about 2% (w/w) to about 8% (w/w), based on the core.

The coating of the protective agent can be carried out by a usual coating method, and specifically, the coating can be carried out by spraying the protective agent by a fluidized bed coating method, pan coating method etc.

II. Coating of Core with a Film Forming Agent

A core obtained in the above-mentioned step I is coated with a film forming agent liquid obtained by heating and dissolving the above-mentioned water-insoluble substance and pH-dependent swellable polymer, and a hydrophilic substance, or by dissolving or dispersing them in a solvent, to give a sustained release preparation.

The method for coating a core with a film forming agent liquid includes, for example, a spray coating method etc.

The composition ratio of a water-insoluble substance, swellable polymer and hydrophilic substance in a film forming agent liquid is appropriately selected so that the contents of these components in a coated film are the above-mentioned contents, respectively.

The coating amount of a film forming agent is from about 1% (w/w) to about 90% (w/w), preferably from about 5% (w/w) to about 50% (w/w), further preferably from about 5% (w/w) to 35% (w/w), based on a core (exclusive of the coating amount of the protective agent)

The solvent in the film forming agent liquid includes water or an organic solvent, alone or in admixture thereof. In the case of use in admixture, the mixing ratio of water to an organic solvent (water/organic solvent: weight ratio) can be varied in the range from 1 to 100%, and preferably from % to about 30%. The organic solvent is not particularly limited as long as it dissolves a water-insoluble substance, and for example, it includes lower alcohols such as methyl alcohol, ethyl alcohol, isopropyl alcohol, n-butyl alcohol, etc., lower alkanones such as acetone, etc., acetonitrile, chloroform, methylene chloride, etc. Among them, lower alcohols are preferable, and ethyl alcohol and isopropyl alcohol are particularly preferable. Water, and a mixture of water with an organic solvent are preferably used as a solvent for a film forming agent. In this case, if necessary, an acid such as tartaric acid, citric acid, succinic acid, fumaric acid, maleic acid, etc. may also be added into a film forming agent liquid for stabilizing the film forming agent liquid.

An operation of coating by spray coating can be conducted by a usual coating method, and specifically, it can be conducted by spray-coating a film forming agent liquid onto a core, for example, by a fluidized bed coating method, pan coating method etc. In this case, if necessary, talc, titanium oxide, magnesium stearate, calcium stearate, light anhydrous silicic acid etc. may also be added as a lubricant, and glycerin fatty ester, hydrogenated castor oil, triethyl citrate, cetyl alcohol, stearyl alcohol etc. may also be added as a plasticizer.

After coating with a film forming agent, if necessary, an antistatic agent such as talc etc. may be mixed.

The rapid release preparation may be liquid (solution, suspension, emulsion etc.) or solid (particle, pill, tablet etc.). It may be oral agents or parenteral agents such as an injection, etc., and preferably, oral agents.

The rapid release preparation, usually, may contain, in addition to an active component drug, also carriers, additives and excipients conventionally used in the field of formulation (hereinafter, sometimes abbreviated as the excipient). The preparation excipient used is not particularly limited as long as it is an excipient ordinarily used as a preparation excipient. For example, the excipient for an oral solid preparation includes lactose, starch, corn starch, crystalline cellulose (Avicel PH101, manufactured by Asahi Kasei Corporation, etc.), powder sugar, granulated sugar, mannitol, light anhydrous silicic acid, magnesium carbonate, calcium carbonate, L-cysteine, etc., and preferably, corn starch and mannitol, etc. These excipients can be used alone or in combination of two or more. The content of the excipient is, for example, from about 4.5 w/w % to about 99.4 w/w %, preferably from about 20 w/w % to about 98.5 w/w %, further preferably from about 30 w/w % to about 97 w/w %, based on the total amount of the rapid release preparation.

The content of a drug in the rapid release preparation can be appropriately selected in the range from about 0.5% to about 95%, preferably from about 1% to about 60% based on the total amount of the rapid release preparation.

When the rapid release preparation is an oral solid preparation, it usually contains a disintegrating agent in addition to the above-mentioned components. The disintegrating agent includes, for example, carboxymethyl cellulose calcium (ECG-505, manufactured by GOTOKU CHEMICAL COMPANY LTD.), croscarmellose sodium (for example, acjizol, manufactured by Asahi Kasei Corporation), crospovidone (for example, colidone CL, manufactured by BASF), low-substituted hydroxypropyl cellulose (manufactured by Shin-Etsu Chemical Co., Ltd.), carboxymethylstarch (manufactured by Matsutani Chemical Industry Co., Ltd.), carboxymethylstarch sodium (Exprotab, manufactured by Kimura Sangyo), partially α-starch (PCS, manufactured by Asahi Kasei Corporation), etc., and for example, includes those which disintegrate a granule by absorbing water in contact with water, causing swelling, or making a channel between an effective ingredient constituting the core and an excipient. These disintegrating agents can be used alone or in combinations of two or more. The amount of the disintegrating agent used is appropriately selected depending on the kind and blending amount of a drug used, formulation design for release property, etc., and for example, from about 0.05 w/w % to about 30 w/w %, preferably from about 0.5 w/w % to about 15 w/w %, based on the total amount of the rapid release preparation.

When the rapid release preparation is an oral solid preparation, it may further contain if desired, additives conventional in solid preparations in addition to the above-mentioned composition. Such an additive includes, for example, a binder (e.g., sucrose, gelatin, arabic gum powder, methyl cellulose, hydroxypropyl cellulose, hydroxypropylmethyl cellulose, carboxylmethyl cellulose, polyvinylpyrrolidone, pullulans, dextrin, etc.), a lubricant (e.g., polyethylene glycol, magnesium stearate, talc, light anhydrous silicic acid (for example, aerosil (Nippon Aerosil)), a surfactant (e.g., anionic surfactants such as sodium alkylsulfate, etc., nonionic surfactants such as polyoxyethylene fatty acid ester and polyoxyethylene sorbitan fatty acid ester, polyoxyethylene castor oil derivatives, etc.), a coloring agent (e.g., tar coloring matter, caramel, iron oxide red, titanium oxide, riboflavins), if necessary, a corrigent (e.g., sweetening agent, flavor, etc.), an adsorbent, an antiseptic, a wetting agent, an antistatic agent, etc. Further, a stabilizer such as an organic acid such as tartaric acid, citric acid, succinic acid, fumaric acid, etc. may also be added.

The above-mentioned binder includes preferably hydroxypropyl cellulose, polyethylene glycol and polyvinylpyrrolidone, etc.

The rapid release preparation can be prepared by mixing the above-mentioned components, and if necessary, further kneading the mixture, and molding it based on a usual technology of producing preparations. The above-mentioned mixing is conducted by generally used methods, for example, mixing, kneading, etc. Specifically, when a rapid release preparation is formed, for example, into a particle, it can be prepared, according to the same means as in the above-mentioned method for preparing a core of a sustained release preparation, by mixing the components using a vertical granulator, universal kneader (manufactured by Hata Iron Works Co., Ltd.), fluidized bed granulator FD-5S (manufactured by Powrex Corporation), etc., then, subjecting the mixture to a wet extrusion granulation method, fluidized bed granulation method, etc.

Thus obtained quick releasing preparation and sustained releasing preparation may be themselves made into products or made into products appropriately together with preparation excipients etc., separately, by an ordinary method, then, may be administered simultaneously or may be administered in combination at any administration interval, or they may be themselves made into one oral preparation (e.g., granule, fine particle, tablet, capsule etc.) or made into one oral preparation together with preparation excipients etc. It may also be permissible that they are made into granules or fine particles, and filled in the same capsule to be used as a preparation for oral administration.

[3] Sublingual, Buccal or Intraoral Quick Disintegrating Agent and Preparation Thereof Sublingual, buccal or intraoral quick disintegrating agents may be a solid preparation such as tablet etc., or may be an oral mucosa membrane patch (film).

The sublingual, buccal or intraoral quick disintegrating agent is preferably a preparation containing the compound of the present invention or the combination drug and an excipient. It may contain also auxiliary agents such as a lubricant, isotonizing agent, hydrophilic carrier, water-dispersible polymer, stabilizer etc. Further, for easy absorption and increased bioavailability, β-cyclodextrin or β-cyclodextrin derivatives (e.g., hydroxypropyl-β-cyclodextrin etc.), etc. may also be contained.

The above-mentioned excipient includes lactose, sucrose, D-mannitol, starch, crystalline cellulose, light anhydrous silicic acid, etc. The lubricant includes magnesium stearate, calcium stearate, talc, colloidal silica, etc., and particularly preferably, magnesium stearate and colloidal silica. The isotonizing agent includes sodium chloride, glucose, fructose, annitol, sorbitol, lactose, saccharose, glycerin, urea, etc., and particularly preferably, mannitol. The hydrophilic carrier includes swellable hydrophilic carriers such as crystalline cellulose, ethyl cellulose, crosslinkable polyvinylpyrrolidone, light anhydrous silicic acid, silicic acid, dicalcium phosphate, calcium carbonate etc., and particularly preferably, crystalline cellulose (e.g., fine crystalline cellulose, etc.). The water-dispersible polymer includes gums (e.g., gum tragacanth, acacia gum, cyamoposis gum), alginates (e.g., sodium alginate), cellulose derivatives (e.g., methyl cellulose, carboxymethyl cellulose, hydroxymethyl cellulose, hydroxypropyl cellulose, hydroxypropylmethyl cellulose), gelatin, water-soluble starch, polyacrylic acids (e.g., Carbomer), polymethacrylic acid, polyvinyl alcohol, polyethylene glycol, polyvinylpyrrolidone, polycarbophil, ascorbate, palmitates, etc., and preferably, hydroxypropylmethyl cellulose, polyacrylic acid, alginate, gelatin, carboxymethyl cellulose, polyvinylpyrrolidone, polyethylene glycol, etc., particularly preferably, hydroxypropylmethyl cellulose. The stabilizer includes cysteine, thiosorbitol, tartaric acid, citric acid, sodium carbonate, ascorbic acid, glycine, sodium sulfite, etc., and particularly preferably, citric acid and ascorbic acid.

The sublingual, buccal or intraoral quick disintegrating agent can be manufactured by mixing the compound of the present invention or the combination drug and an excipient by a per se known method. Further, if desired, auxiliary agents such as a lubricant, isotonizing agent, hydrophilic carrier, water-dispersible polymer, stabilizer, coloring agent, sweetening agent, antiseptic etc. may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol etc. if desired before and after the tablet making process, and after the molding, the materials are dried, to obtain a product.

In the case of molding into a mucosa membrane patch (film), the compound of the present invention or the combination drug and the above-mentioned water-dispersible polymer (preferably, hydroxypropyl cellulose, hydroxypropylmethyl cellulose), excipient etc. are dissolved in a solvent such as water etc., and the resulted solution is cast to give a film. Further, additives such as a plasticizer, a stabilizer, an antioxidant, an antiseptic, a coloring agent, a buffer, a sweetening agent etc. may also be added. For imparting suitable elasticity to the film, glycols such as polyethylene glycol, propylene glycol, etc. may be contained, or for enhancing adhesion of the film to an intraoral mucosa membrane lining, a bio-adhesive polymer (e.g., polycarbophil, carbopol) may also be contained. In the casting, a solution is poured on the non-adhesive surface, spread to uniform thickness (preferably, about 10 micron to about 1,000 micron) by an application tool such as a doctor blade etc., then, the solution is dried to form a film. It may be advantageous that thus formed film is dried at room temperature or under heat, and cut into given area.

The intraoral quick disintegrating preparation is preferably solid quick diffuse preparation composed of a network body comprising the compound of the present invention or the combination drug, and a water-soluble or water-diffusible carrier which is inert to the compound of the present invention or the combination drug. This network body is obtained by sublimating a solvent from the solid composition constituted of a solution prepared by dissolving the compound of the present invention or the combination drug in a suitable solvent.

The composition of an intraoral quick disintegrating agent preferably contains a matrix forming agent and a secondary component in addition to the compound of the present invention or the combination drug.

The matrix forming agent includes animal proteins or vegetable proteins such as gelatins, dextrins, soybean, wheat and psyllium seed protein etc.; rubber substances such as arabic gum, guar gum, agar, xanthane gum, etc.; polysaccharides; alginic acids; carboxymethyl celluloses; carrageenans; dextrans; pectins; synthetic polymers such as polyvinylpyrrolidone, etc.; substances derived from a gelatin-arabic gum complex, etc. Further, it includes saccharides such as mannitol, dextrose, lactose, galactose, trehalose, etc.; cyclic saccharides such as cyclodextrin etc.; inorganic salts such as sodium phosphate, sodium chloride and aluminum silicate, etc.; amino acids having 2 to 12 carbon atoms such as glycine, L-alanine, L-aspartic acid, L-glutamic acid, L-hydroxyproline, L-isoleucine, L-leucine, L-phenylalanine, etc.

One or more of the matrix forming agent(s) can be introduced in a solution or suspension before solidification. Such matrix forming agent may be present in addition to a surfactant, or may be present with the surfactant excluded. The matrix forming agents may help to keep the compound of the present invention or the combination drug diffused in the solution or suspension, in addition to formation of the matrix.

The composition may contain secondary components such as a preservative, an antioxidant, a surfactant, a thickening agent, a coloring agent, a pH controlling agent, a flavoring agent, a sweetening agent, a food taste masking agent, etc. The coloring agent includes red, black and yellow iron oxides, and FD & C dyes such as FD & C Blue 2, FD & C Red 40, etc. manufactured by Elis and Eberald. Examples of the suitable flavoring agent include mint, raspberry, licorice, orange, lemon, grape fruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatine, etc. Examples of the suitable food taste masking agent include sodium bicarbonate, ion exchange resin, cyclodextrin-inclusion compounds, adsorbent substances and microcapsulated apomorphine.

The preparation contains the compound of the present invention or the combination drug in an amount usually from about 0.1% by weight to about 50% by weight, preferably from about 0.1% by weight to about 30% by weight, and is preferably a preparation (such as the above-mentioned sublingual agent, buccal etc.) which can dissolve 90% or more the compound of the present invention or the combination drug (into water) within the time range of about 1 minute to about 60 minutes, preferably of about 1 minute to 15 minutes, more preferably of about 2 minutes to about 5 minutes, and intraoral quick disintegrating preparations which are disintegrated within the range of 1 second to 60 seconds, preferably of 1 to 30 seconds, further preferably of 1 to 10 seconds after being placed in the oral cavity.

The content of the above-mentioned excipient in the whole preparation is from about 10% by weight to about 99% by weight, preferably from about 30% by weight to about 90% by weight. The content of β-cyclodextrin or β-cyclodextrin derivative in the whole preparation is from 0 to about 30% by weight. The content of the lubricant in the whole preparation is from about 0.01% by weight to about 10% by weight, preferably from about 1% by weight to about 5% by weight.

The content of the isotonizing agent in the whole preparation is from about 0.1% by weight to about 90% by weight, preferably, from about 10% by weight to about 70% by weight. The content of the hydrophilic carrier agent in the whole preparation is from about 0.1% by weight to about 50% by weight, preferably, from about 10% by weight to about 30% by weight. The content of the water-dispersible polymer in the whole preparation is from about 0.1 to about 30% by weight, preferably, from about 10% by weight to about 25% by weight. The content of the stabilizer in the whole preparation is from about 0.1% by weight to about 10% by weight, preferably, from about 1% by weight to about 5% by weight. The above-mentioned preparation may further contain additives such as a coloring agent, a sweetening agent, an antiseptic, etc., if necessary.

The dose of a combination preparation of the present invention differs depending on the kind of the compound (I) of the present invention, age, body weight, condition, drug form, administration method, administration period etc., and for example, for a prostate cancer patient (adult, body weight: about 60 kg), the combination preparation is administered intravenously, at a dose of about 0.01 to about 1,000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the combination drug, respectively, once or several times a day in divided portions. Of course, since the dose as described above varies depending on various conditions, it may be sometimes sufficient to administer smaller amounts than the above-mentioned dosage, and further, it may be sometimes necessary to administer greater amounts than that.

The amount of the combination drug can be set at any value unless side effects are problematical. The daily dosage in terms of the combination drug differs depending on the severity of symptoms, age, sex, body weight, sensitivity difference of the subject, administration time and interval, property, prescription, and kind of the pharmaceutical preparation, kind of effective ingredient, etc., and not particularly limited; for example, in the case of oral administration, the dose of the drug is usually from about 0.001 mg to 2,000 mg, preferably from about 0.01 mg to 500 mg, further preferably from about 0.1 mg to 100 mg, per 1 kg body weight of a mammal, which is usually administered once to four times a day in divided portions.

In administration of the combination preparation, the compound of the present invention may be administered after administration of the combination drug or the combination drug may be administered after administration of the compound of the present invention, though they may be administered simultaneously. When administered at a time interval, the interval differs depending on the effective ingredient, drug form and administration method. For example, when the combination-drug is administered first, the compound of the present invention is administered within time range of from 1 minute to 3 days, preferably from 10 minutes to 1 day, more preferably from 15 minutes to 1 hour after administration of the combined drug. When the compound of the present invention is administered first, the combined drug is administered within time range of from 1 minute to 1 day, preferably from 10 minutes to 6 hours, more preferably from 15 minutes to 1 hour after administration of the compound of the present invention.

In a preferable administration method, for example, the combination drug formulated into an oral administration preparation is administered orally at a daily dose of about 0.001 mg/kg to 200 mg/kg, and 15 minutes later, the compound of the present invention formulated into an oral administration preparation is administered orally at a daily dose of about 0.005 mg/kg to 100 mg/kg.

In addition, the pharmaceutical composition of the present invention or the combination preparation of the present invention can be combined with a non-drug therapy such as (1) surgery, (2) hypertensive chemotherapy using angiotensin II etc., (3) gene therapy, (4) thermotherapy, (5) cryotherapy, (6) laser cauterization, (7) radiotherapy, etc.

For example, the pharmaceutical composition of the present invention or the combination preparation of the present invention exhibits effects of inhibiting an expression of resistance, extending disease-free survival, suppressing cancer metastasis or recurrence, prolonging survival, etc. when used before or after surgery, etc., or a combination treatment comprising 2 or 3 of these therapies.

Also, treatment with the pharmaceutical composition of the present invention or the combination preparation of the present invention can be combined with supportive therapies [e.g., (i) administration of antibiotics (e.g., β-lactams such as pansporin, etc., macrolides such as clarithromycin, etc.) to a combined expression of various infectious diseases, (ii) administration of intravenous hyperalimentations, amino acid preparations and general vitamin preparations for improvement of malnutrition, (iii) morphine administration for pain mitigation, (iv) administration of drugs which mitigate adverse reactions such as nausea, vomiting, anorexia, diarrhea, leukopenia, thrombocytopenia, hemoglobin concentration reduction, hair loss, hepatopathy, renopathy, DIC, fever, etc., (v) administration of drugs for inhibition of multiple drug resistance in cancer, etc.].

As a drug for such purpose, for example, the "antiemetic agents" includes specifically 5-HT3 antagonist such as ondansetron, tropisetron hydrochloride, azasetron, ramosetron, granisetron, dorasetronmesilate and palonosetron; NK1 receptor antagonist such as sendide, CP-99994, CP-100263, CP-122721-1, CP-96345, FK224, RPR100893, NKP608 and aprepitant (EMEND (trademark)); a gastrointestinal tract motility promoter such as $5-HT_4$ antagonist such as domperidone, mosapride and metoclopramide; a gastrointestinal tract motility regulator such as trimebutine; phenothiazine drugs such as prochlorperazine maleate, promethazine and thiethylperazine; anxiolytics such as haloperidole, phenol phthalate chlorpromazine, diazepam and droperidole; steroids such as dexamethasone, prednisolone, betamethasone, triamcinolone, etc.; other drugs such as dimethylhydric acid, diphenhydramine, hyoscin, hyoscin bromide, tetrabenazine, etc.

Preferably, the pharmaceutical composition of the present invention or the combination preparation of the present invention is administered orally (including sustained-release preparations), intravenously (including boluses, infusions and clathrates), subcutaneously and intramuscularly (including boluses, infusions and sustained-release preparations), transdermally, intratumorally or proximally before or after conducting the above-described treatment.

As a period for administering the pharmaceutical composition of the present invention or the combination preparation of the present invention before surgery, etc., for example, it can be administrated once about 30 minutes to 24 hours before surgery, etc., or in 1 to 3 cycles about 3 months to 6 months before surgery, etc. In this way, surgery, etc. can be conducted easily because, for example, cancer tissue would be reduced by administering the pharmaceutical composition of the present invention or the combination preparation of the present invention before surgery, etc.

For administering time of the pharmaceutical composition of the present invention or the combination preparation of the present invention after surgery, etc., for example, it can be administrated repeatedly in a unit of a few weeks to 3 months, about 30 minutes to 24 hours after surgery, etc. In this way, it increases the effect of the surgery, etc. by administering the pharmaceutical composition of the present invention or the combination preparation of the present invention after the surgery, etc.

The present inventors have found unexpectedly that an androgen receptor agonist suppresses growth of a hormone-resistant cancer, and further that an androgen receptor agonist having non-steroidal backbone such as the compound of the present invention is useful for preventing and/or treating the hormone-resistant cancer.

Further object of the present invention is to provide a method for preventing and/or treating hormone-resistant cancer comprising administering an androgen receptor agonist, and an agent for preventing and/or treating hormone-resistant cancer comprising an androgen receptor agonist.

The androgen receptor agonist includes a steroidal androgen receptor agonist and a non-steroidal androgen receptor agonist.

The steroidal androgen receptor agonist includes endogenous androgens such as dehydroepiandrosterone, testosterone, dihydrotestosterone (DHT) and androstendione, synthetic androgens (anabolic steroid) such as mestanolone, oxymesterone, ethandrostenolone, fluoxymesterone, chlorotestosterone acetate, ethenolone acetate, oxymetholone, stanozolol, furazabol, oxandrolone, 19-nortestosterone, norethandrolone and ethylestrenol, norbolethone, etc.

The non-steroidal androgen receptor agonist includes LGD-2226, etc. in addition to the compound of the present invention (I).

The androgen receptor agonist includes the above-mentioned compounds, alone or in combination of two or more, especially preferably, a non-steroidal androgen receptor agonist.

The cancer includes prostate cancer, etc.

The hormone-resistant cancer includes, for example, LHRH derivative-resistant cancer, etc., preferably, LHRH derivative-resistant prostate cancer, more preferably, LHRH agonist-resistant cancer, further preferably, LHRH agonist-resistant prostate cancer.

Herein, the LHRH derivative and the LHRH agonist are as the compounds defined above.

The method of preventing and/or treating hormone-resistant cancer comprising administering an androgen receptor agonist includes, (a) administering an effective amount of an androgen receptor agonist (especially a non-steroidal androgen receptor agonist) or a salt thereof, etc. to a mammal having hormone-resistant prostate cancer cells, (b) administering an effective amount of a LHRH derivative or a salt thereof, etc. to a mammal having prostate cancer cells, and after prostate cancer cells become hormone-resistant, administering an effective amount of an androgen receptor agonist (especially a non-steroidal androgen receptor agonist) or a salt thereof, (c) administering a combination of an effective amount of a LHRH derivative or a salt thereof and an effective amount of an androgen receptor agonist (especially a non-steroidal androgen receptor agonist) or a salt thereof to a mammal having prostate cancer cells, (d) administering a combination of an effective amount of a LHRH derivative or a salt thereof and an effective amount of an androgen receptor agonist (especially a non-steroidal androgen receptor agonist) or a salt thereof to a mammal having prostate cancer cells to reduce prostate cancer, followed by conducting surgical operation or radiotherapy, (e) 1) administering an androgen receptor agonist (especially a non-steroidal androgen receptor agonist) or a salt thereof for a prescribed period to hormone-resistant prostate cancer cells, 2) then if the cancer cells become hormone-dependent, administering an effective amount of one or more compounds selected from a LHRH derivative, a lyase inhibitor, an aromatase inhibitor and an antiandrogen or a salt thereof, or if the cancer cell become hormone-resistant, administering an effective amount of an androgen receptor agonist (especially a non-steroidal androgen receptor agonist) or a salt thereof, and 3) if necessary, repeating the process of 2) until the object of the cancer treatment is achieved, (f) administering alternatively an effective amount of 1) an androgen receptor agonist (especially a non-steroidal androgen receptor agonist) or a salt thereof and 2) one or more compounds selected from a LHRH derivative, a lyase inhibitor, an aromatase inhibitor and an antiandrogen or a salt thereof (e.g., during the period of 3 months to 5 years), etc.

By administering an effective amount of a LHRH derivative, a lyase inhibitor, an aromatase inhibitor or antiandrogens or a salt thereof for the prescribed period (e.g., 3 months to 5 years), hormone-resistance of prostate cancer cells may be increased. Then, by administering an effective amount of an androgen receptor agonist (especially a non-steroidal androgen receptor agonist) or a salt thereof, growth of prostate cancer cells may be suppressed or the cancer may be reduced. By continuing administration of an androgen receptor agonist (especially a non-steroidal androgen receptor agonist), hormone-resistance of the prostate cancer cells may return again to the level of normal cells. Alternatively, if the prostate cancer growth is initiated (tumor accumulation, etc. is increased), it is converted to administration of one or more compounds selected from a LHRH derivative, a lyase inhibitor, an aromatase inhibitor and an antiandrogen or a salt thereof. Then, depending on level of the hormone-resistance of the cancer, it is converted selectively to (i) administration of one or two compounds selected from a LHRH derivative, a lyase inhibitor, an aromatase inhibitor and an antiandrogen or a salt thereof (when the hormone-resistance of the cancer is in the same level as normal cells [for example, LNCaP 104-Scell (Cancer Res, 54, p 1566-1573), LNCaP-FGC cell, etc.]), or (ii) administration of an androgen receptor agonist (especially a non-steroidal androgen receptor agonist) or a salt thereof (when the hormone-resistance of the cancer is elevated than normal cells [for example, LNCaP 104-R$^2$cell (Cancer Res, 54, p 1566-1573), LNCaP-hr cell, etc.]), which allows to carry out optimal therapy for the prostate cancer.

The conversion timing for such administrations may be suitably set for every therapy, but for example, it is in the range of 3 months to 5 years, preferably, 6 months to 4 years, more preferably, 1 year to 3 years, further preferably, 1 year to 2 years.

Therefore, if MAB (Maximum androgen blockade) therapy, etc. is conducted by administering a LHRH derivative (e.g., LHRH agonist, etc.), a lyase inhibitor, an aromatase inhibitor or antiandrogens, etc. for the prescribed period, the chance increases that the prostate cancer become more hormone-resistant, and then the therapy by combination of an androgen receptor agonist (especially a non-steroidal androgen receptor agonist) or a salt thereof of the present invention may exert the effects. In this case, an androgen receptor agonist (especially a non-steroidal androgen receptor agonist) may be administered with continuing the administration of the LHRH derivative, or it may be converted to administration of the androgen receptor agonist (especially the non-steroidal androgen receptor agonist) with discontinuing administration of the LHRH derivative, both of which are included in the present invention.

Hormone-resistance of cancer can be measured by a method of examining reactivity of cancer cells to an androgen, or can be estimated by a tumor marker or a physiological index under administration of a prescribed drug, or increase or decrease of tumor accumulation.

EXAMPLES

The present invention is hereinafter described in detail by means of the following Reference Examples, Examples, Formulation Examples and Experimental Examples, but is not limited thereto.

In the reference examples and examples, elution of column chromatography was conducted under observation by TLC (thin layer chromatography). In TLC observation, the TLC plate used was the Merck Kieselgel 60F$_{254}$ plate, the developing solvent used was the solvent used as the eluent for column chromatography, and the means of detection used was a UV detector. The silica gel for the column chromatography was also Merck Kieselgel 60F$_{254}$ (70 to 230 mesh). NMR spectrum was proton-NMR, and was measured with tetramethylsilane as the internal standard, by using the Varian Gemini-200 (200 MHz type spectrometer), Varian Mercury-300 (300 MHz) or the JMTC0400/54 (400 MHz) type spectrometer manufactured by JEOL; δ values are expressed in ppm.

Infrared spectrum (IR) was measured using Paragon 1000 manufactured by PerkinElmer.

Specific rotation ($[\alpha]_D$) was measured by HIGH SENSITIVE POLARIMETER manufactured by HORIBA or DIP-370 type polarimeter manufactured by Jasco.

The abbreviations used in the reference examples and examples are defined as follows:
s: Singlet
br: Broad
d: Doublet
t: Triplet
q: Quartet
dd: Double doublet
ddd: Double double doublet
dt: Double triplet
m: Multiplet
J: Coupling constant
Hz: Hertz Reference Example 1

To a mixture of copper sulfate (11.4 g) and water (80 ml) was added sodium iodide (13.9 g) at room temperature, and the mixture was stirred at 0° C. for 10 minutes. Sulfuric acid (3.0 ml) and nitric acid (3.0 ml) were added thereto, and after 5 minutes, 4-nitro-1-naphthylamine (5.00 g) was added thereto. After 5 minutes, a mixture of sodium nitrite (2.57 g) and water (5.0 ml) was added thereto at 0° C. for 1 hour. The mixture was extracted with ethyl acetate, and the extracts were washed with sodium thiosulfate solution and brine, dried, and concentrated. The obtained residue was purified by silica gel column chromatography to give 1-iodo-4-nitronaphthalene (1.70 g).

$^1$H-NMR (300 MHz, CDCl$_3$) δ: 7.69-7.80 (2H, m), 7.87 (1H, d, J=8.1 Hz), 8.22 (1H, d, J=8.1 Hz), 8.25-8.28 (1H, m), 8.46-8.49 (1H, m).

Reference Example 2

A mixture of 1-iodo-4-nitronaphthalene (1.70 g), sodium trifluoroacetate (3.07 g), copper iodide (I) (2.10 g) and 1-methyl-2-pyrrolidone (40 ml) was stirred at 160° C. for 5 hours under argon atmosphere. After cooling to room temperature, brine and ethyl acetate were added thereto, and the insolubles were filtered off using celite. The mother liquor was distributed, and the organic layer was washed with brine, dried, and concentrated. The obtained residue was purified by silica gel column chromatography to give 1-nitro-4-(trifluoromethyl)naphthalene (897 mg).

$^1$H-NMR (300 MHz, CDCl$_3$) δ: 7.74-7.83 (2H, m), 7.96 (1H, d, J=7.8 z), 8.09 (1H, d, J=7.8 Hz), 8.28-8.32 (1H, m), 8.39-8.45 (1H, m).

Reference Example 3

A mixture of 1-nitro-4-(trifluoromethyl)naphthalene (813 mg), 10% palladium carbon (50% water content, 717 mg), methanol (16 ml) was stirred at room temperature for 1.5 hours under hydrogen atmosphere. The palladium carbon was filtered off using celite. The mother liquor was concentrated and the obtained residue was purified by silica gel column chromatography to give 4-(trifluoromethyl)-1-naphthylamine (634 mg).

$^1$H-NMR (300 MHz, CDCl$_3$) δ: 4.46 (2H, br.s), 6.71 (1H, d, J=8.1 Hz), 7.49-7.62 (2H, m), 7.66 (1H, d, J=8.1 Hz), 7.82-7.85 (1H, m), 8.12-8.16 (1H, m).

Reference Example 4

To a mixture of 4-amino-1-naphthonitrile (250 mg) and dichloromethane (10 ml) was added bromine (75 μL) at room temperature. After stirring for 2.5 hours, sodium hydrogen carbonate solution was added thereto, and the mixture was extracted with ethyl acetate. The extracts were washed with sodium thiosulfate solution, and brine, dried, and concentrated. The obtained residue was purified by silica gel column chromatography to give 4-amino-3-bromo-1-naphthonitrile (301 mg).

$^1$H-NMR (CDCl$_3$) δ: 5.23 (2H, br.s), 7.59 (1H, ddd, J=8.4, 6.8 and 1.4 Hz), 7.68 (1H, ddd, J=8.4, 6.8 and 1.4 Hz), 7.93 (1H, s), 8.14-8.18 (1H, m).

IR (KBr) 3366, 2215, 1632 cm$^{-1}$

Reference Example 5

To a mixture of (S)-ethyl nipecotate (1.15 g) and tetrahydrofuran (16 ml) was added lithium aluminum hydride (278 mg) at 0° C. The mixture was stirred for 3 hours with elevating the temperature to room temperature. Water (0.28 ml), 25% potassium hydroxide solution (0.28 ml) and water (0.84 ml) were added thereto in this order, and the mixture was stirred for 15 hours. The insolubles were filtered off using celite and the mother liquor was concentrated, to give (S)-3-(hydroxymethyl)piperidine (797 mg).

[α]$_D$=−11.3° (c=0.730, MeOH).

$^1$H-NMR (300 Hz, CDCl$_3$) δ: 1.07-1.20 (1H, m), 1.40-1.54 (1H, m), 1.61-1.82 (3H, m), 2.39 (1H, dd, J=12.0 and 9.9 Hz), 2.54-2.62 (3H, m), 2.95-3.01 (1H, m), 3.13-3.18 (1H, m), 3.40-3.54 (2H, m).

Reference Example 6

To a mixture of (R)-ethyl nipecotate (1.15 g) and tetrahydrofuran (16 ml) was added lithium aluminum hydride (278 mg) at 0° C. The mixture was stirred for 3 hours with elevating the temperature to room temperature. Water (0.28 ml), 25% potassium hydroxide solution (0.28 ml) and brine (0.84 ml) were added thereto in this order, and the mixture was stirred for 15 hours. The insolubles were filtered off using celite and the mother liquor was concentrated, to give (R)-3-(hydroxymethyl)piperidine (852 mg).

[α]$_D$=+11.7° (c=0.730, MeOH).

$^1$H-NMR (300 Hz, CDCl$_3$) δ: 1.07-1.20 (1H, m), 1.40-1.54 (1H, m), 1.61-1.82 (3H, m), 2.39 (1H, dd, J=12.0 and 9.9 Hz), 2.54-2.62 (3H, m), 2.95-3.01 (1H, m), 3.13-3.18 (1H, m), 3.40-3.54 (2H, m).

Reference Example 7

To a mixture of 4-amino-1-nitronaphthalene (5.00 g) and dichloromethane (120 ml) was added a mixture of bromine (4.25 g) and dichloromethane (10 ml) at room temperature. After stirring for 3 hours, sodium sulfite solution was added thereto, and the mixture was extracted with ethyl acetate. The extracts were washed with sodium carbonate solution, and brine, dried, and concentrated. The obtained residue was purified by silica gel column chromatography to give 4-amino-3-bromo-1-nitronaphthalene (1.33 g).

$^1$H-NMR (300 MHz, DMSO-d$_6$) δ: 7.55 (2H, br.s), 7.61 (1H, ddd, J=8.4, 6.9 and 1.5 Hz), 7.79 (1H, ddd, J=8.4, 6.9 and 1.5 Hz), 8.45-8.48 (1H, m), 8.56 (1H, s), 8.78-8.81 (1H, m).

Reference Example 8

To a mixture of sodium nitrite (336 mg) and sulfuric acid (1.7 ml) was added a mixture of 4-amino-3-bromo-1-nitronaphthalene (500 mg) and acetic acid (3.5 ml) at 0° C. After 30 minutes of stirring, diethyl ether was added thereto. The produced precipitate was taken by filtration, and washed with 95% ethanol at 0° C. The obtained solid was added to water at 0° C., and the mixture was immediately added to a mixture of potassium cyanide (792 mg), copper chloride (I) (463 mg) and water (25 ml). After 30 minutes of stirring, and the mixture was extracted with ethyl acetate. The extracts were washed with brine, dried and concentrated, and the obtained residue was purified by silica gel column chromatography to give 2-bromo-4-nitro-1-naphthonitrile (141 mg).

$^1$H-NMR (300 MHz, CDCl$_3$) δ: 7.84-7.92 (2H, m), 8.32 (1H, s), 8.36-8.47 (2H, m).

IR (KBr) 2236, 1532 cm$^{-1}$

Reference Example 9

A mixture of 2-bromo-4-nitro-1-naphthonitrile (141 mg), iron (134 mg), ammonium chloride (12 mg), ethanol (5.0 ml) and water (1.5 ml) was stirred at 90° C. for 30 minutes. The reaction solution was cooled to room temperature, and poured into brine. The mixture was extracted with ethyl acetate, and the extracts were washed with brine, dried, and concentrated. The obtained residue was purified by silica gel column chromatography to give 4-amino-2-bromo-1-naphthonitrile (81 mg).

$^1$H-NMR (300 MHz, CDCl$_3$) δ: 4.79 (2H, br.s), 6.93 (1H, s), 7.56 (1H, ddd, J=8.4, 6.9 and 1.2 Hz), 7.68 (1H, ddd, J=8.4, 6.9 and 1.2 Hz), 7.77 (1H, d, J=8.4 Hz), 8.15 (1H, d, J=8.4 Hz).

IR (KBr) 2215, 1572, 1514 cm$^{-1}$

Reference Example 10

To a mixture of 2-(hydroxymethyl)piperidine (10.0 g), 1 M potassium carbonate solution (250 ml) and tetrahydrofuran (150 ml) was added benzyloxycarbonyl chloride (16.3 g) at 0° C. The temperature was elevated to room temperature, and the mixture was stirred for 24 hours. The mixture was acidified with 2 N hydrochloric acid, and extracted with ethyl acetate. The extracts were washed with brine, dried, and concentrated. The obtained residue was purified by silica gel column chromatography to give benzyl 2-(hydroxymethyl)-1-piperidinecarboxylate (15.2 g).

$^1$H-NMR (300 MHz, CDCl$_3$) δ: 1.40-1.70 (6H, m), 2.91-2.99 (1H, m) 3.63 (1H, dt, J=11.1 and 6.0 Hz), 3.84 (1H, ddd, J=11.1, 9.0 and 6.0 Hz), 4.01-4.05 (1H, m), 4.32-4.39 (2H, m), 5.13 (2H, ABq, J=12.3 Hz), 7.27-7.38 (5H, m).

Reference Example 11

To a mixture of benzyl 2-(hydroxymethyl)-1-piperidinecarboxylate (3.00 g), diisopropylethylamine (6.3 mL) and dichloromethane (30 mL) was added chloromethylmethyl ether (80%, 2.42 g) at 0° C. The temperature was elevated to room temperature, and the mixture was stirred for 14 hours. The reaction solution was washed with water, dried and concentrated. The obtained residue was purified by silica gel column chromatography to obtain benzyl 2-(methoxymethoxymethyl)-1-piperidinecarboxylate (3.43 g).

$^1$H-NMR (300 MHz, CDCl$_3$) δ: 1.41-1.78 (6H, m), 2.83-2.92 (1H, m), 3.31 (3H, s), 3.59 (1H, dd, J=9.9 and 7.2 Hz), 3.67 (1H, dd, J=9.9 and 7.2 Hz), 4.06-4.11 (1H, m), 4.46-4.52 (1H, m), 5.13 (2H, ABq, J=12.3 Hz), 7.27-7.37 (5H, m).

Reference Example 12

A mixture of benzyl 2-(methoxymethoxymethyl)-1-piperidinecarboxylate (3.23 g), 10% palladium-carbon (50% water content, 1.17 g) and methanol (50 mL) was stirred at room temperature for 5 hours under hydrogen atmosphere. The catalyst was filtered off using celite and the mother liquor was concentrated to obtain 2-(methoxymethoxymethyl)piperidine (1.27 g).

$^1$H-NMR (300 MHz, CDCl$_3$) δ: 1.04-1.83 (6H, m), 2.23 (1H, br.s), 2.58-2.81 (2H, m), 3.06-3.12 (1H, m), 3.30-3.39 (1H, m), 3.36 (3H, s), 3.50 (1H, dd, J=9.2 and 5.2 Hz), 4.63 (2H, s).

Reference Example 13

Sodium hydride (60% in oil, 5.28 g) was washed with hexane and suspended in tetrahydrofuran (150 mL). 5-hydroxy-2-nitrobenzaldehyde (14.7 g) was added at room temperature and the mixture was stirred for 20 minutes. Chloromethylmethyl ether (80%, 15.9 g) was added and the mixture was stirred for 1 hour. The reaction solution was poured into water and extracted with diethyl ether. The extracts were washed with a 1 N aqueous sodium hydroxide solution and brine, dried, and concentrated. The obtained residue was purified by silica gel column chromatography to obtain 5-methoxymethoxy-2-nitrobenzaldehyde (16.5 g).

$^1$H-NMR (300 MHz, CDCl$_3$) δ: 3.49 (3H, s), 5.29 (2H, s), 7.29 (1H, dd, J=9.0 and 3.0 Hz), 7.47 (1H, d, J=3.0 Hz), 8.15 (1H, d, J=9.0 Hz), 10.46 (1H, s).

Reference Example 14

To a mixture of 5-methoxymethoxy-2-nitrobenzaldehyde (17.0 g) and methanol (150 mL) was added sodium borohydride (910 mg) at room temperature. After stirring for 20 minutes, the mixture was concentrated and the residue was distributed between ethyl acetate and water. The organic layer was washed with brine, dried, and concentrated. The obtained residue was purified by silica gel column chromatography to obtain 5-methoxymethoxy-2-nitrobenzyl alcohol (15.6 g).

$^1$H-NMR (300 MHz, CDCl$_3$) δ: 2.73 (1H, t, J=6.6 Hz), 3.49 (3H, s), 4.98 (2H, d, J=6.6 Hz), 5.28 (2H, s), 7.05 (1H, dd, J=8.8 and 3.0 Hz), 7.36 (1H, d, J=3.0 Hz), 8.17 (1H, d, J=8.8 Hz).

Reference Example 15

To a mixture of 5-methoxymethoxy-2-nitrobenzyl alcohol (8.65 g), triethylamine (8.48 mL) and tetrahydrofuran (130 mL) was added methanesulfonyl chloride (3.77 mL) at 0° C. After stirring for 30 minutes, the mixture was concentrated. To the obtained residue was added acetone (150 mL) and sodium iodide (21.2 g). After stirring at room temperature for 1 hour, the mixture was concentrated and the residue was distributed between ethyl acetate and water. The organic layer was washed with brine, dried, and concentrated. The obtained residue was processed with silica gel column chromatography to obtain a pale yellow solid matter (10.8 g). To a mixture of diethyl malonate (8.00 g) and dimethylsulfoxide (80 mL) was added sodium hydride (60% in oil, 2.00 g) at room temperature and the mixture was stirred for 20 minutes. The above-described pale yellow solid matter (10.8 g) was added thereto, and the mixture was stirred for 5 minutes. The reactant was poured into water and extracted with ethyl acetate. The extracts were washed with water, dried and concentrated. The obtained residue was purified by silica gel column chromatography to obtain diethyl 2-[5-(methoxymethoxy)-2-nitrobenzyl] malonate (10.4 g).

$^1$H-NMR (300 MHz, CDCl$_3$) δ: 1.22 (6H, t, J=7.2 Hz), 3.47 (3H, s), 3.53 (2H, d, J=7.8 Hz), 3.88 (1H, t, J=7.8 Hz), 4.18 (4H, q, J=7.2 Hz), 5.22 (2H, s), 6.98 (1H, d, J=2.4 Hz), 7.01 (1H, dd, J=9.0 and 2.4 Hz), 8.10 (1H, d, J=9.0 Hz).

Reference Example 16

A mixture of diethyl 2-[5-(methoxymethoxy)-2-nitrobenzyl] malonate (8.68 g), trifluoroacetic acid (30 mL) and dichloromethane (30 mL) was stirred at room temperature for 4 hours. The reaction solution was concentrated, and the obtained residue was processed with silica gel column chromatography to obtain a pale yellow oily matter (7.44 g). Under argon atmosphere, a mixture of the obtained matter (7.28 g), methyl iodide (3.65 g), potassium carbonate (3.88 g) and N,N-dimethylformamide (80 mL) was stirred at room temperature for 1 hour. The reaction solution was poured into water and extracted with ethyl acetate. The extracts were washed with water, dried and concentrated. The obtained residue was purified by silica gel column chromatography to obtain diethyl 2-(5-methoxy-2-nitrobenzyl) malonate (6.30 g).

$^1$H-NMR (300 MHz, CDCl$_3$) δ: 1.22 (6H, t, J=7.2 Hz), 3.53 (2H, d, J=7.8 Hz), 3.86 (3H, s), 3.88 (1H, t, J=7.8 Hz), 4.16 (2H, q, J=7.2 Hz), 4.17 (2H, q, J=7.2 Hz), 6.83-6.87 (2H, m), 8.10-8.13 (1H, m).

Reference Example 17

To a mixture of diethyl 2-(5-methoxy-2-nitrobenzyl) malonate (6.04 g) and hydrochloric acid (80 mL) was stirred at 105° C. for 21 hours. After cooling to room temperature, the mixture was extracted with ethyl acetate. The extracts were washed with brine, dried and concentrated. The obtained residue was purified by silica gel column chromatography to obtain 3-(5-methoxy-2-nitrophenyl) propionic acid (3.30 g).

¹H-NMR (300 MHz, CDCl₃) δ: 2.80 (2H, t, J=7.8 Hz), 3.27 (2H, t, J=7.8 Hz), 3.88 (3H, s), 6.82-6.85 (2H, m), 8.07-8.10 (1H, m).

Reference Example 18

3-(5-Methoxy-2-nitrophenyl) propionic acid (3.23 g) was added to polyphosphoric acid (32 g) at 80° C. and the mixture was stirred for 20 minutes. After cooling to room temperature, the mixture was iced water and extracted with ethyl acetate. Produced insolubles were filtered off using celite, and then the organic layer was washed with brine, dried and concentrated. The obtained residue was purified by silica gel column chromatography to obtain 7-methoxy-4-nitro-1-indanone (1.60 g).
¹H-NMR (300 MHz, CDCl₃) δ: 2.74-2.78 (2H, m), 3.56-3.60 (2H, m), 4.08 (3H, s), 6.96 (1H, d, J=9.0 Hz), 8.47 (1H, d, J=9.0 Hz).

Reference Example 19

A mixture of 7-methoxy-4-nitro-1-indanone (1.60 g) and dichloromethane (50 mL) was cooled to −78° C., and a 1M boron tribromide-dichloromethane solution (10.7 mL) was added thereto for 30 minutes. After stirring for 30 minutes, the temperature was elevated to room temperature, and the mixture was stirred for 1.5 hours. The reaction solution was poured into iced water and insolubles were filtered off using celite. The organic layer was washed with brine, dried and concentrated. The obtained residue was purified by silica gel column chromatography to obtain 7-hydroxy-4-nitro-1-indanone (1.26 g).
¹H-NMR (300 MHz, DMSO-d₆) δ: 2.83-2.87 (2H, m), 3.63-3.67 (2H, m), 6.94 (1H, d, J=9.0 Hz), 8.42 (1H, d, J=9.0 Hz), 10.03 (1H, s).

Reference Example 20

Diisopropylamine (2.83 g) was dissolved in anhydrous ether (40 mL) and a 1.6 M n-butyllithium solution (15 mL) was added dropwise with stirring under cooling to −60° C. 1-Benzyl-5-methylpyrrolidin-2-one (3.78 g) was dissolved in anhydrous ether (15 mL). The resulting solution was kept and added dropwise at −60° C., and then returned to 5° C. and stirred for 2 hours. The cooling bath was removed, dry carbon disulfide was introduced for 30 minutes. To the mixture was added iced water, the aqueous layer was separated. The organic layer was twice extracted with 2 N sodium hydroxide. The aqueous layers were combined, washed with ether, and then made acidic with concentrated hydrochloric acid under cooling. The aqueous layer was twice extracted with ethyl acetate, the extract was washed with water, dried and concentrated to obtain 1-benzyl-5-methyl-2-oxopyrrolidine-3-carboxylic acid (3.45 g) as a pale yellow oily matter.
¹H-NMR (200 MHz, CDCl₃) δ: 1.21(1.5H, d, J=6.6 Hz), 1.27(1.5H, d, J=5.2 Hz), 1.80-2.20(1H, m), 2.39-2.70(1H, m), 3.40-3.76(2H, m), 4.00-4.20(1H, m), 4.98(1H, dd, J=4.0 and 15.0 Hz), 7.10-7.50(5H, m).

Reference Example 21

1-Benzyl-5-methyl-2-oxopyrrolidine-3-carboxylic acid (3.45 g) dissolved in anhydrous tetrahydrofuran (40 mL) was added dropwise to lithium aluminum hydride (1.2 g) in anhydrous tetrahydrofuran (80 mL) under stirring. The reaction solution was heated under reflux for 5 hours, and then water (2 mL) under ice-cooling, 4 N-sodium hydroxide (1.5 mL) and water (5.0 mL) was sequentially added dropwise thereto. The produced precipitate was taken by filtration and washed with tetrahydrofuran. After concentrating and drying the filtrate, the residue was purified by basic silica gel column chromatography to obtain cis-(1-benzyl-5-methylpyrrolidin-3-yl)methanol (0.8 g) and trans-(1-benzyl-5-methylpyrrolidin-3-yl)methanol (0.75 g) as colorless oily matters.
cis-isomer ¹H-NMR (200 MHz, CDCl₃) δ: 1.24(3H, d, J=5.8 Hz), 1.36-1.52(1H, m), 2.10-2.60(4H, m), 2.80(1H, d, J=10.0 Hz), 3.01(1H, d, J=12.8 Hz), 7.16-7.42(5H, m).
trans-isomer ¹H-NMR (200 MHz, CDCl₃) δ: 1.16(3H, d, J=6.2 Hz), 1.50-1.82(2H, m), 1.95(1H, dd, J=8.0 and 8.2 Hz), 2.20-2.40(2H, m), 3.03(1H, dd, J=7.2 and 7.4 Hz), 3.15(1H, d, J=12.8 Hz), 3.40-3.64(2H, m), 4.00(1H, d, J=12.8 Hz), 7.12-7.40(5H, m).

Reference Example 22

A mixture of cis-(1-benzyl-5-methylpyrrolidin-3-yl)methanol (350 mg), methyl alcohol (10 mL), 1 N-hydrochloric acid (1.5 mL) and 10% palladium carbon (water content 300 mg) was stirred for 15 hours under hydrogen atmosphere. The catalyst was filtered off and the filtrate was concentrated and dried to obtain cis-(5-methylpyrrolidin-3-yl)methanol hydrochloride (220 mg).
¹H-NMR (200 MHz, CD₃OD) δ: 1.30-1.55(1H, m) 1.42 (3H, d, J=6.6 Hz), 2.20-2.40(1H, m), 2.48-2.72(1H, m), 3.10-3.22(1H, 3.30-3.48(1H, m), 3.48-3.80(3H, m).

Reference Example 23

A mixture of trans-(1-benzyl-5-methylpyrrolidin-3-yl)methanol (350 mg), methyl alcohol (10 mL), 1 N-hydrochloric acid (1.5 mL) and 10% palladium carbon (water content 300 mg) was stirred for 15 hours under hydrogen atmosphere. The catalyst was filtered off and the filtrate was concentrated and dried to obtain trans-(5-methylpyrrolidin-3-yl)methanol hydrochloride (220 mg).
¹H-NMR (200 MHz, CD₃OD) δ: 1.39(3H, d, J=6.6 Hz), 1.70-1.90(1H, m), 1.98-2.16(1H, m), 2.54-2.80(1H, m), 3.02-3.20(1H, m).

Reference Example 24

To a mixture of nipecotic acid (10.0 g) and a 1 N sodium hydroxide solution (77 mL) was added at 0° C. benzyloxycarbonyl chloride (13.2 g) and a 1 N sodium hydroxide solution (77 mL). The temperature was elevated to room temperature and the mixture was stirred for 14 hours. The reaction solution was washed with diethyl ether and acidified with 1 N hydrochloric acid. The mixture was extracted with ethyl acetate, the extract was washed with water, dried and concentrated to obtain 1-[(benzyloxy)carbonyl]-3-piperidinecarboxylic acid (20.1 g).
¹H-NMR (CDCl₃) δ: 1.42-1.76 (3H, m), 2.05-2.11 (1H, m), 2.48-2.53 (1H, m), 2.89-3.44 (2H, m), 3.94-4.00 (1H, m), 4.05-4.64 (1H, m), 5.14 (2H, ABq, J=12.6 Hz), 7.27-7.37 (5H, m).

Reference Example 25

A mixture of 1-[(benzyloxy)carbonyl]-3-piperidinecarboxylic acid (20.0 g), iodoethane (14.2 g), potassium carbonate (15.7 g), and N,N-dimethylformamide (150 mL) was stirred at room temperature for 5 hours. The reaction solution was poured into water and extracted with ethyl acetate. The extracts were washed with water, dried and concentrated. The obtained residue was purified by silica gel column chromatography to obtain ethyl 1-[(benzyloxy)carbonyl]-3-piperidinecarboxylate (20.0 g).

$^1$H-NMR (300 MHz, CDCl$_3$) δ: 1.24 (3H, t, J=7.5 Hz), 1.45-1.74 (3H, m), 2.02-2.08 (1H, m), 2.42-2.48 (1H, m), 2.85-3.13 (2H, m), 3.95-4.02 (1H, m), 4.12 (2H, q, J=7.5 Hz), 4.18-4.30 (1H, m), 5.12 (2H, s), 7.27-7.36 (5H, m).

Reference Example 26

To a solution of 15% potassium hexamethyldisilazide-toluene (31 mL) was added tetrahydrofuran (5.0 mL) under argon atmosphere, and the mixture was cooled to −78° C. A mixture of ethyl 1-[(benzyloxy)carbonyl]-3-piperidinecarboxylate (4.00 g) and tetrahydrofuran (3.0 mL) was added and the mixture was stirred for 20 minutes. A mixture of iodomethane (1.3 mL) and tetrahydrofuran (2.0 mL) was added and the temperature was elevated to room temperature. After stirring for 12 hours, the reaction solution was poured into water and extracted with ethyl acetate. The extracts were washed with brine, dried and concentrated. The obtained residue was purified by silica gel column chromatography to obtain ethyl 1-[(benzyloxy)carbonyl]-3-methyl-3-piperidinecarboxylate (3.76 g).

$^1$H-NMR (300 MHz, CDCl$_3$) δ: 1.16-1.26 (6H, m), 1.40-1.49 (1H, m), 1.52-1.65 (2H, m), 2.03-2.10 (1H, m), 3.11-3.30 (2H, m), 3.52-3.64 (1H, m), 3.98-4.13 (3H, m), 5.12 (2H, s), 7.27-7.37 (5H, m).

Reference Example 27

A mixture of ethyl 1-[(benzyloxy)carbonyl]-3-methyl-3-piperidinecarboxylate (3.57 g), 10% palladium-carbon (50% water content, 1.24 g) and methanol (50 mL) was stirred at room temperature for 2.5 hours under hydrogen atmosphere. The catalyst was filtered off using celite, and mother liquor was concentrated to obtain ethyl 3-methyl-3-piperidinecarboxylate (1.86 g).

$^1$H-NMR (300 MHz, CDCl$_3$) δ: 1.09 (3H, s), 1.27 (3H, t, J=7.2 Hz), 1.33-1.82 (3H, m), 2.14-2.22 (1H, m), 2.40 (1H, d, J=12.9 Hz), 2.53-2.62 (1H, m), 2.89-2.95 (1H, m), 3.31 (1H, dd, J=12.9 and 1.5 Hz), 4.09-4.24 (2H, m).

Reference Example 28

To a mixture of ethyl 3-methyl-3-piperidinecarboxylate (1.68 g) and tetrahydrofuran (21 mL) was added at 0° C. lithium aluminum hydride (372 mg). The mixture was stirred for 3 hours with elevating the temperature to room temperature. Water (0.37 ml), a 25% potassium hydroxide solution (0.37 ml) and water (1.10 ml) were sequentially added thereto, and the mixture was stirred for 15 hours. The insolubles were filtered off using celite and then the mother liquor was concentrated to obtain 3-(hydroxymethyl)-3-methylpiperidine (1.01 g).

$^1$H-NMR (300 MHz, CDCl$_3$) δ: 0.81 (3H, s), 1.28-1.37 (1H, m), 1.49-1.68 (2H, m), 1.80-1.93 (1H, m), 2.54 (1H, d, J=11.7 Hz), 2.60-2.69 (1H, m), 2.85-3.11 (3H, m), 3.58 (2H, s).

Reference Example 29

A mixture of 5,6,7,8-tetrahydro-1-naphthol (4.96 g), benzylbromide (4.3 mL), potassium carbonate (6.94 g), and N,N-dimethylformamide (70 mL) was stirred at room temperature for 21 hours. The reactant was poured into water and extracted with ethyl acetate. The extracts were washed with water, dried and concentrated. The obtained residue was purified by silica gel column chromatography to obtain 5-(benzyloxy)-1,2,3,4-tetrahydronaphthalene (7.85 g).

$^1$H-NMR (300 MHz, CDCl$_3$) δ: 1.72-1.84 (4H, m), 2.72-2.78 (4H, m), 5.05 (2H, s), 6.68-6.72 (2H, m), 7.04 (1H, d, J=7.8 Hz), 7.27-7.45 (5H, m).

Reference Example 30

To a mixure of 5-(benzyloxy)-1,2,3,4-tetrahydronaphthalene (6.30 g), dichloromethylmethyl ether (4.8 mL), and dichloromethane (50 mL) was added dropwise at 0° C. for 30 minutes a mixture of titanium tetrachloride (7.3 mL) and dichloromethane (5.0 mL). After stirring for 15 minutes, the reactant was poured into iced water and stirred vigorously for 30 minutes. The organic layer was washed with water, dried and concentrated. The obtained residue was purified by silica gel column chromatography to obtain 4-(benzyloxy)-5,6,7,8-tetrahydro-1-naphthalenecarboxaldehyde (4.86 g).

$^1$H-NMR (300 MHz, CDCl$_3$) δ: 1.77-1.81 (4H, m), 2.74-2.77 (2H, m), 3.18-3.22 (2H, m), 5.15 (2H, s), 6.86 (1H, d, J=8.4 Hz), 7.32-7.45 (5H, m), 7.63 (1H, d, J=8.4 Hz), 10.09 (1H, s).

Reference Example 31

To a mixture of 4-(benzyloxy)-5,6,7,8-tetrahydro-1-naphthalenecarboxaldehyde (4.64 g) and dichloromethane (50 mL) was added dropwise a 0.5 M boron tribromide-dichloromethane solution (40 mL) at −78° C. for 30 minutes. After stirring for 40 minutes, the temperature was elevated to room temperature. The reactant was poured into water and extracted with ethyl acetate. The extracts were washed with brine, dried and concentrated. The obtained residue was purified by silica gel column chromatography to obtain 4-hydroxy-5,6,7,8-tetrahydro-1-naphthalenecarboxaldehyde (2.73 g).

$^1$H-NMR (300 MHz, CDCl$_3$) δ: 1.77-1.87 (4H, m), 2.65-2.68 (2H, m), 3.19-3.22 (2H, m), 5.93 (1H, s), 6.76 (1H, d, J=8.1 Hz), 7.58 (1H, d, J=8.1 Hz), 10.08 (1H, s).

Reference Example 32

A mixture of 4-hydroxy-5,6,7,8-tetrahydro-1-naphthalenecarboxaldehyde (2.72 g), hydroxylamine hydrochloride (1.29 g), sodium acetate (1.90 g), ethanol (60 mL), and water (30 mL) was stirred at room temperatur for 1 hour. The reactant was concentrated and the residue was distributed between ethyl acetate and water. The organic layer was washed with brine, dried and concentrated to obtain a yellowish-brown solid matter. A mixture of the obtained solid and anhydride acetic acid (50 mL) was stirred at 150° C. for 12 hours. The reactant was concentrated, and the obtained residue was processed with a silica gel column to obtain a colorless solid matter. A mixture of the obtained solid, a 1 N sodium hydroxide solution (28 mL), and tetrahydrofuran (50 mL) was stirred at room temperature for 1.5 hours. The mixture was neutralized with 1N hydrochloric acid and extracted with ethyl acetate. The extracts were washed with brine, dried and concentrated to obtain 4-hydroxy-5,6,7,8-tetrahydro-1-naphthalenecarbonitrile (2.24 g).

$^1$H-NMR (300 MHz, CDCl$_3$) δ: 1.79-1.88 (4H, m), 2.60-2.64 (2H, m), 2.90-2.94 (2H, m), 5.65 (1H, s), 6.66 (1H, d, J=8.4 Hz), 7.35 (1H, d, J=8.4 Hz). IR (KBr) 3256, 2938, 2228, 1584 cm$^{-1}$

Reference Example 33

To a mixture of 4-hydroxy-5,6,7,8-tetrahydro-1-naphthalenecarbonitrile (300 mg), triethylamine (0.72 mL), and dichloromethane (3.0 mL) was added dropwise at −40° C. a mixture of trifluoromethanesulfonic anhydride (0.44 mL) and dichloromethane (1.0 mL). After stirring for 15 minutes, the temperature was elevated to room temperature, and the mixture was concentrated. The obtained residue was purified by silica gel column chromatography to obtain 4-cyano-5,6,7,8-tetrahydro-1-naphthalenyltrifluoromethanesulfonate (500 mg).

$^1$H-NMR (300 MHz, CDCl$_3$) δ: 1.81-1.93 (4H, m), 2.81 (2H, t, J=5.4 Hz), 3.01 (2H, t, J=5.4 Hz), 7.18 (1H, d, J=8.4 Hz), 7.54 (1H, d, J=8.4 Hz).

Reference Example 34

To a mixture of 1-methoxy-3-(methoxymethoxy)benzene (5.00 g), N,N,N',N',-tetramethylethylenediamine (5.20 mL), and tetrahydrofuran (250 mL) was added a 1.6 Mn-butyllithium-hexane solution (21.4 mL) at 0° C. for 20 minutes. The temperature was elevated to room temperature, the mixture was stirred for 2 hours, and then cooled to −78° C. Copper (I) iodide (6.82 g) was added thereto and the mixture was stirred for 2 hours with elevating the temperature to −40° C. After cooling to −78° C., a mixture of metallyl bromide (3.81 mL) and tetrahydrofuran (20 mL) was added for 30 minutes. The temperature was elevated to room temperature, and the mixture was stirred for 12 hours. The reaction solution was poured into water and extracted with ethyl acetate. The extracts were washed with a sodium hydrogen carbonate solution and brine, dried and concentrated. The obtained residue was purified by silica gel column chromatography to obtain 1-methoxy-3-(methoxymethoxy)-2-(2-methyl-2-propenyl)benzene (4.77 g).

$^1$H-NMR (300 MHz, CDCl$_3$) δ: 1.79 (3H, d, J=0.6 Hz), 3.37 (2H, s), 3.45 (3H, s), 3.79 (3H, s), 4.44-4.45 (1H, m), 4.65-4.67 (1H, m), 5.15 (2H, s), 6.58 (1H, dd, J=8.4 and 0.6 Hz), 6.73 (1H, dd, J=8.4 and 0.6 Hz), 7.12 (1H, t, J=8.4 Hz).

Reference Example 35

To a mixture of 1-methoxy-3-(methoxymethoxy)-2-(2-methyl-2-propenyl)benzene (4.50 g), N,N,N',N',-tetramethylethylenediamine (3.36 mL), and hexane (250 mL) was added at 0° C. for 15 minutes a 1.6 Mn-butyllithium-hexane solution (13.9 mL). The temperature was elevated to room temperature, the mixture was stirred for 3 hours and then cooled to −78° C. N,N-dimethylformamide (3.92 mL) was added, and the mixture was stirred for 1 hour. The temperature was elevated to room temperature and the mixture was stirred for 13 hours. The reaction solution was washed with water, dried and concentrated. The obtained residue was purified by silica gel column chromatography to obtain 4-methoxy-2-(methoxymethoxy)-3-(2-methyl-2-propenyl)benzaldehyde (3.20 g).

$^1$H-NMR (300 MHz, CDCl$_3$) δ: 1.82 (3H, s), 3.38 (2H, s), 3.58 (3H, s), 3.89 (3H, s), 4.37 (1H, br.s), 4.71-4.74 (1H, m), 5.05 (2H, s), 6.81 (1H, d, J=8.7 Hz), 7.81 (1H, d, J=8.7 Hz), 10.19 (1H, s).

Reference Example 36

A mixture of 4-methoxy-2-(methoxymethoxy)-3-(2-methyl-2-propenyl)benzaldehyde (3.20 g), 4 N hydrochloric acid (50 mL), and 2-propanol (50 mL) was stirred at room temperature for 18 hours. The reaction solution was concentrated, the residue was saturated with saline and then extracted with ethyl acetate. After the extract was washed with a sodium hydrogen carbonate solution and brine, the extract was dried and concentrated. The obtained residue was processed with a silica gel column to obtain a yellow material. A mixture of the obtained material, Amberlyst 15 (3.00 g), and toluene (30 mL) was stirred vigorously at room temperature for 3 days. The mixture was filtrated using celite and the residue was washed with toluene. Mother liquor and washing liquid were combined and concentrated. The obtained residue was purified by silica gel column chromatography to obtained 4-methoxy-2,2-dimethyl-2,3-dihydro-1-benzofuran-7-carboxaldehyde (1.72 g).

$^1$H-NMR (300 MHz, CDCl$_3$) δ: 1.53 (6H, s), 2.92 (2H, s), 3.88 (3H, s), 6.47 (1H, d, J=8.4 Hz), 7.63 (1H, d, J=8.4 Hz), 10.05 (1H, s).

Reference Example 37

To a mixture of tert-hexadecanethiol (2.16 g) and hexamethylphosphoric triamide (HMPA) (9.0 mL) was added at 0° C. a 1.6 Mn-butyllithium-hexane solution (5.7 mL). After stirring for 20 minutes, the mixture was added at the same temperature to a mixture of 4-methoxy-2,2-dimethyl-2,3-dihydro-1-benzofuran-7-carboxaldehyde (860 mg) and HMPA (20 mL). The temperature was elevated to room temperature, and the mixture was stirred for 13 hours. The reaction solution was poured into a 1 N sodium hydroxide solution and washed with diethyl ether. The aqueous layer was acidified with 1 N hydrochloric acid and extracted with diethyl ether. The extracts were washed with brine, dried and concentrated. The obtained residue was purified by silica gel column chromatography to obtain 4-hydroxy-2,2-dimethyl-2,3-dihydro-1-benzofuran-7-carboxaldehyde (860 mg).

$^1$H-NMR (300 MHz, CDCl$_3$) δ: 1.55 (6H, s), 2.96 (2H, s), 6.39 (1H, d, J=8.4 Hz), 7.53 (1H, d, J=8.4 Hz), 10.01 (1H, s).

Reference Example 38

A mixture of 4-hydroxy-2,2-dimethyl-2,3-dihydro-1-benzofuran-7-carboxaldehyde (500 mg), hydroxylamine hydrochloride (217 mg), sodium acetate (320 mg), ethanol (10 mL), and water (5.0 mL) was stirred at room temperature for 1 hour. The reactant was concentrated and the residue was distributed between ethyl acetate and water. The organic layer was washed with brine, dried and concentrated, to obtain a brown oily matter. A mixture of the obtained matter and acetic acid anhydride (7.5 mL) was stirred at 150° C. for 12 hours. The reactant was concentrated, and the obtained residue was processed with a silica gel column, to obtain a pale yellow oily matter. A mixture of the obtained matter and a 1 N sodium hydroxide solution (4.7 mL), and tetrahydrofuran (9.0 mL) was stirred at room temperature for 2.5 hours. The mixture was neutralized with 1 N hydrochloric acid and extracted with ethyl acetate. The extracts were washed with brine, dried and concentrated to obtain 4-hydroxy-2,2-dimethyl-2,3-dihydro-1-benzofuran-7-carbonitrile (431 mg).

$^1$H-NMR (300 MHz, CDCl$_3$) δ: 1.54 (6H, s), 2.98 (2H, s), 5.57 (1H, br.s), 6.34 (1H, d, J=8.7 Hz), 7.22 (1H, d, J=8.7 Hz). IR (KBr) 2230, 1609, 1453 cm$^{-1}$

Reference Example 39

To a mixture of 4-hydroxy-2,2-dimethyl-2,3-dihydro-1-benzofuran-7-carbonitrile (250 mg), triethylamine (552 µL), and dichloromethane (5.0 mL) was added dropwise at −40° C. a mixture of trifluoromethanesulfonic anhydride (333 µL) and dichloromethane (2.0 mL). After stirring for 15 minutes, the temperature was elevated to room temperature and the mixture was concentrated. The obtained residue was purified by silica gel column chromatography to obtain 7-cyano-2,2-dimethyl-2,3-dihydro-1-benzofuran-4-yl trifluoromethanesulfonate (405 mg).

$^1$H-NMR (300 MHz, CDCl$_3$) δ: 1.58 (6H, s), 3.17 (2H, s), 6.80 (1H, d, J=8.7 Hz), 7.42 (1H, d, J=8.7 Hz).

Reference Example 40

To 4-bromo-1-naphthonitrile (0.232 g) and triisopropyl borate (2.8 mL) was added toluene (4 mL) and tetrahydrofuran (1 mL) and dissolved therein, and then the mixture was with stirring under cooling to −70° C. Then, 1.6 M n-butyllithium (in a hexane solution, 0.75 mL) was added thereto and the mixture was kept to −70° C. to be stirred for 1.5 hours. After adjusting the temperature to −50° C., 3 N-hydrochloric acid (2 mL) was added, and the temperature was elevated to room temperature. Ethyl acetate was added, and the mixture was extracted and washed with water, dried and concentrated. To the obtained residue was added acetonitrile, and the resulting material was crystallized to obtain 4-cyano-1-naphthylboronic acid (0.102 g).

$^1$H-NMR (200 MHz, CDCl$_3$+CD$_3$OD) δ: 7.50-8.00(5H, m), 8.20-8.40(1H, m).

Reference Example 41

A mixture of ethyl 3-(2-methyl-2-oxiranyl) propionate (400 mg), benzylamine (2.76 mL), and ethanol (4.0 mL) was stirred at 90° C. for 14 hours. After cooling to room temperature, the mixture was concentrated and the obtained residue was distributed between ethyl acetate and 1 N hydrochloric acid. The organic layer was washed with 1 N hydrochloric acid and brine, dried and concentrated. The obtained residue was purified by silica gel column chromatography to obtain 1-benzyl-5-hydroxy-5-methyl-2-piperidinone (120 mg).

$^1$H-NMR (300 MHz, CDCl$_3$) δ: 1.28 (3H, s), 1.83-1.89 (2H, m), 2.47 (1H, ddd, J=18.0, 6.0 and 4.2 Hz), 2.72 (1H, ddd, J=18.0, 10.2 and 7.5 Hz), 3.05-3.09 (1H, m), 3.20 (1H, d, J=12.6 Hz), 4.59 (2H, ABq, J=14.4 Hz), 7.23-7.35 (5H, m).

Reference Example 42

To a mixture of methane sulfonamide (1.96 g), triethylamine (3.2 mL), 4-(dimethylamino)pyridine (252 mg), and dichloromethane (30 mL) was added a mixture of di-tert-butyl dicarbonate (5.17 g) and dichloromethane (40 mL) at room temperature for 30 minutes. The mixture was concentrated after stirring for 2 hours, and the residue was distributed with ethyl acetate and 1 N hydrochloric acid. The organic layer was washed with water, dried and concentrated. The obtained residue was purified by silica gel column chromatography to obtain tert-butyl methylsulfonyl carbamate (2.44 g).

$^1$H-NMR (300 MHz, CDCl$_3$) δ: 1.52 (9H, s), 3.28 (3H, s).

Reference Example 43

To a mixture of 2-bromo-5-methoxyphenol (22.0 g), 1,8-diazabicyclo[2,2,2]octane (24.3 g), and N,N-dimethylformamide (120 mL) was added N,N-dimethylthiocarbamoyl chloride (26.8 g) at room temperature for 30 minutes. After stirring for 13 hours, the mixture was poured into water and extracted with ethyl acetate. The extracts were washed with water, dried and concentrated. The obtained solid was washed with methanol to obtain O-(2-bromo-5-methoxyphenyl)dimethylthiocarbamate (26.6 g).

$^1$H-NMR (300 MHz, CDCl$_3$) δ: 3.39 (3H, s), 3.47 (3H, s), 3.79 (3H, s), 6.69-6.72 (2H, m), 7.43-7.47 (1H, m).

Reference Example 44

A mixture of O-(2-bromo-5-methoxyphenyl)dimethylthiocarbamate (26.4 g) and diethylaniline (66 mL) was stirred at 240° C. for 4 hours. After cooling to room temperature, the mixture was poured into 1 N hydrochloric acid with ice-cooling and extracted with ethyl acetate. After the extract was washed with 1 N hydrochloric acid and brine, the extract was dried and concentrated. The obtained residue was purified by silica gel column chromatography to obtain S-(2-bromo-5-methoxyphenyl)dimethylthiocarbamate (22.2 g).

$^1$H-NMR (300 MHz, CDCl$_3$) δ: 3.06 (3H, br.s), 3.11 (3H, br.s), 3.79 (3H, s), 6.82 (1H, dd, J=8.7 and 3.0 Hz), 7.19 (1H, d, J=3.0 Hz), 7.55 (1H, d, J=8.7 Hz).

Reference Example 45

To a mixture of potassium hydroxide (85%, 17.1 g) and methanol (70 mL) was added S-(2-bromo-5-methoxyphenyl)dimethylthiocarbamate (10.0 g), and the mixture was stirred at 85° C. for 2 hours under argon atmpsphere. After cooling to room temperature, 6 N hydrochloric acid was added with ice-cooling, the mixture was acidified and extracted with hexane. The extracts were washed with hexane, dried and concentrated to obtain a colorless oily matter. A mixture of the obtained matter, potassium carbonate (9.53 g), and N,N-dimethylformamide (80 mL) was stirred at room temperature for 20 minutes under argon atmosphere. 1-bromo-2,2-dimethoxyethane (10.5 g) was added thereto, the mixture was stirred at room temperature for 2 hours. The reactant was poured into water, and extracted with hexane. The extracts were washed with water, dried and concentrated. The obtained residue was purified by silica gel column chromatography to obtain 1-bromo-2-[(2,2-dimethoxyethyl)sulfanyl]-4-methoxybenzene (9.37 g).

$^1$H-NMR (300 MHz, CDCl$_3$) δ: 3.12 (2H, d, J=5.7 Hz), 3.39 (6H, s), 3.78 (3H, s), 4.59 (1H, t, J=5.7 Hz), 6.60 (1H, dd, J=8.7 and 3.0 Hz), 6.90 (1H, d, J=3.0 Hz), 7.41 (1H, d, J=8.7 Hz).

Reference Example 46

A mixture of 1-bromo-2-[(2,2-dimethoxyethyl)sulfanyl]-4-methoxybenzene (9.37 g), polyphosphoric acid (18.7 g), and xylene (200 mL) was stirred at 150° C. for 1 hour. After cooling to room temperature, the insolubles were removed by decantation and the supernatant was concentrated. The obtained residue was purified by silica gel column chromatography to obtain 7-bromo-4-methoxy-1-benzothiophene (7.07 g).

$^1$H-NMR (300 MHz, CDCl$_3$) δ: 3.95 (3H, s), 6.66 (1H, d, J=8.1 Hz), 7.38-7.41 (2H, m), 7.58 (1H, d, J=5.4 Hz).

Reference Example 47

A mixture of 7-bromo-4-methoxy-1-benzothiophene (3.00 g), zinc cyanide (1.09 g), tetrakis(triphenylphosphine)palladium(0) (1.43 g), and N,N-dimethylformamide (75 mL) was stirred at 100° C. for 12 hours under argon atmosphere. After cooling to room temperature, the reactant was poured into water and extracted with ethyl acetate. Insolubles were filtered off using celite. The organic layer was washed with brine, dried and concentrated. The obtained residue was purified by silica gel column chromatography to obtain 4-methoxy-1-benzothiophene-7-carbonitrile (2.25 g).

$^1$H-NMR (300 MHz, CDCl$_3$) δ: 4.02 (3H, s), 6.79 (1H, d, J=8.1 Hz), 7.46 (1H, d, J=5.4 Hz), 7.53 (1H, d, J=5.4 Hz), 7.66 (1H, d, J=8.1 Hz).

IR (KBr) 2215, 1561 cm$^{-1}$

Reference Example 48

To a mixture of 2-methyl-2-pentadecanethiol (6.12 g) and hexamethylphosphoric triamide (25 mL) was added at 0° C. a 1.6 Mn-butyllithium-hexane solution (15.5 mL). After stirring for 20 minutes, the mixture was added at 0° C. to a mixture of 4-methoxy-1-benzothiophene-7-carbonitrile (2.24 g) and hexamethylphosphoric triamide (50 mL). After stirring at room temperature for 1.5 hours, the reaction solution was poured into 1 N sodium hydroxide and washed with diethyl ether. The aqueous layer was acidified with 1 N hydrochloric acid, and then was extracted with diethyl ether. The extracts were washed with brine, dried and concentrated. The obtained residue purified by silica gel column chromatography to obtain 4-hydroxy-1-benzothiophene-7-carbonitrile (1.93 g).

$^1$H-NMR (300 MHz, CDCl$_3$) δ: 6.88 (1H, d, J=8.4 Hz), 7.57 (1H, d, J=5.4 Hz), 7.76 (1H, d, J=8.4 Hz), 7.78-7.81 (1H, m), 11.32 (1H, br.s).

IR (KBr) 3326, 2220, 1566 cm$^{-1}$

Reference Example 49

To a mixture of 4-hydroxy-1-benzothiophene-7-carbonitrile (1.43 g), triethylamine (3.4 mL), and dichloromethane (25 mL) was added dropwise at −50° C. a mixture of trifluoromethanesulfonic anhydride (2.1 mL) and dichloromethane (13 mL). The mixture was stirred for 15 minutes and concentrated. The obtained residue was purified by silica gel column chromatography to obtain 7-cyano-1-benzothien-4-yl trifluoromethanesulfonate (2.36 g).

$^1$H-NMR (300 MHz, CDCl$_3$) δ: 7.43 (1H, d, J=8.4 Hz), 7.55 (1H, d, J=5.4 Hz), 7.77 (1H, dd, J=5.4 and 0.6 Hz), 7.79 (1H, dd, J=8.4 and 0.6 Hz).

IR 2226, 1427, 1221, 1140 cm$^{-1}$

Reference Example 50

To a mixture of 2-bromo-5-fluorophenol (19.4 g), 1,8-diazabicyclo[2,2,2]octane (22.8 g), and N,N-dimethylformamide (130 mL) was added N,N-dimethylthiocarbamoyl chloride (25.1 g) at room temperature for 30 minutes. After stirring for 4 hours, the mixture was poured into water and extracted with ethyl acetate. The extracts were washed with water, dried and concentrated. The obtained solid was washed with methanol to obtain O-(2-bromo-5-fluorophenyl)dimethylthiocarbamate (27.1 g).

$^1$H-NMR (300 MHz, CDCl$_3$) δ: 3.39 (3H, s), 3.47 (3H, s), 6.86-6.95 (2H, m), 7.51-7.56 (2H, m).

Reference Example 51

A mixture of O-(2-bromo-5-fluorophenyl)dimethylthiocarbamate (21.9 g) and diethylaniline (60 mL) was stirred at 240° C. for 4 hours. After cooling to room temperature, the mixture was poured into 1 N hydrochloric acid with ice-cooling and extracted with ethyl acetate. The extracts were washed with 1 N hydrochloric acid and brine, and then dried and concentrated. The obtained residue was purified by silica gel column chromatography to obtain S-(2-bromo-5-fluorophenyl)dimethylthiocarbamate (21.2 g).

$^1$H-NMR (300 MHz, CDCl$_3$) δ: 3.06 (3H, br.s), 3.11 (3H, br.s), 6.98 (1H, ddd, J=9.0, 7.8 and 3.0 Hz), 7.38 (1H, dd, J=8.4 and 3.0 Hz), 7.62 (1H, dd, J=9.0 and 5.4 Hz).

Reference Example 52

To a mixture of potassium hydroxide (85%, 35.6 g) and methanol (150 mL) was added S-(2-bromo-5-fluorophenyl)dimethylthiocarbamate (20.0 g), and the mixture was stirred under argon atmosphere at 85° C. for 2 hours. After cooling to room temperature, 6 N hydrochloric acid was added thereto with ice-cooling and the mixture was acidified and extracted with hexane. The extracts were washed with hexane, dried and concentrated to obtain a pale yellow oily matter. A mixture of the obtained matter, potassium carbonate (19.9 g), and N,N-dimethylformamide (160 mL) was stirred under argon atmosphere at room temperature for 20 minutes. 1-bromo-2,2-dimethoxyethane (21.9 g) was added thereto, and the mixture was stirred at room temperature for 2 hours. The reactant was poured into water and extracted with hexane. The extracts were washed with water, dried and concentrated. The obtained residue was purified by silica gel column chromatography to 1-bromo-2-[(2,2-dimethoxyethyl)sulfanyl]-4-fluorobenzene (19.9 g).

$^1$H-NMR (300 MHz, CDCl$_3$) δ: 3.12 (2H, d, J=5.4 Hz), 3.40 (6H, s), 4.60 (1H, t, J=5.4 Hz), 6.75 (1H, ddd, J=8.4, 7.8 and 3.0 Hz), 7.03 (1H, dd, J=9.3 and 3.0 Hz), 7.43 (1H, dd, J=8.4 and 5.4 Hz).

Reference Example 53

A mixture of 1-bromo-2-[(2,2-dimethoxyethyl)sulfanyl]-4-fluorobenzene (19.9 g), polyphosphoric acid (33.0 g), and xylene (400 mL) was stirred at 150° C. for 5 hours. After cooling to room temperature, the insolubles were removed by decantation and the supernatant was concentrated. The obtained residue was purified by silica gel column chromatography to obtain 7-bromo-4-fluoro-1-benzothiophene (9.52 g).

$^1$H-NMR (300 MHz, CDCl$_3$) δ: 6.95 (1H, dd, J=9.6 and 8.4 Hz), 7.42 (1H, ddd, J=8.4, 4.2 and 0.3 Hz), 7.50 (1H, dt, J=5.4 and 0.3 Hz), 7.54 (1H, d, J=5.4 Hz).

Reference Example 54

A mixture of 7-bromo-4-fluoro-1-benzothiophene (4.50 g), zinc cyanide (1.37 g), tetrakis(triphenylphosphine)palladium(0) (2.25 g), and N,N-dimethylformamide (120 mL) was stirred at 100° C. for 2.5 hours under argon atmosphere. After cooling to room temperature, the reactant was poured into water and extracted with ethyl acetate. Insolubles were filtered off using celite. The organic layer was washed with brine, dried and concentrated. The obtained residue was purified by silica gel column chromatography to obtain 4-fluoro-1-benzothiophene-7-carbonitrile (3.30 g).

$^1$H-NMR (300 MHz, CDCl$_3$) δ: 7.12 (1H, dd, J=9.6 and 8.4 Hz), 7.52 (1H, dt, J=5.4 Hz), 7.60 (1H, d, J=5.4 Hz), 7.69 (1H, dd, J=8.4 and 4.8 Hz).

IR (KBr) 2224, 1568, 1464, 1366, 1248 cm$^{-1}$

Reference Example 55

A mixture of 2-bromo-5-fluorophenol (14.6 g), 1-bromo-2,2-dimethoxyethane (32.2 g), potassium carbonate (21.1 g), and N,N-dimethylformamide (200 mL) was stirred at 100° C. for 5 hours. After cooling to room temperature, the reactant was poured into water and extracted with hexane. The extracts were washed with 1 N sodium hydroxide and brine, dried and concentrated. The obtained residue was purified by silica gel column chromatography to obtain 1-bromo-2-(2,2-dimethoxyethoxy)-4-fluorobenzene (20.6 g).

$^1$H-NMR (300 MHz, CDCl$_3$) δ: 3.51 (6H, s), 4.02 (2H, d, J=5.1 Hz), 4.74 (1H, t, J=5.1 Hz), 6.56-6.67 (2H, m), 7.46 (1H, dd, J=8.4 and 6.0 Hz).

Reference Example 56

A mixture of 1-bromo-2-(2,2-dimethoxyethoxy)-4-fluorobenzene (20.6 g), polyphosphoric acid (45.1 g), and xylene (500 mL) was stirred at 150° C. for 7.5 hours. After cooling to room temperature, the insolubles were removed by decantation and the supernatant was concentrated. The obtained residue was purified by silica gel column chromatography to obtain 7-bromo-4-fluoro-1-benzofuran (5.30 g).

$^1$H-NMR (300 MHz, CDCl$_3$) δ: 6.86 (1H, d, J=8.7 Hz), 6.93 (1H, d, J=2.1 Hz), 7.38 (1H, dd, J=8.7 and 4.5 Hz), 7.66 (1H, d, J=2.1 Hz).

Reference Example 57

A mixture of 7-bromo-4-fluoro-1-benzofuran (5.30 g), zinc cyanide (1.74 g), tetrakis(triphenylphosphine)palladium (0) (2.85 g), and N,N-dimethylformamide (160 mL) was stirred at 100° C. for 2.5 hours under argon atmosphere. After cooling to room temperature, the reactant was poured into water and extracted with ethyl acetate. Insolubles were filtered off using celite. The organic layer was washed with brine, dried and concentrated. The obtained residue was purified by silica gel column chromatography to obtain 4-fluoro-1-benzofuran-7-carbonitrile (3.63 g).

$^1$H-NMR (300 MHz, CDCl$_3$) δ: 6.96 (1H, d, J=2.4 Hz), 7.03 (1H, d, J=8.7 Hz), 7.60 (1H, dd, J=8.7 and 5.1 Hz), 7.74 (1H, d, J=2.4 Hz).

IR (KBr) 2232, 1497, 1271 cm$^{-1}$

Reference Example 58

A mixture of tert-butyl hydroxycarbamate (5.00 g), 1,4-dibromobutane (3.18 g), potassium hydroxide (85%, 2.92 g), ethanol (30 mL) was heated under reflux for 7 hours. Insolubles were filtered off, and then washed with ethanol. Mother liquor was concentrated. The obtained residue was purified by silica gel column chromatography to obtain tert-butyl 1,2-oxazinane-2-carboxylate (2.24 g).

$^1$H-NMR (300 MHz, CDCl$_3$) δ: 1.50 (9H, s), 1.64-1.82 (4H, m), 3.60-3.66 (2H, m), 3.92-3.97 (2H, m).

Reference Example 59

To tert-butyl 1,2-oxazinane-2-carboxylate (2.18 g) was added 4 N hydrogen chloride-ethyl acetate (7.5 mL), and the mixture was stirred at room temperature for 3 hours. The produced precipitate was taken by filtration and washed with diethyl ether, to obtain 1,2-oxazinane hydrochloride (1.24 g).

$^1$H-NMR (300 MHz, DMSO-d$_6$) δ: 1.70-1.77 (2H, m), 1.83-1.90 (2H, m), 3.25-3.29 (2H, m), 4.20-4.24 (2H, m).

Reference Example 60

To a mixture of isonipecotic acid (10.0 g) and 1 N sodium hydroxide (77 mL) was added 0° C. for 10 minutes benzyloxycarbonyl chloride (13.2 g) and 1 N sodium hydroxide (77 mL). After stirring for 14 hours, the mixture was washed with diethyl ether. The aqueous layer was acidified with hydrochloric acid and extracted with ethyl acetate. The extracts were washed with brine, dried and concentrated to obtain 1-[(benzyloxy)carbonyl]-4-piperidinecarboxylic acid (18.3 g).

$^1$H-NMR (300 MHz, CDCl$_3$) δ: 1.61-1.72 (2H, m), 1.91-1.95 (2H, m), 2.46-2.56 (1H, m), 2.91-2.99 (2H, m), 4.04-4.14 (2H, m), 5.12 (2H, s), 7.27-7.36 (5H, m).

Reference Example 61

A mixture of 1-[(benzyloxy)carbonyl]-4-piperidinecarboxylic acid (18.3 g), ethyl iodide (12.9 g), potassium carbonate (14.3 g), and N,N-dimethylformamide (160 mL) was stirred at room temperature for 6 hours. The reactant was poured into water and extracted with ethyl acetate. The extracts were washed with water, dried and concentrated. The obtained residue was purified by silica gel column chromatography to obtain 1-benzyl 4-ethyl 1,4-piperidinedicarboxylate (16.5 g).

$^1$H-NMR (300 MHz, CDCl$_3$) δ: 1.25 (3H, t, J=7.5 Hz), 1.58-1.71 (2H, m), 1.84-1.94 (2H, m), 2.46 (1H, tt, J=8.1 and 3.9 Hz), 2.88-2.96 (2H, m), 4.04-4.16 (2H, m), 4.14 (2H, q, J=7.5 Hz), 7.30-7.39 (5H, m).

Reference Example 62

To a mixture of potassium hexamethyldisilazide (in a 20% toluene solution, 23.1 mL) and tetrahydrofuran (5 mL) was added at −78° C. a mixture of 1-benzyl 4-ethyl 1,4-piperidinedicarboxylate (4.00 g) and tetrahydrofuran (4 mL), and the mixture was stirred for 20 minutes. A mixture of methyl iodide (2.92 g) and tetrahydrofuran (15 mL) was added thereto, the resulting mixture was stirred for 10 minutes, and then the temperature was elevated to room temperature. The mixture was stirred for 19 hours. The reactant was poured into water and extracted with ethyl acetate. The extracts were washed with water, dried and concentrated. The obtained residue was purified by silica gel column chromatography to obtain 4-methyl-1-benzyl 4-ethyl 1,4-piperidinedicarboxylate (3.66 g).

$^1$H-NMR (300 MHz, CDCl$_3$) δ: 1.20 (3H, s), 1.26 (3H, t, J=7.2 Hz), 1.32-1.41 (2H, m), 2.06-2.10 (2H, m), 3.01-3.09 (2H, m), 3.84-3.88 (2H, m), 4.16 (2H, q, J=7.2 Hz), 5.11 (2H, s), 7.27-7.35 (5H, m).

Reference Example 63

A mixture of 4-methyl-1-benzyl 4-ethyl 1,4-piperidinedicarboxylate (3.60 g), 10% palladium carbon (50% water content, 1.25 g), methanol (50 mL) was stirred under hydrogen atmosphere at room temperature for 16 hours. Palladium carbon was filtered off using celite and washed with methanol. Mother liquor was concentrated to obtain ethyl 4-methyl-4-piperidine dicarboxylate (1.76 g).

¹H-NMR (300 MHz, CDCl₃) δ: 1.19 (3H, s), 1.26 (3H, t, J=7.2 Hz), 1.39 (2H, ddd, J=13.5, 10.2 and 3.9 Hz), 2.06-2.12 (2H, m), 2.65-2.78 (3H, m), 2.94 (2H, dt, J=12.9 and 3.9 Hz), 4.19 (2H, q, J=7.2 Hz).

Reference Example 64

To a mixture of ethyl 4-methyl-4-piperidine dicarboxylate (1.70 g) and tetrahydrofuran (22 mL) was added at 0° C. lithium aluminum hydride (376 mg), and the mixture was stirred for 4 hours. Water (0.4 mL), a 25% potassium hydroxide solution (0.4 mL) and water (1.2 mL) was sequentially added, and the mixture was stirred for 3 hours. Insolubles were filtered off using celite, and then mother liquor was concentrated to obtain (4-methyl-4-piperidinyl)methanol (1.28 g).
¹H-NMR (300 MHz, CDCl₃) δ: 0.98 (3H, s), 1.24-1.34 (2H, m), 1.35-1.49 (2H, m), 1.75 (2H, br.s), 2.75-2.90 (4H, m), 3.36 (2H, s).

Reference Example 65

To a mixture of ethyl isonipecotate (10.0 g), benzaldehyde (6.75 g), and ethanol (100 mL) was added sodium cyanotrihydroborate (4.00 g) at room temperature. After stirring for 3 hours, the mixture was concentrated and distributed into hexane and water. The organic layer was extracted with 1 N hydrochloric acid, the aqueous layer was alkalified with sodium hydrogen carbonate, and then the reactant was extracted with hexane. The extracts were washed with brine, dried and concentrated. The obtained residue was purified by silica gel column chromatography to obtain ethyl 1-benzyl-4-piperidinecarboxylate (2.34 g).
¹H-NMR (300 MHz, CDCl₃) δ: 1.24 (3H, t, J=7.2 Hz), 1.68-1.91 (5H, m), 2.02 (2H, td, J=11.4 and 2.7 Hz), 2.27 (2H, tt, J=10.8 and 4.2 Hz), 2.82-2.88 (2H, m), 3.49 (2H, s), 4.12 (2H, q, J=7.2 Hz), 7.25-7.38 (5H, m).

Reference Example 66

To a mixture of ethyl 1-benzyl-4-piperidinecarboxylate and tetrahydrofuran (50 mL) was added at −78° C. for 1 hour a 1 M methyl magnesium bromide-tetrahydrofuran solution (1.2 mL). After stirring for 6 hours, the temperature was elevated to room temperature, and the mixture was stirred for 14 hours. The reactant was poured into an ammonium chloride solution and extracted with ethyl acetate. The extracts were washed with water, dried and concentrated. The obtained residue was purified by silica gel column chromatography to obtain 2-(1-benzyl-4-piperidinyl)-2-propanol (820 mg).
¹H-NMR (300 MHz, CDCl₃) δ: 1.16-1.45 (4H, m), 1.17 (6H, s), 1.68-1.73 (2H, m), 1.87-1.95 (2H, m), 2.94-2.99 (2H, m), 3.49 (2H, s) 7.24-7.32 (5H, m).

Reference Example 67

To a mixture of Boc L-prolinol (2.10 g) and dimethylsulfoxide (14 mL) was added at 10° C. triethylamine (5.1 mL) and pyridine-sulfur trioxide (5.81 g). After stirring for 2.5 hours, the mixture was poured into iced water and extracted with dichloromethane. The extracts were washed with a 50% citric acid solution, a sodium hydrogen carbonate solution and water, dried and concentrated to obtain a pale yellow oily matter. A mixture of sodium hydride (60% in oil, 416 mg) and dimethylsulfoxide (10 mL) was stirred at 55° C. for 1 hour. A mixture of methyltriphenylphosphonium bromide (3.72 g) and dimethylsulfoxide (15 mL) was added, and the mixture was stirred for 45 minutes. After cooling to room temperature, the mixture was added to a mixture of the obtained oily matter and dimethylsulfoxide (30 mL). The resulting mixture was stirred for 15 hours. The reactant was poured into water and extracted with dichloromethane. The extracts were water-washed, dried and concentrated. The obtained residue was purified by silica gel column chromatography to obtain tert-butyl (2S)-2-vinyl-1-pyrrolidine carboxylate (490 mg).
¹H-NMR (300 MHz, CDCl₃) δ: 1.44 (9H, s), 1.64-2.10 (4H, m), 3.34-3.45 (2H, m), 4.20-4.38 (1H, m), 5.03-5.06 (2H, m), 5.66-5.80 (1H, m).

Reference Example 68

A mixture of tert-butyl (2S)-2-vinyl-1-pyrrolidine carboxylate (200 mg), 10% palladium carbon (50% water content, 216 mg), and methanol (3.0 mL) was stirred under hydrogen atmosphere at room temperature for 20 hours. Palladium carbon was filtered off using celite and washed with methanol. Mother liquor was concentrated to obtain tert-butyl (2R)-2-ethyl-1-pyrrolidinecarboxylate (170 mg).
¹H-NMR (300 MHz, CDCl₃) δ: 0.86 (3H, t, J=7.5 Hz), 1.25-1.37 (1H, m), 1.46 (9H, s), 1.59-1.99 (5H, m), 3.26-3.74 (3H, m).

Reference Example 69

To a mixture of ethyl diethoxyphosphorylacetate (2.69 g), lithium chloride (509 mg), diisopropylethylamine (1.74 mL), and acetonitrile (100 mL) was added benzyl 4-formylpiperidine-1-carboxylate (2.47 g), and the mixture was stirred at room temperature for 20 hours. The reaction solution was concentrated and the residue was distributed between ethyl acetate and brine. The organic layer was washed with brine, dried and concentrated. The obtained residue was purified by silica gel column chromatography to obtain benzyl 4-[(1E)-3-ethoxy-3-oxoprop-1-en-1-yl]piperidine-1-carboxylate (2.45 g).
¹H-NMR (300 MHz, CDCl₃) δ: 1.29 (3H, t, J=7.2 Hz), 1.31-1.42 (2H, m), 1.73-1.77 (2H, m), 2.25-2.37 (1H, m), 2.85 (2H, t, J=12.0 Hz), 4.16-4.24 (4H, m), 5.80 (1H, dd, J=15.9 and 1.8 Hz), 6.88 (1H, dd, J=15.9 and 6.6 Hz), 7.29-7.40 (5H, m).

Reference Example 70

A mixture of benzyl 4-[(1E)-3-ethoxy-3-oxoprop-1-en-1-yl]piperidine-1-carboxylate (2.38 g), 10% palladium carbon (50% water content, 1.60 g), and ethanol (50 mL) was stirred at room temperature for 2 days under hydrogen atmosphere. Palladium carbon was filtered off using celite and washed with ethanol. Mother liquor was concentrated to obtain ethyl 3-(4-piperidinyl)propionate (1.09 g).
¹H-NMR (300 MHz, CDCl₃) δ: 1.03-1.17 (2H, m), 1.26 (3H, t, J=7.2 Hz), 1.23-1.43 (2H, m), 1.57 (2H, dt, J=15.0 and 7.5 Hz), 1.65-1.69 (2H, m), 2.31 (2H, t, J=7.5 Hz), 2.57 (1H, td, J=12.0 and 2.7 Hz), 3.04-3.08 (2H, m), 4.12 (2H, q, J=7.2 Hz).

Reference Example 71

To a mixture of Boc D-prolinol (5.10 g) and dimethylsulfoxide (35 mL) was added at 10° C. triethylamine (12.1 mL) and pyridine-sulfur trioxide (13.8 g). After stirring for 2.5 hours, the mixture was poured into iced water and extracted with dichloromethane. The extracts were washed with a 50% citric acid solution, a sodium hydrogen carbonate solution and water, dried and concentrated to obtain a pale yellow oily matter (2.30 g). A mixture of sodium hydride (60% in oil, 402 mg) and dimethylsulfoxide (10 mL) was stirred at 55° C. for 1 hour. A mixture of methyltriphenylphosphonium bromide (3.59 g) and dimethylsulfoxide (15 mL) was added, and the mixture was stirred for 45 minutes. After cooling to room temperature, the mixture was added to a mixture of the obtained oily matter (2.00 g) and dimethylsulfoxide (30 mL). The resulting mixture was stirred for 15 hours. The reactant was poured into water and extracted with dichloromethane. The extracts were water-washed, dried and concentrated. The obtained residue was purified by silica gel column chromatography to obtain tert-butyl (2R)-2-vinyl-1-pyrrolidine carboxylate (191 mg).

$^1$H-NMR (300 MHz, CDCl$_3$) δ: 1.44 (9H, s), 1.64-2.10 (4H, m), 3.34-3.45 (2H, m), 4.20-4.38 (1H, m), 5.03-5.06 (2H, m), 5.66-5.80 (1H, m).

Reference Example 72

A mixture of tert-butyl (2R)-2-vinyl-1-pyrrolidine carboxylate (110 mg), 10% palladium carbon (50% water content, 119 mg), and methanol (3.0 mL), and the mixture was stirred at room temperature for 20 hours under hydrogen atmosphere. Palladium carbon was filtered off using celite and washed with methanol. Mother liquor was concentrated to obtain tert-butyl (2S)-2-ethyl-1-pyrrolidine carboxylate (80 mg).

$^1$H-NMR (300 MHz, CDCl$_3$) δ: 0.86 (3H, t, J=7.5 Hz), 1.25-1.37 (1H, m), 1.46 (9H, s), 1.59-1.99 (5H, m), 3.26-3.74 (3H, m).

Reference Example 73

To a mixture of 1-bromo-4-fluoronaphthalene (1.57 g) and tetrahydrofuran (30 mL) was added at −78° C. a 1.6 Mn-butyllithium-hexane solution (4.8 mL). The mixture was stirred for 20 minutes, and then added to a mixture of ethyl trifluoroacetate (1.7 mL) and tetrahydrofuran (20 mL) at the same temperature. After stirring for 20 minutes, the mixture was stirred for 30 minutes with elevating to room temperature. The reactant was poured into brine and extracted with ethyl acetate. The extracts were washed with brine, dried and concentrated. The obtained residue was purified by silica gel column chromatography to obtain 2,2,2-trifluoro-1-(4-fluoro-1-naphthyl)ethanone (865 mg).

$^1$H-NMR (300 MHz, CDCl$_3$) δ: 7.25 (1H, dd, J=9.6 and 8.4 Hz), 7.69 (1H, ddd, J=8.4, 6.9 and 1.2 Hz), 7.79 (1H, ddd, J=8.4, 6.9 and 1.8 Hz), 8.21-8.27 (2H, m), 8.95-8.99 (1H, m).

Reference Example 74

To a mixture of 1-fluoronaphthalene (2.50 g), aluminum chloride (2.74 g), and dichloromethane (13 mL) was added mixture of acetyl chloride (1.22 mL) and dichloromethane (2.0 mL) at 0° C. for 15 minutes. The temperature was elevated to room temperature and the mixture was stirred for 4 hours. The reactant was poured into water and extracted with hexane. The extracts were washed with a sodium carbonate solution and brine, dried and concentrated. The obtained residue was purified by silica gel column chromatography to obtain 1-(4-fluoro-1-naphthyl)ethanone (1.20 g).

$^1$H-NMR (300 MHz, CDCl$_3$) δ: 2.73 (3H, s), 7.15 (1H, dd, J=9.9 and 8.1 Hz), 7.56-7.69 (2H, m), 7.96 (1H, dd, J=8.1 and 5.4 Hz), 8.13-8.16 (1H, m), 8.86-8.90 (1H, m).

Reference Example 75

To a mixture of 4-fluoro-1-naphthonitrile (865 mg) and N,N-dimethylacetamide (5.0 mL) was added hydrazine monohydrate (0.45 mL), and the mixture was stirred at 30° C. for 40 minutes. Water was added to the reactant and the produced precipitate was taken by filtration. After washing with water, the precipitate was dissolved in ethyl acetate, dried and concentrated to obtain 4-hydrazino-1-naphthonitrile (530 mg).

$^1$H-NMR (300 MHz, DMSO-d$_6$) δ: 4.47 (2H, br.s), 7.05 (1H, d, J=8.4 Hz), 7.49 (1H, ddd, J=8.1, 6.9 and 1.5 Hz), 7.66 (1H, ddd, J=8.1, 6.9 and 1.5 Hz), 7.86 (1H, d, J=8.4 Hz), 7.89-7.92 (1H, m), 8.23-8.26 (1H, m), 8.59 (1H, br.s).

IR (KBr) 3312, 2205, 1578 cm$^{-1}$

Reference Example 76

To a mixture of 2-bromo-5-fluorophenol (10.3 g), potassium carbonate (11.2 g), and N,N-dimethylformamide (60 mL) was added a mixture of propargyl bromide (8.64 g) and N,N-dimethylformamide (6 mL) at room temperature for 10 minutes. After stirring for 2 hours, the mixture was poured into water and extracted with hexane. The extracts were washed with water, dried and concentrated. The obtained residue was purified by silica gel column chromatography to obtain 1-bromo-4-fluoro-2-(2-propynyloxy)benzene (9.27 g).

$^1$H-NMR (300 MHz, CDCl$_3$) δ: 2.58 (1H, t, J=2.4 Hz), 4.77 (2H, d, J=2.4 Hz), 6.64 (1H, ddd, J=8.7, 7.8 and 2.7 Hz), 6.84 (1H, dd, J=10.5 and 2.7 Hz), 7.49 (1H, dd, J=8.7 and 6.3 Hz).

Reference Example 77

A mixture of 1-bromo-4-fluoro-2-(2-propynyloxy)benzene (9.00 g), cesium carbonate (8.36 g), and diethylaniline (60 mL) was stirred at 240° C. for 2.5 hours. The mixture was cooled to room temperature, diluted with diethyl ether, washed with 1 N hydrochloric acid and brine, dried and concentrated. The obtained residue was purified by silica gel column chromatography to obtain 7-bromo-4-fluoro-2-methyl-1-benzofuran (7.06 g).

$^1$H-NMR (300 MHz, CDCl$_3$) δ: 2.50 (3H, d, J=0.9 Hz), 6.52 (1H, q, J=0.9 Hz), 6.79 (1H, t, J=8.7 Hz), 7.26 (1H, dd, J=8.7 and 4.8 Hz).

Reference Example 78

A mixture of 7-bromo-4-fluoro-2-methyl-1-benzofuran (4.50 g), zinc cyanide (1.38 g), tetrakis(triphenylphosphine) palladium(0) (2.27 g) and N,N-dimethylformamide (120 mL) was stirred at 100° C. for 2.5 hours under argon atmosphere. After cooling to room temperature, the reactant was poured into water and extracted with ethyl acetate. Insolubles were filtered off using celite. The organic layer was washed with brine, dried and concentrated. The obtained residue was purified by silica gel column chromatography to obtain 4-fluoro-2-methyl-1-benzofuran-7-carbonitrile (3.34 g).

$^1$H-NMR (300 MHz, CDCl$_3$) δ: 2.53 (3H, d, J=0.9 Hz), 6.55 (1H, q, J=0.9 Hz), 6.97 (1H, t, J=8.7 Hz), 7.49 (1H, dd, J=8.7 and 4.8 Hz).

IR (KBr) 2234, 1605, 1505 cm$^{-1}$

Reference Example 79

To a mixture of benzyl 3-hydroxy-1-pyrrolidine carboxylate (5.00 g) and pyridine (50 mL) was added p-toluenesulfonyl chloride (4.74 g) at 0° C. After the mixture was stirred at room temperature for 20 hours, the reactant was poured into water and extracted with ethyl acetate. The extracts were washed with 1 N hydrochloric acid, a sodium hydrogen carbonate solution and brine, dried and concentrated. The obtained residue was purified by silica gel column chromatography to obtain benzyl 3-[[(4-methylphenyl)sulfonyl]oxy]-1-pyrrolidine carboxylate (4.98 g).

$^1$H-NMR (300 MHz, CDCl$_3$) δ: 1.95-2.24 (2H, m), 2.45 (3H, d, J=2.7 Hz), 3.45-3.64 (4H, m), 5.05-5.12 (3H, m), 7.33-7.36 (7H, m), 7.77-7.80 (2H, m).

Reference Example 80

A mixture of benzyl 3-[[(4-methylphenyl)sulfonyl]oxy]-1-pyrrolidine carboxylate (3.92 g), potassium fluoride (3.64 g), and ethylene glycol (16 mL) was stirred at 85° C. for 24 hours under argon atmosphere. After cooling to room temperature, the reactant was poured into water and extracted with ethyl acetate. The extracts were washed with water, dried and concentrated. The obtained residue was purified by silica gel column chromatography to obtain benzyl 3-fluoro-1-pyrrolidine carboxylate (1.32 g).

$^1$H-NMR (300 MHz, CDCl$_3$) δ: 1.88-2.32 (2H, m), 3.44-3.85 (4H, m), 5.12-5.32 (1H, m), 5.14 (2H, s), 7.29-7.37 (5H, m).

Reference Example 81

A mixture of benzyl 3-fluoro-1-pyrrolidine carboxylate (1.32 g), 10% palladium carbon (50% water content, 503 mg), and acetic acid (13 mL) was stirred at room temperature for 2 days under hydrogen atmosphere. Palladium carbon was filtered off using celite and washed with methanol. 4 N Hydrogen chloride-ethyl acetate (4.5 mL) was added to mother liquor, which was concentrated. The obtained residue was washed with diethyl ether to obtain 3-fluoropyrrolidine hydrochloride (711 mg).

$^1$H-NMR (300 MHz, DMSO-d$_6$) δ: 1.95-2.28 (2H, m), 3.15-3.50 (4H, m), 5.43 (1H, dt, J=52.5 and 3.6 Hz), 9.58 (2H, br.s).

Reference Example 82

A mixture of benzyl 3-hydroxy-1-pyrrolidine carboxylate (10.0 g), pyridinium nichromate (14.6 g), and dichloromethane (150 mL) was stirred at room temperature for 3 days. Insolubles were filtered off using celite and washed with dichloromethane. Mother liquor was concentrated, and the obtained residue was purified by silica gel column chromatography to obtain benzyl 3-oxo-1-pyrrolidine carboxylate (4.39 g).

$^1$H-NMR (300 MHz, CDCl$_3$) δ: 2.61 (2H, t, J=7.5 Hz), 3.83-3.89 (4H, m), 5.18 (2H, s), 7.33-7.39 (5H, m).

Reference Example 83

A mixture of benzyl 3-oxo-1-pyrrolidine carboxylate (4.00 g), diethylaminosulfur trifluoride (90%, 10.0 g), and toluene (50 mL) was stirred at room temperature for 4 days. The reactant was poured into water and extracted with ethyl acetate. The extracts were washed with water, dried and concentrated. The obtained residue was purified by silica gel column chromatography to obtain benzyl 3,3-difluoro-1-pyrrolidine carboxylate (3.23 g).

$^1$H-NMR (300 MHz, CDCl$_3$) δ: 2.27-2.41 (2H, m), 3.62-3.80 (4H, m), 5.15 (2H, s), 7.32-7.38 (5H, m).

Reference Example 84

A mixture of benzyl 3,3-difluoro-1-pyrrolidine carboxylate (3.00 g), 10% palladium carbon (50% water content, 1.06 g), and acetic acid (30 mL) was stirred under hydrogen atmosphere at room temperature for 2 days. Palladium carbon was filtered off using celite and washed with methanol. 4 N Hydrogen chloride-ethyl acetate (5.0 mL) was added to mother liquor, which was concentrated. The obtained residue was washed with ethyl acetate to obtain 3,3-difluoropyrrolidine hydrochloride (1.65 g).

$^1$H-NMR (200 MHz, DMSO-d$_6$) δ: 2.37-2.59 (2H, m), 3.42 (2H, t, J=7.6 Hz), 3.63 (2H, t, J=12.4 Hz).

Reference Example 85

A mixture of [1-(tert-butoxycarbonyl)-4-piperidinyl]acetic acid (500 mg), ethyl iodide (385 mg), potassium carbonate (926 mg), and N,N-dimethylformamide (5.0 mL) was stirred at room temperature for 3 hours. The reactant was poured into water and extracted with ethyl acetate. The extracts were washed with water, dried and concentrated. The obtained residue was purified by silica gel column chromatography to obtain tert-butyl 4-(2-ethoxy-2-oxoethyl)-1-piperidinecarboxylate (558 mg).

$^1$H-NMR (300 MHz, CDCl$_3$) δ: 1.08-1.22 (2H, m), 1.26 (3H, t, J=7.2 Hz), 1.45 (9H, s), 1.66-1.71 (2H, m), 1.86-2.00 (1H, m), 2.23 (2H, d, J=7.2 Hz), 2.67-2.76 (2H, m), 4.00-4.16 (4H, m).

Reference Example 86

A mixture of 4-bromo-1-naphthaldehyde (1.00 g), hydroxylamine hydrochloride (355 mg), sodium acetate (523 mg), ethanol (16 mL), and water (8.0 mL) was stirred at room temperature for 2 hours. The reaction solution was concentrated and the residue was distributed between ethyl acetate and water. The organic layer was washed with brine, dried and concentrated. The obtained residue was purified by silica gel column chromatography to obtain 4-bromo-1-naphthaldehyde oxime (1.05 g). 4 N hydrogen chloride-ethyl acetate (0.96 mL) and OXONE (2.36 g) were added to a mixture of the obtained material (800 mg) and N,N-dimethylformamide (8.0 mL), and the mixture was stirred at room temperature for 20 hours. The reaction solution was poured into water, and extracted with ethyl acetate. The extracts were sequentially washed with 0.5 N hydrochloric acid and water, dried and concentrated. The residue was purified by silica gel column chromatography to obtain 4-bromo-N-hydroxynaphthalene-1-carboxyimidoyl chloride (660 mg).

$^1$H-NMR (300 MHz, CDCl$_3$) δ: 7.54 (1H, d, J=7.8 Hz), 7.60-7.68 (2H, m), 7.83 (1H, d, J=7.8 Hz), 8.12 (1H, s), 8.21-8.24 (1H, m), 8.30-8.33 (1H, m).

Reference Example 87

To a mixture of methyl acetoacetate (10.0 g), potassium carbonate (29.8 g), and acetone (145 mL) was added 1,2-dibromoethane (21.0 g) at room temperature, and the mixture was heated under reflux for 8 hours. The reactant was concentrated after cooling to room temperature. The obtained residue was purified by silica gel column chromatography to obtain methyl 1-acetylcyclopropanecarboxylate (1.90 g).

¹H-NMR (300 MHz, CDCl₃) δ: 1.49 (4H, s), 2.47 (3H, s), 3.75 (3H, s).

Reference Example 88

A mixture of methyl 1-acetylcyclopropanecarboxylate (1.40 g), [(1S)-1-phenylethyl]amine (1.26 mL), and toluene (18 mL) was heated under reflux for 12 hours. The reactant was concentrated after cooling to room temperature. The obtained residue was purified by silica gel column chromatography to obtain methyl 2-methyl-1-[(1S)-1-phenylethyl]-4,5-dihydro-1H-pyrrole-3-carboxylate (1.29 g).
¹H-NMR (300 MHz, CDCl₃) δ: 1.54 (3H, d, J=7.2 Hz), 2.33 (3H, s), 2.64-2.72 (2H, m), 3.10-3.20 (1H, m), 3.37-3.48 (1H, m), 3.63 (3H, s), 4.88 (1H, q, J=7.2 Hz), 7.21-7.38 (5H, m).

Reference Example 89

To a mixture of sodium triacetoxyhydroborate (2.02 g), acetic acid (4.7 mL), and acetonitrile (4.7 mL) was added at 0° C. a mixture of methyl 2-methyl-1-[(1S)-1-phenylethyl]-4,5-dihydro-1H-pyrrole-3-carboxylate (780 mg) and acetonitrile (1.7 mL), and the mixture was stirred for 3 hours. The reactant was poured into a sodium carbonate solution and extracted with ethyl acetate. The extracts were sequentially washed with a sodium carbonate solution and brine, dried and concentrated to obtain methyl (2S,3S)-2-methyl-1-[(1S)-1-phenylethyl]pyrrolidine-3-carboxylate (778 mg).
$[\alpha]_D$=−28.4° (c=2.08, EtOH).
¹H-NMR (300 MHz, CDCl₃) δ: 0.79 (3H, d, J=6.3 Hz), 1.35 (3H, d, J=6.9 Hz), 1.82-1.93 (1H, m), 2.11-2.24 (1H, m), 2.54 (1H, t, J=7.2 Hz), 2.70 (1H, td, J=9.3 and 3.9 Hz), 3.02-3.15 (1H, m), 3.44-3.62 (2H, m), 3.67 (3H, s), 7.21-7.36 (5H, m).

Reference Example 90

To a mixture of (2S,3S)-2-methyl-1-[(1S)-1-phenylethyl]pyrrolidine-3-carboxylate (1.04 g) and tetrahydrofuran (11 mL) was added lithium aluminum hydride (160 mg) at 0° C., and the mixture was stirred for 3 hours. Water (0.16 mL), a 25% potassium hydroxide solution (0.16 mL) and water (0.48 mL) was sequentially added and the resulting mixture was stirred at room temperature for 16 hours. Insolubles were filtered off using celite and mother liquor was concentrated to obtain [(2S,3S)-2-methyl-1-[(1S)-1-phenylethyl]pyrrolidin-3-yl]methanol (920 mg). The obtained compound was used in the next reaction without further purification.
¹H-NMR (300 MHz, CDCl₃) δ: 1.14 (3H, d, J=6.3 Hz), 1.29 (3H, d, J=6.9 Hz), 1.67-1.79 (1H, m), 1.85-1.97 (1H, m), 2.04-2.09 (1H, m), 2.36-2.46 (1H, m), 2.62 (1H, td, J=9.9 and 3.6 Hz), 2.87-2.95 (1H, m), 3.47 (1H, dd, J=9.9 and 3.3 Hz), 3.86-3.99 (2H, m), 7.22-7.33 (5H, m).

Reference Example 91

10% palladium carbon (50% water content, 895 mg) was washed with methanol and suspended in methanol (15 mL). [(2S,3S)-2-methyl-1-[(1S)-1-phenylethyl]pyrrolidin-3-yl]methanol (920 mg) was added thereto, and the mixture was stirred at room temperature for 24 hours under hydrogen atmosphere. Palladium carbon was filtered off using celite and washed with methanol. Mother liquor was concentrated to obtain (2S,3S)-3-hydroxymethyl-2-methylpyrrolidine (483 mg). The obtained compound was used in the next reaction without further purification.

¹H-NMR (300 MHz, CDCl₃) δ: 1.23 (3H, d, J=6.6 Hz), 1.76-1.87 (1H, m), 1.96-2.10 (2H, m), 2.82-2.90 (1H, m), 3.06-3.23 (2H, m), 3.56 (1H, dd, J=10.2 and 4.2 Hz), 3.81 (1H, dd, J=10.2 and 4.2 Hz).

Reference Example 92

To a mixture of Boc-L-alanine (20.0 g), meldrum's acid (16.0 g), 4-dimethylaminopyridine (29.7 g), and dichloromethane (460 mL) was added a mixture of isopropenyl chloroformate (12.5 mL) and dichloromethane (40 mL) at −5° C. for 1 hour, and the mixture was stirred for 3 hours. A 5% potassium hydrogensulfate solution (500 mL) at 0° C. was added, and the mixture was distributed. The organic layer was washed with brine, dried and concentrated to obtain a yellow oily matter. A mixture of the obtained matter and ethyl acetate (500 mL) was heated under reflux for 30 minutes. After cooling to room temperature, the mixture was extracted with a 5% sodium hydrogen carbonate solution (500 mL). The extracts were adjusted to about pH 3 with citric acid and extracted with ethyl acetate. The extracts were washed with brine, dried and concentrated. The obtained residue was washed with ethyl acetate to obtain tert-butyl (2S)-3-hydroxy-2-methyl-5-oxo-2,5-dihydro-1H-pyrrole-1-carboxylate (15.2 g).
$[\alpha]_D$=+86.8° (c=0.515, MeOH).
¹H-NMR (300 MHz, CDCl₃) δ: 1.51 (3H, d, J=6.9 Hz), 1.56 (9H, s), 3.15-3.31 (2H, m), 4.42 (1H, qd, J=6.9 and 0.9 Hz).

Reference Example 93

To a mixture of tert-butyl (2S)-3-hydroxy-2-methyl-5-oxo-2,5-dihydro-1H-pyrrole-1-carboxylate (15.0 g), acetic acid (35 mL), and dichloromethane (70 mL) was added sodium tetrahydroborate (985 mg) at 0° C. for 1 hour and the mixture was stirred for 20 hours. Water was added thereto, the mixture was stirred at 0° C. for 10 minutes and the organic layer was separated. The organic layer was washed with brine, dried and concentrated to obtain a pale yellow oily matter. To a mixture of the obtained oily matter, acetic acid (4.7 mL), and dichloromethane (70 mL) was added sodium tetrahydroborate (985 mg) at 0° C. for 1 hour and the mixture was stirred for 20 hours. Water was added thereto, the mixture was stirred at 0° C. for 10 minutes and the organic layer was separated. The organic layer was washed with brine, dried and concentrated. The obtained residue was washed with a mixed solution of diisopropyl ether and hexane to obtain tert-butyl (2S,3S)-3-hydroxy-2-methyl-5-oxopyrrolidine-1-carboxylate (2.25 g).
$[\alpha]_D$=−24.6° (c=0.735, MeOH).
¹H-NMR (300 MHz, CDCl₃) δ: 1.33 (3H, d, J=6.6 Hz), 1.53 (9H, s), 2.58 (1H, dd, J=17.1 and 9.0 Hz), 2.72 (1H, dd, J=17.1 and 7.8 Hz), 4.26 (1H, qui, J=6.6 Hz), 4.47-4.54 (1H, m).

Reference Example 94

To trifluoroacetic acid (4.0 mL) was added tert-butyl (2S,3S)-3-hydroxy-2-methyl-5-oxopyrrolidine-1-carboxylate (3.00 g) at 0° C. and the mixture was stirred at room temperature for 15 minutes. The reactant was concentrated and tetrahydrofuran (5.0 mL) was added to the residue. The obtained mixture was neutralized with potassium carbonate and insolubles were filtered off using celite. The mixture was concentrated to obtain a colorless solid matter (1.56 g). A mixture of the solid matter and tetrahydrofuran (13 mL) was added to a mixture of lithium aluminum hydride (1.29 g) and tetrahydrofuran (35 mL) at room temperature for 15 minutes and the mixture was stirred at 70° C. for 24 hours. After cooling to 0° C., water (1.3 mL), a 25% potassium hydroxide solution (1.3 mL) and water (4.0 mL) were sequentially added and the mixture was stirred at room temperature 1.5 hours. Insolubles were filtered off using celite. Mother liquor was concentrated. To the obtained residue was added tetrahydrofuran (13 mL), and then the obtained mixture was added to a mixture of lithium aluminum hydride (1.03 g) and tetrahydrofuran (35 mL) at room temperature for 15 minutes and the mixture was stirred at 70° C. for 18 hours. After cooling to 0° C., water (1.0 mL), a 25% potassium hydroxide solution (1.0 mL), and water (3.0 mL) were sequentially added, and the mixture was stirred at room temperature for 1.5 hours. Insolubles were filtered off using celite. Mother liquor was concentrated to obtain (2S,3S)-3-hydroxy-2-methylpyrrolidine (1.19 g). The obtained compound was used in the next reaction without further purification.

$^1$H-NMR (300 MHz, DMSO-$d_6$) δ: 0.99 (3H, d, J=6.6 Hz), 1.50-1.60 (1H, m), 1.78-1.89 (1H, m), 2.49-2.66 (2H, m), 2.89-2.97 (1H, m), 3.83-3.87 (1H, m).

Reference Example 95

To a mixture of Boc-D-alanine (4.78 g), meldrum's acid (3.78 g), 4-dimethylaminopyridine (7.02 g), and dichloromethane (120 mL) was added a mixture of isopropenyl chloroformate (2.95 mL) and dichloromethane (10 mL) at −5° C. for 1 hour, and the mixture was stirred for 3 hours. A 5% potassium hydrogensulfate solution (100 mL) at 0° C. was added thereto, and the mixture was distributed. The organic layer was washed with brine, dried and concentrated to obtain a yellow oily matter. A mixture of the obtained matter and ethyl acetate (120 mL) was heated under reflux for 30 minutes. After cooling to room temperature, the mixture was extracted with a 5% sodium hydrogen carbonate solution (100 mL). The extracts were adjusted to about pH 3 with citric acid and extracted with ethyl acetate. The extracts were washed with brine, dried and concentrated, and then the obtained residue was washed with ethyl acetate to obtain tert-butyl (2R)-3-hydroxy-2-methyl-5-oxo-2,5-dihydro-1H-pyrrole-1-carboxylate (3.11 g).

$[α]_D$=−86.5° (c=0.204, MeOH).

$^1$H-NMR (300 MHz, CDCl$_3$) δ: 1.51 (3H, d, J=6.9 Hz), 1.56 (9H, s), 3.15-3.31 (2H, m), 4.42 (1H, qd, J=6.9 and 0.9 Hz).

Reference Example 96

To a mixture of tert-butyl (2R)-3-hydroxy-2-methyl-5-oxo-2,5-dihydro-1H-pyrrole-1-carboxylate (3.00 g), acetic acid (4.7 mL), and dichloromethane (70 mL) was added sodium tetrahydroborate (985 mg) at 0° C. for 1 hour and the mixture was stirred for 20 hours. Water was added thereto, the mixture was stirred at 0° C. for 10 minutes and the organic layer was separated. The organic layer was washed with brine, dried and concentrated to obtain a pale yellow oily matter. To a mixture of the obtained oily matter, acetic acid (4.7 mL), and dichloromethane (70 mL) was added sodium tetrahydroborate (985 mg) at 0° C. for 1 hour and the mixture was stirred for 20 hours. Water was added thereto, the mixture was stirred at 0° C. for 10 minutes and the organic layer was separated. The organic layer was washed with brine, dried and concentrated. The obtained residue was washed with a mixed solution of diisopropyl ether and hexane to obtain tert-butyl (2R,3R)-3-hydroxy-2-methyl-5-oxopyrrolidine-1-carboxylate (2.25 g). $[α]_D$=+24.0° (c=0.515, MeOH).

$^1$H-NMR (300 MHz, CDCl$_3$) δ: 1.33 (3H, d, J=6.6 Hz), 1.53 (9H, s), 2.58 (1H, dd, J=17.1 and 9.0 Hz), 2.72 (1H, dd, J=17.1 and 7.8 Hz), 4.26 (1H, qui, J=6.6 Hz), 4.47-4.54 (1H, m).

Reference Example 97

To a mixture of tert-butyl (2R,3R)-3-hydroxy-2-methyl-5-oxopyrrolidine-1-carboxylate (2.20 g) and ethyl acetate (18 mL) was added 4 N hydrogen chloride-ethyl acetate (6.0 mL) and the mixture was stirred at room temperature for 1 hour. The reactant was concentrated to obtain a yellow oily matter. A mixture of the obtained matter and tetrahydrofuran (50 mL) was added to lithium aluminum hydride (1.15 g) at room temperature for 15 minutes and the mixture was stirred at 70° C. for 12 hours. After cooling to 0° C., water (1.0 mL), a 25% potassium hydroxide solution (1.0 mL) and water (3.0 mL) were sequentially added and the mixture was stirred at room temperature for 1.5 hours. Insolubles were filtered off using celite. Mother liquor was concentrated to obtain (2R,3R)-3-hydroxy-2-methylpyrrolidine (1.00 g). The obtained compound was used in the next reaction without further purification.

$^1$H-NMR (300 MHz, DMSO-$d_6$) δ: 0.99 (3H, d, J=6.6 Hz), 1.50-1.60 (1H, m), 1.78-1.89 (1H, m), 2.49-2.66 (2H, m), 2.89-2.97 (1H, m), 3.83-3.87 (1H, m).

Reference Example 98

(4R)-1-(tert-butoxycarbonyl)-4-hydroxy-D-proline (0.94 g) was dissolved in anhydrous tetrahydrofuran (6 mL). Under stirring with ice-cooling, a 1 M tetrahydrofuran-borane tetrahydrofuran solution (20 mL) was added dropwise and the mixture was stirred for 1 hour. Then, the temperature was returned to room temperature, and the mixture was further stirred for 1 hour. To the reaction solution was added iced water, which was decomposed. Then, saturated brine was added thereto, and the resulting solution was extracted with ethyl acetate. The extracts were washed with brine, dried and concentrated to obtain tert-butyl (2R,4R)-4-hydroxy-2-(hydroxymethyl)pyrrolidine-1-carboxylate (0.99 g) as a colorless oily matter.

$^1$H-NMR (200 MHz, CDCl$_3$) δ: 1.47 (9H, s), 2.20-2.50 (2H, m), 3.30-4.40 (6H, m).

Reference Example and 99

1-benzyl-5-methyl-2-oxopyrrolidine-3-carboxylic acid (2.34 g) was dissolved in N,N-dimethylformamide (40.0 mL), and sodium hydride (60% in oil, 0.99 g) was added thereto with ice-cooling, and the mixture was stirred at room temperature for 1 hour. Methyl iodide (3 mL) was added under ice-cooling and stirring, and the mixture was stirred at room temperature for 16 hours. Water was poured into the reactant and extracted with ethyl acetate. The extracts were washed with water, dried and concentrated. The obtained residue was purified by silica gel column chromatography (ethyl acetate) and crystallized from hexane:ethyl acetate=8:1, to obtain methyl 1-benzyl-3,5-dimethyl-2-oxopyrrolidin-3-carboxylate (1.40 g).

$^1$H-NMR (200 MHz, CDCl$_3$) δ: 1.22 (3H, d, J=6.4 Hz), 1.44 (3H, s), 1.95-2.25 (2H, m), 3.36-3.55 (1H, m), 3.78 (3H, s), 4.00 (1H, d, J=15.0 Hz), 5.00 (1H, d, J=15.0 Hz), 7.22-7.40 (5H, m).

Anal. Calcd. for $C_{15}H_{19}N_2O_3$: C, 68.94; H, 7.33; N, 5.36. Found: C, 68.80; H, 7.08; N, 5.24.

Reference Example 100

While stirring with ice-cooling, lithium aluminum hydride (0.784 g) was suspended in tetrahydrofuran (60 mL), methyl 1-benzyl-3,5-dimethyl-2-oxopyrrolidin-3-carboxylate (2.7 g) was dissolved in tetrahydrofuran (50 mL) and added in small amount. Then the temperature was returned to room temperature, the mixture was stirred for 1 hour and heated under reflux for 20 hours. The reaction solution was ice-cooled, 4 N-sodium hydroxide (20 mL) and water (20 mL) were added, and decomposed. Tetrahydrofuran was added thereto, and decantation was conducted three times. The tetrahydrofuran layer was combined, concentrated and dried. To the residue was added saturated brine, which was extracted with ethyl acetate. The extracts were dried and concentrated. The residue was purified by basic silica gel column chromatography (Chromatorex NH, a product made in Fuji Silysia Chemical Ltd.) to obtain 1-benzyl-4-hydroxymethyl-2,4-dimethylpyrrolidine (1.88 g).

$^1$H-NMR (200 MHz, $CDCl_3$) δ: 0.92 (3H, s), 1.24 (3H, d, J=6.2 Hz), 1.64-1.95 (2H, m), 2.05 (1H, dd, J=2.2 Hz and 9.2 Hz), 2.46-2.68 (1H, m), 2.79 (1H, d, J=9.2 Hz), 2.95 (1H, d, J=12.8 Hz), 3.26 (1H, dd, J=2.2 Hz and 9.4 Hz), 3.43 (1H, d, J=9.4 Hz), 4.05 (1H, d, J=12.8 Hz), 7.20-7.40 (5H, m).

Reference Example 101

(4R)-1-(tert-butoxycarbonyl)-4-hydroxy-D-proline (0.93 g) was dissolved in N,N-dimethylformamide (12.0 mL), sodium hydride (60% in oil, 400 mg) was added thereto with ice-cooling and the mixture was further stirred at room temperature for 0.5 hour. After methyl iodide (1 mL) was added thereto under stirring with ice-cooling, the mixture was stirred at room temperature for 16 hours. Water was poured into the reactant and extracted with ethyl acetate. The extracts were washed with water, dried and concentrated. To the obtained residue was added methyl alcohol (30 mL), and dissolved. 4 N Sodium hydroxide (4 mL) was added thereto, and the mixture was sitrred at room temperature for 3 hours. The reaction solution was concentrated, the aqueous layer was washed with ether, adjusted to pH=2 with potassium hydrogensulfate water and then extracted with ethyl acetate. The extracts were dried and concentrated to obtain (4R)-1-(tert-butoxycarbonyl)-4-methoxy-D-proline (0.85 g). The resulting material was dissolved in anhydrous tetrahydrofuran (6 mL). A 1 M tetrahydrofuran-borane tetrahydrofuran solution (10 mL) was added dropwise thereto under stirring with ice-cooling and the mixture was stirred for 1 hour. Then, the temperature was returned to room temperature, and the mixture was stirred for 2 hours. Iced water was added thereto and distributed. Saturated brine was added and the reaction solution was extracted with ethyl acetate. The extracts were washed with brine, dried and concentrated to obtain tert-butyl (2R,4R)-2-(hydroxymethyl)-4-methoxypyrrolidine-1-carboxylate (0.7 g).

$^1$H-NMR (200 MHz, $CDCl_3$) δ: 1.48 (9H, s), 2.00-2.40 (2H, m), 3.33 (3H, s), 3.40-4.20 (6H, m), 4.30-4.60 (1H, m).

Reference Example 102

To 2-phenylsuccinic acid (3.88 g) was added acetyl chloride (10.0 mL), and the mixture was heated under reflux for 2 hours. After toluene was added to reaction solution, concentrated and dried. The resulting mixture was dissolved in toluene (10 mL), benzylamine (2.2 g) was added, and then the mixture was stirred at room temperature for 15 minutes. Then, acetyl chloride (10 mL) was added and the mixture was heated under reflux for 2 hours. The reaction solution was concentrated. Water was poured into the reactant and extracted with ethyl acetate. The extracts were washed with water, dried and concentrated. The obtained residue was purified by silica gel column chromatography to obtain 1-benzyl-3-phenylpyrrolidine-2,5-dione (4.1 g).

$^1$H-NMR (200 MHz, $CDCl_3$) δ: 2.82 (1H, dd, J=4.8 Hz and J=18.2 Hz), 3.21 (1H, dd, J=9.6 Hz and 18.2 Hz), 4.02 (1H, dd, J=4.8 Hz and 9.6 Hz), 4.60-4.85 (2H, m), 7.10-7.50 (10H, m).

Reference Example 103

With stirring under ice-cooling, lithium aluminum hydride (1.15 g) was suspended in tetrahydrofuran (50 mL), 1-benzyl-3-phenylpyrrolidine-2,5-dione (4.1 g) was dissolved in tetrahydrofuran (30 mL), and added dropwise. Then, the temperature was returned to room temperature, the mixture was stirred for 1 hour and further heated under reflux for 12 hours. After the reaction solution was ice-cooled, 4 N-sodium hydroxide (10 mL) and water (10 mL) were added thereto, and the mixture was distributed. Tetrahydrofuran was added, and the mixture was decanted 3 times. The tetrahydrofuran layer was combined, dried and concentrated. Saturated brine was added to the residue, which was extracted with dichloromethane. The extracts were dried and concentrated. The residue was purified by basic silica gel column chromatography to obtain 1-benzyl-3-phenylpyrrolidine (2.35 g).

$^1$H-NMR (200 MHz, $CDCl_3$) δ: 1.80-2.00 (1H, m), 2.22-2.45 (1H, m), 2.87 (1H, dd, J=1.4 Hz and 7.8 Hz), 2.60-2.92 (2H, m), 3.04 (1H, dd, J=1.4 Hz and 7.8 Hz), 3.28-3.47 (1H, m), 3.62 (2H, s), 7.12-7.40 (10H, m).

Reference Example 104

To D-malic acid (8 g) was added acetyl chloride (25 mL), the mixture was heated under reflux for 2.5 hours and then concentrated and dried. Toluene was added thereto, the mixture was twice concentrated and dried. Toluene (25 ml) was added to the residue, and benzylamine (6.7 g) was added dropwise with stirring under ice-cooling. The temperature was returned to room temperature, and the mixture was agitated for 30 minutes. Then, acetyl chloride (25 mL) was added thereto, the mixture was heated under reflux for 2.5 hours and then concentrated and dried. Toluene was added thereto, the mixture was twice concentrated and dried. The residue was purified by silica gel column chromatography to obtain (3R)-3-acetoxy-1-benzyl-2,5-dioxopyrrolidine (14.9 g).

$^1$H-NMR (200 MHz, $CDCl_3$) δ: 2.16(1H, s), 2.67(1H, dd, J=4.6 Hz and 18.4 Hz), 3.17(1H, d, J=8.8, 18.4 Hz), 4.70(2H, s), 5.45(1H, dd, J=4.4 Hz and 8.8 Hz), 7.28-7.45(5H, m).

Reference Example 105

(3R)-3-acetoxy-1-benzyl-2,5-dioxopyrrolidine (14.9 g) was dissolved in ethyl alcohol (150 mL) and acetyl chloride (8 mL) was added dropwise at room temperature. The mixture was agitated with warming at 50° C. for 4 hours. After ice-cooling, the mixture was concentrated and dried. Toluene was added thereto, which was further concentrated and dried. The residue was crystallized from toluene to obtain (3R)-1-benzyl-3-hydroxypyrrolidine-2,5-dione (7.85 g).

$^1$H-NMR (200 MHz, $CDCl_3$) δ: 2.68(1H, dd, J=4.8 Hz, and 18.2 Hz), 3.06(1H, dd, J=8.4 Hz, and 18.2 Hz), 3.5(1H, d, J=2.8 Hz), 4.52-4.70(1H, m), 4.65(2H, s), 5.45 (1H, dd, J=4.4 Hz and 8.8 Hz), 7.20-7.50(5H, m).

Reference Example 106

(3R)-1-benzyl-3-hydroxypyrrolidine-2,5-dione (19.7 g) was dissolved in diethyl ether (600 mL). Benzyl bromide (49.3 g) and silver (I) oxide (66.8 g) were added thereto, under light shielding, the mixture was agitated at room temperature for 3 days. Insolubles were filtered off and washed with diethyl ether. The filtrate was combined, concentrated and dried. The residue was purified by silica gel column chromatography to obtain (3R)-1-benzyl-3-benzyloxy pyrrolidine-2,5-dione (25.5 g).
$^1$H-NMR (200 MHz, CDCl$_3$) δ: 2.66(1H, dd, J=4.4 Hz and 18.4 Hz), 2.96(1H, dd, J=8.0 Hz and 8.6 Hz), 4.36(1H, dd, J=8.0 Hz and 8.6 Hz), 4.66(2H, s), 4.78(1H, d, J=11.8 Hz), 4.99(1H, d, J=11.8 Hz), 7.20-7.40(10H, m).

Reference Example 107

(3R)-1-benzyl-3-benzyloxy pyrrolidine-2,5-dione (12 g) was dissolved in tetrahydrofuran (200 mL), which was cooled to −70° C. under nitrogen atmosphere. 1 M-methyl magnesium bromide (in a THF solution, 100 mL) was added dropwise thereto, the mixture was kept to −70° C. and agitated for 3 hours. To the reaction solution was added an aqueous saturated ammonium chloride solution (200 mL), the resulting mixutre was twice extracted with ethyl acetate and washed with saturated brine. The extracts were dried over anhydrous sodium sulfate, concentrated and then dried. To the residue was added hexane:ethyl acetate=4:1, to obtain (4R)-1-benzyl-4-(benzyloxy)-5-hydroxy-5-methylpyrrolidin-2-one (9.5 g).
$^1$H-NMR (200 MHz, CDCl$_3$) δ: 1.29(3H, s), 2.50-2.80(2H, m), 3.72(1H, s), 3.87(1H, dd, J=4.2 Hz and 5.4 Hz), 4.42(1H, d, 15.4 Hz), 4.57(1H, d, J=11.8 Hz), 4.59(1H, d, 15.4 Hz), 4.70 (1H, d, 11.8 Hz), 7.20-7.45(10H, m).

Reference Example 108

(4R)-1-benzyl-4-(benzyloxy)-5-hydroxy-5-methylpyrrolidin-2-one (12.43 g) was dissolved in dichloromethane (200 mL), triethylsilane (13.93 g) was added thereto, and the mixture was ice-cooled to −70° C. under nitrogen atmosphere. Boron trifluoride ethyl ether complex (6 mL) was added thereto, and the resulting mixture was agitated for 10 minutes. Then, the mixture was further agitated for 1 hour. A saturated sodium hydrogen carbonate solution was added, which was extracted with dichloromethane. The extracts were dried over anhydrous sodium sulfate, concentrated and dried. The residue was purified by silica gel column chromatography to obtain (4R,5S)-1-benzyl-4-(benzyloxy)-5-methylpyrrolidin-2-one (11.3 g).
$^1$H-NMR (200 MHz, CDCl$_3$) δ: 1.14(3H, d, J=6.6 Hz), 2.53(1H, dd, J=3.2 Hz and 17.2 Hz), 2.77(1H, ddd, J=0.8 Hz and 6.6 Hz and 17.2 Hz), 3.56(1H, dq, J=2.6 Hz and 6.6 Hz), 3.79(1H, ddd, J=2.6 Hz and 3.2 Hz and 6.6 Hz), 3.98(1H, d, J=15.4 Hz), 4.42(1H, d, J=11.8 Hz), 4.50(1H, d, J=11.8 Hz), 5.03(1H, d, J=15.4 Hz), 7.10-7.501(10H, m).

Reference Example 109

(4R,5S)-1-benzyl-4-(benzyloxy)-5-methylpyrrolidin-2-one (11.7 g) was dissolved in methyl alcohol (300 mL), 10% palladium carbon (50% water content, 8 g) was added thereto, and the mixture was agitated under hydrogen atmosphere for 18 hours. The catalyst was filtered off and the filtrate was concentrated and dried. The residue was purified by silica gel column chromatography to obtain (4R,5S)-1-benzyl-4-(hydroxy)-5-methylpyrrolidin-2-one (7.48 g).
$^1$H-NMR (200 MHz, CDCl$_3$) δ: 1.14(3H, d, J=6.6), 2.11 (1H, d, J=4.4 Hz), 2.40(1H, dd, J=3.2 Hz and 17.2 Hz), 2.81(1H, ddd, J=1.0 Hz and 6.6 Hz and 17.2 Hz), 3.38(1H, m), 3.98(1H, d, J=15.0 Hz), 4.00-4.15(1H, m), 4.99(1H, d, J=15.0 Hz), 7.15-7.40(5H, m).

Reference Example 110

Lithium aluminum hydride (6.9 g) was suspended in tetrahydrofuran (containing a stabilizing agent, 100 mL) and (4R,5S)-1-benzyl-4-(hydroxy)-5-methylpyrrolidin-2-one (12.4 g) was dissolved in tetrahydrofuran (100 mL). The resulting solution was added dropwise at room temperature and heated under reflux for 4.5 hours. While agitating the reaction solution with ice-cooling, an aqueous 4 N-sodium hydroxide solution (75 mL) was added dropwise (reacted severely), further water (50 mL) was added, and the mixture was agitated for 30 minutes. Decant was conducted to separate the tetrahydrofuran layer and tetrahydrofuran (containing a stabilizing agent) was added to the residue to repeatedly conduct decantation three times. The tetrahydrofuran solution was combined and concentrated. Dichloromethane was added to the residue, and the mixture was twice extracted and washed with saturated brine. The extracts were dried over anhydrous sodium sulfate, concentrated and dried. The residue was purified by basic silica gel column chromatography to obtain (2S,3R)-1-benzyl-2-methylpyrrolidin-3-ol (10.1 g).
$[α]_D$ +68.61° (C=3.0, CHCl$_3$).
$^1$H-NMR (200 MHz, CDCl$_3$) δ: 1.14(3H, d, J=6.6 Hz), 2.11(1H, d, J=4.4 Hz), 2.40(1H, dd, J=3.2 Hz and 17.2 Hz), 2.81(1H, ddd, J=1.0 Hz and 6.6 Hz and 17.2 Hz), 3.38(1H, m), 3.98(1H, d, J=15.0 Hz), 4.00-4.15(1H, m), 4.99(1H, d, J=15.0 Hz), 7.15-7.40(5H, m).

Reference Example 111

Ethyl (diethoxy phosphoryl) acetate (3.54 g) was dissolved in anhydrous tetrahydrofuran (20 mL), and sodium hydride (60% in oil, 0.63 g) was added with stirring under ice-cooling. The temperature was returned to room temperature and the mixture was stirred for 10 minutes. Then, after tert-butyl 3-oxopyrrolidine-1-carboxylate (1.47 g) was dissolved in anhydrous tetrahydrofuran (6 mL) and added with stirring under ice-cooling, the mixture was stirred at room temperature for 1.5 hours. Water was poured into the reactant, and adjusted to pH=2 with potassium hydrogensulfate water and extracted with ethyl acetate. The extracts were washed with water, dried and concentrated. The obtained residue was purified by silica gel column chromatography (hexane:ethyl=2:1) to obtain a mixture of tert-butyl 3-(2-ethoxy-2-oxoethylidene)pyrrolidine-1-carboxylate and tert-butyl 3-(2-ethoxy-2-oxoethyl)-2,5-dihydro-1H-pyrrole-1-carboxylate (1.78 g). Total amount of the mixture was dissolved in methyl alcohol (50 mL), 10% palladium carbon (containing water) (0.9 g) was added thereto, and the mixture was stirred under hydrogen atmosphere for 11 hours. The catalyst was filtered off and the filtrate was concentrated and dried to obtain tert-butyl 3-(2-ethoxy-2-oxoethy)pyrrolidine-1-carboxylate (1.75 g).
$^1$H-NMR (200 MHz, CDCl$_3$) δ: 1.27(3H, t, J=7.2 Hz), 1.38-1.68(1H, m), 1.46(9H, s), 1.96-2.18(1H, m), 2.34-2.43 (2H, m), 2.44-2.68(1H, m), 2.84-3.04(1H, m), 3.16-3.68(3H, m), 4.14 (2H, q, J=7.2 Hz).

Reference Example 112

To dimethylsulfoxide (20 mL) was added sodium hydride (60% in oil, 0.6 g) at room temperature, the mixture was kept to 55° C. and stirred for 1 hour. Ethyl (triphenyl)phosphonium bromide (5.57 g) was added and the mixture was stirred at 55° C. for 45 minutes. The reaction solution was returned to room temperature, and tert-butyl (2R)-2-formylpyrrolidine-1-carboxylate (2 g) was dissolved in dimethyl sulfoxide (4 mL), added, and the mixture was stirred for 16 hours. Iced water was poured into the reactant, and extracted with ethyl acetate. The extracts were washed with water, dried and concentrated. The obtained residue was purified by silica gel column chromatography to obtain tert-butyl 2-[(1E)-prop-1-enyl]pyrrolidine-1-carboxylate (1.6 g).
$^1$H-NMR (200 MHz, CDCl$_3$) δ: 1.44(9H, s), 1.50-2.20(7H, m), 3.30-3.50(2H, m), 4.10-4.65(1H, m), 5.20-5.60(2H, m).

Reference Example 113

Methyl-(2S,3S)-2-methyl-1-[(1S)1-phenylethyl]pyrrolidine-3-carboxylate (1.0 g) was dissolved in dehydrated tetrahydrofuran (10 mL). Under nitrogen atmosphere, the resulting solution was cooled to −50° C., 1 M-methyl magnesium bromide (in a THF solution, 12 mL) was added dropwise. The temperature was returned to room temperature and the mixture was agitated for 3 hours. After an aquoues saturated ammonium chloride solution (8 mL) was added to the reaction solution, and twice extracted with ethyl acetate and washed with saturated brine. After the extract was dried over anhydrous sodium sulfate, the obtained material was concentrated and dried. The residue was purified by basic silica gel column chromatography to obtain 2-[(2S,3S)-2-methyl-1-[(1S)-1-phenylethyl]pyrrolidin-3-yl]propan-2-ol (0.9 g).
$^1$H-NMR (200 MHz, CDCl$_3$) δ: 1.03(3H, d, J=6.6 Hz), 1.21(3H, s), 1.32(3H, s), 1.33(3H, d, J=6.6 Hz), 1.60-1.90 (3H, m), 2.05-2.25(1H, m), 2.40-2.64(2H, m), 3.30-3.70(2H, m), 7.15-7.40(5H, m).

Reference Example 114

Benzyl 1-acetylcyclopropane carboxylate (13 g) and (1R)-1-phenylethylamine (7.6 g) was dissolved in toluene (100 mL) and the obtained solution was heated under reflux for 22 hours with dehydration. After cooling, the mixture was concentrated and the residue was purified by silica gel column chromatography and to obtain benzyl 2-methyl-1-[(1S)-1-phenylethyl]-4,5-dihydro-1H-pyrrole-3-carboxylate (13.2 g).
$^1$H-NMR (200 MHz, CDCl$_3$) δ: 1.55(3H, d, J=6.8 Hz), 2.34(3H, s), 2.65-2.85(2H, m), 3.05-3.55(2H, m), 4.89(1H, q, J=6.8 Hz), 5.15(2H, s), 7.20-7.50(10H, m).

Reference Example 115

Acetic acid (70 mL) was kept to 15 to 20° C., sodium borohydride (4.66 g) was added dropwise and the mixture was stirred at the same temperature for 30 minutes. Acetonitrile (35 mL) was added, and benzyl 2-methyl-1-[(1S)-1-phenylethyl]-4,5-dihydro-1H-pyrrole-3-carboxylate (13.2 g) was dissolved in acetonitrile (35 mL), and added dropwise with stirring under cooling to 5° C. The reactant was kept to 0 to 8° C., and stirred for 3 hours. After the reaction solution was concentrated and dried, the residue was alkalified with saturated sodium carbonate water. The resulting residue was twice extracted with ethyl acetate and washed with saturated brine. The extracts were dried over anhydrous sodium sulfate, concentrated and dried. The residue was purified by basic silica gel column chromatography to obtain benzyl (2S,3S)-2-methyl-1-[(1S)-1-phenylethyl]pyrrolidine-3-carboxylate (11.7 g).
$^1$H-NMR (200 MHz, CDCl$_3$) δ: 0.78(3H, d, J=6.6 Hz), 1.33(3H, d, J=6.6 Hz), 1.80-2.35(2H, m), 2.45-2.85(2H, m), 3.00-3.22(1H, m), 3.40-3.70(2H, m), 5.00-5.20(2H, m), 7.20-7.40(10H, m).

Reference Example 116

Benzyl (2S,3S)-2-methyl-1-[(1S)-1-phenylethyl]pyrrolidine-3-carboxylate (11.7 g) was dissolved in methyl alcohol (100 mL), 10% palladium carbon (containing water) (3.0 g) was added thereto, and the mixture was stirred under hydrogen atmosphere for 16 hours. The catalyst was filtered off and the filtrate was concentrated and dried. The residue was crystallized from acetone to obtain (2S,3S)-2-methylpyrrolidine-3-carboxylic acid (4.77 g). The obtained compound (2.0 g) was dissolved in water (40 mL), sodium carbonate (2.65 g) and acetone (10 mL) were added thereto, and then di-t-butyl dicarbonate (5.07 g) was added, and the mixture was stirred at room temperature for 16 hours. Acetone was distilled off, water was added, and adjusted to pH=2 with potassium hydrogensulfate and extracted with ethyl acetate. The extracts were washed with water, dried and concentrated. The obtained residue was crystallized from hexane to obtain (2S,3S)-1-(tert-butoxycarbonyl)-2-methylpyrrolidine-3-carboxylic acid (3.19 g).
$[α]_D$=+13.3° (c=0.328, MeOH).
$^1$H-NMR (200 MHz, CDCl$_3$) δ: 1.13(3H, d, J=6.6 Hz), 1.47(9H, s), 1.95-2.40(2H, m), 3.00-3.60(3H, m), 4.05-4.40 (1H, m).

Reference Example 117

(2S,3S)-1-(tert-butoxycarbonyl)-2-methylpyrrolidine-3-carboxylic acid (0.917 g) was dissolved in dioxane (20 mL), pyridine (0.2 mL) was added and then di-t-butyl carbonate (1.14 g) was added. The mixture was stirred for 10 minutes. Ammonium carbonate (0.4 g) was added thereto, and the reactant was stirred at room temperature for 20 hours. After dioxane was distilled off, water was added, and adjusted to pH=2 with potassium hydrogensulfate and extracted with ethyl acetate. The extracts were washed with water, dried and concentrated to obtain tert-butyl (2S,3S)-3-(aminocarbonyl)-2-methylpyrrolidine-1-carboxylate (0.76 g).
$^1$H-NMR (200 MHz, CDCl$_3$) δ: 1.12(3H, d, J=6.6 Hz), 1.46(9H, s), 1.90-2.45(2H, m), 2.85-3.10(1H, m), 3.20-3.60 (2H, m), 4.10-4.30(1H, m), 4.45(1H, br.s), 5.10(1H, br.s).

Example 1 (Preparation of Compound 1)

To a mixture of 4-amino-1-naphthonitrile (1.75 g) and N,N-dimethylformamide (20 mL) was added sodium hydride (60% in oil, 1.25 g) at room temperature, and the mixture was stirred for 20 minutes. After adding 1,4-dibromobutane (2.24 g), the mixture was stirred at 50° C. for 15 hours. The reactant was poured into water and extracted with ethyl acetate. The extracts were washed with water, dried and concentrated. The obtained residue was purified by silica gel column chromatography to obtain 4-(1-pyrrolidinyl)-1-naphthonitrile (1.76 g) (Compound 1).
mp 109-110° C.
$^1$H-NMR (200 MHz, CDCl$_3$) δ: 2.01-2.08 (4H, m), 3.59-3.66 (4H, m), 6.69 (1H, d, J=8.4 Hz), 7.39-7.48 (1H, m), 7.55-7.62 (1H, m), 7.72 (1H, d, J=8.0 Hz), 8.13-8.17 (1H, m), 8.26 (1H, d, J=8.2 Hz).

IR (KBr) 2203, 1563, 1518 cm$^{-1}$
Anal. Calcd. for $C_{15}H_{14}N_2$: C, 81.05; H, 6.35; N, 12.60. Found: C, 80.99; H, 6.33; N, 12.47.

Example 2 (Preparation of Compound 2)

A mixture of 4-(1-pyrrolidinyl)-1-naphthonitrile (1.76 g), a 2 N potassium hydroxide solution (2.7 mL), and ethanol (2.7 mL) was stirred at 100° C. for 2 days. Insolubles were filtered off and the filtrate was washed with water. Washing liquid and mother liquor were combined, and acidified with 1 N hydrochloric acid and extracted with ethyl acetate. The extracts were washed with brine, dried and concentrated to obtain 4-(1-pyrrolidinyl)-1-naphthoic acid (17 mg) (Compound 2).
mp 194° C. (dec).
$^1$H-NMR (200 MHz, DMSO-d$_6$) δ: 1.94-2.00 (4H, m), 3.48-3.54 (4H, m), 6.82 (1H, d, J=8.4 Hz), 7.38-7.47 (1H, m), 7.50-7.58 (1H, m), 8.09 (1H, d, J=8.4 Hz), 8.22-8.26 (1H, m), 9.05-9.09 (1H,m), 12.27 (1H, br.s).

Example 3 (Preparation of Compound 3)

To a mixture of 4-amino-1-naphthonitrile (500 mg) and N,N-dimethylformamide (5.5 mL) was added sodium hydride (60% in oil, 346 mg) at room temperature, and the mixture was stirred for 20 minutes. After adding 1,5-dibromopentane (663 mg), the mixture was stirred at 50° C. for 15 hours. The reactant was poured into water and extracted with ethyl acetate. The extracts were washed with water, dried and concentrated. The obtained residue was purified by silica gel column chromatography to obtain 4-(1-piperidinyl)-1-naphthonitrile (597 mg) (Compound 3).
$^1$H-NMR (300 MHz, CDCl$_3$) δ: 1.66-1.73 (2H, m), 1.82-1.90 (4H, m), 3.11-3.14 (4H, m), 6.98 (1H, d, J=8.1 Hz), 7.52-7.58 (1H, m), 7.60-7.66 (1H, m), 7.80 (1H, d, J=8.1 Hz), 8.14-8.19 (2H, m).
IR (KBr) 2938, 2215, 1572 cm$^{-1}$ Example 4 (Preparation of Compound 4)

To 4-(1-piperidinyl)-1-naphthonitrile (130 mg) was added 4N hydrogen chloride-ethyl acetate (1.5 mL), and the mixture was stirred at room temperature for 1 hour. The precipitated compound was filtered off and the filtrate was washed with diethyl ether, to obtain 4-(1-piperidinyl)-1-naphthonitrile hydrochloride (120 mg) (Compound 4).
$^1$H-NMR (300 MHz, DMSO-d$_6$) δ: 1.62-1.67 (2H, m), 1.76-1.84 (4H, m), 3.08-3.11 (2H, m), 7.14 (1H, d, J=7.8 Hz), 7.67 (1H, ddd, J=8.4, 6.6 and 1.2 Hz), 7.75 (1H, ddd, J=8.4, 6.6 and 1.2 Hz), 8.02-8.06 (2H, m), 8.13-8.16 (1H, m).

Example 5 (Preparation of Compound 5)

To a mixture of 4-bromo-1-naphthylamine (500 mg) and N,N-dimethylformamide (6.0 mL) was adde sodium hydride (60% in oil, 262 mg) at room temperature, and the mixture was stirred for 20 minutes. After adding 1,5-dibromopentane (502 mg), the mixture was stirred at 50° C. for 15 hours. The reactant was poured into water and extracted with ethyl acetate. The extracts were washed with water, dried and concentrated. The obtained residue was purified by silica gel column chromatography to obtain 1-(4-bromo-1-naphthyl) piperidine (120 mg) (Compound 5).
$^1$H-NMR (200 MHz, CDCl$_3$) δ: 1.68 (2H, br.s), 1.84 (4H, qui, J=5.4 Hz), 3.03 (4H, br.s), 6.91 (1H, d, J=8.2 Hz), 7.48-7.68 (3H, m), 8.17-8.24 (2H, m).

Example 6 (Preparation of Compound 6)

A mixture of 4-(trifluoromethyl)-1-naphthylamine (200 mg), 1,5-dibromopentane (544 mg), potassium carbonate (654 mg), sodium iodide (710 mg), and N,N-dimethylformamide (3.0 mL) was stirred at 90° C. for 13 hours. After cooling to room temperature, the reactant was poured into water and extracted with ethyl acetate. The extracts were washed with water, dried and concentrated. The obtained residue was purified by silica gel column chromatography to obtain 1-[4-(trifluoromethyl)-1-naphthyl]piperidine (108 mg) (Compound 6).
$^1$H-NMR (300 MHz, CDCl$_3$) δ: 1.68 (2H, br.s), 1.85 (4H, qui, J=5.4 Hz), 3.08 (4H, br.s), 6.99 (1H, d, J=8.1 Hz), 7.50-7.60 (2H, m), 7.75 (1H, dd, J=8.1 and 0.9 Hz), 8.10-8.15 (1H, m), 8.22-8.25 (1H, m).
IR (KBr) 2938, 1582, 1516 cm$^{-1}$ Example 7 (Preparation of Compound 7)

A mixture of 4-fluoro-1-naphthonitrile (100 mg), morpholine (0.10 mL), potassium carbonate (162 mg), and dimethylsulfoxide (1.0 mL) was stirred at 100° C. for 3 hours. After cooling to room temperature, the reactant was poured into water and extracted with ethyl acetate. The extracts were washed with water, dried and concentrated. The obtained residue was purified by silica gel column chromatography to obtain 4-(4-morpholinyl)-1-naphthonitrile (113 mg) (Compound 7).
mp 128-129° C.
$^1$H-NMR (300 MHz, CDCl$_3$) δ: 3.17-3.20 (4H, m), 3.99-4.02 (4H, m), 7.05 (1H, d, J=7.8 Hz), 7.57-7.70 (2H, m), 7.86 (1H, d, J=7.8 Hz), 8.19-8.24 (2H, m).
IR (KBr) 2216, 1574 cm$^{-1}$
Anal. Calcd. for $C_{15}H_{14}N_2O$: C, 75.61; H, 5.92; N, 11.76. Found: C, 75.69; H, 6.15; N, 11.65.

Examle 8 (Preparation of Compound 8)

A mixture 4-fluoro-1-naphthonitrile (500 mg), thiomorpholine (0.57 mL), potassium carbonate (808 mg), and dimethylsulfoxide (5.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain 4-(4-thiomorpholinyl)-1-naphthonitrile (560 mg) (Compound 8).
mp 130-131° C.
$^1$H-NMR (300 MHz, CDCl$_3$) δ: 2.94-2.97 (4H, m), 3.41-3.45 (4H, m), 7.06 (1H, d, J=8.1 Hz), 7.60 (1H, ddd, J=8.4, 6.6 and 1.2 Hz), 7.68 (1H, ddd, J=8.4, 6.6 and 1.2 Hz), 7.85 (1H, d, J=8.1 Hz), 8.13-8.17 (1H, m), 8.20-8.23 (1H, m).
IR (KBr) 2216, 1574 cm$^{-1}$
Anal. Calcd. for $C_{15}H_{14}N_2S$: C, 70.83; H, 5.55; N, 11.01. Found: C, 70.84; H, 5.60; N, 10.87.

Example 9 (Preparation of Compound 9)

To a mixture of 4-(4-thiomorpholinyl)-1-naphthonitrile (500 mg) and dichloromethane (3.0 mL) was added at −78° C. a mixture of m-chloroperbenzoic acid (70%, 242 mg) and dichloromethane (3.0 mL), and the mixture was stirred for 1 hour. After adding a sodium sulfite solution, the temperature was elevated to room temperature, and the resulting mixture was extracted with ethyl acetate. The extracts were washed with sodium carbonate solution, brine, dried and concentrated. The obtained residue was purified by silica gel column chromatography to obtain 4-(1-oxide-4-thiomorpholinyl)-1-naphthonitrile (239 mg) (Compound 9).

mp 183-184° C.

$^1$H-NMR (300 MHz, CDCl$_3$) δ: 3.11-3.14 (4H, m), 3.34-3.40 (2H, m), 3.85-3.93 (2H, m), 7.18 (1H, d, J=8.1 Hz), 7.62 (1H, ddd, J=8.1, 6.6 and 1.2 Hz), 7.70 (1H, ddd, J=8.1, 6.6 and 1.2 Hz), 7.87 (1H, d, J=8.1 Hz), 8.10-8.13 (1H, m), 8.22-8.25 (1H, m).

IR (KBr) 2218, 1574 cm$^{-1}$

Anal. Calcd. for C$_{15}$H$_{14}$N$_2$OS: C, 66.64; H, 5.22; N, 10.36. Found: C, 66.63; H, 4.98; N, 10.21.

Example 10 (Preparation of Compound 10)

A mixture of 4-fluoro-1-naphthonitrile (100 mg), azepane (116 mg), potassium carbonate (161 mg), and dimethylsulfoxide (1.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain 4-(1-azepaneyl)-1-naphthonitrile (116 mg) (Compound 10).

$^1$H-NMR (300 MHz, CDCl$_3$) δ: 1.77-1.92 (8H, m), 3.40-3.44 (4H, m), 7.02 (1H, d, J=8.1 Hz), 7.52 (1H, ddd, J=8.4, 6.9 and 1.2 Hz), 7.62 (1H, ddd, J=8.4, 6.9 and 1.2 Hz), 7.77 (1H, d, J=8.1 Hz), 8.15-8.18 (1H, m), 8.19-8.23 (1H, m).

IR (KBr) 2930, 2213, 1568 cm$^{-1}$

Example 11 (Preparation of Compound 11)

A mixture of 4-fluoro-1-naphthonitrile (300 mg), 4-hydroxypiperidine (355 mg), potassium carbonate (485 mg), and dimethylsulfoxide (3.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain 4-(4-hydroxy-1-piperidinyl)-1-naphthonitrile (380 mg) (Compound 11).

mp 126-127° C.

$^1$H-NMR (300 MHz, CDCl$_3$) δ: 1.85-1.96 (2H, m), 2.05-2.20 (2H, m), 2.94-3.02 (2H, m), 3.40-3.47 (2H, m), 3.95-4.03 (1H, m), 7.02 (1H, d, J=7.8 Hz), 7.58 (1H, ddd, J=8.1, 6.6 and 1.5 Hz), 7.65 (1H, ddd, J=8.1, 6.6 and 1.5 Hz), 7.81 (1H, d, J=7.8 Hz), 8.13-8.21 (2H, m).

IR (KBr) 2216, 1574 cm$^{-1}$

Anal. Calcd. for C$_{16}$H$_{16}$N$_2$O: C, 76.16; H, 6.39; N, 11.10. Found: C, 76.01; H, 6.29; N, 10.92.

Example 12 (Preparation of Compound 12)

To a mixture of 4-(4-thiomorpholinyl)-1-naphthonitrile (150 mg) and dichloromethane (2.0 mL) was added at −78° C. a mixture of m-chloroperbenzoic acid (70%, 291 mg) and dichloromethane (2.0 mL), and the mixture was stirred for 5 hours with elevating to 0° C. After adding a sodium sulfite solution, the mixture was extracted with ethyl acetate. The extracts were washed with a sodium carbonate solution and brine, dried and concentrated. The obtained residue was purified by silica gel column chromatography to obtain 4-(1,1-dioxide-4-thiomorpholinyl)-1-naphthonitrile (112 mg) (Compound 12).

mp 265° C.(dec).

$^1$H-NMR (300 MHz, CDCl$_3$) δ: 3.36-3.39 (4H, m), 3.68-3.71 (4H, m), 7.17 (1H, d, J=7.8 Hz), 7.65-7.77 (2H, m), 7.89 (1H, d, J=7.8 Hz), 8.11-8.14 (1H, m), 8.25-8.29 (1H, m).

IR (KBr) 2218, 1574 cm$^{-1}$

Anal. Calcd. for C$_{15}$H$_{14}$N$_2$O$_2$S: C, 62.92; H, 4.93; N, 9.78. Found: C, 62.83; H, 5.05; N, 9.71.

Example 13 (Preparation of Compound 13)

A mixture of 4-fluoro-1-naphthonitrile (1.00 g), 1,4-dioxane-8-azaspiro[4,5]decane (1.67 g), potassium carbonate (1.62 g), and dimethylsulfoxide (10 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain 4-(1,4-dioxane-8-azaspiro[4,5]deca-8-yl)-1-naphthonitrile (1.42 g) (Compound 13).

mp 142-143° C.

$^1$H-NMR (300 MHz, CDCl$_3$) δ: 2.02 (4H, t, J=5.7 Hz), 3.26-3.29 (4H, m), 4.04 (4H, s), 7.05 (1H, d, J=7.8 Hz), 7.59 (1H, ddd, J=8.4, 6.9 and 1.5 Hz), 7.65 (1H, ddd, J=8.4, 6.9 and 1.5 Hz), 7.83 (1H, d, J=7.8 Hz), 8.16-8.22 (2H, m).

IR (KBr) 2216, 1574 cm$^{-1}$

Anal. Calcd. for C$_{18}$H$_{18}$N$_2$O$_2$: C, 73.45; H, 6.16; N, 9.52. Found: C, 73.34; H, 6.19; N, 9.40.

Example 14 (Preparation of Compound 14)

A mixture of 4-(1,4-dioxane-8-azaspiro[4,5]deca-8-yl)-1-naphthonitrile (423 mg), p-toluenesulfonic acid monohydrate (410 mg), acetone (17 mL), and water (2.5 mL) was stirred at 75° C. for 3.5 hours. The reaction solution was concentrated and a sodium carbonate solution was added thereto, which was extracted with ethyl acetate. The extracts were washed with brine, dried and concentrated. The obtained residue was purified by silica gel column chromatography to obtain 4-(4-oxo-1-piperidinyl)-1-naphthonitrile (105 mg) (Compound 14).

mp 143-144° C.

$^1$H-NMR (300 MHz, CDCl$_3$) δ: 2.77 (4H, t, J=6.0 Hz), 3.49 (4H, t, J=6.0 Hz), 7.09 (1H, d, J=7.8 Hz), 7.62-7.73 (2H, m), 7.85 (1H, d, J=7.8 Hz), 8.22-8.26 (2H, m).

IR (KBr) 2216, 1717, 1574 cm$^{-1}$

Anal. Calcd. for C$_{16}$H$_{14}$N$_2$O: C, 76.78; H, 5.64; N, 11.19. Found: C, 76.63; H, 5.87; N, 10.98.

Example 15 (Preparation of Compound 15)

A mixture of 4-fluoro-1-naphthonitrile (500 mg), isonipecotamide (749 mg), potassium carbonate (808 mg), and dimethylsulfoxide (5.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain 1-(4-cyano-1-naphthyl)-4-piperidine carboxamide (651 mg) (Compound 15).

mp 249-250° C.

$^1$H-NMR (300 MHz, DMSO-d$_6$) δ: 1.88-1.94 (4H, m), 2.29-2.40 (1H, m), 2.78-2.87 (2H, m), 3.45-3.49 (2H, m), 6.85 (1H, br.s), 7.16 (1H, d, J=7.8 Hz), 7.35 (1H, br.s), 7.68 (1H, ddd, J=8.4, 6.9 and 1.2 Hz), 7.76 (1H, ddd, J=8.4, 6.9 and 1.2 Hz), 8.02-8.06 (2H, m), 8.13-8.16 (1H, m).

IR (KBr) 2211, 1663 cm$^{-1}$

Anal. Calcd. for $C_{17}H_{17}N_3O$: C, 73.10; H, 6.13; N, 15.04. Found: C, 72.92; H, 6.22; N, 14.87.

Example 16 (Preparation of Compound 16)

To a mixture of 4-amino-3-bromo-1-naphthonitrile (250 mg) and N,N-dimethylformamide (3.0 mL) was added sodium hydride (60% in oil, 121 mg) at room temperature, and the mixture was stirred for 20 minutes. After adding 1,5-dibromopentane (233 mg), the resulting mixture was stirred at 50° C. for 15 hours. The reactant was poured into water, and extracted with ethyl acetate. The extracts were washed with water, dried and concentrated. The obtained residue was purified by silica gel column chromatography to obtain 3-bromo-4-(1-piperidinyl)-1-naphthonitrile (198 mg) (Compound 16).

$^1$H-NMR (300 MHz, $CDCl_3$) δ: 1.48-1.90 (6H, m), 3.14 (2H, br), 3.49 (2H, br), 7.59-7.70 (2H, m), 7.80 (1H, s), 8.14-8.17 (1H, m), 8.38-8.43 (1H, m).

IR (KBr) 2934, 2222, 1551 $cm^{-1}$

Example 17 (Preparation of Compound 17)

A mixture of 4-fluoro-1-naphthonitrile (100 mg), 1-methylpiperazine (117 mg), potassium carbonate (161 mg), and dimethylsulfoxide (1.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain 4-(4-methyl-1-piperazinyl)-1-naphthonitrile (100 mg) (Compound 17).

mp 128-129° C.

$^1$H-NMR (300 MHz, $CDCl_3$) δ: 2.43 (3H, s), 2.73 (4H, br.s), 3.22 (4H, br.s), 7.03 (1H, d, J=7.8 Hz), 7.56 (1H, ddd, J=8.4, 6.6 and 1.2 Hz), 7.65 (1H, ddd, J=8.4, 6.6 and 1.2 Hz), 7.83 (1H, d, J=7.8 Hz), 8.16-8.21 (2H, m).

IR (KBr) 2795, 2215, 1574 $cm^{-1}$

Anal. Calcd. for $C_{16}H_{17}N_3$: C, 76.46; H, 6.82; N, 16.72. Found: C, 76.29; H, 6.62; N, 16.48

Example 18 (Preparation of Compound 18)

A mixture of 4-fluoro-1-naphthonitrile (400 mg), 3-hydroxypyrrolidine (467 mg), potassium carbonate (646 mg), and dimethylsulfoxide (4.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain 4-(3-hydroxy-1-pyrrolidinyl)-1-naphthonitrile (447 mg) (Compound 18).

mp 138-139° C.

$^1$H-NMR (300 MHz, $CDCl_3$) δ: 1.93 (1H, d, J=6.6 Hz), 2.08-2.29 (2H, m), 3.49-3.56 (2H, m), 3.84-3.98 (2H, m), 4.62-4.68 (1H, m), 6.73 (1H, d, J=8.1 Hz), 7.46 (1H, ddd, J=8.4, 6.9 and 1.2 Hz), 7.60 (1H, ddd, J=8.4, 6.9 and 1.2 Hz), 7.72 (1H, d, J=8.1 Hz), 8.13-8.16 (1H, m), 8.22-8.25 (1H, m).

IR (KBr) 3434, 2205, 1561 $cm^{-1}$

Anal. Calcd. for $C_{15}H_{14}N_2O$: C, 75.61; H, 5.92; N, 11.76. Found: C, 75.37; H, 5.90; N, 11.57.

Example 19 (Preparation of Compound 19)

A mixture of 4-fluoro-1-naphthonitrile (400 mg), 3-(hydroxymethyl) piperidine (539 mg), potassium carbonate (646 mg), and dimethylsulfoxide (4.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain 4-[3-(hydroxymethyl)-1-piperidinyl]-1-naphthonitrile (560 mg) (Compound 19).

$^1$H-NMR (300 Hz, $CDCl_3$) δ: 1.20-1.32 (1H, m), 1.59 (1H, br.s), 1.86-1.96 (3H, m), 2.09-2.20 (1H, m), 2.66 (1H, t, J=10.5 Hz), 2.77-2.86 (1H, m), 3.38-3.42 (1H, m), 3.54-3.68 (3H, m), 7.01 (1H, d, J=7.8 Hz), 7.56 (1H, ddd, J=8.1, 6.9 and 1.2 Hz), 7.62 (1H, ddd, J=8.1, 6.9 and 1.2 Hz), 7.79 (1H, d, J=7.8 Hz), 8.13-8.18 (2H, m).

IR (KBr) 2932, 2216, 1572 $cm^{-1}$

Example 20 (Preparation of Compound 20)

To 4-[3-(hydroxymethyl)-1-piperidinyl]-1-naphthonitrile (560 mg) was added 4 N hydrogen chloride-ethyl acetate (2.0 mL), and the mixture was stirred at room temperature for 5 minutes and concentrated. The obtained residue was processed with diethyl ether to obtain 4-[3-(hydroxymethyl)-1-piperidinyl]-1-naphthonitrile hydrochloride (631 mg) (Compound 20).

$^1$H-NMR (300 Hz, DMSO-$d_6$) δ: 1.10-1.24 (1H, m), 1.74-2.04 (4H, m), 2.54 (1H, t, J=10.8 Hz), 2.76-2.84 (1H, m), 3.29-3.52 (4H, m), 7.14 (1H, d, J=8.1 Hz), 7.67 (1H, ddd, J=8.1, 6.9 and 1.5 Hz), 7.75 (1H, ddd, J=8.1, 6.9 and 1.5 Hz), 8.02-8.06 (2H, m), 8.14-8.17 (1H, m).

Example 21 (Preparation of Compound 21)

A mixture of 4-fluoro-1-naphthonitrile (100 mg), (S)-3-(hydroxymethyl)piperidine (135 mg), potassium carbonate (161 mg), and dimethylsulfoxide (1.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain 4-[(3S)-3-(hydroxymethyl)-1-piperidinyl]-1-naphthonitrile (133 mg) (Compound 21).

$[α]_D$=+4.9° (c=0.460, MeOH).

$^1$H-NMR (300 Hz, $CDCl_3$) δ: 1.20-1.32 (1H, m), 1.59 (1H, br.s), 1.86-1.96 (3H, m), 2.09-2.20 (1H, m), 2.66 (1H, t, J=10.5 Hz), 2.77-2.86 (1H, m), 3.38-3.42 (1H, m), 3.54-3.68 (3H, m), 7.01 (1H, d, J=7.8 Hz), 7.56 (1H, ddd, J=8.1, 6.9 and 1.2 Hz), 7.62 (1H, ddd, J=8.1, 6.9 and 1.2 Hz), 7.79 (1H, d, J=7.8 Hz), 8.13-8.18 (2H, m).

Compound 21 was obtained using optical resolution as shown in Example 23 as an alternative method.

Example 22 (Preparation of Compound 22)

A mixture of 4-fluoro-1-naphthonitrile (100 mg), (R)-3-(hydroxymethyl)piperidine (135 mg), potassium carbonate (161 mg), and dimethylsulfoxide (1.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain 4-[(3R)-3-(hydroxymethyl)-1-piperidinyl]-1-naphthonitrile (139 mg) (Compound 22).

$[α]_D$=−4.4° (c=0.460, MeOH).

$^1$H-NMR (300 Hz, $CDCl_3$) δ: 1.20-1.32 (1H, m), 1.59 (1H, br.s), 1.86-1.96 (3H, m), 2.09-2.20 (1H, m), 2.66 (1H, t, J=10.5 Hz), 2.77-2.86 (1H, m), 3.38-3.42 (1H, m), 3.54-3.68

(3H, m), 7.01 (1H, d, J=7.8 Hz), 7.56 (1H, ddd, J=8.1, 6.9 and 1.2 Hz), 7.62 (1H, ddd, J=8.1, 6.9 and 1.2 Hz), 7.79 (1H, d, J=7.8 Hz), 8.13-8.18 (2H, m).

Compound 22 was obtained using optical resolution as shown in Example 23 as an alternative method.

Example 23 (Preparation of Compounds 21 and 22) 4-[3-(hydroxymethyl)-1-piperidinyl]-1-naphthonitrile (3.53 g) was optically resolved by CHILALCEL OD (50×500 mm), to obtain 4-[(3S)-3-(hydroxymethyl)-1-piperidinyl]-1-naphthonitrile (Compound 21, 1.77 g) and 4-[(3R)-3-(hydroxymethyl)-1-piperidinyl]-1-naphthonitrile (Compound 22, 1.77 g).

Example 24 (Preparation of Compound 23)

To 4-[(3S)-3-(hydroxymethyl)-1-piperidinyl]-1-naphthonitrile (1.66 g) was added 4 N hydrogen chloride-ethyl acetate (2.0 mL), and the mixture was stirred at room temperature for 5 minutes. The precipitated compound was filtered off, which was washed with ethyl acetate to obtain 4-[(3S)-3-(hydroxymethyl)-1-piperidinyl]-1-naphthonitrile hydrochloride (1.71 g) (Compound 23).

mp 179-180° C.

$[\alpha]_D$=+1.3° (c=0.535, MeOH).

$^1$H-NMR (300 Hz, DMSO-$d_6$) δ: 1.10-1.24 (1H, m), 1.74-2.04 (4H, m), 2.54 (1H, t, J=10.8 Hz), 2.76-2.84 (1H, m), 3.29-3.52 (4H, m), 7.14 (1H, d, J=8.1 Hz), 7.67 (1H, ddd, J=8.1, 6.9 and 1.5 Hz), 7.75 (1H, ddd, J=8.1, 6.9 and 1.5 Hz), 8.02-8.06 (2H, m), 8.14-8.17 (1H, m).

Anal. Calcd. for $C_{17}H_{18}N_2O \cdot HCl$: C, 67.43; H, 6.32; N, 9.25. Found: C, 67.21; H, 6.40; N, 9.07.

Example 25 (Preparation of Compound 24)

To 4-[(3R)-3-(hydroxymethyl)-1-piperidinyl]-1-naphthonitrile (1.66 g) was added 4 N hydrogen chloride-ethyl acetate (2.0 mL), and the mixture was stirred at room temperature for 5 minutes. The precipitated compound was filtered off, which was washed with ethyl acetate to obtain 4-[(3R)-3-(hydroxymethyl)-1-piperidinyl]-1-naphthonitrile hydrochloride (1.72 g) (Compound 24).

mp 178-179° C.

$[\alpha]_D$=-0.45° (c=0.520, MeOH).

$^1$H-NMR (300 Hz, DMSO-$d_6$) δ: 1.10-1.24 (1H, m), 1.74-2.04 (4H, m), 2.54 (1H, t, J=10.8 Hz), 2.76-2.84 (1H, m), 3.29-3.52 (4H, m), 7.14 (1H, d, J=8.1 Hz), 7.67 (1H, ddd, J=8.1, 6.9 and 1.5 Hz), 7.75 (1H, ddd, J=8.1, 6.9 and 1.5 Hz), 8.02-8.06 (2H, m), 8.14-8.17 (1H, m).

Anal. Calcd. for $C_{17}H_{18}N_2O \cdot HCl$: C, 67.43; H, 6.32; N, 9.25. Found: C, 67.32; H, 6.30; N, 9.01.

Example 26 (Preparation of Compound 25)

A mixture of 4-fluoro-1-naphthonitrile (500 mg), tert-butyl 3-pyrrolidinyl carbamate (1.09 g), potassium carbonate (808 mg), and dimethylsulfoxide (10 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain tert-butyl 1-(4-cyano-1-naphthyl)-3-pyrrolidinyl carbamate (765 mg) (Compound 25).

mp 157-158° C.

$^1$H-NMR (300 MHz, CDCl$_3$) δ: 1.46 (9H, s), 1.92-2.08 (1H, m), 2.26-2.43 (1H, m), 3.41-3.61 (2H, m), 3.72-3.87 (2H, m), 4.35-4.45 (1H, m), 4.78 (1H, br.s), 6.74 (1H, d, J=8.0 Hz), 7.48 (1H, ddd, J=8.8, 6.8 and 1.2 Hz), 7.62 (1H, ddd, J=8.8, 6.8 and 1.2 Hz), 7.75 (1H, d, J=8.0 Hz), 8.15-8.22 (2H, m).

IR (KBr) 2978, 2209, 1694 cm$^{-1}$

Anal. Calcd. for $C_{20}H_{23}N_3O_2$: C, 71.19; H, 6.87; N, 12.45. Found: C, 70.56; H, 6.93; N, 12.20.

Exampe 27 (Preparation of Compound 26)

To a mixture of 4-amino-2-bromo-1-naphthonitrile (70 mg) and N,N-dimethylformamide (3.5 mL) was added sodium hydride (60% in oil, 134 mg) at room temperature, the mixture was stirred for 20 minutes. After adding 1,5-dibromopentane (93 mg), the mixture was stirred for 30 minutes. The reactant was poured into water, and extracted with ethyl acetate. The extracts were washed with water, dried and concentrated. The obtained residue was purified by silica gel column chromatography to obtain 2-bromo-4-(1-piperidinyl)-1-naphthonitrile (58 mg) (Compound 26).

mp 179-180° C.

$^1$H-NMR (300 MHz, CDCl$_3$) δ: 1.67-1.74 (2H, m), 1.82-1.90 (4H, m), 3.12-3.16 (4H, m), 7.13 (1H, s), 7.55 (1H, ddd, J=8.4, 7.2 and 1.5 Hz), 7.64 (1H, ddd, J=8.4, 7.2 and 1.5 Hz), 8.07-8.10 (1H, m), 8.12-8.16 (2H, m).

IR (KBr) 2938, 2218, 1570 cm$^{-1}$

Anal. Calcd. for $C_{16}H_{15}BrN_2$: C, 60.97; H, 4.80; N, 8.89. Found: C, 60.89; H, 4.70; N, 8.90.

Example 28 (Preparation of Compound 27)

To a mixture of dimethylsulfoxide (0.10 mL) and dichloromethane (3.0 mL) was added oxalyl chloride (60 μL) at −78° C. Five minutes later, a mixture of 4-(3-hydroxy-1-pyrrolidinyl)-1-naphthonitrile (150 mg), dichloromethane (3.0 mL), and dimethylsulfoxide (0.20 mL) was added, and the mixture was stirred for 15 minutes. Triethylamine (0.44 mL) was added thereto, and the resulting mixture was stirred for 30 minutes with elevating the temperature to room temperature. The reaction solution was poured into water, and extracted with ethyl acetate. The extracts were washed with 1 N hydrochloric acid, a sodium carbonate solution and brine, dried and concentrated. The obtained residue was purified by silica gel column chromatography to obtain 4-(3-oxo-1-pyrrolidinyl)-1-naphthonitrile (83 mg) (Compound 27).

mp 153-154° C.

$^1$H-NMR (300 MHz, CDCl$_3$) δ: 2.76 (2H, t, J=7.2 Hz), 3.73 (2H, t, J=7.2 Hz), 3.77 (2H, s), 7.04 (1H, d, J=8.1 Hz), 7.61 (1H, ddd, J=8.4, 6.9 and 1.2 Hz), 7.69 (1H, ddd, J=8.4, 6.9 and 1.2 Hz), 7.85 (1H, d, J=8.1 Hz), 8.16-8.18 (1H, m), 8.22-8.25 (1H, m).

IR (KBr) 2215, 1759, 1572 cm$^{-1}$

Anal. Calcd. for $C_{15}H_{12}N_2O$: C, 76.25; H, 5.12; N, 11.86. Found: C, 75.89; H, 5.13; N, 11.69.

Example 29 (Preparation of Compound 28)

To tert-butyl 1-(4-cyano-1-naphthyl)-3-pyrrolidinyl carbamate (600 mg) was added 4 N hydrogen chloride-ethyl acetate (3.0 mL) at room temperature, and the mixture was stirred for 30 minutes. The produced precipitate was filtered off, which was washed with ethyl acetate to obtain 4-(3-amino-1-pyrrolidinyl)-1-naphthonitrile dihydrochloride (558 mg) (Compound 28).

mp 161-163° C.

$^1$H-NMR (300 MHz, DMSO-$d_6$) δ: 2.11-2.21 (1H, m), 2.29-2.40 (1H, m), 3.48-3.55 (1H, m), 3.67 (1H, dd, J=10.8 and 3.6 Hz), 3.82-3.96 (3H, m), 6.89 (1H, d, J=8.4 Hz), 7.57-7.62 (1H, m), 7.71-7.76 (1H, m), 7.95 (1H, d, J=8.4 Hz), 8.01-8.04 (1H, m), 8.38 (1H, d, J=8.4 Hz), 8.58 (3H, br.s).
IR (KBr) 2209, 1518 cm$^{-1}$ Example 30 (Preparation of Compound 29)

Sodium hydride (60% in oil, 40 mg) was washed with hexane and suspended in N,N-dimethylformamide (1.0 mL). 4-(3-hydroxy-1-pyrrolidinyl)-1-naphthonitrile (100 mg) was added, and the mixture was stirred for 10 minutes. After adding methyl iodide (78 μL), the mixture was stirred for 40 minutes. The reactant was poured into water, and extracted with ethyl acetate. The extracts were washed with water, dried and concentrated. The obtained residue was purified by silica gel column chromatography to obtain 4-(3-methoxy-1-pyrrolidinyl)-1-naphthonitrile (102 mg) (Compound 29).
$^1$H-NMR (300 MHz, CDCl$_3$) δ: 2.10-2.24 (2H, m), 3.37 (3H, s), 3.52 (1H, ddd, J=12.0, 7.5 and 4.5 Hz), 3.57-3.62 (1H, m), 3.76-3.85 (2H, m), 4.09-4.14 (1H, m), 6.72 (1H, d, J=8.1 Hz), 7.46 (1H, ddd, J=8.7, 6.9 and 1.5 Hz), 7.60 (1H, ddd, J=8.7, 6.9 and 1.5 Hz), 7.73 (1H, d, J=8.1 Hz), 8.14-8.18 (1H, m), 8.22-8.25 (1H, m).
IR (KBr) 2205, 1563, 1518 cm$^{-1}$ Example 31 (Preparation of Compound 30)

A mixture of 4-fluoro-1-naphthonitrile (100 mg), 4-(hydroxymethyl) piperidine (135 mg), potassium carbonate (161 mg), and dimethylsulfoxide (1.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain 4-[4-(hydroxymethyl)-1-piperidinyl]-1-naphthonitrile (150 mg) (Compound 30).
mp 135-136° C.
$^1$H-NMR (300 MHz, CDCl$_3$) δ: 1.47 (1H, t-like), 1.58-1.80 (3H, m), 1.93-1.98 (2H, m), 2.79-2.87 (2H, m), 3.55 (1H, d.t-like, J=12.3 Hz), 3.65 (2H, t, J=5.4 Hz), 7.01 (1H, d, J=7.8 Hz), 7.56 (1H, ddd, J=8.4, 6.9 and 1.5 Hz), 7.64 (1H, ddd, J=8.4, 6.9 and 1.5 Hz), 7.81 (1H, d, J=7.8 Hz), 8.13-8.20 (2H, m).
IR (KBr) 2915, 2216, 1572 cm$^{-1}$
Anal. Calcd. for C$_{17}$H$_{18}$N$_2$O: C, 76.66; H, 6.81; N, 10.52. Found: C, 76.35; H, 6.88; N, 10.42.

Example 32 (Preparation of Compound 31)

A mixture of 4-fluoro-1-naphthonitrile (300 mg), (S)-ethyl nipecotate (551 mg), potassium carbonate (485 mg), and dimethylsulfoxide (3.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain ethyl (3S)-1-(4-cyano-1-naphthyl)-3-piperidinecarboxylate (508 mg) (Compound 31).
[α]$_D$=+49.6° (c=0.580, MeOH).
$^1$H-NMR (200 MHz, CDCl$_3$) δ: 1.26 (3H, t, J=7.0 Hz), 1.70-2.03 (3H, m), 2.14-2.20 (1H, m), 2.79-2.95 (2H, m), 3.07 (1H, t, J=10.6 Hz), 3.35-3.41 (1H, m), 3.57-3.62 (1H, m), 4.17 (2H, q, J=7.0 Hz), 7.06 (1H, d, J=8.2 Hz), 7.54-7.70 (2H, m), 7.84 (1H, d, J=8.2 Hz), 8.13-8.23 (2H, m).
IR (KBr) 2216, 1730, 1574 cm$^{-1}$ Example 33 (Preparation of Compound 32)

A mixture of 4-fluoro-1-naphthonitrile (300 mg), (R)-ethyl nipecotate (551 mg), potassium carbonate (485 mg), and dimethylsulfoxide (3.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain ethyl (3R)-1-(4-cyano-1-naphthyl)-3-piperidinecarboxylate (451 mg) (Compound 32).
[α]$_D$=−56.4° (c=0.475, MeOH).
$^1$H-NMR (200 MHz, CDCl$_3$) δ: 1.26 (3H, t, J=7.0 Hz), 1.70-2.03 (3H, m), 2.14-2.20 (1H, m), 2.79-2.95 (2H, m), 3.07 (1H, t, J=10.6 Hz), 3.35-3.41 (1H, m), 3.57-3.62 (1H, m), 4.17 (2H, q, J=7.0 Hz), 7.06 (1H, d, J=8.2 Hz), 7.54-7.70 (2H, m), 7.84 (1H, d, J=8.2 Hz), 8.13-8.23 (2H, m).
IR (KBr) 2216, 1730, 1574 cm$^{-1}$ Example 34 (Preparation of Compound 33)

A mixture of ethyl (3S)-1-(4-cyano-1-naphthyl)-3-piperidinecarboxylate (396 mg), a 1 N sodium hydroxide solution (2.6 mL), and tetrahydrofuran (4.4 mL) was stirred at room temperature for 20 hours. The mixture was acidified with 1 N hydrochloric acid, and extracted with ethyl acetate. The extracts were washed with brine, dried and concentrated to obtain (3S)-1-(4-cyano-1-naphthyl)-3-piperidinecarboxylate (351 mg) (Compound 33).
[α]$_D$=+60.9° (c=0.495, MeOH).
$^1$H-NMR (300 MHz, CDCl$_3$) δ: 1.74-2.24 (4H, m), 2.86-3.00 (2H, m), 3.04-3.14 (1H, m), 3.29-3.36 (1H, m), 3.58-3.62 (1H, m), 7.05 (1H, d, J=7.8 Hz), 7.55-7.68 (2H, m), 7.83 (1H, d, J=7.8 Hz), 8.12-8.15 (1H, m), 8.18-8.21 (1H, m).
IR (KBr) 2947, 2216, 1705, 1474 cm$^{-1}$ Example 35 (Preparation of Compound 34)

A mixture of ethyl (3S)-1-(4-cyano-1-naphthyl)-3-piperidinecarboxylate (340 mg), a 1 N sodium hydroxide solution (2.2 mL), and tetrahydrofuran (4.0 mL) was stirred at room temperature for 20 hours. The mixture was acidified with 1 N hydrochloric acid, and extracted with ethyl acetate. The extracts were washed with brine, dried and concentrated to obtain (3R)-1-(4-cyano-1-naphthyl)-3-piperidinecarboxylate (287 mg) (Compound 34).
[α]$_D$=−63.9° (c=0.500, MeOH).
$^1$H-NMR (300 MHz, CDCl$_3$) δ: 1.74-2.24 (4H, m), 2.86-3.00 (2H, m), 3.04-3.14 (1H, m), 3.29-3.36 (1H, m), 3.58-3.62 (1H, m), 7.05 (1H, d, J=7.8 Hz), 7.55-7.68 (2H, m), 7.83 (1H, d, J=7.8 Hz), 8.12-8.15 (1H, m), 8.18-8.21 (1H, m).
IR (KBr) 2947, 2216, 1705, 1474 cm$^{-1}$ Example 36 (Preparation of Compound 35)

A mixture of 4-fluoro-1-naphthonitrile (400 mg), 2-(methoxymethoxymethyl)piperidine (744 mg), potassium carbonate (646 mg), and dimethylsulfoxide (4.0 mL) was stirred at 100° C. for 60 hours. After cooling to room temperature, the reactant was poured into water, and then extracted with ethyl acetate. The extracts were washed with water, dried and concentrated, to obtain a yellowish-brown oily matter. A mixture of the obtained matter and trifluoroacetic acid (2.0 mL) was stirred at room temperature for 10 hours. The reaction solution was alkalified with a 1 N sodium hydroxide solution, and extracted with diethyl ether. The extracts were washed with brine, dried and concentrated. The obtained residue was purified by silica gel column chromatography to obtain 4-[2-(hydroxymethyl)-1-piperidinyl]-1-naphthonitrile (37 mg) (Compound 35).

¹H-NMR (300 MHz, CDCl₃) δ: 1.42-1.92 (6H, m), 1.96-2.06 (1H, m), 2.88-2.96 (1H, m), 3.30-3.37 (1H, m), 3.52-3.62 (3H, m), 7.21 (1H, d, J=8.1 Hz), 7.55-7.67 (2H, m), 7.82 (1H, d, J=8.1 Hz), 8.17 (1H, d, J=8.1 Hz), 8.29 (1H, d, J=8.1 Hz).
IR (KBr) 2935, 2216, 1570, 1508 cm⁻¹

Example 37 (Preparation of Compound 36)

A mixture of 7-hydroxy-4-nitro-1-indanone (1.02 g), triethylamine (2.21 mL), and dichloromethane (20 mL) was cooled to −25° C., and a mixture of trifluoromethanesulfonic anhydride (1.33 mL) and dichloromethane (5.0 mL) was added for 15 minutes. After stirring at the same temperature for 10 minutes, the temperature was elevated to room temperature. The reaction solution was concentrated. The obtained residue was processed with silica gel column chromatography to obtain a brown solid matter (1.42 g). A mixture of the obtained solid (140 mg), 3-(hydroxymethyl)piperidine (99 mg), potassium carbonate (119 mg), and dimethylsulfoxide (1.5 mL) was stirred at room temperature for 30 minutes. The reactant was poured into water, and extracted with ethyl acetate. The extracts were washed with water, dried and concentrated. The obtained residue was purified by silica gel column chromatography to obtain 7-[3-(hydroxymethyl)-1-piperidinyl]-4-nitro-1-indanone (95 mg) (Compound 36).
¹H-NMR (300 MHz, CDCl₃) δ: 1.13-1.18 (1H, m), 1.76-1.91 (4H, m), 2.03-2.18 (1H, m), 2.69-2.73 (2H, m), 2.94 (1H, dd, J=12.6 and 9.6 Hz), 3.11 (1H, ddd, J=12.6, 9.6 and 3.3 Hz), 3.52-3.70 (5H, m), 3.77-3.83 (1H, m), 6.85 (1H, d, J=9.0 Hz), 8.28 (1H, d, J=9.0 Hz).
IR (KBr) 1699, 1586, 1319 cm⁻¹

Example 38 (Preparation of Compound 37)

To a mixture of 7-[3-(hydroxymethyl)-1-piperidinyl]-4-nitro-1-indanone (91 mg) and methanol (2.0 mL) was added sodium borohydride (5.9 mg) at room temperature. After stirring for 30 minutes, the reaction solution was concentrated. The residue was purified by silica gel column chromatography to obtain 7-[3-(hydroxymethyl)-1-piperidinyl]-4-nitro-1-indanol (92 mg) (Compound 37).
¹H-NMR (300 MHz, CDCl₃) δ: 1.19-1.31 (1H, m), 1.64-2.18 (6H, m), 2.49-2.81 (2H, m), 2.93-3.04 (1H, m), 3.16-3.67 (6H, m), 4.28 (1H, br.s), 5.51 (1H, t, J=6.6 Hz), 6.94 (1H, d, J=9.0 Hz), 8.09 (1H, d, J=9.0 Hz).

Example 39 (Preparation of Compounds 38 and 39)

A mixture of 7-[3-(hydroxymethyl)-1-piperidinyl]-4-nitro-1-indanol (79 mg), 0.5 N hydrochloric acid (9.0 mL), and ethanol (4.0 mL) was stirred at 100° C. for 6 hours. After cooling to room temperature, the reaction solution was concentrated. The residue was neutralized with a sodium hydrogen carbonate solution, and extracted with ethyl acetate. The extracts were washed with water, dried and concentrated. The obtained residue was purified by silica gel column chromatography to obtain [1-(7-nitro-1H-inden-4-yl)-3-piperidinyl]methanol (37 mg) (Compound 38) and [1-(4-nitro-1H-indene-7-yl)-3-piperidinyl]methanol (20 mg) (Compound 39).

Compound 38
¹H-NMR (300 MHz, CDCl₃) δ: 1.21-1.33 (1H, m), 1.71-2.07 (5H, m), 2.77 (1H, dd, J=12.0 and 9.6 Hz), 2.87-2.96 (1H, m), 3.49-3.70 (4H, m), 3.89 (2H, t, J=1.8 Hz), 6.64 (1H, dt, J=5.7 and 1.8 Hz), 6.86 (1H, d, J=8.7 Hz), 6.97 (1H, dt, J=5.7 and 1.8 Hz), 8.02 (1H, d, J=8.7 Hz).
IR (KBr) 2928, 1582, 1327 cm⁻¹

Compound 39
¹H-NMR (300 MHz, CDCl₃) δ: 1.24-1.35 (1H, m), 1.68-2.04 (5H, m), 2.81 (1H, dd, J=12.3 and 9.6 Hz), 2.93-3.01 (1H, m), 3.49 (2H, t, J=1.8 Hz), 3.56-3.71 (3H, m), 3.75-3.80 (1H, m), 6.78 (1H, d, J=9.0 Hz), 6.81 (1H, dt, J=5.7 and 1.8 Hz), 7.68 (1H, dt, J=5.7 and 1.8 Hz), 8.09 (1H, d, J=9.0 Hz).
IR (KBr) 2936, 1584, 1318 cm⁻¹

Example 40 (Preparation of Compound 40)

A mixture of 4-fluoro-1-naphthonitrile (200 mg), 3-hydroxypiperidine (236 mg), potassium carbonate (322 mg), and dimethylsulfoxide (2.5 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain 4-(3-hydroxy-1-piperidinyl)-1-naphthonitrile (259 mg) (Compound 40).
¹H-NMR (300 MHz, CDCl₃) δ: 1.66-2.28 (5H, m), 3.02-3.16 (3H, m), 3.22-3.36 (1H, m), 4.08-4.15 (1H, m), 7.03 (1H, d, J=7.8 Hz), 7.59 (1H, ddd, J=8.1, 6.6 and 1.5 Hz), 7.66 (1H, ddd, J=8.1, 6.6 and 1.5 Hz), 7.82 (1H, d, J=7.8 Hz), 8.18-8.21 (2H, m).
IR (KBr) 2216, 1572 cm⁻¹

Example 41 (Preparation of Compound 41)

Sodium hydride (60% in oil, 84 mg) was washed with hexane and suspened to N,N-dimethylformamide (2.5 mL). 4-(3-hydroxy-1-piperidinyl)-1-naphthonitrile (220 mg) was added thereto, and the mixture was stirred for 10 minutes. After adding methyl iodide (160 µl), the resulting mixture was stirred for 40 minutes. The reactant was poured into water, and extracted with ethyl acetate. The extracts were washed with water, dried and concentrated. The obtained residue was purified by silica gel column chromatography to obtain 4-(3-methoxy-1-piperidinyl)-1-naphthonitrile (220 mg) (Compound 41).
mp 92-93° C.
¹H-NMR (300 MHz, CDCl₃) δ: 1.48-1.60 (1H, m), 1.79-2.03 (2H, m), 2.14-2.27 (1H, m), 2.82-2.90 (2H, m), 3.28-3.34 (1H, m), 3.44 (3H, s), 3.51-3.64 (2H, m), 7.02 (1H, d, J=7.8 Hz), 7.57 (1H, ddd, J=8.4, 6.6 and 1.5 Hz), 7.65 (1H, ddd, J=8.4, 6.6 and 1.5 Hz), 7.82 (1H, d, J=7.8 Hz), 8.17-8.20 (2H, m).
IR (KBr) 2215, 1574 cm⁻¹
Anal. Calcd. for C₁₇H₁₈N₂O: C, 76.66; H, 6.81; N, 10.52. Found: C, 76.44; H, 6.73; N, 10.44.

Example 42 (Preparation of Compound 42)

A mixture of 4-fluoro-1-naphthonitrile (100 mg), N-pyrrolidin-3-yl acetamide (240 mg), potassium carbonate (87 mg) and dimethylsulfoxide (2.0 mL) was stirred at 100° C. for 16 hours. After cooling to room temperature, the reactant was poured into water, and then extracted with ethyl acetate. The extracts were washed with water, dried and concentrated. The obtained residue was purified by silica gel column chromatography (ethyl acetate) and crystallized from hexane:ethyl acetate=4:1, to obtain N-[1-(4-cyano-1-naphthyl)pyrrolidin-3-yl]acetamide (136 mg) (Compound 42).
mp 154-155° C.
¹H-NMR (200 MHz, CDCl₃) δ: 1.90-2.15(1H, m), 2.02 (3H, s), 2.35-2.48(1H, m), 3.40-3.60 (2H, m), 3.70-3.92(2H, m), 4.55-4.78(1H,m), 5.90(1H, d, J=5.0 Hz), 6.72(1H, d,J=5.0 Hz), 7.42-7.68(2H, m).

IR (KBr) 2203, 1649, 1563, 1518 cm$^{-1}$

Anal. Calcd. for $C_{17}H_{17}N_3O$: C, 73.10; H, 6.13; N, 15.04. Found: C, 72.92; H, 6.04; N, 14.85.

Example 43 (Preparation of Compound 43)

A mixture of 4-fluoro-1-naphthonitrile (100 mg), (2S)-pyrrolidin-2-yl methanol (177 mg), potassium carbonate (87 mg) and dimethylsulfoxide (2.0 mL) was stirred at 100° C. for 16 hours. After cooling to room temperature, the reactant was poured into water, and then extracted with ethyl acetate. The extracts were washed with water, dried and concentrated. The obtained residue was purified by silica gel column chromatography (hexane:ethyl acetate=2:1). The residue was dissolved in ethyl acetate. A 4N-hydrochloric acid/ethyl acetate solution (0.3 mL) was added, and the resulting mixture was crystallized to obtain 4-[(2S)-2-(hydroxymethyl)pyrrolidin-1-yl]-1-naphthonitrile hydrochloride (148 mg) (compound 43).

mp 123-125° C.

$[\alpha]_D$=+119.7° (c=0.870, MeOH).

$^1$H-NMR (200 MHz, DMSO-d$_6$) δ: 1.60-2.05(3H, m), 2.15-2.32(1H, m), 3.25-3.57(3H, m), 3.90-4.20(2H, m), 7.02 (1H, d, J=8.4 Hz), 7.48-7.55(2H, m), 7.89(1H, d, J=8.4 Hz), 7.98(1H, d, J=8.4 Hz), 8.26(1H, d, J=8.4 Hz).

IR (KBr) 2225, 1522, 772 cm$^{-1}$

Anal. Calcd. for $C_{16}H_{16}N_2O·HCl$: C, 66.55; H, 5.93; N, 9.70. Found: C, 66.27; H, 5.88; N, 9.58.

Example 44 (Preparation of Compound 44)

A mixture of 4-fluoro-1-naphthonitrile (100 mg), (2R)-pyrrolidin-2-yl methanol (117 mg), potassium carbonate (87 mg) and dimethylsulfoxide (2.0 mL) was stirred at 100° C. for 16 hours. After cooling to room temperature, the reactant was poured into water, and then extracted with ethyl acetate. The extracts were washed with water, dried and concentrated. The obtained residue was purified by silica gel column chromatography (hexane:ethyl acetate=2:1). The residue was dissolved in ethyl acetate and a 4N-hydrochloric acid/ethyl acetate solution (0.3 mL) was added thereto. The resulting solution was concentrated and dried. The obtained residue was crystallized from hexane:ethyl acetate=1:2, to obtain 4-[(2R)-2-(hydroxymethyl)pyrrolidin-1-yl]-1-naphthonitrile hydrochloride (148 mg) (Compound 44).

mp 125-127° C.

$[\alpha]_D$=−117.5° (c=0.922, MeOH).

$^1$H-NMR (200 MHz, DMSO-d$_6$) δ: 1.60-2.09(3H, m), 2.14-2.34(1H, m), 3.25-3.55(3H, m), 3.85-4.20(2H, m), 7.01 (1H, d, J=8.4 Hz), 7.48-7.74(2H, m), 7.89(1H, d, J=8.4 Hz), 7.98(1H, dd, J=1.2 and 8.4 Hz), 8.26(1H, d, J=8.4 Hz).

IR (KBr) 2225, 1522, 772 cm$^{-1}$

Anal. Calcd. for $C_{16}H_{16}N_2O·HCl·0.2H_2O$: C, 65.73; H, 6.00; N, 9.58. Found: C, 65.96; H, 5.93; N, 9.52.

Example 45 (Preparation of Compound 45)

A mixture of 4-fluoro-1-naphthonitrile (100 mg), (2R)-2-(methoxymethyl)pyrrolidine (200 mg), potassium carbonate (87 mg) and dimethylsulfoxide (2.0 mL) was stirred at 100° C. for 16 hours. After cooling to room temperature, the reactant was poured into water, and then extracted with ethyl acetate. The extracts were washed with water, dried and concentrated. The obtained residue was purified by silica gel column chromatography (hexane:ethyl acetate=2:1). The residue was dissolved in ethyl acetate and a 4N-hydrochloric acid/ethyl acetate solution (0.3 mL) was added thereto. The resulting solution was concentrated and dried. The obtained residue was crystallized from hexane:ethyl acetate=1:1, to obtain 4-[(2R)-2-(methoxymethyl)pyrrolidin-1-yl]-1-naphthonitrile hydrochloride (63 mg) (Compound 45).

mp 88-89° C.

$[\alpha]_D$=−136.6° (c=0.696, MeOH).

$^1$H-NMR (200 MHz, DMSO-d$_6$) δ: 1.65-2.05(3H, m), 2.12-2.34(1H, m), 3.15(3H, s), 3.20-3.46(2H, m), 3.93-4.05 (1H, m), 4.15-4.36(1H, m), 7.06(1H, d, J=8.4 Hz), 7.50-7.76 (2H, m), 7.90(1H, d, J=8.4 Hz), 8.00(1H, dd, J=1.0 and 8.4 Hz), 8.23(1H, d, J=8.4 Hz).

IR (KBr) 2218, 1598, 1519, 1386, 773 cm$^-$

Anal. Calcd. for $C_{17}H_{18}N_2O·HCl·0.1H_2O$: C, 67.03; H, 6.35; N, 9.20. Found: C, 66.97; H, 6.35; N, 9.05.

Example 46 (Preparation of Compound 46)

A mixture of 4-fluoro-1-naphthonitrile (100 mg), L-prolinamide (200 mg), potassium carbonate (87 mg), and dimethylsulfoxide (2.0 mL) was stirred at 100° C. for 15 hours. After cooling to room temperature, the reactant was poured into water, and then extracted with ethyl acetate. The extracts were washed with water, dried and concentrated. The obtained residue was purified by silica gel column chromatography (hexane:ethyl acetate=1:2) and crystallized from hexane: ethyl acetate=1:2, to obtain 1-(4-cyano-1-naphthyl)-L-prolinamide (101 mg) (Compound 46).

mp 177-178° C.

$[\alpha]_D$=+218.7° (c=0.608, MeOH).

$^1$H-NMR (200 MHz, CDCl$_3$) δ: 1.80-2.30(3H, m), 2.30-2.72(1H, m), 3.28-3.46(1H, m), 4.10-4.30(1H, m), 4.38(1H, t, J=8.0 Hz), 5.32(1H, brs), 6.39(1H, brs), 6.97(1H, d, J=8.0 Hz), 7.52-7.75(2H, m), 7.78(1H, d, J=8.0 Hz), 8.18-8.32(2H, m).

IR (KBr) 2210, 1691, 1323 cm$^{-1}$

Anal. Calcd. for $C_{16}H_{15}N_3O$: C, 72.43; H, 5.70; N, 15.84. Found: C, 72.25; H, 5.52; N, 15.68.

Example 47 (Preparation of Compound 47)

A mixture of 4-fluoro-1-naphthonitrile (100 mg), 2-methylpyrrolidine (150 mg), potassium carbonate (87 mg) and dimethylsulfoxide (2.0 mL) was stirred at 100° C. for 15 hours. After cooling to room temperature, the reactant was poured into water, and then extracted with ethyl acetate. The extracts were washed with water, dried and concentrated. The obtained residue was purified by silica gel column chromatography (hexane:ethyl acetate=8:1). The residue was dissolved in ethyl acetate and a 4N-hydrochloric acid/ethyl acetate solution (0.3 mL) was added thereto. The resulting solution was concentrated and dried, to obtain 4-(2-methylpyrrolidin-1-yl)-1-naphthonitrile hydrochloride (150 mg) as a hygroscopic amorphous matter (Compound 47).

$^1$H-NMR (200 MHz, DMSO-d$_6$) δ: 1.13(3H, d, J=5.8 Hz), 1.58-2.10(3H, m), 2.20-2.40(1H, m), 3.20-3.60(1H, m), 3.95-4.20(2H, m), 6.92(1H, d, J=8.4 Hz), 7.49-7.76(2H, m), 7.90 (1H, d, J=8.4 Hz), 7.99(1H, d, J=8.4 Hz), 8.25(1H, d, J=8.4 Hz).

IR (KBr) 2209, 1566, 1515, 1328, 764 cm$^{-1}$

Example 48 (Preparation of Compound 48)

A mixture of 4-fluoro-1-naphthonitrile (400 mg), 2-methylpyrrolidine (410 mg), potassium carbonate (350 mg) and dimethylsulfoxide (8.0 mL) was stirred at 100° C. for 5 hours. After cooling to room temperature, the reactant was poured into water, and then extracted with ethyl acetate. The extracts were washed with water, dried and concentrated. The obtained residue was purified by silica gel column chromatography (hexane:ethyl acetate=8:1), to obtain 4-(2-methylpyrrolidin-1-yl)-1-naphthonitrile (516 mg) (Compound 48).

$^1$H-NMR (200 MHz, CDCl$_3$) δ: 1.18 (3H, d, J=5.8 Hz), 1.60-2.15 (3H, m), 2.20-2.40 (1H, m), 3.25-3.40 (1H, m), 3.90-4.15 (2H, m), 6.82 (1H, d, J=8.0 Hz), 7.40-7.70 (2H, m) 7.76(1H, d, J=8.0 Hz), 8.15-8.25(2H, m).

IR (KBr) 2209, 1565, 1514, 1327, 763 cm$^{-1}$

Example 49 (Preparation of Compound 49)

A mixture of 4-fluoro-1-naphthonitrile (100 mg), N-methyl-N-pyrrolidin-3-yl acetamide (249 mg), potassium carbonate (87 mg) and dimethylsulfoxide (2.0 mL) was stirred at 100° C. for 15 hours. After cooling to room temperature, the reactant was poured into water, and then extracted with ethyl acetate. The extracts were washed with water, dried and concentrated. The obtained residue was purified by silica gel column chromatography (hexane:ethyl acetate=1:2) and crystallized from hexane:ethyl acetate=1:1, to obtain N-[1-(4-cyano-1-naphthyl)pyrrolidin-3-yl]-N-methylacetamide (130 mg) (Compound 49).

mp 144-145° C.

$^1$H-NMR (200 MHz, CDCl$_3$) δ: 2.00-2.40(2H, m), 2.15 (2.1H, s), 2.20(0.9H, s), 3.03(0.9H, s), 3.08(2.1H, s), 3.40-3.78(4H, m), 4.52-4.62(0.3H, m), 5.28-5.50(0.7H, m), 6.80 (0.7H, d, J=8.4 Hz), 6.84(0.3H, d, J=8.4 Hz), 7.45-7.70(2H, m), 7.77(0.7H, J=8.4 Hz), 7.79(0.3H, d, J=8.4 Hz), 8.12(2H, d, J=8.4 Hz).

IR (KBr) 2199, 1655, 1565 cm$^{-1}$

Anal. Calcd. for C$_{18}$H$_{19}$N$_3$O: C, 73.69; H, 6.53; N, 14.32. Found: C, 73.48; H, 6.56; N, 14.12.

Example 50 (Preparation of Compound 50)

A mixture of 4-fluoro-1-naphthonitrile (100 mg), pyrrolidin-3-yl methanol hydrochloride (240 mg), potassium carbonate (330 mg) and dimethylsulfoxide (2.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography (hexane:ethyl acetate=1:1). The residue was dissolved in ethyl acetate and a 4N-hydrochloric acid/ethyl acetate solution (0.3 mL) was added thereto. The resulting solution was concentrated and dried to obtain 4-[3-(hydroxymethyl)pyrrolidin-1-yl]-1-naphthonitrile hydrochloride (153 mg) as hygroscopic amorphous matter (Compound 50).

$^1$H-NMR (200 MHz, CDCl$_3$+CD$_3$OD+D$_2$O) δ: 1.75-2.00 (1H, m), 2.05-2.38(1H, m), 2.45-2.80(1H, m), 3.40-3.90(6H, m), 6.81(1H, d, J=8.4 Hz), 7.40-7.80(3H, m), 8.14(1H, d, J=8.4 Hz), 8.29(1H, d, J=8.4 Hz).

IR (KBr) 2205, 1561 cm$^{-1}$

Example 51 (Preparation of Compound 51)

4-(3-(hydroxymethyl)pyrrolidin-1-yl)-1-naphthonitrile hydrochloride (85 mg) was dissolved in N,N-dimethylformamide (2.0 mL), sodium hydride (60% in oil, 28 mg) was added at room temperature, and the mixture was stirred for 1 hour. After adding methyl iodide (0.1 mL), the mixture was stirred at room temperature for 2 hours. The reactant was poured into water, and extracted with ethyl acetate. The extracts were washed with water, dried and concentrated. The obtained residue was purified by silica gel column chromatography (hexane:ethyl acetate=1:2) to obtain 4-[3-(methoxymethyl)pyrrolidin-1-yl]-1-naphthonitrile (77 mg) (Compound 51).

$^1$H-NMR (200 MHz, CDCl$_3$) δ: 1.70-1.96(1H, m), 2.06-2.30(1H, m), 3.39(3H, s), 3.42-3.78(6H, m), 6.72(1H, d, J=8.2 Hz), 7.40-7.68(2H, m), 7.73(1H, d, J=8.2 Hz), 8.12-8.30(2H, m).

IR (KBr) 2206, 1569 cm$^{-1}$

Example 52 (Preparation of Compound 52)

A mixture of 4-fluoro-1-naphthonitrile (100 mg), cis-(5-methylpyrrolidin-3-yl) methanol hydrochloride (220 mg), potassium carbonate (330 mg) and dimethylsulfoxide (2.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain cis-4-[4-(hydroxymethyl)-2-methylpyrrolidin-1-yl]-1-naphthonitrile (139 mg) (Compound 52).

$^1$H-NMR (200 MHz, CDCl$_3$) δ: 1.25(3H, d, J=6.2 Hz), 1.40-1.70(1H, m), 2.28-2.58(2H, m), 3.30-3.45(1H, m), 3.62-4.20(4H, m), 6.85(1H, d, J=8.4 Hz), 7.44-7.68(2H, m), 7.77 (1H, d, J=8.4 Hz), 8.18(2H, t, J=8.4 Hz).

IR (KBr) 2209, 1566, 1514, 1327 cm$^{-1}$

Example 53 (Preparation of Compound 53)

A mixture of 4-fluoro-1-naphthonitrile (100 mg), trans-(5-methylpyrrolidin-3-yl) methanol hydrochloride (220 mg), potassium carbonate (330 mg) and dimethylsulfoxide (2.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain trans-4-[4-(hydroxymethyl)-2-methylpyrrolidin-1-yl]-1-naphthonitrile (148 mg) (Compound 53).

$^1$H-NMR (200 MHz, CDCl$_3$) δ: 1.10(3H, d, J=5.8 Hz), 1.18-1.99(1H, m), 2.10-2.30(1H, m), 2.40-2.70(1H, m), 3.10-3.20(1H, m), 3.40-3.70(2H, m), 4.00-4.20(2H, m), 6.86(1H, d, J=8.0 Hz), 7.48-7.70(2H, m), 7.76(1H, d, J=8.0 Hz), 8.12-8.24(2H, m).

IR (KBr) 2210, 1566, 1514, 1327 cm$^{-1}$

Example 54 (Preparation of Compound 54)

Cis-4-[4-(hydroxymethyl)-2-methylpyrrolidin-1-yl]-1-naphthonitrile (120 mg) was dissolved in N,N-dimethylformamide (3.0 mL), sodium hydride (60% in oil, 35 mg) was added at room temperature, and the mixture was stirred for 1 hour. After adding methyl iodide (0.2 mL), the mixture was stirred at room temperature for 15 hours. The reactant was poured into water, and extracted with ethyl acetate. The extracts were washed with water, dried and concentrated. The obtained residue was purified by silica gel column chromatography to obtain cis-4-[4-(methoxymethyl)-2-methylpyrrolidin-1-yl]-1-naphthonitrile (78 mg) (Compound 54).

$^1$H-NMR (200 MHz, CDCl$_3$) δ: 1.36(3H, d, J=6.2 Hz), 1.60-1.82(1H, m), 2.44-2.76(2H, m), 3.44-3.78(3H, m), 3.56 (3H, s), 4.01(1H, t, J=8.8 Hz), 4.10-4.34(1H, m), 7.01(1H, d, J=8.4 Hz), 7.60-7.86(2H, m), 7.94(1H, d, J=8.0 Hz), 8.28-8.42(2H, m).

IR (KBr) 2210, 1567, 1514, 1330 cm$^{-1}$

Example 55 (Preparation of Compound 55)

Trans-4-[4-(hydroxymethyl)-2-methylpyrrolidin-1-yl]-1-naphthonitrile (129 mg) was dissolved in N,N-dimethylformamide (3.0 mL), sodium hydride (60% in oil, 32 mg) was added at room temperature, and the mixture was stirred for 1 hour. After adding methyl iodide (0.2 mL), the mixture was stirred at room temperature for 15 hours. The reactant was poured into water, and extracted with ethyl acetate. The extracts were washed with water, dried and concentrated. The obtained residue was purified by silica gel column chromatography to obtain trans-4-[4-(methoxymethyl)-2-methylpyrrolidin-1-yl]-1-naphthonitrile (100 mg) (Compound 55).

$^1$H-NMR (200 MHz, CDCl$_3$) δ: 1.12(3H, d, J=5.8 Hz), 1.80-1.97(1H, m), 2.08-2.22(1H, m), 2.55-2.75(1H, m), 3.03-3.40(3H, m), 3.29(3H, s), 4.00-4.20(2H, m), 6.86(1H, d, J=8.6 Hz), 7.42-7.64(2H, m), 7.77(1H, d, J=8.0 Hz), 8.12-8.24(2H, m).

IR (KBr) 2211, 1566, 1515, 1332 cm$^{-1}$

Example 56 (Preparation of Compound 56)

A mixture of 4-fluoro-1-naphthonitrile (200 mg), 3-(hydroxymethyl)-3-methylpiperidine (301 mg), potassium carbonate (322 mg) and dimethylsulfoxide (2.5 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain 4-[3-(hydroxymethyl)-3-methyl-1-piperidinyl]-1-naphthonitrile (264 mg) (Compound 56).

$^1$H-NMR (300 MHz, CDCl$_3$) δ: 1.13 (3H, s), 1.40-1.48 (1H, m), 1.63-2.04 (4H, m), 2.86-3.20 (4H, m), 3.63-3.76 (2H, m), 7.03 (1H, d, J=8.1 Hz), 7.54-7.67 (2H, m), 7.81 (1H, d, J=8.1 Hz), 8.17-8.22 (2H, m).

IR (KBr) 2216, 1572 cm$^{-1}$

Example 57 (Preparation of Compound 57)

Sodium hydride (60% in oil, 34 mg) was washed with hexane and suspended in N,N-dimethylformamide (1.0 mL). 4-[3-(hydroxymethyl)-3-methyl-1-piperidinyl]-1-naphthonitrile (100 mg) was added thereto, and the mixture was stirred for 10 minutes. After adding methyl iodide (66 μl), the resulting mixture was stirred for 40 minutes. The reactant was poured into water, and extracted with ethyl acetate. The extracts were washed with water, dried and concentrated. The obtained residue was purified by silica gel column chromatography to obtain 4-[3-(methoxymethyl)-3-methyl-1-piperidinyl]-1-naphthonitrile (100 mg) (Compound 57).

$^1$H-NMR (300 MHz, CDCl$_3$) δ: 1.14 (3H, s), 1.37-1.45 (1H, m), 1.62-1.70 (1H, m), 1.84-1.94 (2H, m), 2.78-2.82 (1H, m), 3.04-3.14 (3H, m), 3.31 (1H, d, J=9.0 Hz), 3.37 (3H, s), 3.48 (1H, d, J=9.0 Hz), 7.02 (1H, d, J=7.8 Hz), 7.57 (1H, ddd, J=8.4, 6.9 and 1.5 Hz), 7.64 (1H, ddd, J=8.4, 6.9 and 1.5 Hz), 7.80 (1H, d, J=7.8 Hz), 8.16-8.19 (1H, m), 8.21-8.24 (1H, m).

IR (KBr) 2934, 2216, 1574 cm$^-$

Example 58 (Preparation of Compound 58)

A mixture of 4-fluoro-1-naphthonitrile (150 mg), 3,5-dimethylpiperidine (198 mg), potassium carbonate (362 mg), and dimethylsulfoxide (2.0 mL) was stirred at 100° C. for 3 hours. After cooling to room temperature, the reactant was poured into water, and then extracted with ethyl acetate. The extracts were washed with water, dried and concentrated. The obtained residue was purified by silica gel column chromatography to obtain 4-(3,5-dimethyl-1-piperidinyl)-1-naphthonitrile (223 mg) (Compound 58).

$^1$H-NMR (300 MHz, CDCl$_3$) δ: 0.72-0.84 (1H, m), 0.95 (6H, d, J=6.6 Hz), 1.91-2.12 (3H, m), 2.32 (2H, t, J=11.4 Hz), 3.39-3.44 (2H, m), 6.98 (1H, d, J=7.8 Hz), 7.55 (1H, ddd, J=8.4, 6.6 and 1.5 Hz), 7.63 (1H, ddd, J=8.4, 6.6 and 1.5 Hz), 7.80 (1H, d, J=7.8 Hz), 8.11-8.14 (1H, m), 8.16-8.19 (1H, m).

IR (KBr) 2953, 2216, 1574 cm$^{-1}$

Example 59 (Preparation of Compound 59)

To a mixture of pyrrolidine (16 μL), palladium acetate (1.9 mg), rac-2,2'-bis(diphenylphosphino)-1,1'-binaphthyl (15 mg), sodium t-butoxide (22 mg) and toluene (1.5 mL) was added a mixture of 4-cyano-5,6,7,8-tetrahydro-1-naphthalenyl trifluoromethanesulfonate (50 mg) and toluene (0.5 mL) at 80° C. for 50 minutes. After stirring for 1 hour, the mixture was cooled to room temperature and poured into water, and extracted with ethyl acetate. The extracts were washed with water, dried and concentrated. The obtained residue was purified by silica gel column chromatography to obtain 4-(1-pyrrolidinyl)-5,6,7,8-tetrahydro-1-naphthalenecarbonitrile (12 mg) (Compound 59).

$^1$H-NMR (300 MHz, CDCl$_3$) δ: 1.66-1.75 (2H, m), 1.78-1.87 (2H, m), 1.92-1.96 (4H, m), 2.61 (2H, t, J=6.6 Hz), 2.95 (2H, t, J=6.6 Hz), 3.25-3.29 (4H, m), 6.65 (1H, d, J=8.4 Hz), 7.33 (1H, d, J=8.4 Hz).

IR (KBr) 2938, 2209, 1588 cm$^{-1}$

Example 60 (Preparation of Compound 60)

To a mixture of piperidine (39 μL), palladium acetate (3.7 mg), rac-2,2'-bis (diphenylphosphino)-1,1'-binaphthyl (33 mg), sodium t-butoxide (44 mg) and toluene (3.0 mL) was added a mixture of 4-cyano,5,6,7,8-tetrahydro-1-naphthalenyl trifluoromethanesulfonate (100 mg) and toluene (1.0 mL) at 80° C. for 50 minutes. After stirring for 2 hours, the mixture was cooled to room temperature, poured into water, and then extracted with ethyl acetate. The extracts were washed with water, dried and concentrated. The obtained residue was purified by silica gel column chromatography to obtain 4-(1-piperidinyl)-5,6,7,8-tetrahydro-1-naphthalenecarbonitrile (5.0 mg) (Compound 60).

$^1$H-NMR (300 MHz, CDCl$_3$) δ: 1.56-1.63 (2H, m), 1.67-1.77 (6H, m), 1.81-1.89 (2H, m), 2.67 (2H, t, J=6.0 Hz), 2.84-2.87 (4H, m), 2.96 (2H, t, J=6.0 Hz), 6.83 (1H, d, J=8.4 Hz), 7.41 (1H, d, J=8.4 Hz).

IR (KBr) 2934, 2220, 1587 cm$^{-1}$

Example 61 (Preparation of Compounds 61 and 62)

A mixture of 4-(3-oxo-1-pyrrolidinyl)-1-naphthonitrile (159 mg), hydroxylamine hydrochloride (70.1 mg), sodium acetate (99.4 mg), ethanol (4.0 mL) and water (2.0 mL) was stirred at room temperature for 1.5 hours. The reactant was concentrated and the residue was distributed between ethyl acetate and water. The organic layer was washed with brine, dried and concentrated. The obtained residue was purified by silica gel column chromatography to obtain 4-[3-(hydroxyimino)-1-pyrrolidinyl]-1-naphthonitrile (76.5 mg) (Compound 61) providing a high Rf value and 4-[3-(hydroxyimino)-1-pyrrolidinyl]-1-naphthonitrile (20.4 mg) (Compound 62) providing a low Rf value.

Compound 61

¹H-NMR (300 MHz, CDCl₃) δ: 2.94 (2H, t, J=6.9 Hz), 3.57 (2H, t, J=6.9 Hz), 4.03 (2H, s), 7.00 (1H, d, J=8.1 Hz), 7.37 (1H, br.s), 7.58 (1H, ddd, J=8.4, 6.9 and 1.5 Hz), 7.67 (1H, ddd, J=8.4, 6.9 and 1.5 Hz), 7.82 (1H, d, J=8.1 Hz), 8.17-8.23 (2H, m).

IR (KBr) 2216, 1572 cm⁻¹

Compound 62

¹H-NMR (300 MHz, CDCl₃) δ: 2.86-2.90 (2H, m), 3.57 (2H, t, J=6.9 Hz), 4.22 (2H, s), 7.01 (1H, d, J=8.1 Hz), 7.23 (1H, br.s), 7.58 (1H, ddd, J=8.4, 6.9 and 1.5 Hz), 7.67 (1H, ddd, J=8.4, 6.9 and 1.5 Hz), 7.82 (1H, d, J=8.1 Hz), 8.17-8.23 (2H, m).

IR (KBr) 2215, 1572 cm⁻¹

Example 62 (Preparation of Compound 63)

To a mixture of pyrrolidine (31 μL), palladium acetate (3.5 mg), rac-2,2'-bis(diphenylphosphino)-1,1'-binaphthyl (29 mg), sodium t-butoxide (42 mg) and toluene (1.5 mL) was added a mixture of 7-cyano-2,2-dimethyl-2,3-dihydro-1-benzofuran-4-yl trifluoromethanesulfonate (100 mg) and toluene (0.8 mL) at 80° C. for 30 minutes. After stirring for 1.5 hours, the mixture was cooled to room temperature, poured into water, and then extracted with ethyl acetate. The extracts were washed with water, dried and concentrated. The obtained residue was purified by silica gel column chromatography to obtain 2,2-dimethyl-4-(1-pyrrolidinyl)-2,3-dihydro-1-benzofuran-7-carbonitrile (30 mg) (Compound 63).

¹H-NMR (300 MHz, CDCl₃) δ: 1.49 (6H, s), 1.93-1.98 (4H, m), 3.27 (2H, s), 3.45-3.49 (4H, m), 6.03 (1H, d, J=8.7 Hz), 7.13 (1H, d, J=8.7 Hz).

IR (KBr) 2201, 1613 cm⁻¹

Example 63 (Preparation of Compound 64)

4-Cyano-1-naphthylboronic acid (760 mg), 2-methyl-3-oxo cyclopenta-1-en-1-yl trifluoromethanesulfonate (940 mg) and tetrakis triphenylphosphine (90 mg), dioxane (24 mL) and a 2 N-sodium hydroxide solution (3.5 mL) were heated under reflux for 2.5 hours under nitrogen atmosphere. After cooling to room temperature, the mixture was concentrated. Water was poured into the reactant and extracted with ethyl acetate. The extracts were washed with water, dried and concentrated. The obtained residue was purified by silica gel column chromatography to obtain 4-(2-methyl-3-oxocyclopenta-1-en-1-yl)-1-naphthonitrile (622 mg) (Compound 64).

mp 163-165° C.

¹H-NMR (200 MHz, CDCl₃) δ: 1.59(3H, dd, J=1.8 Hz and 2.2 Hz), 2.65-2.75 (2H, m), 2.90-3.01 (2H, m), 7.40 (1H, d, J=7.4 Hz), 7.60-7.95 (3H, m), 7.99 (1H, d, J=7.4 Hz), 8.30-8.40 (1H, m).

IR (KBr) 2223, 1689, 1644 cm⁻¹

Anal. Calcd. for C₁₇H₁₃NO.0.1H₂O: C, 81.97; H, 5.33; N, 5.62. Found: C, 81.99; H, 5.33; N, 5.49.

Example 64 (Preparation of Compound 65)

4-(2-methyl-3-oxocyclopenta-1-en-1-yl)-1-naphthonitrile (125 mg) was dissolved in methyl alcohol (5 mL), sodium borohydride (50 mg) was added thereto, and the mixture was stirred at room temperature for 15 minutes. Water was poured into the reactant and extracted with ethyl acetate. The extracts were washed with water, dried and concentrated. The obtained residue purified by silica gel column chromatography to obtain 4-(3-hydroxy-2-methylcyclopenta-1-en-1-yl)-1-naphthonitrile (63 mg) (Compound 65).

mp 113-114° C.

¹H-NMR (200 MHz, CDCl₃) δ: 1.53-1.65(3H, m), 1.80-2.05 (2H, m), 2.45-2.98 (3H, m), 4.85-5.05 (1H, m), 7.33 (1H, d, J=7.6 Hz), 7.55-7.76 (2H, m), 7.85-7.96 (2H, m), 8.22-8.35 (1H, m).

IR (KBr) 3505, 2222 cm⁻¹

Anal. Calcd. for C₁₇H₁₅NO: C, 81.90; H, 6.06; N, 5.62. Found: C, 81.84; H, 6.25; N, 5.40.

Example 65 (Preparation of Compound 66)

4-(3-hydroxy-2-methylcyclopenta-1-en-1-yl)-1-naphthonitrile (50 mg) was dissolved in N,N-dimethylformamide (2 mL), and the mixture was stirred with ice-cooling. Sodium hydride (60% in oil, 15 mg) was added thereto, and the mixture was further stirred at room temperature for 0.5 hours. After adding methyl iodide (0.1 mL), the reaction solution was stirred at room temperature for 16 hours. Water was poured into the reactant and extracted with ethyl acetate. The extracts were washed with water, dried and concentrated. The obtained residue purified by silica gel column chromatography to obtain 4-(3-methoxy-2-methylcyclopenta-1-en-1-yl)-1-naphthonitrile (19 mg) (Compound 66).

¹H-NMR (200 MHz, CDCl₃) δ: 1.50-1.60(3H, s), 1.19-2.10 (1H, m), 2.30-2.50 (2H, m), 3.46(3H, m), 4.40-4.60 (1H, m), 7.32 (1H, d, J=7.2 Hz), 7.50-7.80 (2H, m), 7.90 (2H, d, J=7.2 Hz), 8.20-8.35 (1H, m).

IR (KBr) 2222, 1102 cm⁻¹

Example 66 (Preparation of Compound 67)

To a mixture of 4-[4-(hydroxymethyl)-1-piperidinyl]-1-naphthonitrile (80 mg) and N,N-dimethylformamide (1.0 mL) was added sodium hydride (60% in oil, 28 mg) at room temperature. After stirring for 20 minutes, methyl iodide (60 μL) was added, the mixture was stirred for 1 hour. The reactant was poured into water and extracted with ethyl acetate. The extracts were washed with water, dried and concentrated. The obtained residue was purified by silica gel column chromatography to obtain 4-[4-(methoxymethyl)-1-piperidinyl]-1-naphthonitrile (79 mg) (Compound 67).

mp 96-97° C.

¹H-NMR (300 MHz, CDCl₃) δ: 1.61-1.70 (2H, m), 1.78-1.95 (3H, m), 2.82 (2H, td, J=12.0 and 2.1 Hz), 3.37 (2H, d, J=6.0 Hz), 3.40 (3H, s), 3.51-3.55 (2H, m), 7.01 (1H, d, J=8.1 Hz), 7.56 (1H, ddd, J=8.4, 6.6 and 1.5 Hz), 7.65 (1H, ddd, J=8.4, 6.6 and 1.5 Hz), 7.82 (1H, d, J=8.1 Hz), 8.17-8.21 (2H, m).

IR (KBr) 2213, 1570 cm⁻¹

Anal. Calcd. for C₁₈H₂₀N₂O: C, 77.11; H, 7.19; N, 9.99. Found: C, 77.00; H, 7.11; N, 9.77.

Example 67 (Preparation of Compound 68)

To a mixture of 1-benzyl-5-hydroxy-5-methyl-2-piperidinone (95 mg) and tetrahydrofuran (2.5 mL) was added lithium aluminum hydride (16 mg) at room temperature, and the mixture was stirred at 75° C. for 5 hours. After cooling to room temperature, water (16 μl), a 25% potassium hydroxide solution (16 μl) and water (48 μl) were sequentially added, and the mixture was stirred for 1 hour. Insolubles were filtered off using celite and mother liquor was concentrated to obtain a yellow oily matter. A mixture of the obtained matter, 10% palladium carbon (50% water content, 92 mg), 4 N hydrochloric acid (0.12 mL) and methanol (1.4 mL) was stirred under hydrogen atmosphere at room temperature for 12 hours. Palladium carbon was filtered off using celite. Mother liquor was concentrated to obtain a pale orange oily matter. A mixture of the obtained matter, 4-fluoro-1-naphthonitrile (50 mg), potassium carbonate (120 mg), and dimethylsulfoxide (1.0 mL) was stirred at 100° C. for 1 hour. After cooling to room temperature, the reactant was poured into water and extracted with ethyl acetate. The extracts were washed with water, dried and concentrated. The obtained residue was purified by silica gel column chromatography to obtain 4-(3-hydroxy-3-methyl-1-piperidinyl)-1-naphthonitrile (15 mg) (Compound 68).

$^1$H-NMR (300 MHz, CDCl$_3$) δ: 1.33 (3H, s), 1.49-1.59 (1H, m), 1.78-1.89 (2H, m), 2.05-2.22 (1H, m), 2.70-2.85 (2H, m), 3.02 (1H, br.s), 3.22-3.26 (1H, m), 3.40-3.53 (1H, m), 7.05 (1H, d, J=7.8 Hz), 7.60-7.70 (2H, m), 7.83 (1H, d, J=7.8 Hz), 8.20-8.29 (2H, m).

IR (KBr) 2216, 1574 cm$^{-1}$

Example 68 (Preparation of Compound 69)

To a mixture of 4-(3-amino-1-pyrrolidinyl)-1-naphthonitrile (120 mg), triethylamine (0.22 mL), and N,N-dimethylformamide (1.5 mL) was added methanesulfonyl chloride (45 μL) at room temperature, and the mixture was stirred for 2 hours. The reactant was poured into water and extracted with ethyl acetate. The extracts were washed with water, dried and concentrated. The obtained residue was purified by silica gel column chromatography to obtain N-[1-(4-cyano-1-naphthyl)-3-pyrrolidinyl]methanesulfonamide (93 mg) (Compound 69).

mp 128-129° C.

$^1$H-NMR (300 MHz, CDCl$_3$) δ: 2.05-2.16 (1H, m), 2.39-2.50 (1H, m), 3.03 (3H, s), 3.47-3.57 (2H, m), 3.74-3.84 (2H, m), 4.17-4.29 (1H, m), 4.80 (1H, d, J=7.8 Hz), 6.78 (1H, d, J=8.4 Hz), 7.52 (1H, ddd, J=8.4, 6.9 and 1.2 Hz), 7.64 (1H, ddd, J=8.4, 6.9 and 1.2 Hz), 7.75 (1H, d, J=8.4 Hz), 8.15-8.19 (2H, m).

IR (KBr) 2207, 1564, 1329, 1152 cm$^{-1}$

Anal. Calcd. for C$_{16}$H$_{17}$N$_3$O$_2$S: C, 60.93; H, 5.43; N, 13.32. Found: C, 60.98; H, 5.57; N, 13.15.

Example 69 (Preparation of Compound 70)

A mixture of 4-fluoro-1-naphthonitrile (100 mg), 1,2,3,4-tetrahydroisoquinoline (150 mg), potassium carbonate (161 mg), and dimethylsulfoxide (1.5 mL) was stirred at 100° C. for 3 hours. After cooling to room temperature, the reactant was poured into water and extracted with ethyl acetate. The extracts were washed with water, dried and concentrated. The obtained residue was purified by silica gel column chromatography to obtain 4-(3,4-dihydro-2(1H)-isoquinolinyl)-1-naphthonitrile (140 mg) (Compound 70).

$^1$H-NMR (300 MHz, CDCl$_3$) δ: 3.15 (2H, t, J=6.0 Hz), 3.55 (2H, t, J=6.0 Hz), 4.39 (2H, s), 7.10-7.14 (2H, m), 7.18-7.26 (3H, m), 7.57 (1H, ddd, J=8.1, 6.9 and 1.2 Hz), 7.66 (1H, ddd, J=8.1, 6.9 and 1.2 Hz), 7.84 (1H, d, J=7.8 Hz), 8.20-8.24 (2H, m).

IR (KBr) 2216, 1572 cm$^{-1}$

Example 70 (Preparation of Compound 71)

To a mixture of 4-[3-(hydroxymethyl)-1-piperidinyl]-1-naphthonitrile (120 mg), tert-butyl methylsulfonyl carbamate (106 mg), triphenylphosphine (142 mg) and tetrahydrofuran (2.0 mL) was added diethyl azodicarboxylate (in a 40% toluene solution, 0.25 mL) at 0° C. The mixture was stirred for 1.5 hours, and then concentrated. The obtained residue was purified by silica gel column chromatography to obtain tert-butyl [[1-(4-cyano-1-naphthyl)-3-piperidinyl]methyl](methylsulfonyl) carbamate (195 mg) (Compound 71).

mp 139-140° C.

$^1$H-NMR (300 MHz, CDCl$_3$) δ: 1.20-1.36 (1H, m), 1.51 (9H, s), 1.87-1.98 (3H, m), 2.30-2.42 (1H, m), 2.59 (1H, t, J=10.8 Hz), 2.77-2.84 (1H, m), 3.28 (3H, s), 3.39-3.50 (2H, m), 3.60-3.75 (2H, m), 7.00 (1H, d, J=7.8 Hz), 7.55 (1H, ddd, J=8.4, 6.9 and 1.5 Hz), 7.63 (1H, ddd, J=8.4, 6.9 and 1.5 Hz), 7.81 (1H, d, J=7.8 Hz), 8.10-8.19 (2H, m).

IR (KBr) 2215, 1726, 1352 cm$^{-1}$

Anal. Calcd. for C$_{23}$H$_{29}$N$_3$O$_4$S: C, 62.28; H, 6.59; N, 9.47. Found: C, 62.06; H, 6.50; N, 9.33.

Example 71 (Preparation of Compound 72)

A mixture of tert-butyl 1-(4-cyano-1-naphthyl)-3-piperidinyl]methyl(methylsulfonyl)carbamate (127 mg), trifluoroacetic acid (0.4 mL), and dichloromethane (1.0 mL) was stirred at room temperature for 1.5 hours. The reaction solution was diluted with diethyl ether, which was washed with 1 N sodium hydroxide and brine, dried and concentrated to obtain N-[[1-(4-cyano-1-naphthyl)-3-piperidinyl]methyl]methanesulfonamide (86 mg) (Compound 72).

$^1$H-NMR (300 MHz, CDCl$_3$) δ: 1.18-1.35 (1H, m), 1.83-2.04 (3H, m), 2.09-2.21 (1H, m), 2.64 (1H, t, J=10.2 Hz), 2.81-2.88 (1H, m), 2.95 (3H, s), 3.10-3.24 (2H, m), 3.35-3.39 (1H, m), 3.44-3.52 (1H, m), 4.45 (1H, t, J=6.6 Hz), 7.01 (1H, d, J=7.8 Hz), 7.57 (1H, ddd, J=8.4, 6.9 and 1.5 Hz), 7.65 (1H, ddd, J=8.4, 6.9 and 1.5 Hz), 7.81 (1H, d, J=7.8 Hz), 8.10-8.13 (1H, m), 8.17-8.19 (1H, m). IR (KBr) 2215, 1572, 1316, 1154 cm$^{-1}$ Example 72 (Preparation of Compound 73)

A mixture of 7-cyano-1-benzothien-4-yl trifluoromethanesulfonate (150 mg) and piperidine (0.45 mL) was stirred at room temperature for 2 hours. The reactant was distributed between ethyl acetate and water. The organic layer was dried and concentrated. The obtained residue was purified by silica gel column chromatography to obtain 4-(1-piperidinyl)-1-benzothiophene-7-carbonitrile (35 mg) (Compound 73).

mp 99-100° C.

$^1$H-NMR (300 MHz, CDCl$_3$) δ: 1.63-1.71 (2H, m), 1.77-1.84 (4H, m), 3.20-3.24 (4H, m), 6.83 (1H, d, J=8.1 Hz), 7.40 (1H, d, J=5.4 Hz), 7.48 (1H, d, J=5.4 Hz), 7.59 (1H, d, J=8.1 Hz).

IR (KBr) 2938, 2213, 1568 cm$^{-1}$

Anal. Calcd. for C$_{14}$H$_{14}$N$_2$S: C, 69.39; H, 5.82; N, 11.56. Found: C, 69.27; H, 5.71; N, 11.40.

Example 73 (Preparation of Compound 74)

A mixture of 4-fluoro-1-naphthonitrile (100 mg), nipecotamide (150 mg), potassium carbonate (161 mg), and dimethylsulfoxide (1.5 mL) was stirred at 100° C. for 3 hours. After cooling to room temperature, the reactact was poured into water and extracted with ethyl acetate. The extracts were washed with water, dried and concentrated. The obtained residue was purified by silica gel column chromatography to obtain 1-(4-cyano-1-naphthyl)-3-piperidinecarboxylic acid amide (140 mg) (Compound 74).

mp 187-18° C.

$^1$H-NMR (300 MHz, DMSO-d$_6$) δ: 1.51-1.64 (1H, m), 1.76-1.87 (2H, m), 1.96-2.02 (1H, m), 2.65-2.81 (2H, m), 2.90 (1H, t, J=11.1 Hz), 3.38-3.48 (2H, m), 6.90 (1H, br.s), 7.17 (1H, d, J=8.4 Hz), 7.40 (1H, br.s), 7.68 (1H, ddd, J=8.1, 6.6 and 1.2 Hz), 7.76 (1H, ddd, J=8.1, 6.6 and 1.2 Hz), 8.02-8.07 (1H, m), 8.15-8.17 (1H, m).

IR (KBr) 3422, 2216, 1661 cm$^{-1}$

Anal. Calcd. for $C_{17}H_{17}N_3O \cdot 0.1H_2O$: C, 72.63; H, 6.17; N, 14.95. Found: C, 72.56; H, 6.16; N, 14.64.

Example 74 (Preparation of Compound 75)

A mixture of 1,2-oxazinane hydrochloride (300 mg), 2-tert-butyl imino-2-diethylamino-1,3-dimethyl-perhydro-1,3,2-diazaphospholine (polystyrene-carried, about 2.2 mmol/g) (1.20 g) and dichloromethane (6.0 mL) was stirred at room temperature for 3 hours. Resin was filtered off, washed with dichloromethane, and then concentrated to obtain a colorless oily matter. A mixture of the obtained matter, 4-fluoro-1-naphthonitrile (225 mg), potassium carbonate (336 mg), and dimethylsulfoxide (3.0 mL) was stirred at 100° C. for 27 hours. After cooling to room temperature, the reactant was poured into water and extracted with ethyl acetate. The extracts were washed with brine, dried and concentrated. The obtained residue was purified by silica gel column chromatography to obtain 4-(1,2-oxazinane-2-yl)-1-naphthonitrile (34 mg) (Compound 75).

mp 111-112° C.

$^1$H-NMR (300 MHz, CDCl$_3$) δ: 1.77-1.85 (2H, m), 2.03-2.10 (2H, m), 3.32-3.36 (2H, m), 4.28 (2H, t, J=5.4 Hz), 7.44 (1H, d, J=7.8 Hz), 7.57 (1H, ddd, J=8.4, 6.9 and 1.5 Hz), 7.65 (1H, ddd, J=8.4, 6.9 and 1.5 Hz), 7.86 (1H, d, J=7.8 Hz), 8.09-8.12 (1H, m), 8.17-8.20 (1H, m).

IR (KBr) 2220, 1576 cm$^{-1}$

Anal. Calcd. for $C_{15}H_{14}N_2O \cdot 0.2H_2O$: C, 74.48; H, 6.00; N, 11.58. Found: C, 74.69; H, 5.87; N, 11.45.

Example 75 (Preparation of Compound 76)

A mixture of 4-fluoro-1-benzothiophene-7-carbonitrile (349 mg), 2-methylpyrrolidine (252 mg), potassium carbonate (544 mg), and dimethylsulfoxide (4.0 mL) was stirred at 100° C. for 1 hour. After cooling to room temperature, the reactant was poured into water and extracted with ethyl acetate. The extracts were washed with water, dried and concentrated. The obtained residue was purified by silica gel column chromatography to obtain 4-(2-methyl-1-pyrrolidinyl)-1-benzothiophene-7-carbonitrile (466 mg) (Compound 76).

$^1$H-NMR (300 MHz, CDCl$_3$) δ: 1.26 (3H, d, J=6.0 Hz), 1.70-1.81 (1H, m), 1.86-2.30 (3H, m), 3.64-3.71 (1H, m), 3.86-3.94 (1H, m), 4.14-4.23 (1H, m), 6.50 (1H, d, J=8.4 Hz), 7.33 (1H, d, J=6.0 Hz), 7.49 (1H, d, J=8.4 Hz), 7.63 (1H, d, J=6.0 Hz).

IR (KBr) 2205, 1566 cm$^{-1}$

Example 76 (Preparation of Compound 77)

A mixture of 4-fluoro-1-naphthonitrile (200 mg) (4-methyl-4-piperidinyl) methanol (242 mg), potassium carbonate (332 mg) and dimethylsulfoxide (3.0 mL) was stirred at 100° C. for 3 hours. After cooling to room temperature, the reactant was poured into water and extracted with ethyl acetate. The extracts were washed with water, dried and concentrated. The obtained residue was purified by silica gel column chromatography to obtain 4-[4-(hydroxymethyl)-4-methyl-1-piperidinyl]-1-naphthonitrile (256 mg) (Compound 77).

mp 136-137° C.

$^1$H-NMR (300 MHz, CDCl$_3$) δ: 1.10 (3H, s), 1.48 (1H, t, J=6.0 Hz), 1.55-1.61 (2H, m), 1.90 (2H, ddd, J=13.2, 10.2 and 4.2 Hz), 3.04-3.12 (2H, m), 3.24-3.31 (2H, m), 3.53 (2H, d, J=6.0 Hz), 7.04 (1H, d, J=8.1 Hz), 7.57 (1H, ddd, J=8.1, 6.9 and 1.5 Hz), 7.65 (1H, ddd, J=8.1, 6.9 and 1.5 Hz), 7.83 (1H, d, J=8.1 Hz), 8.15-8.21 (2H, m).

IR (KBr) 2216, 1574 cm$^{-1}$

Anal. Calcd. for $C_{18}H_{20}N_2O$: C, 77.11; H, 7.19; N, 9.99. Found: C, 76.88; H, 7.12; N, 9.72.

Example 77 (Preparation of Compound 78)

A mixture of 4-fluoro-1-naphthonitrile (100 mg), 4-piperidine ethanol (151 mg), potassium carbonate (161 mg) and dimethylsulfoxide (1.5 mL) was stirred at 100° C. for 3 hours. After cooling to room temperature, the reactant was poured into water and extracted with ethyl acetate. The extracts were washed with water, dried and concentrated. The obtained residue was purified by silica gel column chromatography to obtain 4-[4-(2-hydroxyethyl)-1-piperidinyl]-1-naphthonitrile (149 mg) (Compound 78).

mp 128-129° C.

$^1$H-NMR (300 MHz, CDCl$_3$) δ: 1.30 (1H, t, J=5.1 Hz), 1.59-1.73 (5H, m), 1.90-1.94 (2H, m), 2.78-2.86 (2H, m), 3.49-3.53 (2H, m), 3.77-3.83 (2H, m), 7.01 (1H, d, J=8.1 Hz), 7.56 (1H, ddd, J=8.4, 6.9 and 1.5 Hz), 7.65 (1H, ddd, J=8.4, 6.9 and 1.5 Hz), 7.82 (1H, d, J=8.1 Hz), 8.14-8.20 (2H, m).

IR (KBr) 2924, 2216, 1572 cm$^{-1}$

Anal. Calcd. for $C_{18}H_{20}N_2O$: C, 77.11; H, 7.19; N, 9.99. Found: C, 76.89; H, 7.03; N, 9.71.

Example 78 (Preparation of Compound 79)

To a mixture of 4-[4-(2-hydroxyethyl)-1-piperidinyl]-1-naphthonitrile (80 mg) and N,N-dimethylformamide (1.0 mL) was added sodium hydride (60% in oil, 34.1 mg) at room temperature, and the mixture was stirred for 20 minutes. After adding methyl iodide (66 μl), the mixture was stirred for 40 minutes. The reactant was poured into water and extracted with ethyl acetate. The extracts were washed with water, dried and concentrated. The obtained residue was purified by silica gel column chromatography to obtain 4-[4-(2-methoxyethyl)-1-piperidinyl]-1-naphthonitrile (79 mg) (Compound 79).

mp 95-96° C.

$^1$H-NMR (300 MHz, CDCl$_3$) δ: 1.54-1.69 (5H, m), 1.88-1.92 (2H, m), 2.77-2.85 (2H, m), 3.37 (3H, s), 3.48-3.52 (4H, m), 7.00 (1H, d, J=7.8 Hz), 7.56 (1H, ddd, J=8.1, 6.9 and 1.5 Hz), 7.64 (1H, ddd, J=8.1, 6.9 and 1.5 Hz), 7.81 (1H, d, J=7.8 Hz), 8.14-8.20 (2H, m).

IR (KBr) 2216, 1574 cm$^{-1}$

Anal. Calcd. for $C_{19}H_{22}N_2O$: C, 77.52; H, 7.53; N, 9.52. Found: C, 77.37; H, 7.31; N, 9.40.

Example 79 (Preparation of Compound 80)

A mixture of 2-(1-benzyl-4-piperidinyl)-2-propanol (790 mg), 10% palladium carbon (50% water content, 720 mg) and methanol (20 mL) was stirred under hydrogen atmosphere at room temperature for 16 hours. Palladium carbon was filtered off using celite and washed with methanol. Mother liquor was concentrated to obtain a colorless solid matter (485 mg). A mixture of the obtained solid (151 mg), 4-fluoro-1-naphthonitrile (100 mg), potassium carbonate (161 mg), and dimethylsulfoxide (1.5 mL) was stirred at 100° C. for 3 hours. After cooling to room temperature, the reactant was poured into water and extracted with ethyl acetate. The extracts were washed with water, dried and concentrated. The obtained residue was purified by silica gel column chromatography to obtain 4-[4-(1-hydroxy-1-methylethyl)-1-piperidinyl]-1-naphthonitrile (150 mg) (Compound 80).

mp 133-134° C.

$^1$H-NMR (300 MHz, CDCl$_3$) δ: 1.29 (6H, s), 1.48-1.59 (1H, m), 1.66-1.80 (2H, m), 1.94-1.98 (2H, m), 2.74-2.82 (2H, m), 3.58-3.62 (2H, m), 7.00 (1H, d, J=8.1 Hz), 7.56 (1H, ddd, J=8.4, 6.9 and 1.5 Hz), 7.64 (1H, ddd, J=8.4, 6.9 and 1.5 Hz), 7.81 (1H, d, J=8.1 Hz), 8.14-8.20 (2H, m).

IR (KBr) 2216, 1574 cm$^{-1}$

Anal. Calcd. for C$_{19}$H$_{22}$N$_2$O: C, 77.52; H, 7.53; N, 9.52. Found: C, 77.31; H, 7.28; N, 9.24.

Example 80 (Preparation of Compounds 81 and 82)

A mixture of tert-butyl (2R)-2-vinyl-1-pyrrolidine carboxylate (70 mg) and 4 N hydrogen chloride-ethyl acetate (1.0 mL) was stirred at room temperature for 1.5 hours. The reactant was concentrated and processed with diethyl ether to obtain a colorless solid matter. A mixture of the obtained solid, 4-fluoro-1-naphthonitrile (50 mg), potassium carbonate (104 mg), and dimethylsulfoxide (1.0 mL) was stirred at 100° C. for 3 hours. After cooling to room temperature, the reactant was poured into water and extracted with ethyl acetate. The extracts were washed with water, dried and concentrated. The obtained residue was purified by silica gel column chromatography to obtain 4-[(2R)-2-vinyl-1-pyrrolidinyl]-1-naphthonitrile (36 mg). The enantiomer excess of the obtained compound was 24.8% e.e.

A mixture of tert-butyl (2S)-2-vinyl-1-pyrrolidine carboxylate (185 mg) and 4 N hydrogen chloride-ethyl acetate (1.0 mL) was stirred at room temperature for 1.5 hours. The reactant was concentrated and processed with diethyl ether to obtain a colorless solid matter. A mixture of the obtained solid, 4-fluoro-1-naphthonitrile (100 mg), potassium carbonate (242 mg), and dimethylsulfoxide (1.5 mL) was stirred at 100° C. for 3 hours. After cooling to room temperature, the reactant was poured into water and extracted with ethyl acetate. The extracts were washed with water, dried and concentrated. The obtained residue was purified by silica gel column chromatography to obtain 4-[(2S)-2-vinyl-1-pyrrolidinyl]-1-naphthonitrile (90 mg). The enantiomer excess of the obtained compound was 22.7% e.e. 4-[(2R)-2-vinylpyrrolidinyl]-1-naphthonitrile (25 mg) and 4-[(2S)-2-vinylpyrrolidinyl]-1-naphthonitrile (70 mg) were combined and the combination was optically resolved using CHIRALPAK AS (50×500 mm), to obtain 4-[(2R)-2-vinyl-1-pyrrolidinyl]-1-naphthonitrile (Compound 81) (43 mg) and 4-[(2S)-2-vinyl-1-pyrrolidinyl]-1-naphthonitrile (Compound 82) (50 mg).

Compound 81

[α]$_D$=−2670.0° (c=0.295, MeOH).

$^1$H-NMR (300 MHz, CDCl$_3$) δ: 1.80-1.98 (2H, m), 2.02-2.10 (1H, m), 2.27-2.35 (1H, m), 3.37-3.43 (1H, m), 4.05-4.13 (1H, m), 4.32-4.40 (1H, m), 5.08 (1H, dt, J=10.2 and 1.2 Hz), 5.23 (1H, dt, J=17.1 and 1.2 Hz), 5.70 (1H, ddd, J=17.1, 10.2 and 7.2 Hz), 6.78 (1H, d, J=8.4 Hz), 7.46 (1H, ddd, J=8.4, 6.9 and 1.2 Hz), 7.59 (1H, ddd, J=8.4, 6.9 and 1.2 Hz), 7.71 (1H, d, J=8.4 Hz), 8.13-8.16 (1H, m), 8.21-8.24 (1H, m).

IR (KBr) 2209, 1566 cm$^{-1}$

Compound 82

[α]$_D$=+267.9° (c=0.345, MeOH).

$^1$H-NMR (300 MHz, CDCl$_3$) δ: 1.80-1.98 (2H, m), 2.02-2.10 (1H, m), 2.27-2.35 (1H, m), 3.37-3.43 (1H, m), 4.05-4.13 (1H, m), 4.32-4.40 (1H, m), 5.08 (1H, dt, J=10.2 and 1.2 Hz), 5.23 (1H, dt, J=17.1 and 1.2 Hz), 5.70 (1H, ddd, J=17.1, 10.2 and 7.2 Hz), 6.78 (1H, d, J=8.4 Hz), 7.46 (1H, ddd, J=8.4, 6.9 and 1.2 Hz), 7.59 (1H, ddd, J=8.4, 6.9 and 1.2 Hz), 7.71 (1H, d, J=8.4 Hz), 8.13-8.16 (1H, m), 8.21-8.24 (1H, m).

IR (KBr) 2209, 1566 cm$^{-1}$

Example 81 (Preparation of Compounds 83 and 84)

A mixture of tert-butyl (2S)-2-ethyl-1-pyrrolidine carboxylate (70 mg) and 4 N hydrogen chloride-ethyl acetate (1.0 mL) was stirred at room temperature for 1.5 hours. The reactant was concentrated and processed with diethyl ether to obtain a colorless solid matter. A mixture of the obtained matter, 4-fluoro-1-naphthonitrile (50 mg), potassium carbonate (104 mg), and dimethylsulfoxide (1.0 mL) was stirred at 100° C. for 3 hours. After cooling to room temperature, the reactant was poured into water and extracted with ethyl acetate. The extracts were washed with water, dried and concentrated. The obtained residue was purified by silica gel column chromatography to obtain 4-[(2S)-2-ethyl-1-pyrrolidinyl]-1-naphthonitrile (33 mg). The enantiomer excess of the obtained compound was 24.4% e.e.

A mixture of tert-butyl (2R)-2-ethyl-1-pyrrolidine carboxylate (130 mg) and 4 N hydrogen chloride-ethyl acetate (1.5 mL) was stirred at room temperature for 1.5 hours. The reactant was concentrated and processed with diethyl ether to obtain a colorless solid matter. A mixture of the obtained matter, 4-fluoro-1-naphthonitrile (75 mg), potassium carbonate (182 mg), and dimethylsulfoxide (1.5 mL) was stirred at 100° C. for 3 hours. After cooling to room temperature, the reactant was poured into water and extracted with ethyl acetate. The extracts were washed with water, dried and concentrated. The obtained residue was purified by silica gel column chromatography to obtain 4-[(2R)-2-ethyl-1-pyrrolidinyl]-1-naphthonitrile (85 mg). The enantiomer excess of the obtained compound was 21.0% e.e. 4-[(2S)-2-ethyl-1-pyrrolidinyl]-1-naphthonitrile (80 mg) and 4-[(2R)-2-ethyl-1-pyrrolidinyl]-1-naphthonitrile (19 mg) were combined and the combination was optically resolved using CHIRALPAK AS (50×500 mm), to obtain 4-[(2S)-2-ethyl-1-pyrrolidinyl]-1-naphthonitrile (Compound 83) (44 mg) and 4-[(2R)-2-ethyl-1-pyrrolidinyl]-1-naphthonitrile (Compound 84 (51 mg).

Compound 83

[α]$_D$=−294.6° (c=0.330, MeOH).

$^1$H-NMR (300 MHz, CDCl$_3$) δ: 0.90 (3H, t, J=7.8 Hz), 1.30-1.45 (1H, m), 1.68-1.86 (3H, m), 1.95-2.05 (1H, m), 2.26-2.34 (1H, m), 3.32-3.38 (1H, m), 3.83-3.92 (1H, m), 3.95-4.03 (1H, m), 6.79 (1H, d, J=8.1 Hz), 7.45 (1H, ddd, J=8.4, 6.9 and 1.2 Hz), 7.59 (1H, ddd, J=8.4, 6.9 and 1.2 Hz), 7.73 (1H, d, J=8.1 Hz), 8.13-8.18 (2H, m).

IR (KBr) 2963, 2209, 1564 cm$^{-1}$

Compound 84

[α]$_D$=+294.9° (c=0.380, MeOH).

$^1$H-NMR (300 MHz, CDCl$_3$) δ: 0.90 (3H, t, J=7.8 Hz), 1.30-1.45 (1H, m), 1.68-1.86 (3H, m), 1.95-2.05 (1H, m), 2.26-2.34 (1H, m), 3.32-3.38 (1H, m), 3.83-3.92 (1H, m), 3.95-4.03 (1H, m), 6.79 (1H, d, J=8.1 Hz), 7.45 (1H, ddd, J=8.4, 6.9 and 1.2 Hz), 7.59 (1H, ddd, J=8.4, 6.9 and 1.2 Hz), 7.73 (1H, d, J=8.1 Hz), 8.13-8.18 (2H, m).

IR (KBr) 2963, 2209, 1564 cm$^{-1}$

Example 82 (Preparation of Compound 85)

tert-Butyl (2S)-2-methylpyrrolidine-1-carboxylate ([α]$_D$=+32.7° (c=2.17, CHCl$_3$)) (1250 mg), which was synthesized by a known method, was dissolved in toluene (2.0 mL), trifluoroacetic acid (4.0 mL) was added, and the mixture was stirred at room temperature for 2 hours. The reaction solution was concentrated and dried. To the residue was added 4-fluoro-1-naphthonitrile (855 mg), potassium carbonate (2800 mg), and dimethylsulfoxide (10.0 mL), and the mixture was stirred at 100° C. for 5.5 hours. After cooling to room temperature, water was poured into the reactant and extracted with ethyl acetate. The extracts were washed with water, dried and concentrated. The obtained residue was purified by silica gel column chromatography to obtain 4-[(2S)-2-methyl-1-pyrrolidinyl]-1-naphthonitrile (780 mg) (Compound 85).

$[\alpha]_D = -244.4°$ (c=0.448, MeOH).
$^1$H-NMR (200 MHz, CDCl$_3$) δ: 1.18 (3H, d, J=5.8 Hz), 1.60-2.15 (3H, m), 2.20-2.40 (1H, m), 3.25-3.40 (1H, m), 3.90-4.15 (2H, m), 6.82 (1H, d, J=8.0 Hz), 7.40-7.70 (2H, m) 7.76(1H, d, J=8.0 Hz), 8.15-8.25(2H, m).

Example 83 (Preparation of Compounds 85 and 86)

4-(2-methyl-1-pyrrolidinyl)-1-naphthonitrile (1.68 g) was subjected to optical resolution using CHIRALPAK AS (50× 500 mm) to obtain 4-[(2S)-2-methyl-1-pyrrolidinyl]-1-naphthonitrile (Compound 85) (804 mg) and 4-[(2R)-2-methyl-1-pyrrolidinyl]-1-naphthonitrile (Compound 86) (805 mg).

Compound 85
mp 73-74° C.
$[\alpha]_D = -251.5°$ (c=0.470, MeOH).
NMR values were identical to those of Compound 85 in Example 81.
IR (KBr) 2209, 1565, 1514, 1327, 763 cm$^{-1}$
Anal. Calcd. for C$_{16}$H$_{16}$N$_2$: C, 81.32; H, 6.82; N, 11.85. Found: C, 81.35; H, 6.87; N, 11.84.

Compound 86
$[\alpha]_D = +257.7°$ (c=0.410, MeOH).
$^1$H-NMR (200 MHz, CDCl$_3$) δ: 1.18 (3H, d, J=5.8 Hz), 1.60-2.15 (3H, m), 2.20-2.40 (1H, m), 3.25-3.40 (1H, m), 3.90-4.15 (2H, m), 6.82 (1H, d, J=8.0 Hz), 7.40-7.70 (2H, m) 7.76(1H, d, J=8.0 Hz), 8.15-8.25(2H, m).
IR (KBr) 2209, 1565, 1514, 1327, 763 cm$^{-1}$ Example 84 (Preparation of Compound 87)

A mixture of 4-fluoro-1-naphthonitrile (70 mg), ethyl 3-(4-piperidinyl)propionate (91 mg), potassium carbonate (78 mg) and dimethylsulfoxide (1.0 mL) was stirred at 100° C. for 1 hour. After cooling to room temperature, the reactant was poured into water and extracted with ethyl acetate. The extracts were washed with water, dried and concentrated. The obtained residue was purified by silica gel column chromatography to obtain ethyl 3-[1-(4-cyano-1-naphthyl)-4-piperidinyl]propionate (110 mg) (Compound 87).
mp 106-107° C.
$^1$H-NMR (300 MHz, CDCl$_3$) δ: 1.28 (3H, t, J=7.2 Hz), 1.54-1.62 (2H, m), 1.69-1.77 (2H, m), 1.88-1.91 (2H, m), 2.41 (2H, t, J=7.5 Hz), 2.79 (2H, t, J=11.1 Hz), 3.46-3.52 (2H, m), 4.16 (2H, q, J=7.2 Hz), 6.99 (1H, d, J=7.8 Hz), 7.55 (1H, ddd, J=8.4, 6.9 and 1.5 Hz), 7.64 (1H, ddd, J=8.4, 6.9 and 1.5 Hz), 7.80 (1H, d, J=7.8 Hz), 8.12-8.19 (2H, m).
IR (KBr) 2216, 1732, 1574 cm$^{-1}$
Anal. Calcd. for C$_{21}$H$_{24}$N$_2$O$_2$: C, 74.97; H, 7.19; N, 8.33. Found: C, 74.71; H, 7.08; N, 7.99.

Example 85 (Preparation of Compound 88)

To a mixture of ethyl 3-(4-piperidinyl)butyrate (870 mg) and tetrahydrofuran (10 mL) was added lithium aluminum hydride (178 mg) at 0° C., and the mixture was stirred for 6 hours. Water (0.18 mL), a 25% potassium hydroxide solution (0.18 mL) and water (0.54 mL) were sequentially added and the mixture was stirred for 14 hours. Insolubles were filtered off using celite and mother liquor was concentrated to obtain a pale yellow oily matter (590 mg). A mixture of the obtained matter (167 mg), 4-fluoro-1-naphthonitrile (100 mg), potassium carbonate (202 mg) and dimethylsulfoxide (1.0 mL) was stirred at 100° C. for 3 hours. After cooling to room temperature, the reactant was poured into water and extracted with ethyl acetate. The extracts were washed with water, dried and concentrated. The obtained residue was purified by silica gel column chromatography to obtain 4-[4-(3-hydroxypropyl)-1-piperidinyl]-1-naphthonitrile (105 mg) (Compound 88).
mp 114-115° C.
$^1$H-NMR (300 MHz, CDCl$_3$) δ: 1.30 (1H, t, J=5.4 Hz), 1.43-1.54 (4H, m), 1.57-1.72 (3H, m), 1.90-1.92 (2H, m), 2.80 (2H, t, J=11.7 Hz), 3.49-3.54 (2H, m), 3.70 (2H, td, J=6.6 and 5.4 Hz), 7.00 (1H, d, J=8.1 Hz), 7.56 (1H, ddd, J=8.4, 6.9 and 1.5 Hz), 7.65 (1H, ddd, J=8.4, 6.9 and 1.5 Hz), 7.82 (1H, d, J=8.1 Hz), 8.14-8.20 (2H, m).
IR (KBr) 2932, 2216, 1572 cm$^{-1}$
Anal. Calcd. for C$_{19}$H$_{22}$N$_2$O: C, 75.92; H, 7.65; N, 8.85. Found: C, 75.79; H, 7.71; N, 8.69.

Example 86 (Preparation of Compound 89)

A mixture of 2,2,2-trifluoro-1-(4-fluoro-1-naphthyl)ethanone (100 mg), 2-methylpyrrolidine (85 mg), potassium carbonate (138 mg), and dimethylsulfoxide (1.0 mL) was stirred at 100° C. for 30 minutes. After cooling to room temperature, the reactant was poured into water and extracted with ethyl acetate. The extracts were washed with water, dried and concentrated. The obtained residue was purified by silica gel column chromatography to obtain 2,2,2-trifluoro-1-[4-(2-methyl-1-pyrrolidinyl)-1-naphthyl]ethanone (86 mg) (Compound 89).
$^1$H-NMR (300 MHz, CDCl$_3$) δ: 1.30 (3H, d, J=6.0 Hz), 1.66-1.84 (2H, m), 1.97-2.04 (1H, m), 2.29-2.42 (1H, m), 3.54-3.60 (1H, m), 4.05-4.16 (2H, m), 6.75 (1H, d, J=9.0 Hz), 7.44 (1H, ddd, J=8.4, 6.9 and 1.5 Hz), 7.63 (1H, ddd, J=8.4, 6.9 and 1.5 Hz), 8.09-8.16 (2H, m), 9.24 (1H, d, J=9.0 Hz).
IR (KBr) 1669, 1559, 1518 cm$^{-1}$ Example 87 (Preparation of Compound 90)

A mixture of 1-(4-fluoro-1-naphthyl)ethanone (141 mg), 2-methylpyrrolidine (96 mg), potassium carbonate (207 mg), and dimethylsulfoxide (1.5 mL) was stirred at 100° C. for 1.5 hours. After cooling to room temperature, the reactant was poured into water and extracted with ethyl acetate. The extracts were washed with water, dried and concentrated. The obtained residue was purified by silica gel column chromatography to obtain 1-[4-(2-methyl-1-pyrrolidinyl)-1-naphthyl]ethanone (50 mg) (Compound 90).
$^1$H-NMR (300 MHz, CDCl$_3$) δ 1.17 (3H, d, J=6.0 Hz), 1.67-1.88 (2H, m), 1.97-2.05 (1H, m), 2.26-2.34 (1H, m), 2.70 (3H, s), 3.20-3.26 (1H, m), 3.95-4.04 (2H, m), 6.83 (1H, d, J=8.1 Hz), 7.43 (1H, ddd, J=8.7, 6.9 and 1.5 Hz), 7.56 (1H, ddd, J=8.7, 6.9 and 1.5 Hz), 7.97 (1H, d, J=8.1 Hz), 8.15-8.19 (1H, m), 9.06-9.09 (1H, m).
IR (KBr) 1653, 1566, 1512 cm$^{-1}$ Example 88 (Preparation of Compound 91)

A mixture of 4-hydrazino-1-naphthonitrile (560 mg), acrylamide (304 mg), sodium ethoxide (20%, 1.5 mL), ethanol (15 mL) and toluene (15 mL) was stirred at 1000° C. for 2 hours. The mixture was cooled to room temperature and then concentrated. To residue was added a potassium hydrogensulfate solution, acidified, and then extracted with ethyl acetate. The extracts were washed with water, dried and concentrated. The obtained residue was purified by silica gel column chromatography to obtain 4-(3-oxo-1-pyrazolidinyl)-1-naphthonitrile (102 mg) (Compound 91).

$^1$H-NMR (300 MHz, DMSO-d$_6$) δ: 2.43 (2H, t, J=8.1 Hz), 4.02 (2H, t, J=8.1 Hz), 7.30 (1H, d, J=8.1 Hz), 7.72 (1H, ddd, J=8.4, 6.9 and 1.5 Hz), 7.81 (1H, ddd, J=8.4, 6.9 and 1.5 Hz), 8.07-8.10 (2H, m), 8.18-8.21 (1H, m), 10.22 (1H, s).

IR (KBr) 2218, 1707 cm$^{-1}$

Example 89 (Preparation of Compound 92 and 93)

To a mixture of 4-(3-oxo-1-pyrazolidinyl)-1-naphthonitrile (72 mg) and N,N-dimethylformamide (4.0 mL) was added sodium hydride (60% in oil, 17 mg) at room temperature, and the mixture was stirred for 15 minutes. After adding methyl iodide (26 μl), the mixture was stirred for 40 minutes. The reactant was poured into water and extracted with ethyl acetate. The extracts were washed with water, dried and concentrated. The obtained residue was purified by silica gel column chromatography to obtain 4-(3-methoxy-4,5-dihydro-1H-pyrazole-1-yl)-1-naphthonitrile (Compound 92) (18 mg) and 4-(2-methyl-3-oxo-1-pyrazolidinyl)-1-naphthonitrile (compound 93) (43 mg).

Compound 92

$^1$H-NMR (300 MHz, CDCl$_3$) δ: 2.95 (2H, t, J=9.3 Hz), 3.94 (2H, t, J=9.3 Hz), 3.99 (3H, s), 7.03 (1H, d, J=8.1 Hz), 7.52 (1H, ddd, J=8.4, 6.9 and 1.2 Hz), 7.63 (1H, ddd, J=8.4, 6.9 and 1.2 Hz), 7.77 (1H, d, J=8.1 Hz), 8.16-8.19 (1H, m), 8.55-8.58 (1H, m).

IR (KBr) 2205, 1640, 1568, 1518 cm$^{-1}$

Compound 93 mp 192-193° C.

$^1$H-NMR (300 MHz, CDCl$_3$) δ: 2.4-2.8 (2H, br), 3.09 (3H, s), 3.7-4.3 (2H, br), 6.98 (1H, d, J=7.8 Hz), 7.67 (1H, ddd, J=8.4, 6.6 and 1.2 Hz), 7.74 (1H, ddd, J=8.4, 6.6 and 1.2 Hz), 7.86 (1H, d, J=7.8 Hz), 8.16-8.19 (1H, m), 8.25-8.28 (1H, m).

IR (KBr) 2218, 1698 cm$^{-1}$

Anal. Calcd. for C$_{15}$H$_{13}$N$_3$O: C, 71.70; H, 5.21; N, 16.72. Found: C, 71.55; H, 5.31; N, 16.59.

Example 90 (Preparation of Compound 94)

A mixture of 4-fluoro-1-benzothiophene-7-carbonitrile (100 mg), 4-(2-hydroxyethyl) piperidine (109 mg), potassium carbonate (156 mg), and dimethylsulfoxide (2.0 mL) was stirred at 100° C. for 1 hour. After cooling to room temperature, the reactant was poured into water and extracted with ethyl acetate. The extracts were washed with water, dried and concentrated. The obtained residue was purified by silica gel column chromatography to obtain 4-[4-(2-hydroxyethyl)]-1-piperidinyl]-1-benzothiophene-7-carbonitrile (145 mg) (Compound 94).

mp 134-135° C.

$^1$H-NMR (300 MHz, CDCl$_3$) δ: 1.26 (1H, t, J=5.1 Hz), 1.46-1.76 (5H, m), 1.88-1.92 (2H, m), 2.85 (2H, td, J=12.0 and 1.8 Hz), 3.63-3.67 (2H, m), 3.77 (2H, td, J=6.3 and 5.1 Hz), 6.83 (1H, d, J=8.1 Hz), 7.39 (1H, d, J=5.4 Hz), 7.48 (1H, d, J=5.4 Hz), 7.59 (1H, d, J=8.1 Hz).

IR (KBr) 2928, 2215, 1566, 1462 cm$^{-1}$

Anal. Calcd. for C$_{16}$H$_{18}$N$_2$OS: C, 67.10; H, 6.33; N, 9.78. Found: C, 67.01; H, 6.28; N, 9.76.

Example 91 (Preparation of Compound 95)

A mixture of 4-fluoro-1-benzofuran-7-carbonitrile (400 mg), 2-methylpyrrolidine (317 mg), potassium carbonate (686 mg), and dimethylsulfoxide (4.0 mL) was stirred at 100° C. for 1 hour. After cooling to room temperature, the reactant was poured into water and extracted with ethyl acetate. The extracts were washed with water, dried and concentrated. The obtained residue was purified by silica gel column chromatography to obtain 4-(2-methyl-1-pyrrolidinyl)-1-benzofuran-7-carbonitrile (542 mg) (Compound 95).

mp 82-83° C.

$^1$H-NMR (300 MHz, CDCl$_3$) δ: 1.26 (3H, d, J=6.3 Hz), 1.76-1.83 (1H, m), 2.01-2.20 (3H, m), 3.54-3.63 (1H, m), 3.74-3.81 (1H, m), 4.20-4.29 (1H, m), 6.27 (1H, d, J=8.7 Hz), 6.95 (1H, d, J=2.1 Hz), 7.38 (1H, d, J=8.7 Hz), 7.54 (1H, d, J=2.1 Hz).

IR (KBr) 2211, 1607, 1508 cm$^{-1}$

Anal. Calcd. for C$_{14}$H$_{14}$N$_2$O: C, 74.31; H, 6.24; N, 12.38. Found: C, 74.10; H, 6.34; N, 12.20.

Example 92 (Preparation of Compound 96)

A mixture of 4-fluoro-1-benzofuran-7-carbonitrile (100 mg), 4-(2-hydroxyethyl) piperidine (120 mg), potassium carbonate (172 mg) and dimethylsulfoxide (2.0 mL) was stirred at 100° C. for 1 hour. After cooling to room temperature, the reactant was poured into water and extracted with ethyl acetate. The extracts were washed with water, dried and concentrated. The obtained residue was purified by silica gel column chromatography to obtain 4-[4-(2-hydroxyethyl)-1-piperidinyl]-1-benzofuran-7-carbonitrile (135 mg) (Compound 96).

mp 103-104° C.

$^1$H-NMR (300 MHz, CDCl$_3$) δ: 1.27 (1H, t, J=5.4 Hz), 1.39-1.80 (5H, m), 1.86-1.91 (2H, m), 2.94 (2H, td, J=12.3 and 2.4 Hz), 3.74-3.84 (4H, m), 6.63 (1H, d, J=8.4 Hz), 6.82 (1H, d, J=2.4 Hz), 7.46 (1H, d, J=8.4 Hz), 7.64 (1H, d, J=2.4 Hz).

IR (KBr) 2926, 2218, 1607, 1503 cm$^{-1}$

Anal. Calcd. for C$_{16}$H$_{18}$N$_2$O$_2$: C, 71.09; H, 6.71; N, 10.36. Found: C, 71.13; H, 6.67; N, 10.38.

Example 93 (Preparation of Compound 97)

A mixture of 4-fluoro-2-methyl-1-benzofuran-7-carbonitrile (100 mg), 2-methylpyrrolidine (73 mg), potassium carbonate (158 mg) and dimethylsulfoxide (2.0 mL) was stirred at 100° C. for 1 hour. After cooling to room temperature, the reactant was poured into water and extracted with ethyl acetate. The extracts were washed with water, dried and concentrated. The obtained residue was purified by silica gel column chromatography to obtain 2-methyl-4-(2-methyl-1-pyrrolidinyl)-1-benzofuran-7-carbonitrile (88 mg) (Compound 97).

mp 78-80° C.

$^1$H-NMR (300 MHz, CDCl$_3$) δ: 1.24 (3H, d, J=6.6 Hz), 1.75-1.80 (1H, m), 1.96-2.22 (3H, m), 2.45 (3H, d, J=0.9 Hz), 3.51-3.59 (1H, m), 3.71-3.78 (1H, m), 4.18-4.27 (1H, m), 6.24 (1H, d, J=8.4 Hz), 6.54-6.55 (1H, m), 7.30 (1H, d, J=8.4 Hz).

IR (KBr) 2209, 1605, 1512 cm$^{-1}$

Anal. Calcd. for C$_{15}$H$_{16}$N$_2$O: C, 74.97; H, 6.71; N, 11.66. Found: C, 74.85; H, 6.67; N, 11.82.

Example 94 (Preparation of Compound 98)

A mixture of 4-fluoro-2-methyl-1-benzofuran-7-carbonitrile (100 mg), 4-(2-hydroxyethyl)piperidine (111 mg), potassium carbonate (158 mg) and dimethylsulfoxide (2.0 mL) was stirred at 100° C. for 1 hour. After cooling to room temperature, the reactant was poured into water and extracted with ethyl acetate. The extracts were washed with water, dried and concentrated. The obtained residue was purified by silica gel column chromatography to obtain 4-[4-(2-hydroxyethyl)-1-piperidinyl]-2-methyl-1-benzofuran-7-carbonitrile (149 mg) (Compound 98).

mp 106-107° C.

$^1$H-NMR (300 MHz, CDCl$_3$) δ: 1.29 (1H, t, J=4.8 Hz), 1.37-1.50 (2H, m), 1.57-1.74 (3H, m), 1.84-1.89 (2H, m), 2.48 (3H, d, J=1.2 Hz), 2.88 (2H, td, J=12.0 and 2.4 Hz), 3.73-3.79 (4H, m), 6.40-6.41 (1H, m), 6.58 (1H, d, J=8.4 Hz), 7.37 (1H, d, J=8.4 Hz).

IR (KBr) 2924, 2220, 1607 cm$^-$

Anal. Calcd. for C$_{17}$H$_{20}$N$_2$O$_2$: C, 71.81; H, 7.09; N, 9.85. Found: C, 71.62; H, 7.29; N, 9.99.

Example 95 (Preparation of Compound 99)

A mixture of 4-fluoro-1-naphthonitrile (40 mg), 3-fluoropyrrolidine hydrochloride (29 mg), potassium carbonate (81 mg) and dimethylsulfoxide (1.0 mL) was stirred at 100° C. for 2 hours. After cooling to room temperature, the reactant was poured into water and extracted with ethyl acetate. The extracts were washed with water, dried and concentrated. The obtained residue was purified by silica gel column chromatography to obtain 4-(3-fluoro-1-pyrrolidinyl)-1-naphthonitrile (32 mg) (Compound 99).

$^1$H-NMR (300 MHz, CDCl$_3$) δ: 2.11-2.46 (2H, m), 3.48-3.55 (1H, m), 3.66-4.00 (3H, m), 5.39 (1H, dt, J=53.7 and 3.9 Hz), 6.78 (1H, d, J=8.1 Hz), 7.49 (1H, ddd, J=8.4, 6.9 and 1.5 Hz), 7.62 (1H, ddd, J=8.4, 6.9 and 1.5 Hz), 7.75 (1H, d, J=8.1 Hz), 8.16-8.22 (2H, m).

IR (KBr) 2207, 1566 cm$^{-1}$

Example 96 (Preparation of Compound 100)

A mixture of 4-fluoro-1-benzothiophene-7-carbonitrile (40 mg), 3-fluoropyrrolidine hydrochloride (28 mg), potassium carbonate (78 mg) and dimethylsulfoxide (1.0 mL) was stirred at 100° C. for 2 hours. After cooling to room temperature, the reactant was poured into water and extracted with ethyl acetate. The extracts were washed with water, dried and concentrated. The obtained residue was purified by silica gel column chromatography to obtain 4-(3-fluoro-1-pyrrolidinyl)-1-benzothiophene-7-carbonitrile (39 mg) (Compound 100).

mp 151-152° C.

$^1$H-NMR (300 MHz, CDCl$_3$) δ: 2.05-2.34 (1H, m), 2.41-2.54 (1H, m), 3.77-4.08 (4H, m), 5.43 (1H, dt, J=52.8 and 3.3 Hz), 6.46 (1H, d, J=8.7 Hz), 7.37 (1H, d, J=5.7 Hz), 7.53 (1H, d, J=5.7 Hz), 7.68 (1H, d, J=8.7 Hz).

IR (KBr) 2201, 1570 cm$^{-1}$

Anal. Calcd. for C$_{13}$H$_{11}$FN$_2$S: C, 63.39; H, 4.50; N, 11.37. Found: C, 63.30; H, 4.64; N, 11.39.

Example 97 (Preparation of Compound 101)

A mixture of 4-fluoro-1-benzothiophene-7-carbonitrile (100 mg), 3-(2-hydroxyethyl)pyrrolidine hydrochloride (163 mg), potassium carbonate (275 mg) and dimethylsulfoxide (1.0 mL) was stirred at 100° C. for 30 minutes. After cooling to room temperature, the reactant was poured into water and extracted with ethyl acetate. The extracts were washed with water, dried and concentrated. The obtained residue was purified by silica gel column chromatography to obtain 4-[3-(2-hydroxyethyl)-1-pyrrolidinyl]-1-benzothiophene-7-carbonitrile (49 mg) (Compound 101).

mp 109-111° C.

$^1$H-NMR (300 MHz, CDCl$_3$) δ: 1.41 (1H, t, J=4.8 Hz), 1.68-1.83 (3H, m), 2.22-2.31 (1H, m), 2.41-2.48 (1H, m), 3.39 (1H, t, J=9.0 Hz), 3.67-3.88 (5H, m), 6.40 (1H, d, J=8.4 Hz), 7.31 (1H, d, J=5.7 Hz), 7.48 (1H, d, J=8.4 Hz), 7.70 (1H, d, J=5.7 Hz).

IR (KBr) 2199, 1570, 1476 cm$^{-1}$

Anal. Calcd. for C$_{15}$H$_{16}$N$_2$OS: C, 66.15; H, 5.92; N, 10.29. Found: C, 66.10; H, 5.92; N, 10.30.

Example 98 (Preparation of Compound 102)

To a mixture of 4-[3-(2-hydroxyethyl)-1-pyrrolidinyl]-1-benzothiophene-7-carbonitrile (43 mg) and N,N-dimethylformamide (1.0 mL) was added sodium hydride (60% in oil, 30.0 mg) at room temperature, and the mixture was stirred for 20 minutes. After adding methyl iodide (60 µl), the mixture was stirred for 40 minutes. The reactant was poured into water and extracted with ethyl acetate. The extracts were washed with water, dried and concentrated. The obtained residue was purified by silica gel column chromatography to obtain 4-[3-(2-methoxyethyl)-1-pyrrolidinyl]-1-benzothiophene-7-carbonitrile (43 mg) (Compound 102).

mp 88-89° C.

$^1$H-NMR (300 MHz, CDCl$_3$) δ: 1.68-1.82 (3H, m), 2.18-2.26 (1H, m), 2.39-2.49 (1H, m), 3.32-3.39 (1H, m), 3.36 (3H s), 3.48 (2H, t, J=6.3 Hz), 3.69-3.84 (3H, m), 6.40 (1H, d, J=8.4 Hz), 7.31 (1H, d, J=6.0 Hz), 7.47 (1H, d, J=8.4 Hz), 7.69 (1H, d, J=6.0 Hz).

IR (KBr) 2201, 1570, 1474 cm$^{-1}$

Anal. Calcd. for C$_{16}$H$_{18}$N$_2$OS: C, 67.10; H, 6.33; N, 9.78. Found: C, 66.91; H, 6.29; N, 9.79.

Example 99 (Preparation of Compound 103)

A mixture of 4-fluoro-1-naphthonitrile (100 mg), 3,3-difluoropyrrolidine hydrochloride (92 mg), potassium carbonate (202 mg) and dimethylsulfoxide (1.0 mL) was stirred at 100° C. for 1 hour. After cooling to room temperature, the reactant was poured into water and extracted with ethyl acetate. The extracts were washed with water, dried and concentrated. The obtained residue was purified by silica gel column chromatography to obtain 4-(3,3-difluoro-1-pyrrolidinyl)-1-naphthonitrile (39 mg) (Compound 103).

mp 68-69° C.

$^1$H-NMR (300 MHz, CDCl$_3$) δ: 2.50-2.64 (2H, m), 3.64 (2H, t, J=7.2 Hz), 3.81 (2H, t, J=12.6 Hz), 6.90 (1H, d, J=8.1 Hz), 7.58 (1H, ddd, J=8.4, 6.9 and 1.5 Hz), 7.68 (1H, ddd, J=8.4, 6.9 and 1.5 Hz), 7.82 (1H, d, J=8.1 Hz), 8.14-8.17 (1H, m), 8.21-8.24 (1H, m).

IR (KBr) 2213, 1574 cm$^{-1}$

Anal. Calcd. for C$_{15}$H$_{12}$F$_2$N$_2$: C, 69.76; H, 4.68; N, 10.85. Found: C, 69.95; H, 4.95; N, 10.91.

Example 100 (Preparation of Compound 104)

A mixture of 4-fluoro-1-benzothiophene-7-carbonitrile (100 mg), 3,3-difluoropyrrolidine hydrochloride (134 mg), potassium carbonate (240 mg) and dimethylsulfoxide (2.0 mL) was stirred at 100° C. for 1 hour. After cooling to room temperature, the reactant was poured into water and extracted with ethyl acetate. The extracts were washed with water, dried and concentrated. The obtained residue was purified by silica gel column chromatography to obtain 4-(3,3-difluoro-1-pyrrolidinyl)-1-benzothiophene-7-carbonitrile (51 mg) (Compound 104).

mp 169-170° C.

$^1$H-NMR (300 MHz, CDCl$_3$) δ: 2.48-2.62 (2H, m), 3.86 (2H, t, J=7.2 Hz), 4.06 (2H, t, J=12.6 Hz), 6.47 (1H, d, J=8.4 Hz), 7.43 (1H, d, J=5.4 Hz), 7.54 (1H, d, J=8.4 Hz), 7.58 (1H, d, J=5.4 Hz).

IR (KBr) 2203, 1570 cm$^{-1}$

Anal. Calcd. for C$_{13}$H$_{10}$F$_2$N$_2$S: C, 59.08; H, 3.81; N, 10.60. Found: C, 59.09; H, 4.11; N, 10.68.

Example 101 (Preparation of Compound 105)

A mixture of tert-butyl 4-(2-ethoxy-2-oxoethyl)-1-piperidinecarboxylate (450 mg) and 4 N hydrogen chloride-ethyl acetate (1.5 mL) was stirred at room temperature for 1 hour. The reactant was concentrated to obtain a colorless solid matter (330 mg). A mixture of the obtained matter (146 mg), 4-fluoro-1-naphthonitrile (100 mg), potassium carbonate (218 mg), and dimethylsulfoxide (2.0 mL) was stirred at 100° C. for 30 minutes. After cooling to room temperature, the reactant was poured into water and extracted with ethyl acetate. The extracts were washed with water, dried and concentrated. The obtained residue was purified by silica gel column chromatography to obtain ethyl [1-(4-cyano-1-naphthyl)-4-piperidinyl]acetate (113 mg) (Compound 105).

$^1$H-NMR (CDCl$_3$) δ: 1.29 (3H, t, J=7.2 Hz), 1.60-1.72 (2H, m), 1.92-2.12 (3H, m), 2.38 (2H, d, J=6.9 Hz), 2.84 (2H, td, J=12.0 amd 1.8 Hz), 3.48-3.52 (2H, m), 4.17 (2H, q, J=7.2 Hz), 7.00 (1H, d, J=8.1 Hz), 7.55 (1H, ddd, J=8.4, 6.9 and 1.5 Hz), 7.64 (1H, ddd, J=8.4, 6.9 and 1.5 Hz), 7.81 (1H, d, J=8.1 Hz), 8.11-8.20 (2H, m).

IR (KBr) 2216, 1732, 1574 cm$^{-1}$

Example 102 (Preparation of Compound 106)

A mixture of ethyl [1-(4-cyano-1-naphthyl)-4-piperidinyl]acetate (80 mg), a 0.67 M sodium carbonate solution (1.5 mL), and methanol (1.5 mL) was stirred at 70° C. for 1 hour. After cooling to room temperature, the reactant was poured into water, acidified with 1 N hydrochloric acid and extracted with ethyl acetate. The extracts were washed with brine, dried and concentrated. The obtained residue was washed with dichloromethane to obtain [1-(4-cyano-1-naphthyl)-4-piperidinyl]acetic acid (30 mg) (Compound 106).

mp 195-196° C.

$^1$H-NMR (300 MHz, CDCl$_3$) δ: 1.62-1.75 (2H, m), 1.97-2.12 (3H, m), 2.46 (2H, d, J=6.6 Hz), 2.82-2.89 (2H, m), 3.47-3.54 (2H, m), 7.02 (1H, d, J=8.1 Hz), 7.57 (1H, ddd, J=8.4, 6.9 and 1.5 Hz), 7.65 (1H, ddd, J=8.4, 6.9 and 1.5 Hz), 7.83 (1H, d, J=8.1 Hz), 8.13-8.21 (2H, m).

IR (KBr) 2216, 1705, 1574 cm$^{-1}$

Anal. Calcd. for C$_{18}$H$_{18}$N$_2$O$_2$.0.5H$_2$O: C, 71.27; H, 6.31; N, 9.23. Found: C, 70.91; H, 6.24; N, 8.86.

Example 103 (Preparation of Compound 107)

To a mixture of sodium triacetoxyhydroborate (2.02 g), acetic acid (4.7 mL), and acetonitrile (3.0 mL) was added a mixture of methyl 2-methyl-1-[(1S)-1-phenylethyl]-4,5-dihydro-1H-pyrrole-3-carboxylate (780 mg) and acetonitrile (1.7 mL) at 0° C., and the mixture was stirred for 3 hours. The reactant was poured into a sodium carbonate solution and extracted with ethyl acetate. The extracts were washed with a sodium carbonate solution and brine, dried and concentrated to obtain a colorless oily matter (778 mg). To a mixture of the obtained oily matter (740 mg) and tetrahydrofuran (8.0 mL) was added lithium aluminum hydride (114 mg) at 0° C., and the mixture was stirred for 3 hours. Water (0.11 mL), a 25% potassium hydroxide solution (0.11 mL) and water (0.33 mL) were sequentially added, and the resulting mixture was stirred at room temperature for 15 hours. Insolubles were filtered off using celite and mother liquor was concentrated to obtain a pale yellow oily matter (656 mg). A mixture of the obtained matter (581 mg), 10% palladium carbon (50% water content, 564 mg), and methanol (9.0 mL) was stirred under hydrogen atmosphere at room temperature for 20 hours. Palladium carbon was filtered off using celite and washed with methanol. Mother liquor was concentrated, and then ethyl acetate was added to the residue. The mixture was dried and concentrated to obtain a pale yellow oily matter (260 mg). A mixture of the obtained oily matter (117 mg), 4-fluoro-1-naphthonitrile (171 mg), potassium carbonate (207 mg), and dimethylsulfoxide (2.0 mL) was stirred at 100° C. for 30 minutes. After cooling to room temperature, the reactant was poured into water and extracted with ethyl acetate. The extracts were washed with water, dried and concentrated. The obtained residue was washed with dichloromethane to obtain 4-[(2S, 3S)-3-(hydroxymethyl)-2-methyl-1-pyrrolidinyl]-1-naphthonitrile (80 mg) (Compound 107).

mp 158-159° C.

[α]$_D$=−258.9° (c=0.320, MeOH).

$^1$H-NMR (300 MHz, CDCl$_3$) δ: 1.44 (3H, d, J=6.3 Hz), 1.99-2.20 (3H, m), 2.55-2.66 (1H, m), 3.01-3.09 (1H, m), 3.79-4.02 (3H, m), 4.11 (1H, qui, J=6.3 Hz), 6.96 (1H, d, J=8.4 Hz), 7.54 (1H, ddd, J=8.4, 6.9 and 1.5 Hz), 7.65 (1H, ddd, J=8.4, 6.9 and 1.5 Hz), 7.82 (1H, d, J=8.4 Hz), 8.14-8.21 (2H, m).

IR (KBr) 2211, 1568, 1323 cm$^{-1}$

Anal. Calcd. for C$_{17}$H$_{18}$N$_2$O.0.2H$_2$O: C, 75.64; H, 6.87; N, 10.38. Found: C, 75.77; H, 6.83; N, 10.46.

Example 104 (Preparation of Compound 108)

To a mixture of sodium triacetoxyhydroborate (2.02 g), acetic acid (4.7 mL), and acetonitrile (3.0 mL) was added a mixture of methyl 2-methyl-1-[(1S)-1-phenylethyl]-4,5-dihydro-1H-pyrrole-3-carboxylate (780 mg) and acetonitrile (1.7 mL) at 0° C., and the mixture was stirred for 3 hours. The reactant was poured into a sodium carbonate solution and extracted with ethyl acetate. The extracts were washed with a sodium carbonate solution and brine, dried and concentrated to obtain a colorless oily matter (778 mg). To a mixture of the obtained oily matter (740 mg) and tetrahydrofuran (8.0 mL) was added lithium aluminum hydride (114 mg) at 0° C., and the mixture was stirred for 3 hours. Water (0.11 mL), a 25% potassium hydroxide solution (0.11 mL) and water (0.33 mL) were sequentially added, and the resulting mixture was stirred at room temperature for 15 hours. Insolubles were filtered off using celite and mother liquor was concentrated to obtain a pale yellow oily matter (656 mg). A mixture of the obtained oily matter (581 mg), 10% palladium carbon (50% water content, 564 mg), and methanol (9.0 mL) was stirred under hydrogen atmosphere at room temperature for 20 hours. Palladium carbon was filtered off using celite and washed with methanol. Mother liquor was concentrated and then, ethyl acetate was added to residue. The mixture was dried and concentrated to obtain a pale yellow oily matter (260 mg). A mixture of the obtained matter (100 mg), 4-fluoro-1-benzothiophene-7-carbonitrile (154 mg), potassium carbonate (180 mg), and dimethylsulfoxide (2.0 mL) was stirred at 100° C. for 30 minutes. After cooling to room temperature, the reactant was poured into water and extracted with ethyl acetate. The extracts were washed with water, dried and concentrated. The obtained residue was washed with diethyl ether to obtain 4-[(2S,3S)-3-(hydroxymethyl)-2-methyl-1-pyrrolidinyl]-1-benzothiophene-7-carbonitrile (109 mg) (Compound 108).

mp 109-111° C.

$[\alpha]_D$=+17.8° (c=0.320, MeOH).

$^1$H-NMR (300 MHz, CDCl$_3$) δ: 1.21 (3H, d, J=6.6 Hz), 1.84-1.98 (1H, m), 2.11-2.20 (1H, m), 2.52-2.66 (1H, m), 3.64-3.98 (4H, m), 4.51 (1H, qui, J=6.6 Hz), 6.47 (1H, d, J=8.7 Hz), 7.33 (1H, d, J=5.7 Hz), 7.49 (1H, d, J=8.7 Hz), 7.71 (1H, d, J=5.7 Hz).

IR (KBr) 2205, 1568, 1472 cm$^{-1}$

Anal. Calcd. for C$_{15}$H$_{16}$N$_2$OS: C, 66.15; H, 5.92; N, 10.29. Found: C, 65.83; H, 5.98; N, 10.05.

Example 105 (Preparation of Compound 109)

To a mixture of tert-butyl (2S,4R)-4-hydroxy-2-methylpyrrolidine-1-carboxylate (200 mg) and dichloromethane (1.5 mL) was added trifluoroacetic acid (1.5 mL) at room temperature, and the mixture was stirred for 30 minutes. The reactant was concentrated to obtain a colorless oily matter. A mixture of the obtained oily matter, 4-fluoro-1-benzothiophene-7-carbonitrile (159 mg), potassium carbonate (622 mg), and dimethylsulfoxide (2.0 mL) was stirred at 100° C. for 30 minutes. After cooling to room temperature, the reactant was poured into water and extracted with ethyl acetate. The extracts were washed with water, dried and concentrated. The obtained residue was purified by silica gel column chromatography to obtain 4-[(2S,4R)-4-hydroxy-2-methyl-1-pyrrolidinyl]-1-benzothiophene-7-carbonitrile (184 mg) (Compound 109).

mp 102-103° C.

$[\alpha]_D$=−78.4° (c=0.305, MeOH).

$^1$H-NMR (300 MHz, CDCl$_3$) δ: 1.37 (3H, d, J=6.0 Hz), 1.81-2.00 (2H, m), 2.49-2.58 (1H, m), 3.82-3.92 (1H, m), 4.17-4.28 (2H, m), 4.53 (1H, qui, J=6.3 Hz), 6.53 (1H, d, J=8.7 Hz), 7.38 (1H, d, J=5.7 Hz), 7.51 (1H, d, J=8.7 Hz), 7.60 (1H, d, J=5.7 Hz).

IR (KBr) 2207, 1568, 1470 cm$^{-1}$

Anal. Calcd. for C$_{14}$H$_{14}$N$_2$OS: C, 65.09; H, 5.46; N, 10.84. Found: C, 64.82; H, 5.47; N, 10.54.

Example 106 (Preparation of Compound 110)

To a mixture of 4-[(2S,4R)-3-(hydroxymethyl)-2-methyl-1-pyrrolidinyl]-1-naphthonitrile (40 mg) and N,N-dimethylformamide (1.0 mL) was added sodium hydride (60% in oil, 29 mg) at room temperature. After stirring for 20 minutes, methyl iodide (60 μl) was added and the mixture was stirred for 1 hour. The reactant was poured into water and extracted with ethyl acetate. The extracts were washed with water, dried and concentrated. The obtained residue was purified by silica gel column chromatography to obtain 4-[(2S,4R)-3-(methoxymethyl)-2-methyl-1-pyrrolidinyl]-1-naphthonitrile (36 mg) (Compound 110).

$[\alpha]_D$=−144.6° (c=0.280, MeOH).

$^1$H-NMR (300 MHz, CDCl$_3$) δ: 1.00 (3H, d, J=6.6 Hz), 1.84-1.94 (1H, m), 2.01-2.13 (1H, m), 2.69-2.81 (1H, m), 3.15-3.23 (1H, m), 3.41 (3H, s), 3.51-3.54 (2H, m), 3.89-3.98 (1H, m), 4.24 (1H, qui, J=6.3 Hz), 6.89 (1H, d, J=8.4 Hz), 7.51 (1H, ddd, J=8.4, 6.9 and 1.5 Hz), 7.62 (1H, ddd, J=8.4, 6.9 and 1.5 Hz), 7.78 (1H, d, J=8.4 Hz), 8.16-8.19 (2H, m).

IR (KBr) 2211, 1568 cm$^{-1}$

Example 107 (Preparation of Compound 111)

To a mixture of 4-[(2S,4R)-4-hydroxy-2-methyl-1-pyrrolidinyl]-1-benzothiophene-7-carbonitrile (184 mg), p-nitrobenzoic acid (286 mg), triphenylphosphine (449 mg) and tetrahydrofuran (3.5 mL) was added diethyl azodicarboxylate (in a 40% toluene solution, 0.75 mL) at 0° C., and the mixture was stirred for 2 hours. The mixture was further stirred at room temperature for 18 hours and then the reactant was concentrated. The residue was purified by silica gel column chromatography to obtain an orange oily matter. To a mixture of the obtained oily matter and methanol (2.5 mL) was added 1 N sodium hydroxide (0.5 mL), and the mixture was stirred at room temperature for 40 minutes. The reactant was poured into brine and extracted with diethyl ether. The extracts were washed with brine, dried and concentrated. The obtained residue was purified by silica gel column chromatography to obtain 4-[(2S,4R)-4-hydroxy-2-methyl-1-pyrrolidinyl]-1-benzothiophene-7-carbonitrile (68 mg) (Compound 111).

$[\alpha]_D$=−65.7° (c=0.235, MeOH).

$^1$H-NMR (300 MHz, CDCl$_3$) δ: 1.28 (3H, d, J=6.0 Hz), 1.63 (1H, d, J=3.9 Hz), 1.90 (1H, ddd, J=13.2, 9.0 and 3.9 Hz), 2.30-2.38 (1H, m), 3.60-3.64 (1H, m), 4.15 (1H, dd, J=10.8 and 3.6 Hz), 4.32-4.43 (1H, m), 4.55-4.60 (1H, m), 6.62 (1H, d, J=8.7 Hz), 7.38 (1H, d, J=6.0 Hz), 7.51-7.53 (2H, m).

IR (KBr) 2209, 1566 cm$^{-1}$

Example 108 (Preparation of Compound 112)

To a mixture of dimethylsulfoxide (0.22 mL) and dichloromethane (4.0 mL) was added oxalyl chloride (0.14 mL) at −78° C., and the mixture was stirred for 10 minutes. A mixture of 4-[(2S,3R)-3-hydroxy-2-methyl-1-pyrrolidinyl]-1-naphthonitrile (207 mg) and dichloromethane (2.0 mL) was added thereto, and the mixture was stirred for 15 minutes. Triethylamine (0.57 mL) was added, and the mixture was stirred for 10 minutes and then further stirred at room temperature for 30 minutes. The reactant was poured into water and extracted with ethyl acetate. The extracts were washed with water, dried and concentrated. The obtained residue was purified by silica gel column chromatography to obtain 4-[(2S)-2-methyl-3-oxo-1-pyrrolidinyl]-1-naphthonitrile (150 mg) (Compound 112).

mp 113-114° C.

$[\alpha]_D$=−253.9° (c=0.270, MeOH).

$^1$H-NMR (300 MHz, CDCl$_3$) δ: 1.17 (3H, d, J=6.6 Hz), 2.69 (1H, ddd, J=18.0, 7.5 and 4.2 Hz), 2.79 (1H, dt, J=18.0 and 7.8 Hz), 3.15 (1H, ddd, J=9.9, 7.8 and 7.5 Hz), 3.89 (1H, q, J=6.6 Hz), 4.07 (1H, ddd, J=9.9, 7.8 and 4.2 Hz), 7.09 (1H, d, J=8.1 Hz), 7.63 (1H, ddd, J=8.4, 6.9 and 1.2 Hz), 7.71 (1H, ddd, J=8.4, 6.9 and 1.2 Hz), 7.89 (1H, d, J=8.1 Hz), 8.24-8.28 (2H, m).

IR (KBr) 2216, 1759, 1574 cm$^{-1}$

Anal. Calcd. for C$_{16}$H$_{14}$N$_2$O: C, 76.78; H, 5.64; N, 11.19. Found: C, 76.52; H, 5.63; N, 11.30.

Example 109 (Preparation of Compound 113)

(2S,3R)-1-benzyl-2-methylpyrrolidin-3-ol (820 mg) was dissolved in methyl alcohol (30 mL), 1 N-hydrochloric acid (4.3 mL) and 10% palladium carbon (containing water) (500 mg) were added, and the mixture was stirred under hydrogen atmosphere for 15 hours. The catalyst was filtered off, and the filtrate was concentrated and dried. To the residue was added 4-fluoro-1-naphthonitrile (582 mg), potassium carbonate (890 mg), and dimethylsulfoxide (12.0 mL), and the mixture was stirred at 100° C. for 15 hours. After cooling to room temperature, water was poured into the reactant, and extracted with ethyl acetate. The extracts were washed with water, dried and concentrated. The obtained residue was purified by silica gel column chromatography and basic silica gel column chromatography (Chromatorex NH, a product made in Fuji Silysia Chemical Ltd.) to obtain 4-[(2S,3R)-3-hydroxy-2-methyl-1-pyrrolidinyl]-1-naphthonitrile (540 mg) (Compound 113).

$[\alpha]_D = -268.6°$ (c=0.515, MeOH).
$^1$H-NMR (200 MHz, CDCl$_3$) δ: 1.15(3H, d, J=6.2 Hz), 1.80-2.20 (2H, m), 2.30-2.50 (1H, m), 3.20-3.38 (1H, m), 3.77-4.00 (2H, m), 4.10-4.30 (1H, m), 6.89 (1H, d, J=8.0 Hz), 7.46-7.68 (2H, m), 7.19 (1H, d, J=8.0 Hz), 8.14-8.26 (2H, m).
IR (KBr) 2211, 1567, 1514 cm$^{-1}$.

Example 110 (Preparation of Compound 114)

To a mixture of 4-[(2S,3R)-3-hydroxy-2-methyl-1-pyrrolidinyl]-1-naphthonitrile (280 mg) and tetrahydrofuran (about 1 mL) was added methanesulfonic acid (72 μL) was added at room temperature. Diethyl ether was added, and the mixture was crystallized to obtain 4-[(2S,3R)-3-hydroxy-2-methyl-1-pyrrolidinyl]-1-naphthonitrile methanesulfonate (205 mg) (Compound 114).

mp 107-108° C.
$[\alpha]_D = -174.5°$ (c=0.350, MeOH).
$^1$H-NMR (CDCl$_3$) δ: 1.44 (3H, d, J=6.3 Hz), 2.40-2.50 (1H, m), 2.80-2.90 (1H, m), 2.89 (3H, s), 3.98-4.36 (3H, m), 4.58-4.64 (1H, m), 7.83-7.94 (3H, m), 8.02 (1H, d, J=7.8 Hz), 8.37-8.40 (1H, m), 8.68-8.71 (1H, m).
IR (KBr) 3320, 2228, 1194 cm$^{-1}$
Anal. Calcd. for C$_{16}$H$_{16}$N$_2$O.CH$_3$SO$_3$H.0.1H$_2$O: C, 58.30; H, 5.81; N, 8.00. Found: C, 58.13; H, 5.77; N, 7.97.

Example 111 (Preparation of Compound 115)

A mixture of 4-fluoro-1-benzothiophene-7-carbonitrile (100 mg), (2S,3R)-2-methyl-3-pyrrolidinol hydrochloride (93 mg), potassium carbonate (195 mg) and dimethylsulfoxide (1.5 mL) was stirred at 100° C. for 1 hour. After cooling to room temperature, the reactant was poured into water and extracted with ethyl acetate. The extracts were washed with water, dried and concentrated. The obtained residue was purified by silica gel column chromatography to obtain 4-[(2S,3R)-3-hydroxy-2-methyl-1-pyrrolidinyl]-1-benzothiophene-7-carbonitrile (108 mg) (Compound 115).

mp 145-146° C.
$[\alpha]_D = +30.6°$ (c=0.345, MeOH).
$^1$H-NMR (300 MHz, CDCl$_3$) δ: 1.28 (3H, d, J=6.6 Hz), 1.80 (1H, d, J=4.5 Hz), 2.01-2.14 (1H, m), 2.31-2.43 (1H, m), 3.82-3.98 (2H, m), 4.11-4.19 (1H, m), 4.23-4.28 (1H, m), 6.49 (1H, d, J=8.4 Hz), 7.35 (1H, d, J=5.7 Hz), 7.49 (1H, d, J=8.4 Hz), 7.68 (1H, d, J=5.7 Hz).
IR (KBr) 2207, 1568 cm$^{-1}$
Anal. Calcd. for C$_{14}$H$_{14}$N$_2$OS: C, 65.09; H, 5.46; N, 10.84. Found: C, 65.03; H, 5.58; N, 10.90.

Example 112 (Preparation of Compound 116)

4-[(2S,3R)-3-hydroxy-2-methyl-1-pyrrolidinyl]-1-naphthonitrile (254 mg), acetic acid (175 mg) and triphenylphosphine (510 mg) were dissolved in toluene (12 mL) and diethyl azodicarboxylate (in a 40% toluene solution, 0.8 mL) was added under nitrogen atmosphere, and the mixture was stirred at room temperature for 16 hours. The obtained insolubles were filtered off and washed with toluene. Then, water was poured into the filtrate, and extracted with ethyl acetate. The extracts were sequentially washed with sodium hydrogen carbonate water and water, dried and concentrated. The obtained residue was purified by silica gel column chromatography to concentrate a solution containing a fractioned objective matter. The residue was dissolved in methyl alcohol (10 mL), potassium carbonate (280 mg) was added thereto and the mixture was stirred at room temperature for 1.0 hours. The reaction solution was concentrated, the residue was poured into water and extracted with ethyl acetate. The extracts were washed with saturated brine, dried and concentrated. The residue was purified by silica gel column chromatography to obtain 4-[(2S,3S)-3-hydroxy-2-methyl-1-pyrrolidinyl]-1-naphthonitrile (105 mg) (Compound 116).

$[\alpha]_D = -270.2°$ (c=0.618, MeOH).
$^1$H-NMR (200 MHz, CDCl$_3$) δ: 1.25(3H, d, J=6.2 Hz), 1.93 (1H, d-like), 2.00-2.20 (2H, m), 3.18-4.02 (1H, m), 4.20-4.40 (1H, m), 4.40-4.58 (1H, m), 6.86 (1H, d, J=8.0 Hz), 7.46-7.70 (2H, m), 7.78 (1H, d, J=8.0 Hz), 8.12-8.28 (2H, m).
IR (KBr) 2211, 1565, 1515 cm$^{-1}$ Example 113 (Preparation of Compound 116)

A mixture of 4-fluoro-1-naphthonitrile (166 mg), (2S,3S)-2-methyl-3-pyrrolidinol (98 mg), potassium carbonate (202 mg) and dimethylsulfoxide (1.5 mL) was stirred at 100° C. for 40 minutes. After cooling to room temperature, the reactant was poured into water and extracted with ethyl acetate. The extracts were washed with water, dried and concentrated. The obtained residue was purified by silica gel column chromatography to obtain 4-[(2S,3S)-3-hydroxy-2-methyl-1-pyrrolidinyl]-1-naphthonitrile (160 mg) (Compound 116).

NMR values were identical to those of Compound 116 in Example 111.

Example 114 (Preparation of Compound 117)

To a mixture of 4-[(2S,3S)-3-hydroxy-2-methyl-1-pyrrolidinyl]-1-naphthonitrile (20 mg) and ethyl acetate (about 1 mL) was added a mixture (0.3 mL) of sulfuric acid (0.5 mL) and ethyl acetate (35.5 mL) at room temperature, and the mixture was crystallized to obtain 4-[(2S,3S)-3-hydroxy-2-methyl-1-pyrrolidinyl]-1-naphthonitrile sulfate (18 mg) (Compound 117).

mp 111-112° C.
$[\alpha]_D = -144.0°$ (c=0.270, MeOH).
$^1$H-NMR (DMSO-d$_6$) δ: 1.10 (3H, d, J=6.3 Hz), 1.86-1.93 (2H, m), 3.25-3.31 (1H, m), 3.96-4.04 (1H, m), 4.21-4.32 (2H, m), 6.89 (1H, d, J=8.4 Hz), 7.55 (1H, ddd, J=8.4, 6.9 and 1.2 Hz), 7.70 (1H, ddd, J=8.4, 6.9 and 1.2 Hz), 7.89 (1H, d, J=8.4 Hz), 7.97-8.00 (1H, m), 8.23-8.26 (1H, m).
IR (KBr) 2228, 1223 cm$^{-1}$
Anal. Calcd. for C$_{16}$H$_{16}$N$_2$O.H$_2$SO$_4$.1.2H$_2$O: C, 51.66; H, 5.53; N, 7.53. Found: C, 51.60; H, 5.52; N, 7.62.

Example 115 (Preparation of Compound 118)

To a mixture of 4-[(2s, 3R)-3-hydroxy-2-methyl-1-pyrrolidinyl]-1-benzothiophene-7-carbonitrile (600 mg), p-nitrobenzoic acid (1.55 g), triphenylphosphine (2.44 g), and tetrahydrofuran (18 mL) was added at 0° C. diethyl azodicarboxylate (in a 40% toluene solution, 4.0 mL), and the mixture was stirred at room temperature for 12 hours. The reactant was concentrated and the residue was purified by silica gel column chromatography to obtain an orange oily matter. To a mixture of the obtained oily matter and methanol (15 mL) was added 1 N sodium hydroxide (3.0 mL) and the mixture was stirred at room temperature for 40 minutes. The reactant was poured into brine and extracted with diethyl ether. The extracts were washed with brine, dried and concentrated. The obtained residue was purified by silica gel column chromatography to obtain 4-[(2S,3S)-3-hydroxy-2-methyl-1-pyrrolidinyl]-1-benzothiophene-7-carbonitrile (228 mg) (Compound 118).

$[\alpha]_D$=-52.0° (c=0.450, MeOH).

$^1$H-NMR (300 MHz, CDCl$_3$) δ: 1.30 (3H, d, J=6.6 Hz), 2.07-2.11 (3H, m), 3.61-3.68 (1H, m), 4.09-4.18 (2H, m), 4.49-4.53 (1H, m), 6.54 (1H, d, J=8.4 Hz), 7.36 (1H, d, J=5.7 Hz), 7.50 (1H, d, J=8.4 Hz), 7.60 (1H, d, J=5.7 Hz).

IR (KBr) 2207, 1568 cm$^{-1}$

Example 116 (Preparation of Compound 118)

A mixture of 4-fluoro-1-benzothiophene-7-carbonitrile (100 mg), (2S,3S)-2-methyl-3-pyrrolidinol (86 mg), potassium carbonate (156 mg) and dimethylsulfoxide (1.5 mL) was stirred at 100° C. for 40 minutes. After cooling to room temperature, the reactant was poured into water and extracted with ethyl acetate. The extracts were washed with water, dried and concentrated. The obtained residue was purified by silica gel column chromatography to obtain 4-[(2S,3S)-3-hydroxy-2-methyl-1-pyrrolidinyl]-1-benzothiophene-7-carbonitrile (113 mg) (Compound 118).

NMR values were identical to those of Compound 118 in Example 114.

Example 117 (Preparation of Compound 119)

To a mixture of 4-[(2S,3S)-3-hydroxy-2-methyl-1-pyrrolidinyl]-1-benzothiophene-7-carbonitrile (175 mg) and ethyl acetate (10 mL) was added a mixture (1.3 mL) of sulfuric acid (1.0 mL) and ethyl acetate (3.5 mL) at room temperature. After stirring for several minutes, the supernatant was removed and the residue was crystallized from diethyl ether-ethanol (9:1) to obtain 4-[(2S,3S)-3-hydroxy-2-methyl-1-pyrrolidinyl]-1-benzothiophene-7-carbonitrile sulfate (53 mg) (Compound 119).

mp 128-129° C.

$[\alpha]_D$=-37.4° (c=0.200, MeOH).

$^1$H-NMR (DMSO-d$_6$) δ: 1.14 (3H, d, J=6.3 Hz), 1.87-2.06 (2H, m), 3.53-3.61 (1H, m), 3.96-4.16 (2H, m), 4.29 (1H, q, J=5.1 Hz), 6.61 (1H, d, J=8.4 Hz), 7.63 (1H, d, J=8.4 Hz), 7.68 (1H, d, J=5.4 Hz), 7.75 (1H, d, J=5.4 Hz).

IR (KBr) 2226, 1221 cm$^{-1}$

Anal. Calcd. for $C_{14}H_{14}N_2OS.H_2SO_4.H_2O$: C, 44.91; H, 4.85; N, 7.48. Found: C, 44.92; H, 5.01; N, 7.52.

Example 118 (Preparation of Compound 120)

To a mixture of tert-butyl (2R, 3R)-3-hydroxy-2-methyl-5-oxopyrrolidine-1-carboxylate (2.20 g) and ethyl acetate (18 mL) was added 4 N hydrogen chloride-ethyl acetate (6.0 mL), and the mixture was stirred at room temperature for 1 hour. The reaction solution was concentrated to obtain a pale yellow oily matter. To a mixture of the obtained matter and tetrahydrofuran (50 mL) was added lithium aluminum hydride (1.15 g) at room temperature, and the mixture was heated under reflux for 18 hours. After cooling to 0° C., water (1.0 mL), a 25% potassium hydroxide solution (1.0 mL) and water (3.0 mL) were sequentially added, and the mixture was stirred for 1 hour. Insolubles were filtered off using celite and mother liquor was concentrated to obtain a light brown oily matter (1.0 g). A mixture of the obtained matter (107 mg), 4-fluoro-1-benzothiophene-7-carbonitrile (170 mg), potassium carbonate (199 mg) and dimethylsulfoxide (2.0 mL) was stirred at 100° C. for 30 minutes. After cooling to room temperature, the reactant was poured into water and extracted with ethyl acetate. The extracts were washed with water, dried and concentrated. The obtained residue was purified by silica gel column chromatography to obtain 4-[(2R,3R)-3-hydroxy-2-methyl-1-pyrrolidinyl]-1-benzothiophene-7-carbonitrile (172 mg) (Compound 120).

$[\alpha]_D$=+51.8° (c=0.265, MeOH).

$^1$H-NMR (300 MHz, CDCl$_3$) δ: 1.30 (3H, d, J=6.6 Hz), 2.07-2.11 (3H, m), 3.61-3.68 (1H, m), 4.09-4.18 (2H, m), 4.49-4.53 (1H, m), 6.54 (1H, d, J=8.4 Hz), 7.36 (1H, d, J=5.7 Hz), 7.50 (1H, d, J=8.4 Hz), 7.60 (1H, d, J=5.7 Hz).

IR (KBr) 2207, 1568 cm$^{-1}$

Example 119 (Preparation of Compound 121)

To a mixture of 4-[(2R,3R)-3-hydroxy-2-methyl-1-pyrrolidinyl]-1-benzothiophene-7-carbonitrile (125 mg), p-nitrobenzoic acid (323 mg), triphenylphosphine (508 mg) and tetrahydrofuran (4.5 mL) was added at 0° C. diethyl azodicarboxylate (in a 40% toluene solution, 0.84 mL), and the mixture was stirred at room temperature for 12 hours. The reactant was concentrated and the residue was purified by silica gel column chromatography to obtain an orange oily matter. To a mixture of the obtained oily matter and methanol (15 mL) was added 1 N sodium hydroxide (3.0 mL), and the mixture was stirred at room temperature for 2 hours. The reactant was poured into brine and extracted with diethyl ether. The extracts were washed with brine, dried and concentrated. The obtained residue was purified by silica gel column chromatography to obtain 4-[(2R, 3S)-3-hydroxy-2-methyl-1-pyrrolidinyl]-1-benzothiophene-7-carbonitrile (61 mg) (Compound 121).

mp 145-146° C.

$[\alpha]_D$=-29.2° (c=0.353, MeOH).

$^1$H-NMR (300 MHz, CDCl$_3$) δ: 1.28 (3H, d, J=6.6 Hz), 1.80 (1H, d, J=4.5 Hz), 2.01-2.14 (1H, m), 2.31-2.43 (1H, m), 3.82-3.98 (2H, m), 4.11-4.19 (1H, m), 4.23-4.28 (1H, m), 6.49 (1H, d, J=8.4 Hz), 7.35 (1H, d, J=5.7 Hz), 7.49 (1H, d, J=8.4 Hz), 7.68 (1H, d, J=5.7 Hz).

IR (KBr) 2207, 1568 cm$^{-1}$

Example 120 (Preparation of Compound 122)

To a mixture of tert-butyl (2R,3R)-3-hydroxy-2-methyl-5-oxopyrrolidine-1-carboxylate (2.20 g) and ethyl acetate (18 mL) was added 4 N hydrogen chloride-ethyl acetate (6.0 mL) and the mixture was stirred at room temperature for 1 hour. The reaction solution was concentrated to obtain a pale yellow oily matter. To a mixture of the obtained matter and tetrahydrofuran (50 mL) was added lithium aluminum hydride (1.15 g) at room temperature, and the mixture was heated under reflux for 18 hours. After cooling to 0° C., water (1.0 mL), a 25% potassium hydroxide solution (1.0 mL) and water (3.0 mL) were sequentially added, and the mixture was stirred for 1 hour. Insolubles were filtered off using celite and mother liquor was concentrated to obtain a light brown oily matter (1.0 g). A mixture of the obtained matter (330 mg), 4-fluoro-1-naphthonitrile (500 mg), potassium carbonate (606 mg) and dimethylsulfoxide (5.0 mL) was stirred at 100° C. for 30 minutes. After cooling to room temperature, the reactant was poured into water and extracted with ethyl acetate. The extracts were washed with water, dried and concentrated. The obtained residue was purified by silica gel column chromatography to obtain 4-[(2R,3R)-3-hydroxy-2-methyl-1-pyrrolidinyl]-1-naphthonitrile (473 mg) (Compound 122).

$[\alpha]_D$=+271.5° (c=0.555, MeOH).

$^1$H-NMR (200 MHz, CDCl$_3$) δ: 1.25(3H, d, J=6.2 Hz), 1.93 (1H, d-like), 2.00-2.20 (2H, m), 3.18-4.02 (1H, m), 4.20-4.40 (1H, m), 4.40-4.58 (1H, m), 6.86 (1H, d, J=8.0 Hz), 7.46-7.70 (2H, m), 7.78 (1H, d, J=8.0 Hz), 8.12-8.28 (2H, m).

IR (KBr) 2211, 1565, 1515 cm$^{-1}$

Example 121 (Preparation of Compound 123)

To a mixture of 4-[(2R,3R)-3-hydroxy-2-methyl-1-pyrrolidinyl]-1-naphthonitrile (272 mg), p-nitrobenzoic acid (719 mg), triphenylphosphine (1.13 mg) and tetrahydrofuran (10 mL) was added at 0° C. diethyl azodicarboxylate (in a 40% toluene solution, 1.9 mL), and the mixture was stirred at room temperature for 12 hours. The reactant was concentrated and the residue was purified by silica gel column chromatography to obtain an orange oily matter. To a mixture of the obtained oily matter and methanol (15 mL) was added 1 N sodium hydroxide (3.0 mL), and the mixture was stirred at room temperature for 40 minutes. The reactant was poured into brine and extracted with diethyl ether. The extracts were washed with brine, dried and concentrated. The obtained residue was purified by silica gel column chromatography to obtain 4-[(2R,3S)-3-hydroxy-2-methyl-1-pyrrolidinyl]-1-naphthonitrile (102 mg) (Compound 123).

$[\alpha]_D$=+269.8° (c=0.590, MeOH).

$^1$H-NMR (200 MHz, CDCl$_3$) δ: 1.15(3H, d, J=6.2 Hz), 1.80-2.20 (2H, m), 2.30-2.50 (1H, m), 3.20-3.38 (1H, m), 3.77-4.00 (2H, m), 4.10-4.30 (1H, m), 6.89 (1H, d, J=8.0 Hz), 7.46-7.68 (2H, m), 7.19 (1H, d, J=8.0 Hz), 8.14-8.26 (2H, m).

IR (KBr) 2211, 1567, 1514 cm$^{-1}$

Example 122 (Preparation of Compound 124)

To a mixture of 4-bromo-N-hydroxynaphthalene-1-carboxyimidoyl chloride (200 mg), allyl alcohol (48 μl) and diethyl ether (20 mL) was added triethylamine (0.10 mL) at room temperature, and the mixture was stirred for 3 days. Insolubles were filtered off and mother liquor was concentrated. The obtained residue was purified by silica gel column chromatography to obtain [3-(4-bromo-1-naphthyl)-4,5-dihydroisoxazol-5-yl]methanol (188 mg) (Compound 124).

$^1$H-NMR (200 MHz, CDCl$_3$) δ: 2.01 (1H, t, J=6.6 Hz), 3.41-3.64 (2H, m), 3.69-3.81 (1H, m), 3.91-4.02 (1H, m), 4.84-4.97 (1H, m), 7.37 (1H, d, J=7.8 Hz), 7.60-7.69 (2H, m), 7.80 (1H, d, J=7.8 Hz), 8.31-8.35 (1H, m), 8.91-8.97 (1H, m).

Example 123 (Preparation of Compound 125)

A mixture of [3-(4-bromo-1-naphthyl)-4,5-dihydroisoxazole-5-yl]methanol (70 mg), zinc cyanide (16 mg), tetrakis triphenylphosphine)palladium(0) (26 mg) and N,N-dimethylformamide (3.0 mL) was stirred under argon atmosphere at 100° C. for 15 hours. After cooling to room temperature, the reactant was poured into water and extracted with ethyl acetate. Insolubles were filtered off using celite and the organic layer was washed with brine. The reaction solution was dried and concentrated. The obtained residue was purified by silica gel column chromatography to obtain 4-[5-(hydroxymethyl)-4,5-dihydroisoxazole-3-yl]-1-naphthonitrile (46 mg) (Compound 125).

mp 138-139° C.

$^1$H-NMR (300 MHz, CDCl$_3$) δ: 1.93 (1H, dd, J=8.1 and 5.4 Hz), 3.49-3.65 (2H, m), 3.74-3.80 (1H, m), 3.97-4.03 (1H, m), 4.93-4.97 (1H, m), 7.59 (1H, d, J=7.5 Hz), 7.70-7.80 (2H, m), 7.93 (1H, d, J=7.5 Hz), 8.30-8.33 (1H, m), 9.01-9.04 (1H, m).

IR (KBr) 2924, 2224 cm$^{-1}$

Anal. Calcd. for C$_{15}$H$_{12}$N$_2$O$_2$: C, 71.42; H, 4.79; N, 11.10. Found: C, 71.22; H, 4.86; N, 11.06.

Example 124 (Preparation of Compound 126)

To a mixture of 4-[5-(hydroxymethyl)-4,5-dihydroisoxazol-3-yl naphthonitrile (46 mg) and N,N-dimethylformamide (1.0 mL) was added sodium hydride (60% in oil, 35 mg) at room temperature. After stirring for 20 minutes, methyl iodide (70 μl) was added, and the mixture was stirred for 1 hour. The reactant was poured into water and extracted with ethyl acetate. The extracts were washed with water, dried and concentrated. The obtained residue was purified by silica gel column chromatography to obtain 4-[5-(methoxymethyl)-4,5-dihydroisoxazol-3-yl naphthonitrile (38 mg) (Compound 126).

mp 110-111° C.

$^1$H-NMR (300 MHz, CDCl$_3$) δ: 3.47 (3H, s), 3.47 (1H, dd, J=16.5 and 7.8 Hz), 3.59 (1H, dd, J=16.5 and 10.8 Hz), 3.66 (2H, d, J=4.5 Hz), 4.94-5.03 (1H, m), 7.58 (1H, d, J=7.8 Hz), 7.70-7.79 (2H, m), 7.93 (1H, d, J=7.8 Hz), 8.30-8.33 (1H, m), 9.06-9.09 (1H, m).

IR (KBr) 2222, 1514 cm$^{-1}$

Anal. Calcd. for C$_{16}$H$_{14}$N$_2$O$_2$: C, 72.16; H, 5.30; N, 10.52. Found: C, 71.91; H, 5.19; N, 10.65.

Example 125 (Preparation of Compound 127)

4-[4-(hydroxymethyl)-2-methyl-1-pyrrolidinyl]-1-naphthonitrile (1.12 g) was dissolved in ethyl acetate (10.0 mL). 4N-hydrochloride-ethyl acetate (2 mL) was added at room temperature and crystallized to obtain 4-[4-(hydroxymethyl)-2-methyl-1-pyrrolidinyl]-1-naphthonitrile hydrochloride (1.06 g) (Compound 127).

mp 114-116° C.

$^1$H-NMR (200 MHz, DMSO-d$_6$) δ: 1.13(3H, d, J=5.8 Hz), 1.30-1.60(1H, m), 2.10-2.40(2H, m), 3.25-4.20(6H, m), 6.92 (1H, d, J=8.4 Hz), 7.50-7.80(2H, m), 7.91(1H, d, J=8.0 Hz), 7.91(1H, d, J=8.0 Hz), 8.24(1H, d, J=8.4 Hz).

IR (KBr) 2225, 1521, 1389 cm$^{-1}$.

Anal. Calcd. for C$_{17}$H$_{18}$N$_2$O.HCl.0.1AcOEt: C, 67.07; H, 6.40; N, 8.99. Found: C, 67.00; H, 6.30; N, 9.20.

Example 126 (Preparation of Compound 128)

Tert-butyl (2R,4R)-4-hydroxy-2-(hydroxymethyl)pyrrolidine-1-carboxylate (700 mg) was dissolved in toluene (2.0 mL), trifluoroacetic acid (4.0 mL) was added, and the mixture was stirred at room temperature for 2 hours. The reaction solution was concentrated and dried. To the residue was added 4-fluoro-1-naphthonitrile (440 mg), potassium carbonate (1.34 g) and dimethylsulfoxide (10.0 mL) were added, and the mixture was stirred at 100° C. for 4 hours. After cooling to room temperature, the reactant was poured into water and extracted with ethyl acetate. The extracts were washed with water, dried and concentrated. The obtained residue was purified by silica gel column chromatography to obtain 4-[(2R, 4R)-4-hydroxy-2-(hydroxymethyl)-1-pyrrolidinyl]-1-naphthonitrile (119 mg) (Compound 128).

mp 146-147° C.

$[\alpha]_D$=−284.7° (c=0.364, MeOH).

¹H-NMR (200 MHz, CDCl₃) δ: 2.05-2.40 (2H, m), 2.46-2.70 (1H, m), 3.10-3.24(1H, m), 3.35-3.80(3H, m), 3.96-4.10 (1H, m), 4.16-4.30(1H, m), 4.35-4.55(1H, m), 7.13 (1H, d, J=8.2 Hz), 7.50-7.75 (2H, m), 7.80(1H, d, J=8.2 Hz), 8.12-8.40(2H, m).

IR (KBr) 2214, 1570 cm⁻¹

Anal. Calcd. for $C_{16}H_{16}N_2O_2 \cdot 0.1AcOEt$: C, 70.08; H, 6.11; N, 10.11. Found: C, 70.00; H, 6.14; N, 9.96.

Example 127 (Preparation of Compound 129)

Tert-butyl (2R,4R)-4-hydroxy-2-(hydroxymethyl)pyrrolidine-1-carboxylate (700 mg) was dissolved in toluene (2.0 mL), trifluoroacetic acid (4.0 mL) was added and the mixture was stirred at room temperature for 2 hours. The reaction solution was concentrated and dried. To the residue was added 4-fluoro-1-naphthonitrile (440 mg), potassium carbonate (1340 mg) and dimethylsulfoxide (10.0 mL) were added, and the mixture was stirred at 100° C. for 4 hours. After cooling to room temperature, the reactant was poured into water and extracted with ethyl acetate. The extracts were washed with water, dried and concentrated. The obtained residue was purified by silica gel column chromatography to obtain 4-{[(2R,4R)-1-(4-cyano-1-naphthyl)-4-hydroxypyrrolidin-2-yl]methoxy}-1-naphthonitrile (50 mg) (Compound 129).

mp 123-126° C.

¹H-NMR (200 MHz, CDCl₃) δ: 2.12-2.30 (2H, m), 2.76-2.94 (1H, m), 3.48-3.52(1H, m), 3.88-4.00(1H, m), 4.15-4.38 (2H, m), 4.60-4.76(2H, m), 6.64 (1H, d, J=8.6 Hz), 7.19 (1H, d, J=8.0 Hz), 7.40-7.85 (7H, m), 8.04-8.30(3H, m).

IR (KBr) 2214, 1570 cm⁻¹.

Anal. Calcd. for $C_{27}H_{21}N_3O_2 \cdot 0.2AcOEt$: C, 76.39; H, 5.21; N, 9.61. Found: C, 76.25; H, 5.18; N, 9.87.

Example 128 (Preparation of Compound 130)

A mixture of (1-benzyl-3,5-dimethylpyrrolidin-3-yl) methanol (1.88 g), methanol (60 mL), 1 N-hydrochloric acid (8.6 mL) and 10% palladium carbon (containing water) (1.10 g) was stirred under hydrogen atmosphere for 16 hours. The catalyst was filtered off, the filtrate was concentrated and dried. To the residue was added 4-fluoro-1-naphthonitrile (1.10 g), potassium carbonate (3.55 g) and dimethylsulfoxide (30.0 mL) were added, and the mixture was stirred at 100° C. for 4 hours. After cooling to room temperature, water was poured into the reactant, and extracted with ethyl acetate. The extracts were washed with water, dried and concentrated. The obtained residue was purified by silica gel column chromatography to obtain 4-[4-(hydroxymethyl)-2,4-dimethyl-1-pyrrolidinyl]-1-naphthonitrile (480 mg) (Compound 130).

mp 100-101° C.

¹H-NMR (200 MHz, CDCl₃) δ: 1.02(3H, s), 1.20(3H, d, J=5.8 Hz), 1.65-2.04(3H, m), 2.98 (1H, dd, J=1.0 Hz and 9.8 Hz), 3.66(2H, d, J=5.4 Hz), 4.00-4.26(2H, m), 6.88(1H, d, J=8.4 Hz), 7.42-7.70(2H, m), 7.23 (1H, d, J=8.0 Hz), 8.12-8.26 (2H, m).

IR (KBr) 2211, 1564, 1515 cm⁻¹

Anal. Calcd. for $C_{18}H_{20}N_2O$: C, 77.11; H, 7.19; N, 9.99. Found: C, 77.09; H, 7.25; N, 9.90.

Example 129 (Preparation of Compound 131)

A mixture of 4-fluoro-1-naphthonitrile (300 mg), isoindoline (250 mg), potassium carbonate (270 mg), and dimethylsulfoxide (6.0 mL) was stirred at 100° C. for 5 hours. After cooling to room temperature, the reactant was poured into water and extracted with ethyl acetate. The extracts were washed with water, dried and concentrated. The obtained residue was purified by silica gel column chromatography to obtain 4-(1,3-dihydro-2H-isoindole-2-yl)-1-naphthonitrile (195 mg) (Compound 131).

mp 156-158° C.

¹H-NMR (200 MHz, CDCl₃) δ: 5.00 (4H, s), 6.94 (1H, d, J=8.2 Hz), 7.30-7.41 (4H, m), 7.48-7.72 (2H, m), 7.82 (1H, d, J=8.2 Hz), 8.22 (1H, d, J=8.0 Hz), 8.48 (1H, d, J=8.0 Hz).

IR (KBr) 2201, 1561, 1413 cm⁻¹

Example 130 (Preparation of Compound 132)

Tert-butyl (2R,4R)-2-(hydroxymethyl)-4-methoxypyrrolidine-1-carboxylate (700 mg) was dissolved in toluene (2.0 mL), trifluoroacetic acid (4.0 mL) was added and the mixture was stirred at room temperature for 2 hours. The reaction solution was concentrated and dried. To the residue was added 4-fluoro-1-naphthonitrile (300 mg), potassium carbonate (730 mg) and dimethylsulfoxide (6.0 mL) were added, and the mixture was stirred at 100° C. for 16 hours. After cooling to room temperature, water was poured into the reactant, and extracted with ethyl acetate. The extracts were washed with water, dried and concentrated. The obtained residue was purified by silica gel column chromatography to obtain 4-[(2R,4R)-2-(hydroxymethyl)-4-methoxy-1-pyrrolidinyl]-1-naphthonitrile (334 mg) (Compound 132).

$[\alpha]_D = -212°$ (c=0.316, MeOH).

¹H-NMR (200 MHz, CDCl₃) δ: 2.00-2.30 (2H, m), 2.40-2.60 (1H, m), 3.20-3.40 (1H, m), 3.44 (3H, s), 3.50-3.76 (2H, m), 3.92-4.26 (3H, m), 7.09 (1H, d, J=8.6 Hz), 7.50-7.74 (2H, m) 7.80(1H, d, J=8.0 Hz), 8.16-8.30(2H, m).

IR (KBr) 3437, 2212, 1568 cm⁻¹

Example 131 (Preparation of Compound 133)

4-[(2R,4R)-4-hydroxy-2-(hydroxymethyl)-1-pyrrolidinyl]-1-naphthonitrile (310 mg) was dissolved in N,N-dimethylformamide (6.0 mL), sodium hydride (60% in oil, 100 mg) was added with ice-cooling, and the mixture was stirred at room temperature for 1 hour. Then, methyl iodide (0.3 mL) was added, and the mixture was stirred at room temperature for 2 hours. Water was poured into the reactant and extracted with ethyl acetate. The extracts were washed with water, dried and concentrated. The obtained residue was purified by silica gel column chromatography to obtain 4-[(2R,4R)-4-methoxy-2-(methoxymethyl)-1-pyrrolidinyl]-1-naphthonitrile (303 mg) (Compound 133).

¹H-NMR (200 MHz, CDCl₃) δ: 1.90-2.50(1H, m), 2.50-2.70(1H, m), 3.25(3H, s), 3.25-3.55(3H, m), 3.41(3H, s), 3.80-4.27(3H, m), 7.00(1H, d, J=8.0 Hz), 7.48-7.70(2H, m), 7.78(1H, d, J=8.0 Hz), 8.14-8.26(2H, m).

IR (KBr) 2212, 1568 cm⁻¹

Example 132 (Preparation of Compound 134)

1-Benzyl-2,2-dimethylpyrrolidine (1.00 g) was dissolved in methyl alcohol (30 mL), 1 N-hydrochloric acid (5.5 mL) and 10% palladium carbon (containing water) (500 mg) were added, and the mixture was stirred under hydrogen atmosphere for 15 hours. The catalyst was filtered off, the filtrate was concentrated and dried. To the residue was added 4-fluoro-1-naphthonitrile (256 mg), potassium carbonate (825 mg) and dimethylsulfoxide (6.0 mL), and the mixture was stirred at 100° C. for 20 hours. Then, imidazole (210 mg) and potassium carbonate (280 mg) were added, and the mixture was stirred at 100° C. for 3 hours. After cooling to room temperature, water was poured into the reactant and extracted with ethyl acetate. The extracts were washed with water, dried and concentrated. The obtained residue was purified by silica gel column chromatography to obtain 4-(2,2-dimethyl-1-pyrrolidinyl)-1-naphthonitrile (46 mg) (Compound 134).

$^1$H-NMR (200 MHz, CDCl$_3$) δ: 1.17 (6H, s), 1.90-2.15 (4H, m), 7.34(1H, d, J=8.0 Hz), 7.48-7.70 (2H, m), 7.83 (1H, d, J=8.0 Hz), 8.14-8.22 (1H, m), 8.42-8.49(1H, m).

IR (KBr) 2218, 1570 cm$^{-1}$

Example 133 (Preparation of Compound 135)

D-prolinamide (800 mg), 4-fluoro-1-naphthonitrile (1000 mg) and potassium carbonate (1000 mg) was added dimethylsulfoxide (15.0 mL), and the mixture was stirred at 100° C. for 23 hours. After cooling to room temperature, water was poured into the reactant, and extracted with ethyl acetate. The extracts were washed with water, dried and concentrated. To the obtained residue was added hexane:ethyl acetate=1:2 and crystallized to obtain 1-(4-cyano-1-naphthyl)-D-prolinamide (570 mg) (Compound 135).

mp 176-177° C.

[α]$_D$=−194.6° (c=0.380, MeOH).

$^1$H-NMR (200 MHz, CDCl$_3$) δ: 1.82-2.30 (3H, m), 2.50-2.72 (1H, m), 3.30-3.42(1H, m), 4.10-4.48(2H, m), 5.29(1H, br.s), 6.38(1H, br.s), 6.97(1H, d, J=8.0 Hz), 7.50-7.75 (2H, m), 7.78 (1H, d, J=8.0 Hz), 8.20-8.32 (2H, m).

IR (KBr) 2210, 1690, 1568 cm$^{-1}$

Example 134 (Preparation of Compound 136)

1-(4-Cyano-1-naphthyl)-D-prolinamide (160 mg) was dissolved in dichloromethane (10 mL), anhydrous trifluoroacetic acid (0.25 mL) and triethylamine (0.56 mL) were added, and the mixture was stirred at room temperature for 0.5 hour. The reaction solution was alkalified with sodium hydrogen carbonate water and extracted with ethyl acetate. The extracts were washed with water, dried and concentrated. The obtained residue was purified by silica gel column chromatography to obtain (2R)-1-(4-cyano-1-naphthyl)pyrrolidine-2-carbonitrile (113 mg) (Compound 136).

[α]$_D$=+92.3° (c=0.39, MeOH).

$^1$H-NMR (200 MHz, CDCl$_3$) δ: 2.00-2.72 (4H, m), 3.35-3.50 (1H, m), 3.65-3.82(1H, m), 4.70-4.80 (1H, m), 7.88(1H, d, J=8.0 Hz), 8.04-8.15 (1H, m), 8.20-8.32 (1H, m).

IR (KBr) 2216, 1573 cm$^{-1}$

Example 135 (Preparation of Compound 137)

1-Benzyl-3-phenylpyrrolidine (2.35 g) was dissolved in methyl alcohol (30 mL), 1 N-hydrochloric acid (10 mL) and 10% palladium carbon (containing water) (1200 mg) were added, and the mixture was stirred under hydrogen atmosphere for 15 hours. The catalyst was filtered off, the filtrate was concentrated and dried. To the residue was added 4-fluoro-1-naphthonitrile (600 mg), potassium carbonate (1500 mg) and dimethylsulfoxide (15.0 mL) and the mixture was stirred at 100° C. for 15 hours. After cooling to room temperature, water was poured into the reactant and extracted with ethyl acetate. The extracts were washed with water, dried and concentrated. The obtained residue was purified by silica gel column chromatography to obtain 4-(3-phenyl-1-pyrrolidinyl)-1-naphthonitrile (628 mg) (Compound 137).

$^1$H-NMR (200 MHz, CDCl$_3$) δ: 2.01-2.57 (2H, m), 3.40-4.02 (5H, m), 6.73 (1H, d, J=8.4 Hz), 7.20-7.50 (5H, m), 7.57-7.70 (1H, m), 7.75 (1H, d, J=8.4 Hz), 8.12-8.32 (2H, m).

IR (KBr) 2205, 1563, 1518 cm$^{-1}$

Example 136 (Preparation of Compound 138)

4-(3-Hydroxy-1-pyrrolidinyl)-1-naphthonitrile (220 mg), phenol (175 mg) and triphenylphosphine (290 mg) were dissolved in toluene (6 mL) and tetrahydrofuran (2 mL), diethyl azodicarboxylate (in a 40% toluene solution, 1.2 mL) was added under nitrogen atmosphere, and the mixture was stirred at room temperature for 15 hours. The reaction solution was concentrated and the residue was purified by silica gel column chromatography to obtain 4-(3-phenoxy-1-pyrrolidinyl)-1-naphthonitrile (180 mg) (Compound 138).

$^1$H-NMR (200 MHz, CDCl$_3$) δ: 2.20-2.50 (2H, m), 3.50-4.10 (4H, m), 5.00-5.15(1H, m), 6.80 (1H, d, J=8.0 Hz), 6.82-7.06 (3H, m), 7.22-7.38 (2H, m), 7.42-7.70(2H, m), 7.76 (1H, d, J=8.0 Hz), 8.12-8.30 (2H, m).

IR (KBr) 2213, 1568, cm$^{-1}$

Example 137 (Preparation of Compound 139)

4-[(2S,3R)-3-hydroxy-2-methyl-1-pyrrolidinyl]-1-naphthonitrile (110 mg) was dissolved in N,N-dimethylformamide (2 mL), and the resulting solution was stirred with ice-cooling. Sodium hydride (60% in oil, 35 mg) was added, the mixture was further stirred at room temperature for 0.5 hour. After adding methyl iodide (0.10 mL), the mixture was stirred in at room temperature for 15 hours. Water was poured into the reactant and extracted with ethyl acetate. The extracts were washed with water, dried and concentrated. The obtained residue purified by silica gel column chromatography to obtain 4-[(2S,3R)-3-methoxy-2-methyl-1-pyrrolidinyl]-1-naphthonitrile (110 mg) (Compound 139).

[α]$_D$=−221° (c=0.45, MeOH).

$^1$H-NMR (200 MHz, CDCl$_3$) δ: 1.14(3H, d, J=6.2 Hz), 1.80-2.20 (1H, m), 2.28-2.46 (1H, m), 3.20-3.38 (1H, m), 3.47(3H, s), 3.50-3.98 (3H, m), 6.90 (1H, d, J=8.2 Hz), 7.46-7.68 (2H, m), 7.79 (1H, d, J=8.2 Hz), 8.14-8.24 (2H, m).

IR (KBr) 2211, 1568, 1514 cm$^{-1}$

Example 138 (Preparation of Compound 140)

Tert-butyl 3-(2-ethoxy-2-oxoethyl)pyrrolidine-1-carboxylate (510 mg) was dissolved in toluene (2.0 mL), trifluoroacetic acid (2.0 mL) was added, and the mixture was stirred at room temperature for 1 hour. The reaction solution was concentrated and dried. To the residue was added 4-fluoro-1-naphthonitrile (171 mg), potassium carbonate (410 mg) and dimethylsulfoxide (4.0 mL) were added, and the mixture was stirred at 100° C. for 1.5 hours. After cooling to room temperature, water was poured into the reactant and extracted with ethyl acetate. The extracts were washed with water, dried and concentrated. The obtained residue was purified by silica gel column chromatography to obtain ethyl [1-(4-cyano-1-naphthyl)pyrrolidin-3-yl]acetate (300 mg) (Compound 140).

$^1$H-NMR (200 MHz, CDCl$_3$) δ: 1.28(3H, d, J=7.2 Hz), 1.64-1.88 (1H, m), 2.20-2.40 (1H, m), 2.53(2H, d, J=7.8 Hz), 2.62-2.70 (1H, m), 3.40(1H, dd, J=7.6 Hz and 7.7 Hz), 3.55-3.84 (3H, m), 4.17(2H, q, J=7.2 Hz), 6.70 (1H, d, J=8.4 Hz), 7.40-7.68 (2H, m), 7.72 (1H, d, J=8.4 Hz), 8.12-8.28 (2H, m).

IR (KBr) 2199, 1732, 1556, 1522 cm$^{-1}$

Example 139 (Preparation of Compound 141)

Tert-butyl 3-(2-ethoxy-2-oxoethyl)pyrrolidine-1-carboxylate (1200 mg) was dissolved in 4 N-hydrochloric acid (ethyl acetate solution) (10 mL), and the mixture was stirred for 1.5 hours. Toluene was added, and the resulting solution was concentrated and dried. To the residue was added tetrahydrofuran (35 mL) was added, and the mixture was stirred with ice-cooling. Lithium aluminum hydride (530 mg) was added dropwise, the temperature was returned to room temperature, and the resulting mixture was stirred for 3 hours. After ice-cooling the reaction solution, 4 N-sodium hydroxide (6 mL) and water (6 mL) were added, and resolved. Tetrahydrofuran was added, and decantation was conducted three times. The tetrahydrofuran layer was combined, concentrated and dried. To the residue was added saturated brine (5 mL) and the reaction solution was extracted with dichloromethane. To the residue was added 4-fluoro-1-naphthonitrile (340 mg), potassium carbonate (410 mg), and dimethylsulfoxide (6.0 mL) were added, and the mixture was stirred at 100° C. for 3.0 hours. After cooling to room temperature, the reactant was poured into water and extracted with ethyl acetate. The extracts were washed with water, dried and concentrated. The obtained residue was purified by silica gel column chromatography to obtain 4-[3-(2-hydroxyethyl)-1-pyrrolidinyl]-1-naphthonitrile (223 mg) (Compound 141).

$^1$H-NMR (200 MHz, CDCl$_3$) δ: 1.45(3H, t, J=5.0 Hz), 1.62-1.90 (3H, m), 2.10-2.60 (2H, m), 3.41(1H, J=9.2 Hz), 3.52-3.90 (5H, m), 6.65 (1H, d, J=8.4 Hz), 7.36-7.68 (2H, m), 7.71 (1H, d, J=8.4 Hz), 8.10-8.30 (2H, m).

IR (KBr) 2204, 1562 cm$^{-1}$

Example 140 (Preparation of Compound 142)

tert-Butyl 2-[(1E)-propa-1-enyl]pyrrolidine-1-carboxylate (1600 mg) was dissolved in methanol (50 mL), acetic acid (2 mL) and 10% palladium carbon (containing water) (1600 mg) were added, and the mixture was stirred under hydrogen atmosphere for 19 hours. The catalyst was filtered off, and the filtrate was concentrated and dried. To the residue was dissolved in toluene (2.0 mL), trifluoroacetic acid (4.0 mL) was added, and the mixture was stirred at room temperature for 1 hour. The reaction solution was concentrated and dried. To the residue was added 4-fluoro-1-naphthonitrile (520 mg), potassium carbonate (1450 mg) and dimethylsulfoxide (10.0 mL) were added and the mixture was stirred at 100° C. for 3.5 hours. After cooling to room temperature, water was poured into the reactant and extracted with ethyl acetate. The extracts were washed with water, dried and concentrated. The obtained residue was purified by silica gel column chromatography to obtain 4-(2-propyl-1-pyrrolidinyl)-1-naphthonitrile (310 mg) (Compound 142).

$^1$H-NMR (200 MHz, CDCl$_3$) δ: 0.89(3H, t, J=7.0 Hz), 1.20-1.45 (3H, m), 1.60-2.10 (4H, m), 2.20-2.40 (2H, m), 3.28-3.40 (1H, m), 3.80-4.10 (2H, m), 6.80 (1H, d, J=8.8 Hz), 7.40-7.70 (2H, m), 7.75 (1H, d, J=8.8 Hz), 8.10-8.30 (2H, m).

IR (KBr) 2209, 1560 cm$^{-1}$

Example 141 (Preparation of Compound 143)

Benzyl (2R)-2-(1-hydroxy-1-methylethyl)pyrrolidine-1-carboxylate (1200 mg) was dissolved in methyl alcohol (30 mL), acetic acid (2.0 mL) and 10% palladium carbon (containing water) (600 mg) were added, and the mixture was stirred under hydrogen atmosphere for 2.5 hours. The catalyst was filtered off, and the filtrate was concentrated and dried. To the residue was added 4-fluoro-1-naphthonitrile (390 mg), potassium carbonate (940 mg), and dimethylsulfoxide (10.0 mL), and the mixture was stirred at 100° C. for 17 hours. After cooling to room temperature, water was poured into the reactant and extracted with ethyl acetate. The extracts were washed with water, dried and concentrated. The obtained residue was purified by silica gel column chromatography and basic silica gel column chromatography (Chromatorex NH, manufactured by Fuji Silysia Chemical Ltd.) to obtain 4-[(2R)-2-(1-hydroxy-1-methylethyl)-1-pyrrolidinyl]-1-naphthonitrile (120 mg) (Compound 143).

[α]$_D$=−337.2° (c=0.776, MeOH).
$^1$H-NMR (200 MHz, CDCl$_3$) δ: 1.10(3H, s), 1.60-2.30 (5H, m), 3.10-3.22 (1H, m), 3.70-3.90 (1H, m), 4.23 (1H, t, J=7.6 Hz), 7.26 (1H, d, J=8.8 Hz), 7.50-7.26 (2H, m), 7.72 (1H, d, J=8.8 Hz), 8.14-8.28 (2H, m).

IR (KBr) 2212, 1568 cm$^{-1}$

Example 142 (Preparation of Compound 144)

Benzyl (2R)-2-isopropylpyrrolidine-1-carboxylate (1700 mg) was dissolved in methanol (30 mL), acetic acid (2.0 mL) and 10% palladium carbon (containing water) (1700 mg) were added, and the mixture was stirred under hydrogen atmosphere for 17 hours. The catalyst was filtered off, and the filtrate was concentrated and dried. To the residue was added 4-fluoro-1-naphthonitrile (510 mg), potassium carbonate (1380 mg) and dimethylsulfoxide (15.0 mL), and the mixture was stirred at 100° C. for 9 hours. After cooling to room temperature, water was poured into the reactant and extracted with ethyl acetate. The extracts were washed with water, dried and concentrated. The obtained residue was purified by silica gel column chromatography to obtain 4-[(2R)-2-isopropyl-1-pyrrolidinyl]-1-naphthonitrile (220 mg) (Compound 144).

[α]$_D$=−337.2° (c=0.776, MeOH).
$^1$H-NMR (200 MHz, CDCl$_3$) δ: 0.81(3H, d, J=7.0 Hz), 0.94(3H, d, J=7.0 Hz), 1.60-2.20 (5H, m), 3.30-3.46 (1H, m), 3.88-4.08 (2H, m), 6.85 (1H, d, J=8.8 Hz), 7.40-7.68 (2H, m), 7.73 (1H, d, J=8.8 Hz), 8.10-8.22 (2H, m).

IR (KBr) 2210, 1560 cm$^{-1}$

Example 143 (Preparation of Compound 145)

4-(3-Hydroxy-1-pyrrolidinyl)-1-naphthonitrile (240 mg) was dissolved in N,N-dimethylformamide (5 mL), and the resulting solution was stirred with ice-cooling. Sodium hydride (60% in oil, 100 mg) was added, the mixture was further stirred at room temperature for 0.5 hour. After adding benzyl bromide (0.17 mL), the mixture was stirred at room temperature for 16 hours. Water was poured into the reactant and extracted with ethyl acetate. The extracts were washed with water, dried and concentrated. The obtained residue was purified by silica gel column chromatography and crystallized from ether, to obtain 4-[3-(benzyloxy)-1-pyrrolidinyl]-1-naphthonitrile (311 mg) (Compound 145).

$^1$H-NMR (200 MHz, CDCl$_3$) δ: 2.10-2.35 (2H, m), 3.50-3.95 (4H, m), 4.26-4.40 (1H, m), 4.57 (2H, q, J=11.8 Hz), 6.73 (1H, d, J=8.0 Hz), 7.30-7.68 (7H, m), 7.74 (1H, d, J=8.0 Hz), 8.12-8.28 (2H, m).

IR (KBr) 2201, 1562 cm$^{-1}$

Example 144 (Preparation of Compound 146)

4-[3-(2-Hydroxyethyl)-1-pyrrolidinyl]-1-naphthonitrile (130 mg) was dissolved in N,N-dimethylformamide (5 mL), and the resulting solution was stirred with ice-cooling. Sodium hydride (60% in oil, 30 mg) was added, the mixture was further stirred at room temperature for 0.5 hour. After adding methyl iodide (0.05 mL), the mixture was stirred at room temperature for 15 hours. Water was poured into the reactant and extracted with ethyl acetate. The extracts were washed with water, dried and concentrated. The obtained residue was purified by silica gel column chromatography, to obtain 4-[3-(2-methoxyethyl)-1-pyrrolidinyl]-1-naphthonitrile (85 mg) as a pale yellow oily matter (Compound 146).

¹H-NMR (200 MHz, CDCl₃) δ: 1.60(3H, m), 2.10-2.55 (2H, m), 3.35 (3H, s), 3.38-3.85 (6H, m), 6.66 (1H, d, J=8.4 Hz), 7.29-7.63 (2H, m), 7.71 (1H, d, J=8.4 Hz), 8.10-8.30 (2H, m).

IR (KBr) 2207, 1563 cm⁻¹

Example 145 (Preparation of Compound 147)

1,4-Dibromonaphthalene (2.86 g) was dissolved in anhydrous tetrahydrofuran (100 mL), and the mixture was stirred at −78° C. with ice-cooling. 1.6 Mn-butyllithium (in a hexane solution, 6.25 mL) was added, and the mixture was stirred for 15 minutes. 2-Methylcyclopentanone (1.07 mL) was added, and the mixture was stirred for 15 minutes. After adding saturated ammonium chloride, the mixture was extracted with ethyl acetate. The extracts were washed with water, dried and concentrated. The obtained residue was purified by silica gel column chromatography to obtain 1-(4-bromo-1-naphthyl)-2-methyl cyclopentanol (1.35 g) (Compound 147).

¹H-NMR (200 MHz, CDCl₃) δ: 1.26(3H, d, J=6.6 Hz), 1.80-2.50 (6H, m), 2.60-3.00 (2H, m), 7.54 (1H, d, J=8.0 Hz), 7.60-7.81 (2H, m), 7.85 (1H, d, J=8.0 Hz), 8.45-8.56 (2H, m), 8.85-8.90 (1H, m).

Example 146 (Preparation of Compound 148)

1-(4-Bromo-1-naphthyl)-2-methyl cyclopentanol (310 mg), zinc cyanide (72 mg) and tetrakis triphenylphosphine (120 mg) was dissolved in N,N-dimethylformamide (6 mL), the mixture was warmed to 100° C. under nitrogen atmosphere and stirred for 2 hours. Water was poured into the reactant and extracted with ethyl acetate. The extracts were washed with water, dried and concentrated. The obtained residue was purified by silica gel column chromatography and crystallized from hexane, to obtain 4-(1-hydroxy-2-methylcyclopentyl)-1-naphthonitrile (174 mg) (Compound 148).

mp 121-122° C.

¹H-NMR (200 MHz, CDCl₃) δ: 1.06(3H, d, J=6.6 Hz), 1.60-2.15 (5H, m), 2.15-2.38 (1H, m), 2.42-2.85 (2H, m), 7.56-7.72 (3H, m), 7.86 (1H, d, J=7.6 Hz), 8.24-8.34 (1H, m), 8.72-8.80 (1H, m).

IR (KBr) 3493, 2965, 2217, 764 cm⁻¹

Anal. Calcd. For $C_{17}H_{17}NO$: C, 81.24; H, 6.82; N, 5.57. Found: C, 81.89; H, 6.92; N, 5.48.

Example 147 (Preparation of Compound 149)

1-Bromo-4-(5-methylcyclopenta-1-en-1-yl)-naphthalene and 1-bromo-4-(2-methylcyclopenta-1-en-1-yl)-naphthalene (a mixture of about 6:4), (290 mg), zinc cyanide (71 mg) and tetrakis triphenylphosphine (120 mg) was dissolved in N,N-dimethylformamide (6 mL), the mixture was warmed to 100° C. under nitrogen atmosphere and stirred for 1 hour. Water was poured into the reactant and extracted with ethyl acetate. The extracts were washed with water, dried and concentrated. The obtained residue was purified by silica gel column chromatography to obtain 4-(5-methylcyclopenta-1-en-1-yl)-1-naphthonitrile and 4-(2-methylcyclopenta-1-en-1-yl)-1-naphthonitrile (a mixture of about 6:4) (224 mg) (Compound 149).

¹H-NMR (200 MHz, CDCl₃) δ: 0.93 (1.8H, d, J=7.0 Hz), 1.48-1.55 (1.2H, m), 1.60-2.85 (4.8H, m), 3.20-3.40 (0.6H, m), 5.85-5.95 (0.6H, m), 7.25-8.50 (6H, m).

IR (KBr) 2220, 766 cm⁻¹

Example 148 (Preparation of Compound 150)

A mixture of 4-fluoro-1-naphthonitrile (514 mg), [1,4]oxepane (506 mg), potassium carbonate (420 mg), and dimethylsulfoxide (5.0 mL) was stirred at 100° C. for 1 hour. After cooling to room temperature, water was poured into the reactant and extracted with ethyl acetate. The extracts were washed with water, dried and concentrated. The obtained residue was purified by silica gel column chromatography to obtain 4-(1,4-oxepan-4-yl)-1-naphthonitrile (281 mg) (Compound 150).

¹H-NMR (200 MHz, CDCl₃) δ: 2.10-2.30 (2H, m), 3.40-3.60 (4H, m), 3.90-4.10 (4H, m), 7.09 (1H, d, J=8.0 Hz), 7.50-7.75 (2H, m), 7.82 (1H, d, J=8.0 Hz), 8.18-8.28 (2H, m).

IR (KBr) 2215, 1571, 1512 cm⁻¹

Example 149 (Preparation of Compound 151 and 152)

4-(5-Methylcyclopenta-1-en-1-yl)-1-naphthonitrile and 4-(2-methylcyclopenta-1-en-1-yl)-1-naphthonitrile (a mixture of about 6:4, 250 mg) was dissolved in methyl alcohol (20 mL), 10% palladium carbon (containing water) (100 mg) was added, and the mixture was stirred under hydrogen atmosphere for 2 hours. The catalyst was filtered off, the filtrate was concentrated and dried. The residue was dissolved in dichloromethane (6 mL), m-chloroperbenzoic acid (170 mg) was added at room temperature, and the mixture was stirred for 1 hour. Water was poured into the reactant and extracted with ethyl acetate. The extracts were sequentially washed with sodium hydrogen carbonate water and water, dried and concentrated. The obtained residue was purified by silica gel column chromatography to obtain 4-(2-methylcyclopentyl)-1-naphthonitrile (Compound 151) (38 mg) and 4-(5-methyl-6-oxabicyclo[3,1,0]hexa-1-yl)-1-naphthonitrile (Compound 152) (62 mg).

Compound 151

¹H-NMR (200 MHz, CDCl₃) δ: 0.39(3H, d, J=7.4 Hz), 1.35-1.58 (1H, m), 1.60-2.40 (5H, m), 2.52-2.80 (1H, m), 3.80-4.00 (1H, m), 7.43 (1H, d, J=7.6 Hz), 7.58-7.74 (2H, m), 7.87 (1H, d, J=7.6 Hz), 8.20-8.32 (2H, m).

IR (KBr) 2221, 1579, 1514 cm⁻

Compound 152

¹H-NMR (200 MHz, CDCl₃) δ: 1.20(3H, s), 1.60-2.40 (6H, m), 7.50-7.90 (4H, m), 7.93 (1H, d, J=7.4 Hz), 8.22-8.35 (1H, m).

IR (KBr) 2223, 1514, 1390 cm⁻¹

Example 150 (Preparation of Compound 153)

Tert-butyl (2S,4R)-4-hydroxy-2-methylpyrrolidine-1-carboxylate (2.01 g) was dissolved in toluene (4.0 mL), trifluoroacetic acid (4.0 mL) was added, and the mixture was stirred at room temperature for 2 hours. The reaction solution was concentrated and dried. To the residue was added 4-fluoro-1-naphthonitrile (1.71 g), potassium carbonate (2.77 g) and dimethylsulfoxide (15.0 mL), and the mixture was stirred at 100° C. for 1.5 hours. After cooling to room temperature, water was poured into the reactant, and extracted with ethyl acetate. The extracts were washed with water, dried and concentrated. The obtained residue was purified by silica gel column chromatography to obtain 4-[(2S,4R)-4-hydroxy-2-methyl-1-pyrrolidinyl]-1-naphthonitrile (119 mg) (Compound 153).

$[α]_D$=−263.9° (c=0.462, MeOH).

¹H-NMR (200 MHz, CDCl₃) δ: 1.23(3H, d, J=6.4 Hz), 1.70-1.90 (1H, m), 2.04 (1H, d, J=6.0 Hz), 2.56-2.74 (1H, m), 3.25-3.39 (1H, m), 3.85-4.10 (2H, m), 4.35-4.55 (1H, m), 6.90 (1H, d, J=8.4 Hz), 7.48-7.69 (2H, m), 7.79 (1H, d, J=8.4 Hz), 8.16-8.30 (2H, m).
IR (KBr) 2212, 1567 cm⁻¹

Example 151 (Preparation of Compound 154)

4-[(2S,4R)-4-hydroxy-2-methyl-1-pyrrolidinyl]-1-naphthonitrile (310 mg), acetic acid (210 mg) and triphenylphosphine (645 mg) were dissolved in toluene (8 mL), diethyl azodicarboxylate (in a 40% toluene solution, 1 mL) was added under nitrogen atmosphere, and the mixture was stirred at room temperature for 15 hours. Hexane (20 mL) was added to the reaction solution and the precipitated insolubles were filtered off. To the filtrate was poured water and extracted with ethyl acetate. The extracts were sequentially washed with sodium hydrogen carbonate water and water, dried and concentrated. The obtained residue was purified by silica gel column chromatography to concentrate a solution containing a fractioned objective matter. The residue was dissolved in methyl alcohol (15 mL), potassium carbonate (680 mg) was added, and the mixture was stirred at room temperature for 1.5 hours. The reaction solution was concentrated. The residue was poured into water and extracted with ethyl acetate. The extracts were washed with saturated brine, dried and concentrated. The residue was purified by silica gel column chromatography to obtain 4-[(2S,4S)-4-hydroxy-2-methyl-1-pyrrolidinyl]-1-naphthonitrile (119 mg) (Compound 154).
mp 149-151° C.
$[\alpha]_D$=−211.8° (c=0.51, MeOH).
¹H-NMR (200 MHz, CDCl₃) δ: 1.20(3H, d, J=5.8 Hz), 1.66 (1H, d, J=3.6 Hz), 1.80-2.00 (1H, m), 2.20-2.40 (1H, m), 3.28 (1H, dd, J=1.8 Hz and 11.0 Hz), 4.18-4.60 (3H, m), 6.90 (1H, d, J=8.4 Hz), 7.40-7.68 (2H, m), 7.76 (1H, d, J=8.4 Hz), 8.08-8.20 (2H, m).
IR (KBr) 3480, 2214, 1564 cm⁻¹

Example 152 (Preparation of Compound 155)

4-[(2S,4R)-4-hydroxy-2-methyl-1-pyrrolidinyl]-1-naphthonitrile (73 mg) was dissolved in N,N-dimethylformamide (2 mL), and the mixture was stirred with ice-cooling. Sodium hydride (60% in oil, 17 mg) was added, and the mixture was further stirred at room temperature for 0.5 hour. After adding methyl iodide (0.1 mL), the mixture was stirred at room temperature for 15 hours. Water was poured into the reactant and extracted with ethyl acetate. The extracts were washed with water, dried and concentrated. The obtained residue was purified by silica gel column chromatography to obtain 4-[(2S,4R)-4-methoxy-2-methyl-1-pyrrolidinyl]-1-naphthonitrile (72 mg) (Compound 155).
mp 88-89° C.
$[\alpha]_D$=−225.1° (c=0.386, MeOH).
¹H-NMR (200 MHz, CDCl₃) δ: 1.20(3H, d, J=6.2 Hz), 1.70-1.90 (1H, m), 2.50-2.70 (1H, m), 3.28-3.44 (1H, m), 3.40 (3H, s), 3.84-4.08 (3H, m), 6.88 (1H, d, J=8.2 Hz), 7.48-7.70 (2H, m), 7.79 (1H, d, J=8.2 Hz), 8.14-8.30 (2H, m).
IR (KBr) 2210, 1569 cm⁻¹

Example 153 (Preparation of Compound 156)

A mixture of methyl (2S,3S)-2-methyl-1-[(1S)-1-phenylethyl]pyrrolidine-3-carboxylate (1.00 g), methanol (20 mL), acetic acid (1.0 mL), and 10% palladium carbon (containing water) (350 mg) was stirred under hydrogen atmosphere for 4 hours. The catalyst was filtered off, the filtrate was concentrated and dried. To the residue was added 4-fluoro-1-naphthonitrile (680 mg), potassium carbonate (1.66 g) and dimethylsulfoxide (10.0 mL), and the mixture was stirred at 100° C. for 1.5 hours. After cooling to room temperature, water was poured into the reactant and extracted with ethyl acetate. The extracts were washed with water, dried and concentrated. The obtained residue was purified by silica gel column chromatography to obtain methyl (2S,3S)-1-(4-cyano-1-naphthyl)-2-methylpyrrolidine-3-carboxylate (262 mg) (Compound 156).
$[\alpha]_D$=−236.3° (c=0.408, MeOH).
¹H-NMR (200 MHz, CDCl₃) δ: 1.35(3H, d, J=6.4 Hz), 2.00-2.52 (2H, m), 3.10-3.48 (2H, m), 3.76 (1H, s), 4.05-4.45 (2H, m), 6.93 (1H, d, J=8.6 Hz), 7.50-7.70 (2H, m), 7.80 (1H, d, J=8.0 Hz), 8.14-8.28 (2H, m).
IR (KBr) 2213, 1737, 1570 cm⁻¹

Example 154 (Preparation of Compound 157)

Methyl (2S,3S)-1-(4-cyano-1-naphthyl)-2-methylpyrrolidine-3-carboxylate (62 mg) was dissolved in methyl alcohol (2 mL), 1 N-sodium hydroxide (0.63 mL) was added, and the mixture was stirred at room temperature for 5 hours. The resulting mixture was adjusted to pH=2 with acetic acid, concentrated and extracted with ethyl acetate. The extracts were washed with water, dried and concentrated. The obtained residue was purified by silica gel column chromatography to obtain (2S,3S)-1-(4-cyano-1-naphthyl)-2-methylpyrrolidine-3-carboxylic acid (8.8 mg) (Compound 157).
¹H-NMR (200 MHz, CDCl₃) δ: 1.15(3H, d, J=6.2 Hz), 2.08-2.55 (2H, m), 3.08-3.24 (1H, m), 3.35-3.50 (1H, m), 4.05-4.40 (2H, m), 6.98 (1H, d, J=8.0 Hz), 7.50-7.76 (2H, m), 7.82 (1H, d, J=8.0 Hz), 8.16-8.30 (2H, m).
IR (KBr) 2213, 1708, 1570 cm⁻¹

Example 155 (Preparation of Compound 158)

2-{(2S,3S)-2-methyl-1-[(1S)-1-phenylethyl]-pyrrolidin-3-yl}propan-2-ol (1.08 g) was dissolved in methanol (20 mL), acetic acid (1.0 mL) and 10% palladium carbon (containing water) (500 mg) were added, and the mixture was stirred under hydrogen atmosphere for 3 hours. The catalyst was filtered off, the filtrate was concentrated and dried. To the residue was added 4-fluoro-1-naphthonitrile (750 mg), potassium carbonate (1.81 g) and dimethylsulfoxide (20.0 mL) were added, and the mixture was stirred at 100° C. for 3.0 hours. After cooling to room temperature, water was poured into the reactant and extracted with ethyl acetate. The extracts were washed with water, dried and concentrated. The obtained residue was purified by silica gel column chromatography to obtain 4-[(2S,3S)-3-(1-hydroxy-1-methylethyl)-2-methyl-1-pyrrolidinyl]-1-naphthonitrile (543 mg) (Compound 158).
$[\alpha]_D$=−225.5° (c=0.20, MeOH).
¹H-NMR (200 MHz, CDCl₃) δ: 0.98(3H, d, J=6.6 Hz), 1.34 (3H, s), 1.39 (3H, s), 1.57 (1H, s), 2.05-2.16 (2H, m), 2.45-2.65 (1H, m), 3.20-3.40 (1H, m), 3.70-3.92 (1H, s), 4.35-4.55 (1H, m), 6.89 (1H, d, J=8.0 Hz), 7.45-7.70 (2H, m), 7.77 (1H, d, J=8.0 Hz), 8.06-8.24 (2H, m).
IR (KBr) 2211, 1569 cm⁻¹

Example 156 (Preparation of Compound 159)

4-[(2S,3S)-3-(1-hydroxy-1-methylethyl)-2-methyl-1-pyrrolidinyl]-1-naphthonitrile (130 mg) was dissolved in dichloromethane (2 mL). With stirring under ice-cooling to −40° C., chlorosulfonyl isocyanate (0.10 mL) was added and the mixture was stirred for 30 minutes. To the reaction solution was added water (10 mL) and dichloromethane (2 mL), and the mixture was heated under reflux for 30 minutes. The reaction solution was alkalified with sodium carbonate water and extracted with ethyl acetate. The extracts were washed with water, dried and concentrated. The obtained residue was purified by silica gel column chromatography to obtain 1-[(2S,3S)-1-(4-cyano-1-naphthyl)-2-methylpyrrolidin-3-yl]-1-methylethyl carbamate (19 mg) (Compound 159).

$^1$H-NMR (200 MHz, CDCl$_3$) δ: 0.94(3H, d, J=6.6 Hz), 1.63 (3H, s), 1.68 (3H, s), 2.10-2.30 (2H, m), 2.68-2.85 (1H, m), 3.70-3.90 (1H, m), 4.35-4.60 (3H, m), 6.90 (1H, d, J=8.0 Hz), 7.46-7.70 (2H, m), 7.78 (1H, d, J=8.0 Hz), 8.06-8.24 (2H, m).

IR (KBr) 2212, 1715, 1568 cm$^{-1}$

Example 157 (Preparation of Compound 160)

Tert-butyl (2S,3S)-3-(aminocarbonyl)-2-methylpyrrolidine-1-carboxylate (760 mg) was dissolved in toluene (4.0 mL), trifluoroacetic acid (4.0 mL) was added, and the mixture was stirred at room temperature for 2 hours. The reaction solution was concentrated and dried. To the residue was added 4-fluoro-1-naphthonitrile (570 mg), potassium carbonate (1370 mg) and dimethylsulfoxide (12 mL), and the mixture was stirred at 100° C. for 5 hours. After cooling to room temperature, water was poured into the reactant and extracted with ethyl acetate. The extracts were washed with water, dried and concentrated. To the residue was added hexane:ethyl acetate=1:2 and crystallized, to obtain (2S,3S)-1-(4-cyano-1-naphthyl)-2-methylpyrrolidine-3-carboxamide (158 mg). Mother liquor was purified by silica gel column chromatography, to obtain the same compound (289 mg) (Compound 160).

mp 204-206° C.

[α]$_D$=−276.7° (c=0.388, MeOH).

$^1$H-NMR (200 MHz, CDCl$_3$+DMSO-d$_6$) δ: 1.17(3H, d, J=6.2 Hz), 2.00-2.50 (2H, m), 3.06-3.30 (2H, m), 4.05-4.30 (2H, m), 5.84 (1H, br.s), 6.51 (1H, br.s), 6.98 (1H, d, J=8.0 Hz), 7.50-7.71 (2H, m), 7.82 (1H, d, J=8.0 Hz), 8.12-8.30 (2H, m).

IR (KBr) 2210, 1664, 1567 cm$^{-1}$

Anal. Calcd. for C$_{17}$H$_{17}$N$_3$O: C, 73.10; H, 6.13; N, 15.04. Found: C, 72.82; H, 6.03; N, 15.09.

Example 158 (Preparation of Compound 161)

(2S,3S)-1-(4-cyano-1-naphthyl)-2-methylpyrrolidine-3-carboxamide (160 mg) was dissolved in dichloromethane (3 mL), anhydrous trifluoroacetic acid (0.2 mL) was added, and the mixture was stirred at room temperature for 5 hours. The reaction solution was alkalified with sodium hydrogen carbonate water and extracted with ethyl acetate. The extracts were washed with water, dried and concentrated. The obtained residue was purified by silica gel column chromatography to obtain (2S,3S)-1-(4-cyano-1-naphthyl)-2-methylpyrrolidine-3-carbonitrile (124 mg) (Compound 161).

mp 143-145° C.

[α]$_D$=−192.6° (c=0.34, MeOH).

$^1$H-NMR (200 MHz, CDCl$_3$) δ: 1.36(3H, d, J=5.8 Hz), 2.20-2.50 (2H, m), 3.08-3.25 (1H, m), 3.38-3.50 (1H, m), 4.00-4.22 (2H, m), 6.96 (1H, d, J=8.0 Hz), 7.50-7.78 (2H, m), 7.83 (1H, d, J=8.0 Hz), 8.18-8.30 (2H, m).

IR (KBr) 2249, 2213, 1567 cm$^{-1}$

The structural formulae of the compounds obtained in Examples were shown in the following tables 1 to 12. "Ex." in the tables represents Example Nos., respectively. Further, in the tables, "HCl", "H$_2$SO$_4$", "MsOH" and the like in the columns regarding B ring represent "hydrochloride", "sulfate", "methanesulfonate" and the like.

TABLE 1

| Ex. | Compound No. | A ring | B ring | R$^1$ | R$^2$ | R$^3$ |
|---|---|---|---|---|---|---|
| 1 | 1 | benzene | pyrrolidine | CN | H | H |
| 2 | 2 | benzene | pyrrolidine | CO$_2$H | H | H |
| 3 | 3 | benzene | piperidine | CN | H | H |
| 4 | 4 | benzene | piperidine · HCl | CN | H | H |
| 5 | 5 | benzene | piperidine | Br | H | H |
| 6 | 6 | benzene | piperidine | CF$_3$ | H | H |
| 7 | 7 | benzene | morpholine | CN | H | H |
| 8 | 8 | benzene | thiomorpholine | CN | H | H |
| 9 | 9 | benzene | thiomorpholine S-oxide | CN | H | H |
| 10 | 10 | benzene | azepane | CN | H | H |

TABLE 1-continued

| Ex. | Compound No. | A ring | B ring | R¹ | R² | R³ |
|---|---|---|---|---|---|---|
| 11 | 11 | dimethylphenyl | 4-hydroxypiperidine | CN | H | H |
| 12 | 12 | dimethylphenyl | thiomorpholine 1,1-dioxide | CN | H | H |
| 13 | 13 | dimethylphenyl | 1,4-dioxa-8-azaspiro[4.5]decane | CN | H | H |
| 14 | 14 | dimethylphenyl | 4-oxopiperidine | CN | H | H |

TABLE 2

| Ex. | Compound No. | A ring | B ring | R¹ | R² | R³ |
|---|---|---|---|---|---|---|
| 15 | 15 | dimethylphenyl | 4-carbamoylpiperidine | CN | H | H |
| 16 | 16 | dimethylphenyl | piperidine | CN | H | Br |
| 17 | 17 | dimethylphenyl | 4-methylpiperazine | CN | H | H |
| 18 | 18 | dimethylphenyl | 3-hydroxypyrrolidine | CN | H | H |

TABLE 2-continued

| Ex. | Compound No. | A ring | B ring | R¹ | R² | R³ |
|---|---|---|---|---|---|---|
| 19 | 19 | benzene | 3-(hydroxymethyl)piperidine | CN | H | H |
| 20 | 20 | benzene | 3-(hydroxymethyl)piperidine·HCl | CN | H | H |
| 21, 23 | 21 | benzene | (S)-3-(hydroxymethyl)piperidine | CN | H | H |
| 22, 23 | 22 | benzene | (R)-3-(hydroxymethyl)piperidine | CN | H | H |
| 24 | 23 | benzene | (S)-3-(hydroxymethyl)piperidine·HCl | CN | H | H |
| 25 | 24 | benzene | (R)-3-(hydroxymethyl)piperidine·HCl | CN | H | H |
| 26 | 25 | benzene | 3-(BocNH)pyrrolidine | CN | H | H |
| 27 | 26 | benzene | piperidine | CN | Br | H |
| 28 | 27 | benzene | 3-oxopyrrolidine | CN | H | H |
| 29 | 28 | benzene | 3-aminopyrrolidine·2HCl | CN | H | H |

TABLE 3
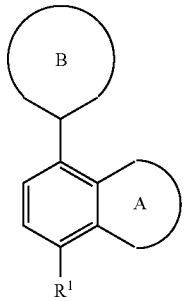
| Ex. | Compound No. | A ring | B ring | R¹ |
|---|---|---|---|---|
| 30 | 29 | 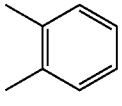 | 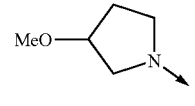 | CN |
| 31 | 30 | 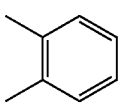 | 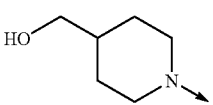 | CN |
| 32 | 31 | 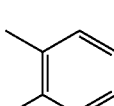 | 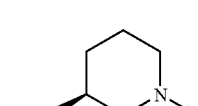 | CN |
| 33 | 32 | 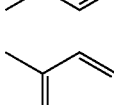 | 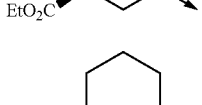 | CN |
| 34 | 33 | 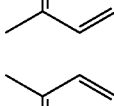 | 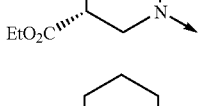 | CN |
| 35 | 34 | 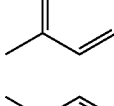 | 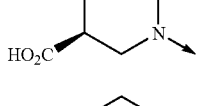 | CN |
| 36 | 35 | 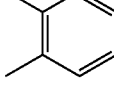 | 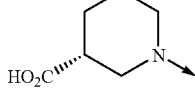 | CN |
| 37 | 36 | 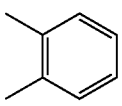 | | NO₂ |
| 38 | 37 | 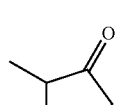 | | NO₂ |
| 39 | 38 | 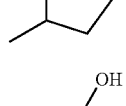 | | NO₂ |
TABLE 3-continued
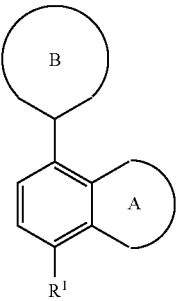
| Ex. | Compound No. | A ring | B ring | R¹ |
|---|---|---|---|---|
| 39 | 39 | 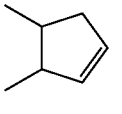 | | NO₂ |
| 40 | 40 | 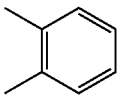 | 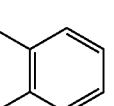 | CN |
| 41 | 41 | 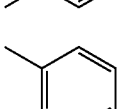 | 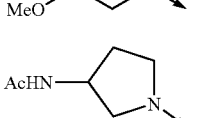 | CN |
| 42 | 42 | 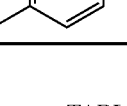 | 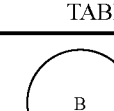 | CN |
TABLE 4
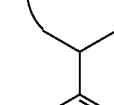
| Ex. | Compound No. | A ring | B ring | R¹ |
|---|---|---|---|---|
| 43 | 43 | 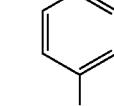 | 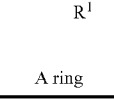 | CN |
| 44 | 44 | 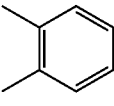 | 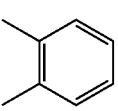 | CN |
| 45 | 45 | 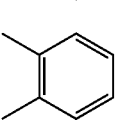 | 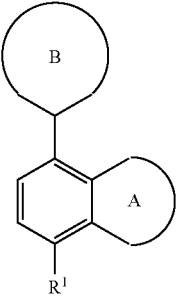 | CN |

TABLE 4-continued

| Ex. | Compound No. | A ring | B ring | R¹ |
|---|---|---|---|---|
| 46 | 46 | (2-methylphenyl) | pyrrolidine-CONH₂ | CN |
| 47 | 47 | (2-methylphenyl) | 2-methylpyrrolidine·HCl | CN |
| 48 | 48 | (2-methylphenyl) | 2-methylpyrrolidine | CN |
| 49 | 49 | (2-methylphenyl) | 3-(N-Ac-N-Me)aminopyrrolidine | CN |
| 50 | 50 | (2-methylphenyl) | 3-(hydroxymethyl)pyrrolidine·HCl | CN |
| 51 | 51 | (2-methylphenyl) | 3-(methoxymethyl)pyrrolidine | CN |
| 52 | 52 | (2-methylphenyl) | cis-2-methyl-4-(hydroxymethyl)pyrrolidine | CN |
| 53 | 53 | (2-methylphenyl) | trans-2-methyl-4-(hydroxymethyl)pyrrolidine | CN |
| 54 | 54 | (2-methylphenyl) | cis-2-methyl-4-(methoxymethyl)pyrrolidine | CN |
| 55 | 55 | (2-methylphenyl) | trans-2-methyl-4-(methoxymethyl)pyrrolidine | CN |

TABLE 4-continued

| Ex. | Compound No. | A ring | B ring | R¹ |
|---|---|---|---|---|
| 56 | 56 | (2-methylphenyl) | 3-methyl-3-(hydroxymethyl)piperidine | CN |

TABLE 5

| Ex. | Compound No. | A ring | B ring | R¹ |
|---|---|---|---|---|
| 57 | 57 | (2-methylphenyl) | 3-methyl-3-(methoxymethyl)piperidine | CN |
| 58 | 58 | (2-methylphenyl) | 3,5-dimethylpiperidine | CN |
| 59 | 59 | cyclohexyl | pyrrolidine | CN |
| 60 | 60 | cyclohexyl | piperidine | CN |
| 61 | 61 | (2-methylphenyl) | 3-(hydroxyimino)pyrrolidine | CN |
| 62 | 62 | (2-methylphenyl) | 3-(hydroxyimino)pyrrolidine | CN |

TABLE 5-continued

| Ex. | Compound No. | A ring | B ring | R¹ |
|---|---|---|---|---|
| 62 | 63 | 2,2,4-trimethyltetrahydrofuran | pyrrolidine | CN |
| 63 | 64 | o-tolyl | 2-methyl-3-oxocyclopentyl | CN |
| 64 | 65 | o-tolyl | 2-methyl-3-hydroxycyclopentenyl | CN |
| 65 | 66 | o-tolyl | 2-methyl-3-methoxycyclopentenyl | CN |
| 66 | 67 | o-tolyl | 4-(methoxymethyl)piperidine | CN |
| 67 | 68 | o-tolyl | 3-hydroxy-3-methylpiperidine | CN |
| 68 | 69 | o-tolyl | 3-(methanesulfonamido)pyrrolidine | CN |
| 69 | 70 | o-tolyl | 1,2,3,4-tetrahydroisoquinoline | CN |

TABLE 6

| Ex. | Compound No. | A ring | B ring | R¹ |
|---|---|---|---|---|
| 70 | 71 | o-tolyl | 3-((N-Boc-N-methanesulfonyl)aminomethyl)piperidine | CN |
| 71 | 72 | o-tolyl | 3-(methanesulfonamidomethyl)piperidine | CN |
| 72 | 73 | 2,3-dimethylthiophene | piperidine | CN |
| 73 | 74 | o-tolyl | 3-carbamoylpiperidine | CN |
| 74 | 75 | o-tolyl | 1,2-oxazinane | CN |
| 75 | 76 | 2,3-dimethylthiophene | 2-methylpyrrolidine | CN |
| 76 | 77 | o-tolyl | 4-(hydroxymethyl)-4-methylpiperidine | CN |
| 77 | 78 | o-tolyl | 4-(2-hydroxyethyl)piperidine | CN |
| 78 | 79 | o-tolyl | 4-(2-methoxyethyl)piperidine | CN |
| 79 | 80 | o-tolyl | 4-(2-hydroxypropan-2-yl)piperidine | CN |

TABLE 6-continued

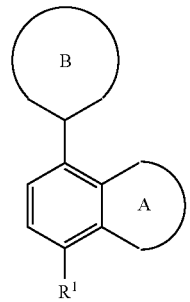

| Ex. | Compound No. | A ring | B ring | R¹ |
|---|---|---|---|---|
| 80 | 81 | (2,3-dimethylphenyl) | (2-vinylpyrrolidin-1-yl) | CN |
| | 82 | (2,3-dimethylphenyl) | (2-vinylpyrrolidin-1-yl) | CN |

TABLE 6-continued

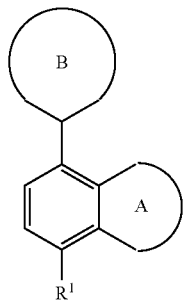

| Ex. | Compound No. | A ring | B ring | R¹ |
|---|---|---|---|---|
| 81 | 83 | (2,3-dimethylphenyl) | (2-ethylpyrrolidin-1-yl) | CN |
| | 84 | (2,3-dimethylphenyl) | (2-ethylpyrrolidin-1-yl) | CN |

TABLE 7

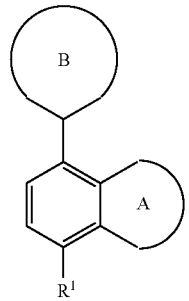

| Ex. | Compound No. | A ring | B ring | R¹ |
|---|---|---|---|---|
| 82, 83 | 85 | (2,3-dimethylphenyl) | (2-methylpyrrolidin-1-yl) | CN |
| 83 | 86 | (2,3-dimethylphenyl) | (2-methylpyrrolidin-1-yl) | CN |
| 84 | 87 | (2,3-dimethylphenyl) | (4-(2-ethoxycarbonylethyl)piperidin-1-yl) | CN |
| 85 | 88 | (2,3-dimethylphenyl) | (4-(2-hydroxyethyl)piperidin-1-yl) | CN |

TABLE 7-continued

| Ex. | Compound No. | A ring | B ring | R¹ |
|---|---|---|---|---|
| 86 | 89 | dimethylbenzene | 2-methylpyrrolidine | COCF₃ |
| 87 | 90 | dimethylbenzene | 2-methylpyrrolidine | COCH₃ |
| 88 | 91 | dimethylbenzene | 5-oxo-pyrazolidine (NH) | CN |
| 89 | 92 | dimethylbenzene | 3-methoxy-4,5-dihydropyrazole | CN |
|  | 93 | dimethylbenzene | 2-methyl-5-oxo-pyrazolidine | CN |
| 90 | 94 | dimethylthiophene | 4-(2-hydroxyethyl)piperidine | CN |
| 91 | 95 | dimethylfuran | 2-methylpyrrolidine | CN |
| 92 | 96 | dimethylfuran | 4-(2-hydroxyethyl)piperidine | CN |
| 93 | 97 | trimethylfuran | 2-methylpyrrolidine | CN |
| 94 | 98 | trimethylfuran | 4-(2-hydroxyethyl)piperidine | CN |

TABLE 8

| Ex. | Compound No. | A ring | B ring | R¹ |
|---|---|---|---|---|
| 95 | 99 | 2,3-dimethylphenyl | 3-fluoropyrrolidine | CN |
| 96 | 100 | 2,3-dimethylthiophene | 3-fluoropyrrolidine | CN |
| 97 | 101 | 2,3-dimethylthiophene | 3-(2-hydroxyethyl)pyrrolidine | CN |
| 98 | 102 | 2,3-dimethylthiophene | 3-(2-methoxyethyl)pyrrolidine | CN |
| 99 | 103 | 2,3-dimethylphenyl | 3,3-difluoropyrrolidine | CN |
| 100 | 104 | 2,3-dimethylthiophene | 3,3-difluoropyrrolidine | CN |
| 101 | 105 | 2,3-dimethylphenyl | 4-(ethoxycarbonylmethyl)piperidine | CN |
| 102 | 106 | 2,3-dimethylphenyl | 4-(carboxymethyl)piperidine | CN |
| 103 | 107 | 2,3-dimethylphenyl | 3-(hydroxymethyl)-2-methylpyrrolidine | CN |
| 104 | 108 | 2,3-dimethylthiophene | 3-(hydroxymethyl)-2-methylpyrrolidine | CN |
| 105 | 109 | 2,3-dimethylthiophene | 4-hydroxy-2-methylpyrrolidine | CN |
| 106 | 110 | 2,3-dimethylphenyl | 3-(methoxymethyl)-2-methylpyrrolidine | CN |
| 107 | 111 | 2,3-dimethylthiophene | 4-hydroxy-2-methylpyrrolidine | CN |
| 108 | 112 | 2,3-dimethylphenyl | 2-methyl-3-oxopyrrolidine | CN |

TABLE 9

| Ex. | Compound No. | A ring | B ring | R¹ |
|---|---|---|---|---|
| 109 | 113 | 2,3-dimethylphenyl | 3-hydroxy-2-methylpyrrolidine | CN |

TABLE 9-continued

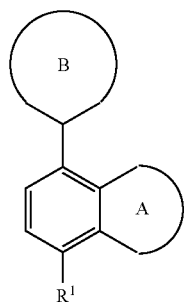

| Ex. | Compound No. | A ring | B ring | R[1] |
|---|---|---|---|---|
| 110 | 114 | (dimethylphenyl) | (hydroxy-methyl-pyrrolidine) MsOH | CN |
| 111 | 115 | (dimethylthiophene) | (hydroxy-methyl-pyrrolidine) | CN |
| 112, 113 | 116 | (dimethylphenyl) | (hydroxy-methyl-pyrrolidine) | CN |
| 114 | 117 | (dimethylphenyl) | (hydroxy-methyl-pyrrolidine) H₂SO₄ | CN |
| 115, 116 | 118 | (dimethylthiophene) | (hydroxy-methyl-pyrrolidine) | CN |
| 117 | 119 | (dimethylthiophene) | (hydroxy-methyl-pyrrolidine) H₂SO₄ | CN |
| 118 | 120 | (dimethylthiophene) | (hydroxy-methyl-pyrrolidine) | CN |
| 119 | 121 | (dimethylthiophene) | (hydroxy-methyl-pyrrolidine) | CN |

TABLE 9-continued

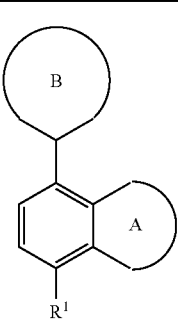

| Ex. | Compound No. | A ring | B ring | R[1] |
|---|---|---|---|---|
| 120 | 122 | (dimethylphenyl) | (hydroxy-methyl-pyrrolidine) | CN |
| 121 | 123 | (dimethylphenyl) | (hydroxy-methyl-pyrrolidine) | CN |
| 122 | 124 | (dimethylphenyl) | (hydroxymethyl-isoxazoline) | Br |
| 123 | 125 | (dimethylphenyl) | (hydroxymethyl-isoxazoline) | CN |
| 124 | 126 | (dimethylphenyl) | (methoxymethyl-isoxazoline) | CN |

TABLE 10

| Ex. | Compound No. | A ring | B ring | R¹ |
|---|---|---|---|---|
| 125 | 127 | o-tolyl | 4-(hydroxymethyl)-2-methylpyrrolidinyl · HCl | CN |
| 126 | 128 | o-tolyl | (4-hydroxy-2-(hydroxymethyl))pyrrolidinyl | CN |
| 127 | 129 | o-tolyl | 4-hydroxy-2-((4-cyano-naphthalenyloxy)methyl)pyrrolidinyl | CN |
| 128 | 130 | o-tolyl | 3-(hydroxymethyl)-3,5-dimethylpyrrolidinyl | CN |
| 129 | 131 | o-tolyl | isoindolinyl | CN |
| 130 | 132 | o-tolyl | 4-methoxy-2-(hydroxymethyl)pyrrolidinyl | CN |
| 131 | 133 | o-tolyl | 4-methoxy-2-(methoxymethyl)pyrrolidinyl | CN |
| 132 | 134 | o-tolyl | 2,2-dimethylpyrrolidinyl | CN |
| 133 | 135 | o-tolyl | 2-carbamoylpyrrolidinyl | CN |
| 134 | 136 | o-tolyl | 2-cyanopyrrolidinyl | CN |

TABLE 10-continued
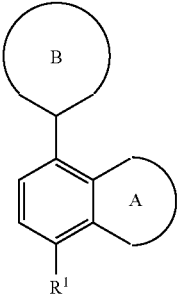
| Ex. | Compound No. | A ring | B ring | R¹ |
|---|---|---|---|---|
| 135 | 137 | (o-dimethylphenyl) | (3-phenylpyrrolidine) | CN |
| 136 | 138 | (o-dimethylphenyl) | (3-phenoxypyrrolidine) | CN |
| 137 | 139 | (o-dimethylphenyl) | (3-MeO, 2-Me pyrrolidine) | CN |
| 138 | 140 | (o-dimethylphenyl) | (3-(EtO₂CCH₂)pyrrolidine) | CN |
TABLE 11
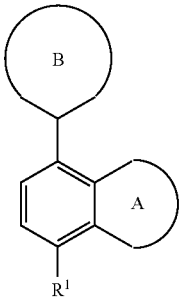
| Ex. | Compound No. | A ring | B ring | R¹ |
|---|---|---|---|---|
| 139 | 141 | (o-dimethylphenyl) | (3-(2-hydroxyethyl)pyrrolidine) | CN |
| 140 | 142 | (o-dimethylphenyl) | (2-propylpyrrolidine) | CN |

TABLE 11-continued
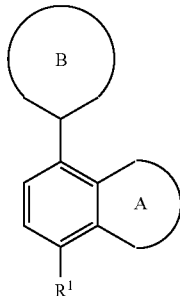
| Ex. | Compound No. | A ring | B ring | R¹ |
|---|---|---|---|---|
| 141 | 143 | 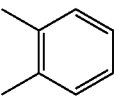 | 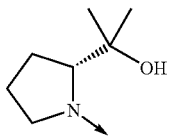 | CN |
| 142 | 144 | 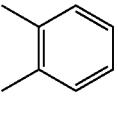 | 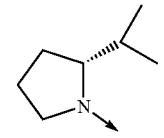 | CN |
| 143 | 145 | 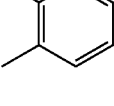 | 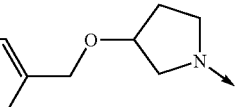 | CN |
| 144 | 146 | 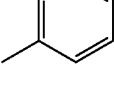 | 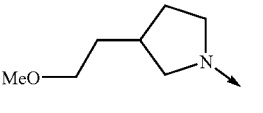 | CN |
| 145 | 147 | 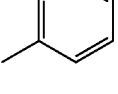 | 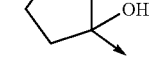 | Br |
| 146 | 148 | 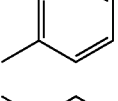 | 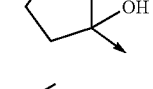 | CN |
| 147 | 149 | 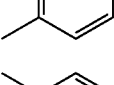 |  | CN |
| 148 | 150 | 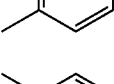 | 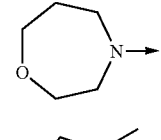 | CN |
| 149 | 151 | 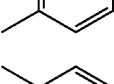 | 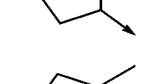 | CN |
|  | 152 | 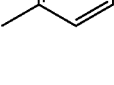 | 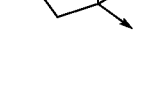 | CN |

TABLE 11-continued
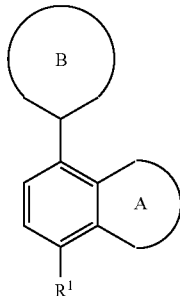
| Ex. | Compound No. | A ring | B ring | R[1] |
|---|---|---|---|---|
| 150 | 153 | 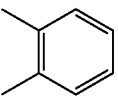 | 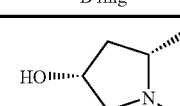 | CN |
| 151 | 154 | 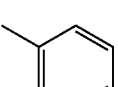 | 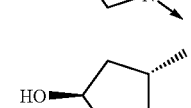 | CN |
TABLE 12
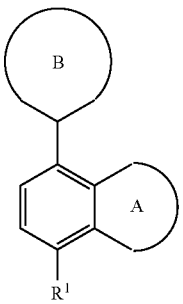
| Ex. | Compound No. | A ring | B ring | R[1] |
|---|---|---|---|---|
| 152 | 155 | 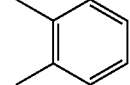 | 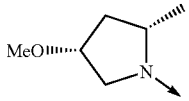 | CN |
| 153 | 156 | 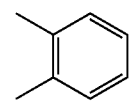 | 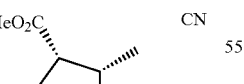 | CN |
| 154 | 157 | 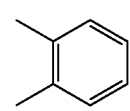 | 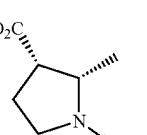 | CN |
TABLE 12-continued
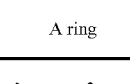
| Ex. | Compound No. | A ring | B ring | R[1] |
|---|---|---|---|---|
| 155 | 158 | 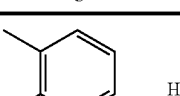 | 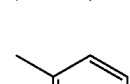 | CN |
| 156 | 159 | 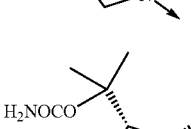 | 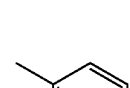 | CN |
| 157 | 160 | 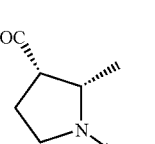 |  | CN |

TABLE 12-continued

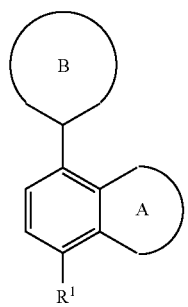

| Ex. | Compound No. | A ring | B ring | R¹ |
|---|---|---|---|---|
| 158 | 161 | (2-methylphenyl) | (NC, CN pyrrolidine) | CN |

Experimental Example 1

AR-Binding Inhibition Test (Wild Type and LNCaP Type)

To a solution of wild type or LNCaP type mutant androgen receptor (AR) was added 3 nM radio-labeled Mibolerone and 100 nM of the compound. The mixture was incubated at 4° C. for 3 hours, and B (Bound) and F (Free) Mibolerones were separated by the dextran/charcoal method. The radioactivity of B was measured and inhibition rate of the compound was calculated. The results are shown in Table 13.

TABLE 13

| Compound No. | Inhibition rate (%) at 100 nM | |
|---|---|---|
| | Wild type | LNCaP type |
| 1 | 88 | 78 |
| 3 | 97 | 97 |
| 8 | 92 | 96 |
| 10 | 112 | 144 |
| 18 | 96 | 79 |
| 19 | 75 | 91 |
| 30 | 105 | 113 |
| 45 | 105 | 110 |
| 47 | 116 | 116 |
| 50 | 91 | 102 |
| 56 | 80 | 91 |
| 73 | 95 | 95 |
| 76 | 102 | 97 |
| 78 | 92 | 97 |
| 81 | 104 | 100 |
| 82 | 85 | 94 |
| 83 | 95 | 102 |
| 84 | 88 | 93 |
| 85 | 95 | 99 |
| 95 | 92 | 105 |
| 99 | 98 | 92 |
| 100 | 97 | 92 |
| 101 | 93 | 97 |
| 107 | 95 | 93 |
| 108 | 99 | 100 |
| 109 | 98 | 99 |
| 111 | 93 | 88 |
| 113 | 97 | 98 |
| 115 | 93 | 97 |

TABLE 13-continued

| Compound No. | Inhibition rate (%) at 100 nM | |
|---|---|---|
| | Wild type | LNCaP type |
| 116 | 99 | 94 |
| 118 | 96 | 95 |
| 139 | 95 | 99 |
| 141 | 96 | 101 |
| 144 | 103 | 102 |
| 155 | 95 | 92 |
| 158 | 134 | 115 |
| 160 | 110 | 115 |
| 161 | 113 | 115 |

Experimental Example 2

Evaluation of a Compound in Reporter Assay System Using Cos-7 Cells

Cos-7 cells were inoculated in a 150 cm² flask at 5,000,000 cells, and incubated in a culture solution (DMEM medium containing 10% Dextran Charcoal (DCC)-Fetal Bovine Serum (FBS) and 2 mM glutamine) for 24 hours. A vector DNA containing AR gene and a vector DNA ligated with luciferase gene downstream of the androgen-responsive promoter, which was constructed by ligating two PSA promoter regions in tandem, were cotransfected by the liposome method. Two hours later, the culture medium was replaced and incubation was further carried out for 3 hours. 1 μM of 5α-dihydrotestosterone or 100 nM of the compound were added, and incubation was further carried out for 24 hours. By measuring luciferase activity, induction rate (%) of the compound was calculated, based on the luciferase activity induced is 100 when 1 μM of 5α-dihydrotestosterone was added. The results are shown in Table 14.

TABLE 14

| Compound No. | Induction rate (%) at 100 nM Wild type |
|---|---|
| 1 | 97 |
| 3 | 119 |
| 73 | 84 |
| 76 | 112 |
| 78 | 78 |
| 81 | 107 |
| 82 | 80 |
| 83 | 90 |
| 84 | 94 |
| 85 | 107 |
| 95 | 112 |
| 99 | 103 |
| 100 | 101 |
| 107 | 113 |
| 108 | 104 |
| 109 | 85 |
| 111 | 89 |
| 113 | 122 |
| 115 | 110 |
| 116 | 99 |
| 118 | 99 |
| 139 | 89 |
| 141 | 85 |
| 144 | 108 |
| 155 | 90 |
| 158 | 91 |
| 160 | 74 |

Experimental Example 3

PSA Production Test in Human Prostate Cancer Cells Strain

Human prostate cancer cell strain LNCaP-FGC was inoculated in 96 well plate at 5,000 cells/100 μL/well. The next day, the test Compound (100 nM of final concentration), or vehicle or testosterone as control (0.35 to 350 nM of final concentration) was added thereto. 3 days after the drug addition, the culture supernatant was collected. Concentration of androgen-dependently produced PSA (Prostate Specific Antigen) in the culture supernatant was measured by ELISA. The promotion-rate on PSA production by the test compound was calculated, based that the vehicle-addition group is 0 and the 350 nM testosterone-addition group is 100. The results are shown in Table 15.

TABLE 15

| Compound No. | Promotion rate (%) on PSA production at 100 nM |
|---|---|
| 3 | 90 |
| 8 | 71 |
| 10 | 75 |
| 19 | 70 |
| 30 | 100 |
| 47 | 88 |
| 50 | 88 |
| 56 | 96 |
| 76 | 85 |
| 78 | 89 |
| 81 | 98 |
| 83 | 95 |
| 85 | 92 |
| 99 | 83 |
| 100 | 82 |
| 101 | 86 |
| 107 | 95 |
| 108 | 102 |
| 109 | 86 |
| 111 | 70 |
| 113 | 88 |
| 115 | 76 |
| 116 | 84 |
| 118 | 88 |
| 139 | 73 |
| 141 | 87 |
| 144 | 87 |
| 155 | 91 |
| 158 | 81 |
| 160 | 82 |
| 161 | 122 |

Experimental Example 4

Influence of an Androgen Receptor Agonist on Growth Rate of Hormone-Resistant Cancer Cell 1) Establishment of Hormone-Resistant Cell Strain (LNCaP-hr and MDA PCa 2b-hr Cell Strains)

LNCaP-FGC and MDA PCa 2b cell strains were incubated in a culture solution free of androgen (RPMI1640+10% Dextran Charcoal (DCC)-Fetal Bovine Serum (FBS) for LNCaP-FGC, Ham's F-12K+25 ng/ml cholera toxin+10 ng/ml EGF+0.005 mM phosphoethanol amine+100 pg/ml hydrocortisone+45 nM selenious acid+0.005 mg/ml insulin+20% DCC-FBS for MDA PCa 2b). Initially, no growth was observed, but 3 to 8 months of continuous incubation led to growth. The cells were designated as LNCaP-hr and MDA PCa 2b-hr, respectively.

2) Influence of an Androgen Receptor Agonist on Growth Rate of Hormone-Resistant Cancer Cell (Method) LNCaP-hr (incubated for 60 weeks in androgen-free culture solution) cells were inoculated in 24 well plate at 40,000 cells/ml/well. The next day, 0.01 to 10 nmol/L of the test compound was added thereto. 3 days after the addition, cell number was counted. Furthermore, MDA PCa 2b-hr (incubated for 61 weeks in androgen-free culture solution) cells were inoculated in 24 well plate at 40,000 cells/ml/well. The next day, 0.01 to 10 μmol/L of the test compound was added thereto. 4 days after the addition, cell number was counted.

(Results) The compound of the present invention inhibited the growth of LNCaP-hr and MDA PCa 2b-hr cells.

Formulation Example 1

Microcapsules Containing Leuprorelin Acetate 5.8 g of leuprorelin acetate was dissolved in 6.7 ml of distilled water. To this was added 138 g of dichloromethane solution containing polylactic acid (weight average molecular weight: 15000) (51.6 g) which had been separately dissolved and filtered, and the mixture was stirred and emulsified with an auto-mini mixer for 9 minutes (rotation number: about 6000 rpm), and adjusted to 15° C. This mixture was added to 13.5 L aqueous solution of 0.1% polyvinyl alcohol (PVA) which had been previously dissolved, filtered and adjusted to the same temperature, to emulsify it. For emulsification, HOMOMIC LINE FLOW (Tokushu Kika Kogyo Co., Ltd.) was used, and the rotation number of the mixer was about 7,000 rpm. Solvent was removed from this W/O/W emulsion with light stirring for about 3 hours (drying method in water).

The obtained microcapsules were put through a sieve of 74 μm to remove coarse particles, and separated by filtration or centrifugation. Those were washed with distilled water, free drug and PVA were removed, and re-dispersed with small amount of water. 8.7 g of D-mannitol was dissolved therein, and the mixture was sieved and lyophilized. The rack temperature was gradually elevated in the drying process, and the microcapsules were dried finally at 52° C. for 69 hours. The microcapsules were sieved and crushed to give microcapsule powders. From this process, 58 g of microcapsule powders containing 15% D-mannitol was obtained.

Formulation Example 2

Injections Containing the Compound of Example 1

| | |
|---|---|
| (1) Compound of Example 1 | 5.0 mg |
| (2) Sodium chloride | 20.0 mg |
| (3) Distilled water to make total volume | 2 ml |

The compound of Example 1 (5.0 mg) and sodium chloride (20.0 mg) are dissolved in distilled water, and to the solution is added water to make the total volume 2 ml. The solution is filtered, and filled into an ampoule (content: 2 ml) under sterilized conditions. The ampoule is sterilized and sealed to obtain an injectable solution.

Formulation Example 3

Tablets Containing Testosterone

| (1) Testosterone | 50 mg |
|---|---|
| (2) Lactose | 34 mg |
| (3) Corn starch | 10.6 mg |
| (4) Corn starch (in paste form) | 5 mg |
| (5) Magnesium stearate | 0.4 mg |
| (6) Carboxymethyl cellulose calcium | 20 mg |
| Total | 120 mg |

In accordance with conventional methods, the above (1) to (6) were mixed and tableted by means of a tablet machine to obtain a tablet.

Formulation Example 4

The preparation obtained in Formulation Example 1 and the preparation obtained in Formulation Example 2 are combined.

Formulation Example 5

The preparation obtained in Formulation Example 1 and the preparation obtained in Formulation Example 3 are combined.

Formulation Example 6

The preparation obtained in Formulation Example 1, the preparation obtained in Formulation Example 2 and the preparation obtained in Formulation Example 3 are combined.

INDUSTRIAL APPLICABILITY

The compound of the present invention has excellent actions as an androgen receptor modulator (especially an agonist), and is useful for preventing and/or treating hypogonadism, male climacteric disturbance, osteoporosis or hormone-resistant cancer (especially LHRH derivative-resistant prostate cancer) for which androgen administration is effective.

The invention claimed is:

1. A compound represented by the general formula:

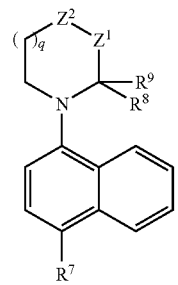

(IIa)

wherein $R^7$ represents a cyano group, a halogen atom, an acyl group optionally substituted with 1 to 5 halogen atoms, a carboxyl group or a $C_{1-6}$ alkyl group substituted with 1 to 5 halogen atoms, $R^8$ and $R^9$ are the same or different and each represents (1) a hydrogen atom, (2) a cyano group, (3) a $C_{1-6}$ alkyl group optionally substituted with a hydroxy group or a $C_{1-6}$ alkoxy group, or (4) an optionally amidated carboxyl group, q represents 0 or 1, $Z^1$ represents a carbonyl group, a carbon atom substituted with a hydroxyimino group, or a group represented by the formula:

wherein $R^{10}$ and $R^{11}$ are the same or different and each represents (1) a hydrogen atom, (2) a halogen atom, (3) a cyano group, (4) a hydroxy group, (5) a $C_{1-6}$ alkyl group optionally substituted with a halogen atom, a hydroxy group or a $C_{1-6}$ alkoxy group, (6) a $C_{1-6}$ alkoxy group, (7) an amino group optionally substituted with a $C_{1-6}$ alkyl group and/or a $C_{1-6}$ acyl group or (8) an optionally esterified or amidated carboxyl group, and $Z^2$ represents a carbonyl group, a carbon atom substituted with a hydroxyimino group, or a group represented by the formula:

wherein $R^{12}$ and $R^{13}$ are the same or different and each represents (1) a hydrogen atom, (2) a halogen atom, (3) a cyano group, (4) a hydroxy group, (5) a $C_{1-6}$ alkyl group optionally substituted with a halogen atom, a hydroxy group or a $C_{1-6}$ alkoxy group, (6) a $C_{1-6}$ alkoxy group, (7) an amino group optionally substituted with a $C_{1-6}$ alkyl group and/or a $C_{1-6}$ acyl group, or (8) an optionally esterified or amidated carboxyl group, or a salt thereof, except the case that the compound is 1-[4-(1-piperidinyl)-1-naphthyl]ethanone, and 4-(1-piperidinyl)-1-naphthonitrile.

2. A compound represented by the general formula:

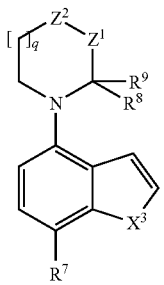

(IIb)

wherein $X^3$ represented a sulfur atom or an oxygen atom,
$R^7$ represents a cyano group, a halogen atom, an acyl group optionally substituted with 1 to 5 halogen atoms, a carboxyl group or a $C_{1-6}$ alkyl group substituted with 1 to 5 halogen atoms,
$R^8$ and $R^9$ are the same or different and each represents (1) a hydrogen atom, (2) a cyano group, (3) a $C_{1-6}$ alkyl group optionally substituted with a hydroxy group or a $C_{1-6}$ alkoxy group, or (4) an optionally amidated carboxyl group,
q represents 0 or 1,
$Z^1$ represents a carbonyl group, a carbon atom substituted with a hydroxyimino group, or a group represented by the formula:

wherein $R^{10}$ and $R^{11}$ are the same or different and each represents (1) a hydrogen atom, (2) a halogen atom, (3) a cyano group, (4) a hydroxy group, (5) a $C_{1-6}$ alkyl group optionally substituted with a halogen atom, a hydroxy group or a $C_{1-6}$ alkoxy group, (6) a $C_{1-6}$ alkoxy group, (7) an amino group optionally substituted with a $C_{1-6}$ alkyl group and/or a $C_{1-6}$ acyl group, or (8) an optionally esterified or amidated carboxyl group, and
$Z^2$ represents a carbonyl group, a carbon atom substituted with a hydroxyimino group, or a group represented by the formula:

wherein $R^{12}$ and $R^{13}$ are the same or different and each represents (1) a hydrogen atom, (2) a halogen atom, (3) a cyano group, (4) a hydroxy group, (5) a $C_{1-6}$ alkyl group optionally substituted with a halogen atom, a hydroxy group or a $C_{1-6}$ alkoxy group, (6) a $C_{1-6}$ alkoxy group, (7) an amino group optionally substituted with a $C_{1-6}$ alkyl group and/or a $C_{1-6}$ acyl group, or (8) an optionally esterified or amidated carboxyl group, or a salt thereof,
except the case that $X^3$ is an oxygen atom, $R^7$ is a halogen atom, q is 0, $R^8$ and $R^9$ are hydrogen atom, $Z^1$ is a group represented by the formula:

wherein one of $R^{10}$ and $R^{11}$ represents a hydrogen atom and the other represents an amino group optionally substituted with a $C_{1-6}$ alkyl group and/or a $C_{1-6}$ acyl group, and $Z^2$ is a methylene group.

3. 4-[4-(hydroxymethyl)-1-piperidinyl]-1-naphthonitrile, 4-[3-(hydroxymethyl)-1-piperidinyl]-1-naphthonitrile, 4-[3-(hydroxymethyl)-3-methyl-1-piperidinyl]-1-naphthonitrile, 4-(2-methyl-1-pyrrolidinyl)-1-naphthonitrile, 4-(2-ethyl-1-pyrrolidinyl)-1-naphthonitrile, 4-(2-isopropyl-1-pyrrolidinyl)-1-naphthonitrile, 4-(3-hydroxy-2-methyl-1-pyrrolidinyl)-1-naphthonitrile, 4-(3-methoxy-2-methyl-1pyrrolidinyl)-1-naphthonitrile, 4-(4-methoxy-2-methyl-1-pyrrolidinyl)-1-naphthonitrile, 4-[3-(hydroxymethyl)-2-methyl-1-pyrrolidinyl]-1-naphthonitrile, 4-[3-(1-hydroxy-1-methylethyl)-2-methyl-1-pyrrolidinyl]-1-naphthonitrile, 1-(4-cyano-1-naphthyl)-2-methylpyrrolidine-3-carboxamide, 1-(4-cyano-1-naphthyl)-2-methylpyrrolidine-3-carbonitrile, 4-(2-methyl-1-pyrrolidinyl)-1-benzothiophene-7-carbonitrile, 4-(3-hydroxy-2-methyl-1-pyrrolidinyl)-1-benzothiophene-7-carbonitrile, 4-(4-hydroxy-2-methyl-1-pyrrolidinyl-1-benzothiophene-7-carbonitrile or an optically active substance or a salt thereof.

4. A pharmaceutical composition comprising an therapeutically effective amount of the compound according to claim 1 or 2 or a salt thereof, and a pharmaceutically acceptable carrier.

5. The pharmaceutical composition according to claim 4, which is an androgen receptor agonist.

6. A method of agonizing an androgen receptor in a mammal, which comprises administering a therapeutically effective amount of the compound according to claim 1 or 2 or a salt thereof.

7. A method for treating hypogonadism or male climacteric disturbance in a mammal, which comprises administering a therapeutically effective amount of the compound according to claim 1 or 2 or a salt thereof.

8. The method according to claim 6, wherein the agonizing is in LHRH agonist-resistant cancer.

9. The method according to claim 8, wherein the cancer is prostate cancer.

* * * * *